US010919870B2

(12) United States Patent
Horiguchi et al.

(10) Patent No.: US 10,919,870 B2
(45) Date of Patent: Feb. 16, 2021

(54) POLYMERIZABLE COMPOUND AND OPTICALLY ANISOTROPIC BODY

(71) Applicant: DIC CORPORATION, Tokyo (JP)

(72) Inventors: Masahiro Horiguchi, Kita-adachi-gun (JP); Yutaka Kadomoto, Kita-adachi-gun (JP); Akihiro Koiso, Kita-adachi-gun (JP); Masanao Hayashi, Kita-adachi-gun (JP); Yoshitaka Saitou, Kita-adachi-gun (JP); Yan Teng, Qingdao (CN); Zhimin Li, Qingdao (CN)

(73) Assignee: DIC CORPORATION, Tokyo (JP)

( * ) Notice: Subject to any disclaimer, the term of this patent is extended or adjusted under 35 U.S.C. 154(b) by 118 days.

(21) Appl. No.: 15/772,981

(22) PCT Filed: Nov. 9, 2015

(86) PCT No.: PCT/CN2015/094100
§ 371 (c)(1),
(2) Date: May 2, 2018

(87) PCT Pub. No.: WO2017/079867
PCT Pub. Date: May 18, 2017

(65) Prior Publication Data
US 2018/0319755 A1   Nov. 8, 2018

(51) Int. Cl.
| | | |
|---|---|---|
| C07D 277/82 | (2006.01) | |
| C09K 19/34 | (2006.01) | |
| C07D 409/04 | (2006.01) | |
| C07D 417/04 | (2006.01) | |
| C07C 251/86 | (2006.01) | |
| C07D 277/64 | (2006.01) | |
| C07D 277/84 | (2006.01) | |
| C09K 19/30 | (2006.01) | |
| C07D 409/14 | (2006.01) | |
| C07C 251/88 | (2006.01) | |
| C07D 305/06 | (2006.01) | |
| C07D 339/06 | (2006.01) | |
| C07C 251/84 | (2006.01) | |
| C07D 409/12 | (2006.01) | |
| C07D 417/12 | (2006.01) | |
| C07D 513/04 | (2006.01) | |

(Continued)

(52) U.S. Cl.
CPC .......... *C07D 277/82* (2013.01); *C07C 251/84* (2013.01); *C07C 251/86* (2013.01); *C07C 251/88* (2013.01); *C07D 277/64* (2013.01); *C07D 277/84* (2013.01); *C07D 305/06* (2013.01); *C07D 339/06* (2013.01); *C07D 409/04* (2013.01); *C07D 409/12* (2013.01); *C07D 409/14* (2013.01); *C07D 417/04* (2013.01); *C07D 417/12* (2013.01); *C07D 513/04* (2013.01); *C09K 19/3066* (2013.01); *C09K 19/32* (2013.01); *C09K 19/322* (2013.01); *C09K 19/34* (2013.01); *C09K 19/3402* (2013.01); *C09K 19/3472* (2013.01); *C09K 19/3477* (2013.01); *C09K 19/3491* (2013.01); *C09K 19/3497* (2013.01); *C07C 2602/40* (2017.05); *C07C 2603/18* (2017.05); *C07C 2603/24* (2017.05); *C07C 2603/32* (2017.05); *C09K 2019/0444* (2013.01); *C09K 2019/0448* (2013.01); *C09K 2019/0466* (2013.01); *C09K 2019/301* (2013.01); *C09K 2019/3408* (2013.01); *C09K 2019/3416* (2013.01)

(58) Field of Classification Search
None
See application file for complete search history.

(56) References Cited

U.S. PATENT DOCUMENTS

| | | |
|---|---|---|
| 6,465,060 B1 | 10/2002 | Wingen et al. |
| 2009/0189120 A1 | 7/2009 | Takeuchi |

(Continued)

FOREIGN PATENT DOCUMENTS

| | | |
|---|---|---|
| CN | 103664868 A | 3/2014 |
| CN | 103772335 A | 5/2014 |

(Continued)

OTHER PUBLICATIONS

Office Action dated Nov. 15, 2017, issued in counterpart Japanese Application No. 2015-240161, with English translation (33 pages).

(Continued)

*Primary Examiner* — Richard A Huhn
(74) *Attorney, Agent, or Firm* — Westerman, Hattori, Daniels & Adrian, LLP

(57) ABSTRACT

There is provided a polymerizable composition, by which discoloration or alignment defects are less likely to occur when a filmy polymer, which is obtained by adding a polymerizable compound to the polymerizable composition and polymerizing this composition, is irradiated with ultraviolet light. There are also provided a polymer obtained by polymerizing the polymerizable composition, and an optically anisotropic body using the polymer. The present invention provides a polymerizable low-wavelength dispersive or polymerizable reverse-wavelength dispersive compound having a partial structure represented by Formula (Z-0). Further, the present invention provides a composition containing the compound; a polymer obtained by polymerizing the composition; and an optically anisotropic body obtained by using the polymer.

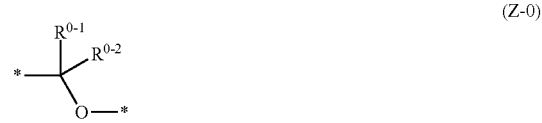

(Z-0)

12 Claims, No Drawings

(51) Int. Cl.
*C09K 19/32* (2006.01)
*C09K 19/04* (2006.01)

(56) References Cited

U.S. PATENT DOCUMENTS

| | | |
|---|---|---|
| 2009/0268143 A1 | 10/2009 | Takeuchi et al. |
| 2011/0237768 A1 | 9/2011 | Katoh et al. |
| 2015/0175564 A1 | 6/2015 | Sakamoto et al. |
| 2015/0274647 A1 | 10/2015 | Sakamoto et al. |
| 2016/0002374 A1 | 1/2016 | Sakamoto et al. |
| 2016/0280672 A1 | 9/2016 | Sakamoto et al. |
| 2017/0260150 A1 | 9/2017 | Nose et al. |
| 2017/0369783 A1 | 12/2017 | Horiguchi et al. |
| 2018/0002276 A1 | 1/2018 | Kadomoto et al. |
| 2018/0002459 A1 | 1/2018 | Endo et al. |
| 2018/0002460 A1 | 1/2018 | Endo et al. |
| 2018/0016502 A1 | 1/2018 | Endo et al. |
| 2018/0031738 A1 | 2/2018 | Ishii et al. |
| 2018/0037817 A1 | 2/2018 | Kuwana et al. |
| 2018/0066189 A1 | 3/2018 | Ishii et al. |
| 2018/0112022 A1 | 4/2018 | Ishii et al. |

FOREIGN PATENT DOCUMENTS

| | | | |
|---|---|---|---|
| JP | 2001206884 A | | 7/2001 |
| JP | 2009-179563 A | | 8/2009 |
| JP | 2009173893 A | * | 8/2009 |
| JP | 2009173893 A | | 8/2009 |
| JP | 2009-265317 A | | 11/2009 |
| JP | 2010-163482 A | | 7/2010 |
| JP | 2011-162678 A | | 8/2011 |
| JP | 2011162678 A | | 8/2011 |
| JP | 2011-207941 A | | 10/2011 |
| JP | 2012-136641 A | | 7/2012 |
| JP | 2016113583 A | | 6/2016 |
| JP | 6066252 B2 | | 1/2017 |
| JP | 6172556 B2 | | 8/2017 |
| JP | 6172557 B2 | | 8/2017 |
| JP | 6213797 B2 | | 10/2017 |
| WO | 2014/010325 A1 | | 1/2014 |
| WO | 2014061709 A1 | | 4/2014 |
| WO | 2014126113 A1 | | 8/2014 |
| WO | 2014/132978 A1 | | 9/2014 |
| WO | 2016/104317 A1 | | 6/2016 |
| WO | 2016088749 A1 | | 6/2016 |
| WO | 2016/114252 A1 | | 7/2016 |
| WO | 2016/114254 A1 | | 7/2016 |
| WO | 2016/114255 A1 | | 7/2016 |
| WO | 2016/114348 A1 | | 7/2016 |
| WO | 2016114253 A1 | | 7/2016 |
| WO | 2017/038265 A1 | | 3/2017 |
| WO | 2017038266 A1 | | 3/2017 |
| WO | 2017038267 A1 | | 3/2017 |
| WO | 2017/068860 A1 | | 4/2017 |
| WO | 2017057020 A1 | | 4/2017 |

OTHER PUBLICATIONS

Office Action dated Jan. 17, 2019, issued in counterpart to JP Application No. 2018-052601, with English translation (12 pages).
International Search Report dated Aug. 12, 2016, issued in counterpart International Application No. PCT/CN2015/094100 (2 pages).

* cited by examiner

POLYMERIZABLE COMPOUND AND OPTICALLY ANISOTROPIC BODY

TECHNICAL FIELD

The present invention relates to a compound having a polymerizable group, a polymerizable composition containing the compound, a polymerizable liquid crystal composition, and an optically anisotropic body using the polymerizable liquid crystal composition.

BACKGROUND ART

A compound having a polymerizable group (polymerizable compound) is used for various optical materials. For example, it is possible to produce a polymer having a uniform alignment by arranging a polymerizable composition containing the polymerizable compound in a liquid crystal state and then polymerizing the polymerizable composition. Such a polymer can be used for a polarization plate, a retardation plate, or the like, necessary for displays. In many cases, in order to satisfy the required optical properties, polymerization rate, solubility, melting point, glass transition temperature, transparency of the polymer, mechanical strength, surface hardness, heat resistance, and light resistance, a polymerizable composition containing two or more kinds of polymerizable compounds is used. In this case, the polymerizable compound to be used is required to provide good physical properties to the polymerizable composition without negatively affecting other properties.

In order to improve the viewing angle of a liquid crystal display, it is required to make the wavelength dispersibility of birefringence of a retardation film lower or make the wavelength dispersibility thereof reverse. As the material for this purpose, various polymerizable liquid crystal compounds having reverse wavelength dispersibility or low wavelength dispersibility have been developed. However, these polymerizable compounds were problematic in that discoloration or alignment defects are likely to occur when a filmy polymer, which is obtained by adding the compound to a polymerizable composition, applying the composition onto a substrate, and polymerizing this composition, is irradiated with ultraviolet light (Patent Documents 1 to 3). For example, when the film in which discoloration or alignment defects occurred is used for displays, there are problems in that the unevenness in brightness of a screen occurs, color tone is unnatural, desired optical properties cannot be obtained, and the quality of display products is greatly deteriorated. Therefore, the development of a polymerizable liquid crystal compound having reverse-wavelength dispersibility or low-wavelength dispersibility, which can solve such problems, has been required.

RELATED ART DOCUMENT

Patent Document

[Patent Document 1] JP-A-2011-162678
[Patent Document 2] WO 2014-010325 A1
[Patent Document 3] JP-A-2009-179563

SUMMARY OF THE INVENTION

Problem that the Invention is to Solve

In order to solve the aforementioned problems, the present invention intends to provide a polymerizable liquid crystal compound having reverse wavelength dispersibility or low wavelength dispersibility, by which discoloration or alignment defects are less likely to occur when a filmy polymer, which is obtained by adding the compound to a polymerizable composition and polymerizing this composition, is irradiated with ultraviolet light. Further, the present invention intends to provide a polymerizable composition containing the polymerizable liquid crystal compound having reverse wavelength dispersibility or low wavelength dispersibility, a polymer obtained by polymerizing the polymerizable composition, and an optically anisotropic body using the polymer.

Means for Solving the Problem

The present inventors have conducted intensive studies in order to solve the above problems. As a result, they have developed a low-wavelength dispersive and/or reverse-wavelength dispersive compound having a partial structure represented by Formula (I-0-1) below in a molecule thereof. That is, the present invention provides a polymerizable low-wavelength dispersive or polymerizable reverse-wavelength dispersive compound having a partial structure represented by Formula (Z-0) below in a molecule thereof:

(Z-0)

(in the formula, $R^{0-1}$ and $R^{0-2}$ each independently represent a hydrogen atom, a fluorine atom, a chlorine atom, a bromine atom, an iodine atom, or a linear or branched alkyl group having 1 to 20 carbon atoms, in which one —$CH_2$— or two or more non-adjacent —$CH_2$—'s may be each independently substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, and any hydrogen atom in the alkyl group may be substituted with a fluorine atom or a chlorine atom, and * is connected to a ring structure). Further, the present invention provides a polymerizable composition containing the compound; a resin, a resin additive, an oil, a filter, an adhesive, a pressure-sensitive adhesive, oil and fat, an ink, pharmaceuticals, cosmetics, a detergent, a building material, a packaging material, a liquid crystal material, an organic EL material, an organic semiconductor material, an electronic material, a display element, an electronic device, a communication apparatus, an automobile part, an aircraft part, a machinery part, an agricultural chemical, and a food, each of which is obtained by using the compound, and a product using these; a polymerizable liquid crystal composition; a polymer obtained by polymerizing the polymerizable liquid crystal composition; and an optically anisotropic body using the polymer.

Advantage of the Invention

The compound of the present invention is useful as a component of the polymerizable composition. Further, the optically anisotropic body using the polymerizable liquid crystal composition containing the compound of the present invention is useful in the application of an optical material such as a retardation film because discoloration or alignment defects are less likely to occur when this optically anisotropic body is irradiated with ultraviolet light.

DESCRIPTION OF EMBODIMENTS

The present invention provides a reversely dispersive compound having a specific structure in the molecule thereof, and also provides a polymerizable composition containing the compound; a resin, a resin additive, an oil, a filter, an adhesive, a pressure-sensitive adhesive, oil and fat, an ink, pharmaceuticals, cosmetics, a detergent, a building material, a packaging material, a liquid crystal material, an organic EL material, an organic semiconductor material, an electronic material, a display element, an electronic device, a communication apparatus, an automobile part, an aircraft part, a machinery part, an agricultural chemical, and a food, each of which is obtained by using the compound, and a product using these; a polymerizable liquid crystal composition; a polymer obtained by polymerizing the polymerizable liquid crystal composition; and an optically anisotropic body using the polymer. In the graph in which the wavelength λ of incident light to a retardation film is taken on the horizontal axis and the birefringence Δn thereof is plotted on the vertical axis, when the birefringence Δn becomes larger as the wavelength λ become shorter, the film is generally referred to as "positively dispersive" by those skilled in the art, and when the birefringence Δn becomes smaller as the wavelength λ becomes shorter, the film is generally referred to as "reverse-wavelength dispersive" or "reversely dispersive" by those skilled in the art. In the present invention, the compound constituting a retardation film having a Re(450)/Re(550) of 0.95 or less, which is a value obtained by dividing an in-plane phase difference at a wavelength of 450 nm (Re 450) by an in-plane phase difference at a wavelength of 550 nm (Re 550), is referred to as a reversely dispersive compound. Further, the compound constituting a retardation film having a Re(450)/Re(550) of more than 0.95 and 1.05 or less is referred to as a low-wavelength dispersive compound. The method of measuring the phase difference is as follows.

Measurement of Phase Difference>

A polyimide solution for alignment film is applied onto a glass substrate having a thickness of 0.7 mm using a spin coating method, dried at 100° C. for 10 minutes, and then baked at 200° C. for 60 minutes, so as to obtain a coating film. The obtained coating film is rubbed using a commercially available rubbing apparatus.

A cyclopentanone solution containing a compound to be evaluated in an amount of 20 mass % is applied onto the rubbed substrate by a spin coating method, and dried at 100° C. for 2 minutes. The obtained coating film is cooled to room temperature, and then irradiated with ultraviolet rays at an intensity of 30 mW/cm$^2$ for 30 seconds using a high-pressure mercury lamp, so as to obtain a film to be evaluated. The phase difference of the obtained film is measured using a retardation film optical material test apparatus RETS-100 (manufactured by OTSUKA ELECTRONICS Co., LTD.).

When the compound to be evaluated is not dissolved in cyclopentanone, chloroform is used as a solvent. Further, when the compound to be evaluated does not exhibit liquid crystallinity alone, a film is formed using a composition obtained by adding the compound to be evaluated (10 mass %, 20 mass %, or 30 mass %) to a mother liquid crystal consisting of a compound represented by Formula (A) below (50 mass %) and a compound represented by Formula (B) below (50 mass %), and the phase difference is measured by extrapolation.

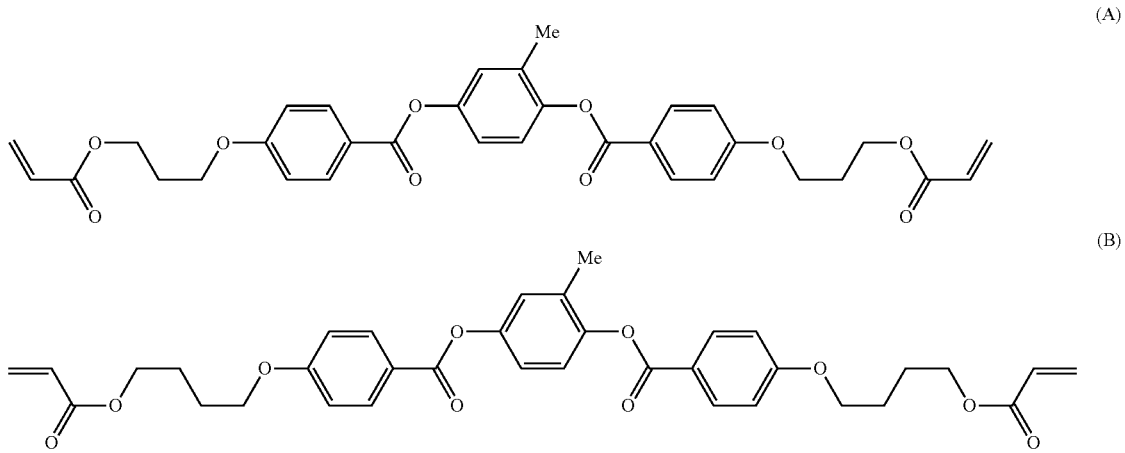

(A)

(B)

In Formula (Z-0), two *'s are each independently connected to a ring structure. The ring structure is preferably a group selected from the following ring structures A and/or ring structures G. The ring structures A each independently represent an unsubstituted ring structure or a ring structure which may be substituted with one or more of substituent groups L, and, from the viewpoint of liquid crystallinity, easiness of synthesis, and easiness of raw material availability, the ring structures A each independently represent preferably a 1,4-phenylene group, a 1,4-cyclohexylene group, a pyridine-2,5-diyl group, a pyrimidine-2,5-diyl group, a naphthalene-2,6-diyl group, a naphthalene-1,4-diyl group, a tetrahydronaphthalene-2,6-diyl group, a decahydronaphthalene-2,6-diyl group, or 1,3-dioxane-2,5-diyl group, each of which may be unsubstituted or may be substituted with one or more of substituent groups L, more preferably a 1,4-phenylene group, a 1,4-cyclohexylene group, or a naphthalene-2,6-diyl group, each of which may be unsubstituted or may be substituted with one or more of substituent groups L, further preferably a group selected from Formulae (A-1) to (A-11) below,

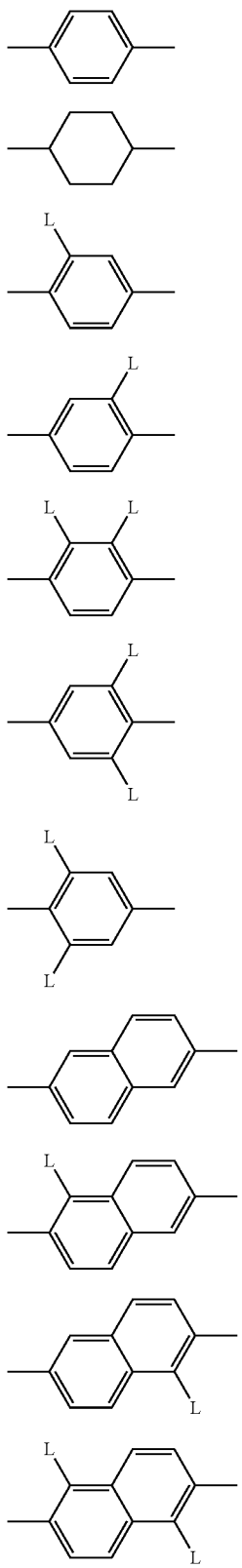

still further preferably a group selected from Formulae (A-1) to (A-8) below, and particularly preferably a group selected from Formulae (A-1) to (A-4) below. The ring structure G represents a divalent group having at least one aromatic ring selected from the group consisting of aromatic hydrocarbon rings and aromatic heterocyclic rings, and the number of π electrons contained in the aromatic ring in the group represented by G is 12 or more, and the group represented by G represents preferably a group which may be unsubstituted or may be substituted with one or more of substituent groups $L^G$. More preferable structure is the same as that of the group represented by $G^1$ below. L represents a fluorine atom, a chlorine atom, a bromine atom, an iodine atom, a pentafluorosulfuranyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms, in which one —CH$_2$— or two or more non-adjacent —CH$_2$—'s may be each independently substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, and any hydrogen atom in the alkyl group may be substituted with a fluorine atom, or L may represent a group represented by $P^L$-(Sp$^L$-X$^L$)$_{kL}$—, where $P^L$ represents a polymerizable group, and a preferable polymerizable group represents the same group as that of $P^0$ below, Sp$^L$ represents a spacer group or single bond, and a preferable spacer group represents the same group as that of Sp$^0$ below, and if a plurality of Sp$^L$'s exist, they may be different from or identical to each other, $X^L$ represents —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—N=CH—, —CF=CF—, —C≡C—, or a single bond, and if a plurality of $X^L$'s exist, they may be different from or identical to each other (provided that, $P^L$-(Sp$^L$-X$^L$)$_{kL}$— does not contain a —O—O— bond), and kL represents an integer of 0 to 10, and if a plurality of L's exist in the compound, they may be different from or identical to each other. From the viewpoint of liquid crystallinity and easiness of synthesis, preferably, L represents a fluorine atom, a chlorine atom, a pentafluorosulfuranyl group, a nitro group, a methylamino group, a dimethylamino group, a diethylamino group, a diisopropylamino group, or a linear or branched alkyl group having 1 to 20 carbon atoms, in which any hydrogen atom may be substituted with a fluorine atom, and one —CH$_2$— or two or more non-adjacent —CH$_2$—'s may be each independently substituted with a group selected from —O—, —S—, —CO—, —COO—, —OCO—, —O—CO—O—, —CH=CH—, —CF=CF—, or —C≡C—, more preferably, L represents a fluorine atom, a chlorine atom, or a linear or branched alkyl group having 1 to 12 carbon atoms, in which any hydrogen atom may be substituted with a fluorine atom, and one —CH$_2$— or two or more non-adjacent —CH$_2$—'s may be each independently substituted with a group selected from —O—, —COO—, or —OCO—, further preferably, L represents a fluorine atom, a chlorine atom, or a linear or branched alkyl group or alkoxy group having 1 to 12 carbon atoms, in which any hydrogen atom may be substituted with a fluorine atom, and particularly preferably, L represents a fluorine atom, a chlorine atom, or a linear alkyl group or linear alkoxy group having 1 to 8 carbon atoms.

In Formula (Z-0), $R^{0-1}$ and $R^{0-2}$ each independently represent a hydrogen atom, a fluorine atom, a chlorine atom, a bromine atom, an iodine atom, or a linear or branched alkyl group having 1 to 20 carbon atoms, in which one —$CH_2$— or two or more non-adjacent —$CH_2$—'s may be each independently substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, and any hydrogen atom in the alkyl group may be substituted with a fluorine atom or a chlorine atom. From the viewpoint of liquid crystallinity, easiness of synthesis, and discoloration and alignment defects at the time of being irradiated with ultraviolet light, preferably, $R^{0-1}$ and $R^{0-2}$ each independently represent a hydrogen atom, a fluorine atom, a chlorine atom, or a linear or branched alkyl group having 1 to 20 carbon atoms, in which one —$CH_2$— or two or more non-adjacent —$CH_2$—'s may be each independently substituted with —O— or —S—, and any hydrogen atom in the alkyl group may be substituted with a fluorine atom or a chlorine atom, more preferably, $R^{0-1}$ and $R^{0-2}$ each independently represent a hydrogen atom, a fluorine atom, or a linear or branched alkyl group having 1 to 6 carbon atoms, in which any hydrogen atom in the alkyl group may be substituted with a fluorine atom, further preferably, $R^{0-1}$ and $R^{0-2}$ each independently represent a hydrogen atom, a fluorine atom, a methyl group, or a trifluoromethyl group, still further preferably, $R^{0-1}$ and $R^{0-2}$ each independently represent a hydrogen atom or a fluorine atom, and particularly preferably $R^{0-1}$ and $R^{0-2}$ each independently represent a hydrogen atom.

From the viewpoint of mechanical strength and liquid crystallinity of a film prepared from the compound, the compound has more preferably at least one group represented by Formula (I-0-R) below in a molecule thereof:

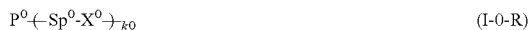      (I-0-R)

(in the formula, $P^0$ represents a polymerizable group, $Sp^0$ represents a spacer group or a single bond, and if a plurality of $Sp^0$'s exist, they may be different from or identical to each other, $X^0$ represents —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—N=CH—, —CF=CF—, —C≡C—, or a single bond, and if a plurality of $X^c$'s exist, they may be different from or identical to each other (provided that, $P^0$-($Sp^0$-$X^0$)$_{k0}$-does not contain a —O—O— bond), and k0 represents an integer of 0 to 10).

In Formula (I-0-R), $P^0$ represents a polymerizable group, and preferably a group selected from Formulae (P-1) to (P-20) below,

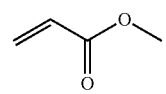 (P-1)

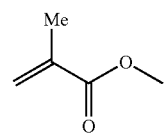 (P-2)

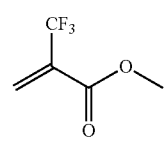 (P-3)

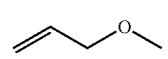 (P-4)

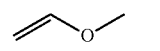 (P-5)

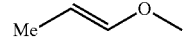 (P-6)

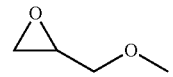 (P-7)

 (P-8)

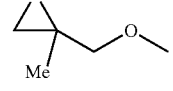 (P-9)

 (P-10)

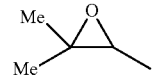 (P-11)

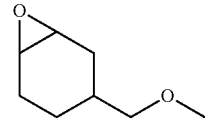 (P-12)

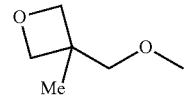 (P-13)

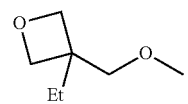 (P-14)

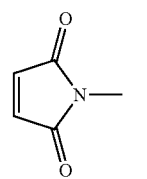 (P-15)

-continued

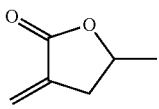
(P-16)

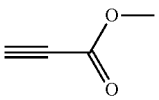
(P-17)

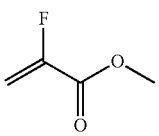
(P-18)

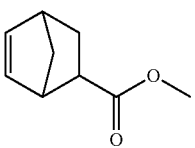
(P-19)

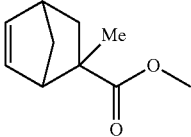
(P-20)

and these polymerizable groups are polymerized by radical polymerization, radical addition polymerization, cationic polymerization, or anionic polymerization. Particularly, when ultraviolet polymerization is performed as the polymerization method. Formula (P-1), (P-2), (P-3), (P-4), (P-5), (P-7), (P-11), (P-13), (P-15), or (P-18) is preferable, Formula (P-1), (P-2), (P-7), (P-11), or (P-13) is more preferable, Formula (P-1), (P-2), or (P-3) is further preferable, and Formula (P-1) or (P-2) is particularly preferable.

In Formula (I-0-R), $Sp^0$ represents a spacer group or a single bond, and if a plurality of $Sp^0$'s exists, they may be different from or identical to each other. Further, the spacer group may be unsubstituted or may be substituted with one or more of the aforementioned substituent groups L. Preferably, the spacer group represents an alkylene group having 1 to 20 carbon atoms, in which one —$CH_2$— or two or more non-adjacent —$CH_2$—'s may be each independently substituted with —O—, —S—, —$OCH_2$—, —$CH_2O$—, —CO—, —COO—, —OCO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —$SCF_2$—, —CH=CH—COO—, —CH=CH—OCO—, —COO—CH=CH—, —OCO—CH=CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH=CH—, —N=N—, —CH=N—N=CH—, —CF=CF—, or —C≡C—. From the viewpoint of easiness of raw material availability and easiness of synthesis, if a plurality of $Sp^0$'s exists, they may be different from or identical to each other, and the plurality of $Sp^0$'s each independently represent preferably an alkylene group having 1 to 20 carbon atoms, in which one —$CH_2$— or two or more non-adjacent —$CH_2$—'s may be each independently substituted with —O—, —COO—, —OCO—, —OCO—O—, —CO—NH—, —NH—CO—, —CH=CH—, or —C≡C—, more preferably an alkylene group having 1 to 10 carbon atoms, in which one —$CH_2$— or two or more non-adjacent —$CH_2$—'s may be each independently substituted with —O—, —COO—, or —OCO—, or a single bond, further preferably an alkylene group having 1 to 10 carbon atoms or a single bond, and particularly preferably an alkylene group having 1 to 8 carbon atoms, where if a plurality of the alkyelene groups exists, they may be different from or identical to each other.

In Formula (I-0-R), $X^0$ represents —O—, —S—, —$OCH_2$—, —$CH_2O$—, —CO—, —COO—, —OCO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —$SCF_2$—, —CH=CH—COO—, —CH=CH—OCO—, —COO—CH=CH—, —OCO—CH=CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH=CH—, —N=N—, —CH=N—N=CH—, —CF=CF—, —C≡C—, or a single bond, and if a plurality of $X^0$'s exist, they may be different from or identical to each other. From the viewpoint of easiness of raw material availability and easiness of synthesis, if a plurality of $X^0$'s exists, they may be different from or identical to each other, and the plurality of $X^0$'s each independently represent preferably —O—, —S—, —$OCH_2$—, —$CH_2O$—, —COO—, —OCO—, —CO—S—, —S—CO—, —O—CO—O—, —CO—NH—, —NH—CO—, —COO—$CH_2CH_2$—, —OCO—$CH_2CH_2$—, —$CH_2CH_2$—COO—, —$CH_2CH_2$—OCO—, or a single bond, more preferably —O—, —$OCH_2$—, —$CH_2O$—, —COO—, —OCO—, —COO—$CH_2CH_2$—, —OCO—$CH_2CH_2$—, —$CH_2CH_2$—COO—, —$CH_2CH_2$—OCO—, or a single bond, and particularly preferably —O—, —COO—, —OCO—, or a single bond, where if a plurality of the groups exists, they may be different from or identical to each other.

In Formula (I-0-R), k0 represents an integer of 0 to 10, preferably an integer of 0 to 5, more preferably an integer of 0 to 2, and particularly preferably 1.

From the viewpoint of liquid crystallinity and the occurrence of discoloration and alignment defects being difficult at the time of being irradiated with ultraviolet light, the low-wavelength dispersive and/or reverse-wavelength dispersive compound according to the present invention is preferably a compound represented by Formula (I) below:

$$R^1\text{-}(A^1\text{-}Z^1\text{-})_{m1}G^1\text{-}(Z^2\text{-}A^2\text{-})_{m2}R^2 \quad (I)$$

(in the formula, $R^1$ and $R^2$ each independently represent a hydrogen atom or a hydrocarbon group having 1 to 80 carbon atoms, the hydrocarbon group may have a substituent group, any carbon atom may be substituted with a heteroatom, and at least one of $R^1$ and $R^2$ represents the group represented by Formula (I-0-R); $A^1$ and $A^2$ each independently represent a 1,4-phenylene group, a 1,4-cyclohexylene group, a pyridine-2,5-diyl group, a pyrimidine-2,5-diyl group, a naphthalene-2,6-diyl group, a naphthalene-1,4-diyl group, a tetrahydronaphthalene-2,6-diyl group, a decahydronaphthalene-2,6-diyl group, or a 1,3-dioxane-2,5-diyl group, and these groups may be unsubstituted or may be substituted with one or more of the aforementioned substituent groups L;

$Z^1$ and $Z^2$ each independently represent —O—, —S—, —$OCH_2$—, —$CH_2O$—, —$CH_2CH_2$—, —CO—, —COO—, —OCO—, —CO—S—, —S—CO—, —O—CO—O—, —CO—NH—, —NH—CO—, —OCO—NH—, —NH—COO—, —NH—CO—NH—, —NH—O—, —O—NH—, —$SCH_2$—, —$CH_2S$—, —$CF_2O$—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—, —N=CH—, —CH=N—N=CH—, —CF=CF—, —C≡C—, a single bond, or a group represented by —CR$^{0-1}$R$^{0-2}$O— or —OCR$^{0-1}$R$^{0-2}$— (in the formula, R$^{0-1}$ and R$^{0-2}$ each independently have the same meaning as R$^{0-1}$ and R$^{0-2}$ in Formula (Z-0)), and if a plurality of Z$^1$'s exist, they may be different from or identical to each other, if a plurality of Z$^2$'s exist, they may be different from or identical to each other, and at least one of Z$^1$ and Z$^2$ represents a group represented by —CR$^{0-1}$R$^{0-2}$O— or —OCR$^{0-1}$R$^{0-2}$—;

G$^1$ represents a divalent group having at least one aromatic ring selected from the group consisting of aromatic hydrocarbon rings antiaromatic heterocyclic rings, the number of π electrons contained in the aromatic ring of the group represented by G$^1$ is 12 or more, and the group represented by G$^1$ may be unsubstituted or may be substituted with one or more of substituent groups L$^G$;

L$^G$ represents a fluorine atom, a chlorine atom, a bromine atom, an iodine atom, a pentafluorosulfuranyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms, in which one —CH$_2$— or two or more non-adjacent —CH$_2$—'s may be each independently substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, and any hydrogen atom in the alkyl group may be substituted with a fluorine atom, or L$^G$ may represent a group represented by P$^{LG}$-(Sp$^{LG}$-X$^{LG}$)$_{kLG}$—, where P$^{LG}$ represents a polymerizable group, and a preferable polymerizable group represents the same group as that defined for P$^0$ above, and Sp$^{LG}$ represents a spacer group or single bond, a preferable spacer group represents the same group as that defined for Sp$^0$ above, and if a plurality of Sp$^{LG}$'s exist, they may be different from or identical to each other, X$^{LG}$ represents —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—N=CH—, —CF=CF—, —C≡C—, or a single bond, and if a plurality of X$^{LG}$'s exist, they may be different from or identical to each other (provided that, P$^{LG}$-(Sp$^{LG}$-X$^{LG}$)$_{kLG}$— does not contain a —O—O— bond), and kLG represents an integer of 0 to 10, and if a plurality of L$^G$'s exist in the compound, they may be different from or identical to each other; and m1 and m2 each independently represent an integer of 0 to 6, and m1+m2 represents an integer of 0 to 6).

In Formula (I), R$^1$ and R$^2$ each independently represent a hydrogen atom or a hydrocarbon group having 1 to 80 carbon atoms which may have a substituent group and in which any carbon atom may be substituted with a heteroatom, and at least one of R$^1$ and R$^2$ represents the group represented by Formula (I-0-R). When R$^1$ or R$^2$ represents a group other than the group represented by Formula (I-0-R), from the viewpoint of liquid crystallinity and easiness of synthesis, R$^1$ or R$^2$ represent preferably a hydrogen atom, a fluorine atom, a chlorine atom, a bromine atom, an iodine atom, a pentafluorosulfuranyl group, a cyano group, a nitro group, an isocyano group, a thioisocyano group, or a linear or branched alkyl group having 1 to 20 carbon atoms, in which any hydrogen atom in the group may be substituted with a fluorine atom and one —CH$_2$— or two or more non-adjacent —CH$_2$—'s may be each independently substituted with —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—N=CH—, —CF=CF—, or —C≡C—, more preferably a hydrogen atom, a fluorine atom, a chlorine atom, or a linear or branched alkyl group having 1 to 12 carbon atoms, in which one —CH$_2$— or two or more non-adjacent —CH$_2$—'s may be each independently substituted with —O—, —COO—, —OCO—, or —O—CO—O—, further preferably a hydrogen atom, a fluorine atom, a chlorine atom, or a linear alkyl group or linear alkoxy group having 1 to 12 carbon atoms, and particularly preferably a linear alkyl group or linear alkoxy group having 1 to 12 carbon atoms. From the viewpoint of mechanical strength and liquid crystallinity of a film prepared from the compound, more preferably, R$^1$ and R$^2$ each independently represent the group represented by Formula (I-0-R).

In Formula (I), A$^1$ and A$^2$ each independently represent a 1,4-phenylene group, a 1,4-cyclohexylene group, a pyridine-2,5-diyl group, a pyrimidine-2,5-diyl group, a naphthalene-2,6-diyl group, a naphthalene-1,4-diyl group, a tetrahydronaphthalene-2,6-diyl group, a decahydronaphthalene-2,6-diyl group, or a 1,3-dioxane-2,5-diyl group, and these groups may be unsubstituted or may be substituted with one or more of the aforementioned substituent groups L. As preferable embodiments of A$^1$ and A$^2$, A$^1$ and A$^2$ each independently represent more preferably a 1,4-phenylene group, a 1,4-cyclohexylene group, or a naphthalene-2,6-diyl group which may be unsubstituted or may be substituted with one or more of the substituent groups L, further preferably a group selected from Formulae (A-1) to (A-11) below,

(A-1)

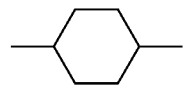

(A-2)

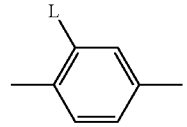

(A-3)

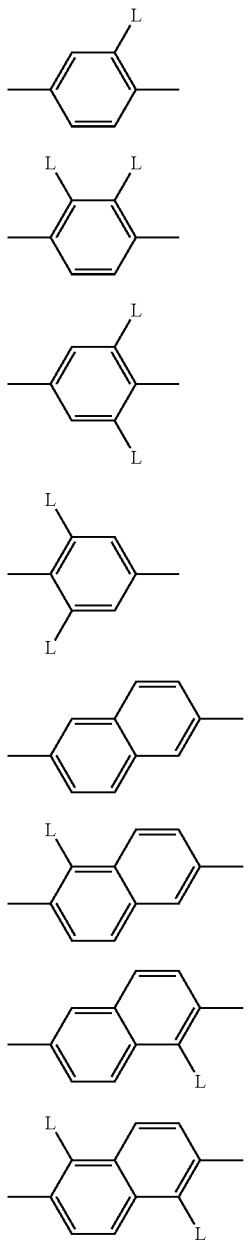

still further preferably a group selected from Formulae (A-1) to (A-8), and particularly preferably a group selected from Formulae (A-1) to (A-4). From the viewpoint of reverse dispersibility, as the group represented by $A^1$ connected to the group represented by $Z^1$ adjacent to the group $G^1$ and the group represented by $A^2$ connected to the group represented by $Z^2$ adjacent to the group $G^1$, $A^1$ and $A^2$ each independently represent preferably a 1,4-cyclohexylene group which may be unsubstituted or may be substituted with one or more of the substituent groups L, and more preferably a group represented by Formula (A-2). Further, when a plurality of the groups represented by $A^1$ and $A^2$ exist, from the viewpoint of refractive index anisotropy, easiness of synthesis, and solubility in a solvent, as the group represented by $A^1$ and $A^2$ other than above groups represented by $A^1$ and $A^2$, $A^1$ and $A^2$ each independently represent preferably a 1,4-phenylene group or a naphthalene-2,6-diyl group which may be unsubstituted or may be substituted with one or more of the substituent groups L, more preferably a group selected from Formulae (A-1) and (A-3) to (A-11), further preferably a group selected from Formulae (A-1) and (A-3) to (A-8), and particularly preferably a group selected from Formulae (A-1), (A-3), and (A-4). In Formula (I), $Z^1$ and $Z^2$ each independently represent —O—, —S—, —OCH$_2$—, —CH$_2$O—, —CH$_2$CH$_2$—, —CO—, —COO—, —OCO—, —CO—S—, —S—CO—, —O—CO—O—, —CO—NH—, —NH—CO—, —OCO—NH—, —NH—COO—, —NH—CO—NH—, —NH—O—, —O—NH—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO, —CH=CH—, —N=N—, —CH=N—, —N=CH—, —CH=N—N=CH—, —CF=CF—, —C≡C—, a single bond, or a group represented by —CR$^{0-1}$R$^{0-2}$O— or —OCR$^{0-1}$R$^{0-2}$— (in the formula, R$^{0-1}$ and R$^{0-2}$ each independently have the same meaning as R$^{0-1}$ and R$^{0-2}$ in Formula (Z-0)). Here, if a plurality of $Z^1$'s exist, they may be different from or identical to each other, if a plurality of $Z^2$'s exist, they may be different from or identical to each other, and at least one of $Z^1$ and $Z^2$ represents a group represented by —CR$^{0-1}$R$^{0-2}$O— or —OCR$^{0-1}$R$^{0-2}$—. When a plurality of $Z^1$'s and $Z^2$'s exist, from the viewpoint of easiness of synthesis and liquid crystallinity, preferably, at least one of $Z^1$ and $Z^2$ directly connected to the $G^1$ group contained in Formula (I) represents a group represented by —CR$^{0-1}$R$^{0-2}$O— or —OCR$^{0-1}$R$^{0-2}$—, and particularly preferably all of $Z^1$ and $Z^2$ directly connected to the $G^1$ group contained in Formula (I) represents a group represented by —CR$^{0-1}$R$^{0-2}$O— or —OCR$^{0-1}$R$^{0-2}$—. Further, when a plurality of $Z^1$'s and $Z^2$'s exist, from the viewpoint of liquid crystallinity, easiness of raw material availability, and easiness of synthesis, preferable groups other than the group represented by —CR$^{0-1}$R$^{0-2}$O— or —OCR$^{0-1}$R$^{0-2}$— each independently represent preferably —OCH$_2$—, —CH$_2$O—, —COO—, —OCO—, —CF$_2$O—, —OCF$_2$—, —CH$_2$CH$_2$—, —CF$_2$CF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —CH=CH—, —CF=CF—, —C≡C—, or a single bond, more preferably —OCH$_2$—, —CH$_2$O—, —COO—, —OCO—, —CF$_2$O—, —OCF$_2$—, —CH$_2$CH$_2$—, —COO—CH$_2$CH$_2$—, —OCO—CH$_2$CH$_2$—, —CH$_2$CH$_2$—COO—, —CH$_2$CH$_2$—OCO—, —CH=CH—, —C≡C—, or a single bond, further preferably -OCH$_2$—, —CH$_2$O—, —COO—, —OCO—, —CF$_2$O—, —OCF$_2$—, or a single bond, still further preferably —OCH$_2$—, —CH$_2$O—, —COO—, —OCO—, or a single bond, and particularly preferably-OCH$_2$—, —CH$_2$O—, —COO—, or —OCO—.

In Formula (I), m1 and m2 each independently represent an integer of 0 to 6, provided that m1+m2 represents an integer of 0 to 6. From the viewpoint of solubility in a solvent, liquid crystallinity, and discoloration and alignment defects at the time of being irradiated with ultraviolet light, m1 and m2 each independently represent preferably an integer of 1 to 3, and particularly preferably an integer of 1 or 2. Further, from the viewpoint of easiness of synthesis, more preferably, m1 and m2 are identical to each other.

In Formula (I), $G^1$ represents a divalent group having at least one aromatic ring selected from the group consisting of aromatic hydrocarbon rings and aromatic heterocyclic rings, the number of π electrons contained in the aromatic ring of the group represented by $G^1$ is 12 or more, and the group represented by $G^1$ may be unsubstituted or may be substituted with one or more of substituent groups $L^G$. From the viewpoint of reverse wavelength dispersibility, $G^1$ is preferably a group having the maximum absorbance at a wavelength of 300 nm to 900 nm, more preferably a group having the maximum absorbance at a wavelength of 310 nm to 500 nm. From the viewpoint of liquid crystallinity of a compound, easiness of raw material availability, and easiness of synthesis, more preferably, $G^1$ represents a group selected from Formulae (M-1) to (M-6) below:

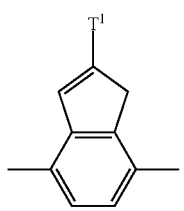 (M-1)

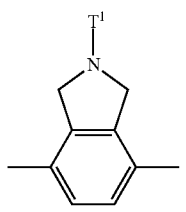 (M-2)

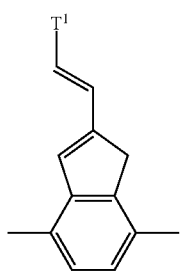 (M-3)

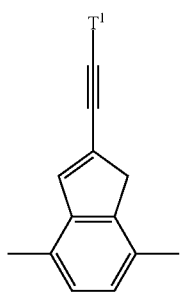 (M-4)

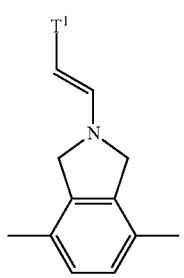 (M-5)

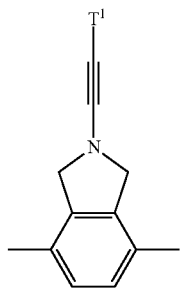 (M-6)

(in the formulae, these groups may be unsubstituted or substituted with one or more of the aforementioned substituent groups $L^G$, any —CH= may be substituted with —N=, —CH$_2$—'s may be each independently substituted with —O—, —S—, —NR$^T$— (in the formula, $R^T$ represents a hydrogen atom or an alkyl group having 1 to 20 carbon atoms), —CS—, or —CO—, and $T^1$ represents a group selected from Formulae (T1-1) to (T1-6) below:

 (T1-1)

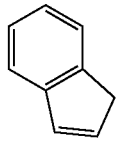 (T1-2)

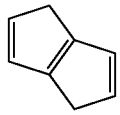 (T1-3)

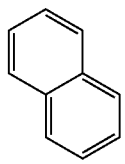 (T1-4)

(T1-5)

(T1-6)

(in the formulae, each of these groups may have a bond at any position, any —CH= may be each independently substituted with —N=, —CH$_2$—'s may be independently substituted with —O—, —S—, —NR$^{1'}$ (in the formula, $R^T$ represents a hydrogen atom or an alkyl group having 1 to 20 carbon atoms), —CS—, or —CO—. Here, the meaning that each of these groups may have a bond at any position is intended to have one bond at any position of Formula (T1-1) when Formula (T1-1) is bonded to $T^1$ of Formulae (M-1) to (M-6) (hereinafter, in the present invention, the meaning that each of these groups may have a bond at any position indicates the same meaning). Further, these groups may be unsubstituted or substituted with one or more of the aforementioned substituent groups $L^G$)); or a group selected from Formulae (M-7) to (M-14) below:

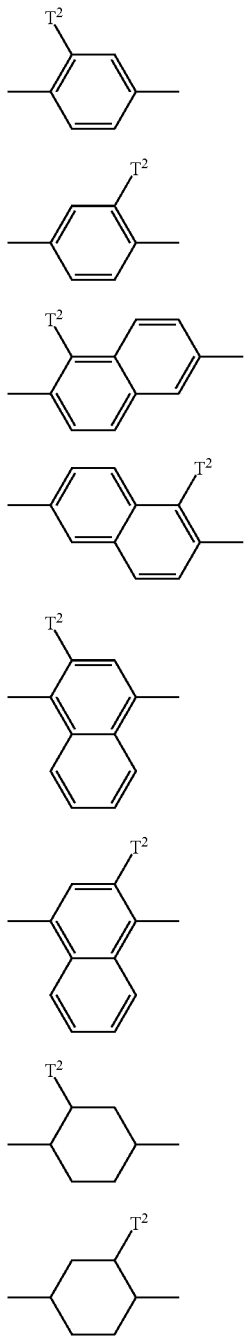

(in the formulae, these groups may be unsubstituted or substituted with one or more of the aforementioned substituent groups $L^G$, any —CH═ may be each independently substituted with —N═, —CH$_2$—'s may be each independently substituted with —O—, —S—, —NR$^T$— (in the formula, R$^T$ represents a hydrogen atom or an alkyl group having 1 to 20 carbon atoms), —CS—, or —CO—, and T$^2$ represents a group selected from Formulae (T2-1) and (T2-2) below:

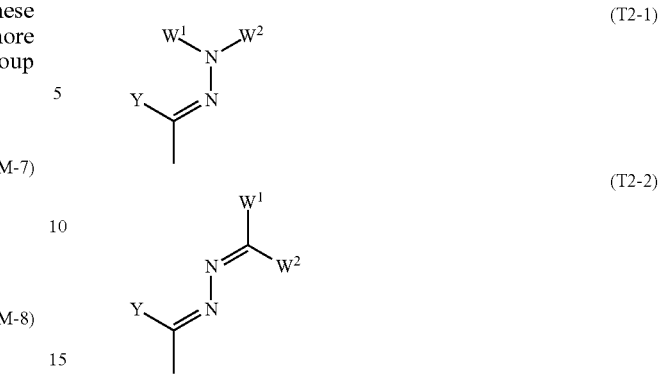

(in the formula, $W^1$ represents a group containing an aromatic group and/or non-aromatic group having 1 to 40 carbon atoms, which may be substituted, the aromatic group may be a hydrocarbon ring or a heterocyclic ring, and the non-aromatic group may be a hydrocarbon group or a group in which any carbon atom in a hydrocarbon group is substituted with a heteroatom (provided that, oxygen atoms are not directly connected with each other), $W^2$ represents a hydrogen atom or a linear or branched alkyl group having 1 to 20 carbon atoms, in which one —CH$_2$— or two or more non-adjacent —CH$_2$—'s may be each independently substituted with —O—, —S—, —CO—, —COO—, —OCO—, —CO—S—, —S—CO—, —O—CO—O—, —CO—NH—, —NH—CO—, —CH═CH—COO—, —CH═CH—OCO—, —COO—CH═CH—, —OCO—CH═CH—$_z$—CH═CH—, —CF═CF—, or —C≡C—, and any hydrogen atom in the alkyl group may be substituted with a fluorine atom, or $W^2$ may represent a group of 2 to 30 carbon atoms having at least one aromatic group, and the group may be unsubstituted or may be substituted with one or more of substituent groups $L^W$, or $W^2$ may represent a group represented by $P^W$—(Sp$^W$-X$^W$)$_{kW}$—, where $P^W$ represents a polymerizable group, a preferable polymerizable group represents the same group as that defined for $P^0$ above, and Sp$^W$ represents a spacer group or single bond, and a preferable spacer group represents the same group as that defined for Sp$^0$ below, and if a plurality of Sp$^W$'s exist, they may be different from or identical to each other, $X^W$ represents —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH═CH—COO—, —CH═CH—OCO—, —COO—CH═CH—, —OCO—CH═CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH═CH—, —N═N—, —CH═N—N═CH—, —CF═CF—, —C≡C—, or a single bond, and if a plurality of $X^W$'s exist, they may be different from or identical to each other (provided that, $P^W$—(Sp$^W$-X$^W$)$_{kW}$— does not contain a —O—O— bond), and kW represents an integer of 0 to 10, $L^W$ represents a fluorine atom, a chlorine atom, a bromine atom, an iodine atom, a pentafluorosulfuranyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms, in which one —CH$_2$— or two or more non-adjacent —CH$_2$—'s may be each independently substituted with —O—, —S—, —CO—, —COO—, —OCO—, —CO—S—, —S—CO—, —O—CO—O—, —CO—NH—, —NH—CO—, —CH═CH—COO—, —CH═CH—OCO—, —COO—CH═CH—, —OCO—CH═CH—, —CH═CH—, —CF═CF—, or —C≡C—, and any hydrogen atom in the alkyl group may be substituted with a fluorine atom, or $L^W$ may represent a group represented by $P^{LW}$-$(Sp^{LW}$-$X^{LW})_{kLW}$—, where $P^{LW}$ represents a polymerizable group, $Sp^{LW}$ represents a spacer group or single bond, and if a plurality of $Sp^{LW}$'s exist, they may be different from or identical to each other, $X^{LW}$ represents —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH═CH—COO—, —CH═CH—OCO—, —COO—CH═CH—, —OCO—CH═CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH═CH—, —N═N—, —CH═N—N═CH—, —CF═CF—, —C≡C—, or a single bond, and if a plurality of $X^{LW}$'s exist, they may be different from or identical to each other (provided that, $P^{LW}$—$(Sp^{LW}$-$X^{LW})_{kLW}$— does not contain a —O—O— bond), and kLW represents an integer of 0 to 10, and if a plurality of $L^W$'s exist in the compound, they may be different from or identical to each other, and Y represents hydrogen atom, a fluorine atom, a chlorine atom, a bromine atom, an iodine atom, a pentafluorosulfuranyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms, in which one —CH$_2$— or two or more non-adjacent —CH$_2$—'s may be each independently substituted with —O—, —S—, —CO—, —COO—, —OCO—, —CO—S—, —S—CO—, —O—CO—O—, —CO—NH—, —NH—CO—, —CH═CH—COO—, —CH═CH—OCO—, —COO—CH═CH—, —OCO—CH═CH—, —CH═CH—, —CF═CF—, or —C≡C—, and any hydrogen atom in the alkyl group may be substituted with a fluorine atom, or Y may represent a group represented by $P^Y$-$(Sp^Y$-$X^Y)_{kY}$—, where $P^Y$ represents a polymerizable group, a preferable polymerizable group represents the same group as that defined for $P^0$ above, and $Sp^Y$ represents a spacer group or single bond, and a preferable spacer group represents the same group as that defined for $Sp^0$ above, and if a plurality of $Sp^Y$'s exist, they may be different from or identical to each other, $X^Y$ represents —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH═CH—COO—, —CH═CH—OCO—, —COO—CH═CH—, —OCO—CH═CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH═CH—, —N═N—, —CH═N—N═CH—, —CF═CF—, —C≡C—, or a single bond, and if a plurality of $X^Y$'s exist, they may be different from or identical to each other (provided that, $P^Y$—$(Sp^Y$-$X^Y)_{kY}$— does not contain a —O—O— bond), and kY represents an integer of 0 to 10, and $W^1$ and $W^2$ may form a ring structure together). From the viewpoint of solubility in a solvent and easiness of synthesis, $G^1$ represents further preferably a group selected from Formulae (M-1), (M-3), (M-4), (M-7), and (M-8), still further preferably a group selected from Formulae (M-1), (M-7), and (M-8), and particularly preferably a group selected from Formulae (M-7) and (M-8). More specifically, the group represented by Formula (M-1) represents preferably a group selected from Formulae (M-1-1) to (M-1-6) below:

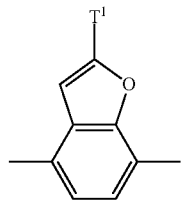

(M-1-1)

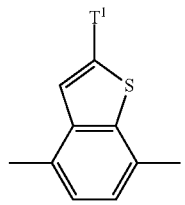

(M-1-2)

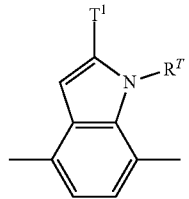

(M-1-3)

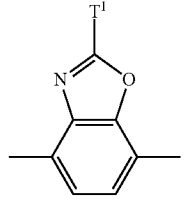

(M-1-4)

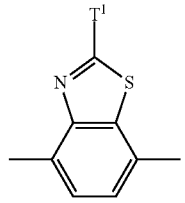

(M-1-5)

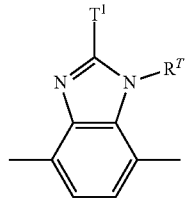

(M-1-6)

(in the formulae, $T^1$ has the same meaning as above, and $R^T$ represents a hydrogen atom or an alkyl group having 1 to 20 carbon atoms), more preferably a group selected from Formulae (M-1-4) and (M-1-5), and particularly preferably a group represented by Formula (M-1-5). The group represented by Formula (M-3) represents preferably a group selected from Formulae (M-3-1) to (M-3-6) below:

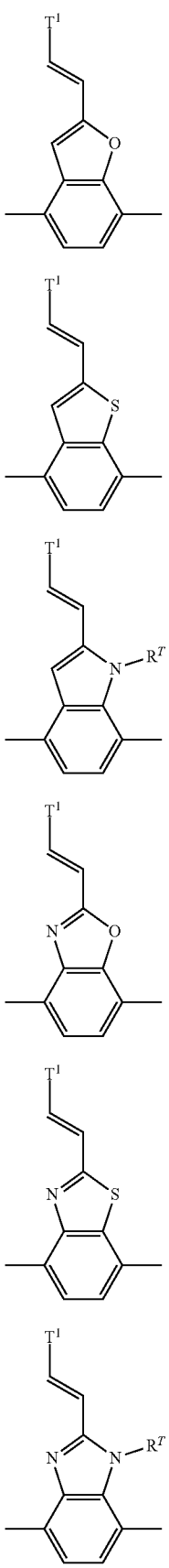
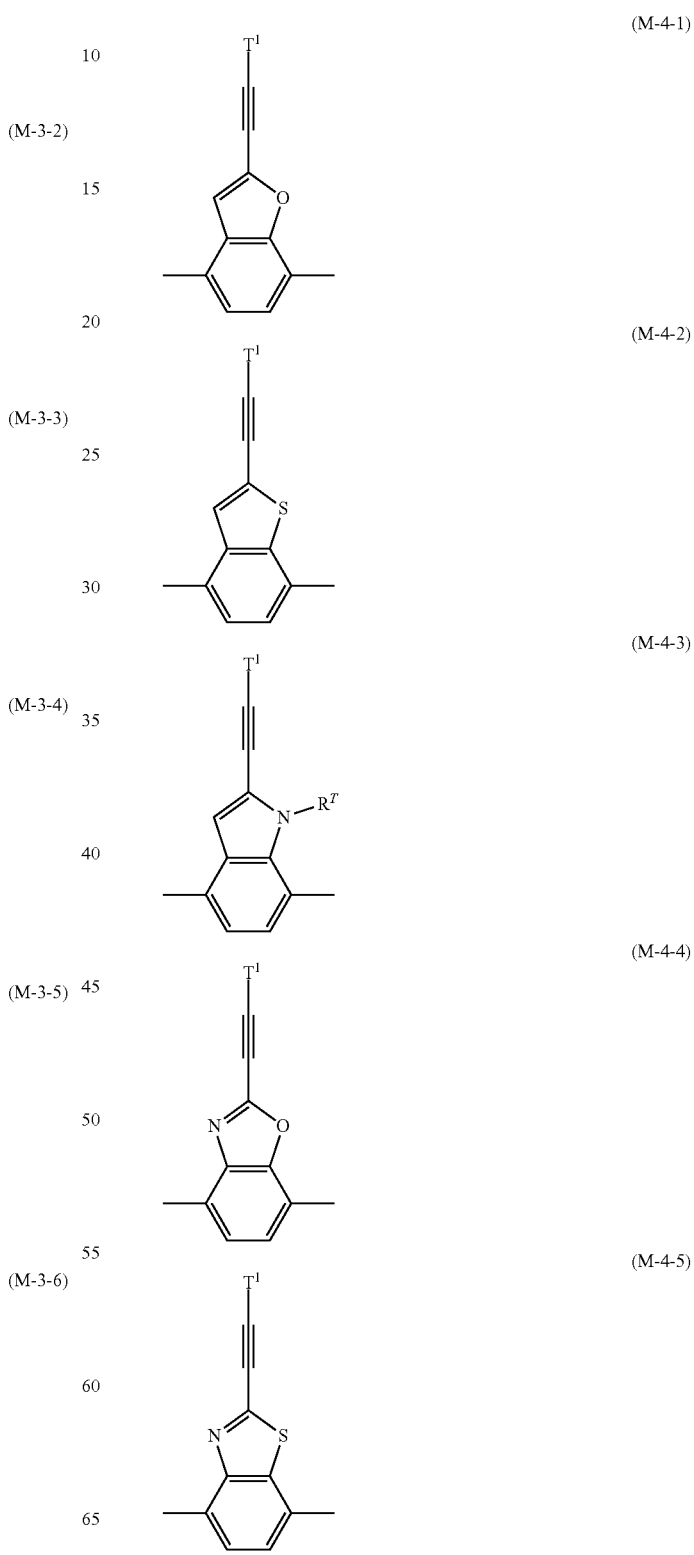
(in the formulae, $T^1$ has the same meaning as above, and $R^T$ represents a hydrogen atom or an alkyl group having 1 to 20 carbon atoms), more preferably a group selected from Formulae (M-3-4) and (M-3-5), and particularly preferably a group represented by Formula (M-3-5). The group represented by Formula (M-4) represents preferably a group selected from Formulae (M-4-1) to (M-4-6) below:

(M-4-6)

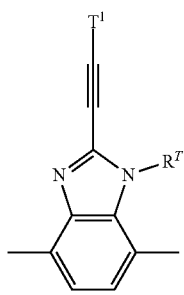

(in the formulae, T¹ has the same meaning as above, and $R^T$ represents a hydrogen atom or an alkyl group having 1 to 20 carbon atoms), more preferably a group selected from Formulae (M-4-4) and (M-4-5), and particularly preferably a group represented by Formula (M-4-5). Each of the groups represented by Formulae (M-7) to (M-14) represents preferably a group selected from Formulae (M-7-1) to (M-14-1) below:

(M-7-1)


(M-8-1)

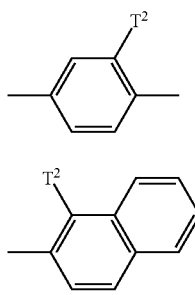

(M-9-1)

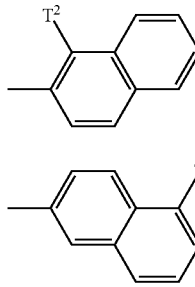

(M-10-1)

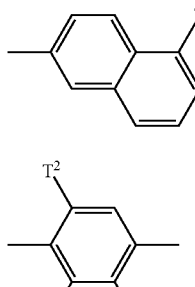

(M-11-1)

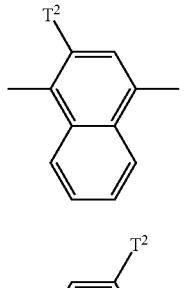

(M-12-1)

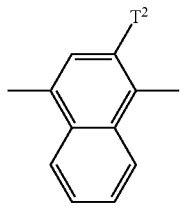

(M-13-1)

(M-14-1)

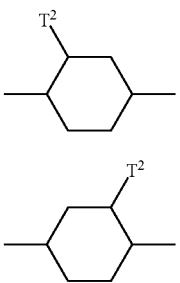

(in the formulae, T² has the same meaning as above), more preferably a group selected from Formulae (M-7-1) to (M-12-1), and particularly preferably a group represented by Formula (M-7-1) or (M-8-1). Further, in Formulae (M-1) to (M-6), from the viewpoint of wavelength dispersibility and easiness of synthesis, T¹ represents preferably a group selected from Formulae (T1-1), (T1-2), (T1-3), and (T1-6), more preferably a group selected from Formulae (T1-3) and (T1-6), and particularly preferably a group represented by Formula (T1-3). More specifically, the group represented by Formula (T1-1) represents preferably a group selected from Formulae (T1-1-1) to (T1-1-7) below:

(T1-1-1)

(T1-1-2)

(T1-1-3)

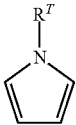

(T1-1-4)

(T1-1-5)

(T1-1-6)

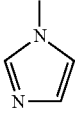

(T1-1-7)

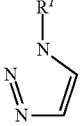

(in the formulae, each of these groups may have a bond at any position, and $R^T$ represents a hydrogen atom or an alkyl group having 1 to 20 carbon atoms. Further, each of these groups may be unsubstituted or may be substituted with one or more of the aforementioned substituent groups $L^G$), and more preferably a group selected from Formulae (T1-1-2), (T1-1-4), (T1-1-5), (T1-1-6), and (T1-1-7). The group represented by Formula (T1-2) represents preferably a group selected from Formulae (T1-2-1) to (T1-2-8) below:

 (T1-2-1)

 (T1-2-2)

 (T1-2-3)

 (T1-2-4)

 (T1-2-5)

 (T1-2-6)

 (T1-2-7)

 (T1-2-8)

(in the formulae, each of these groups may have a bond at any position. Further, each of these groups may be unsubstituted or may be substituted with one or more of the aforementioned substituent groups $L^G$), and more preferably a group represented by Formula (T1-2-1). The group represented by Formula (T1-3) represents preferably a group selected from Formulae (T1-3-1) to (T1-3-8) below:

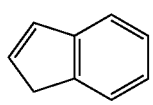 (T1-3-1)

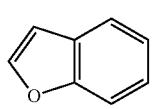 (T1-3-2)

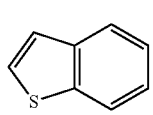 (T1-3-3)

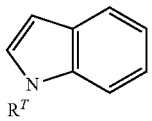 (T1-3-4)

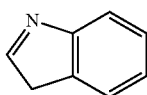 (T1-3-5)

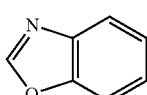 (T1-3-6)

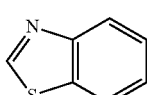 (T1-3-7)

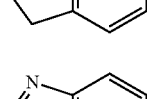 (T1-3-8)

(in the formulae, each of these groups may have a bond at any position, and $R^T$ represents a hydrogen atom or an alkyl group having 1 to 20 carbon atoms. Further, each of these groups may be unsubstituted or may be substituted with one or more of the aforementioned substituent groups $L^G$), and more preferably a group represented by Formulae (T1-3-2), (T1-3-3), (T1-3-6), or (T1-3-7). The group represented by Formula (T1-4) represents preferably a group selected from Formulae (T1-4-1) to (T1-4-6) below:

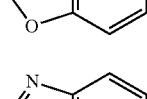 (T1-4-1)

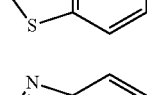 (T1-4-2)

(T1-4-3)

(T1-4-4)

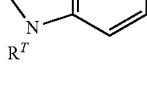 (T1-4-5)

-continued (T1-4-6)

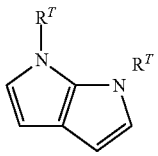

(in the formulae, each of these groups may have a bond at any position, and $R^T$ represents a hydrogen atom or an alkyl group having 1 to 20 carbon atoms. Further, each of these groups may be unsubstituted or may be substituted with one or more of the aforementioned substituent groups $L^G$). The group represented by Formula (T1-5) represents preferably a group selected from Formulae (T1-5-1) to (T1-5-9) below:

(T1-5-1)

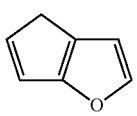

(T1-5-2)

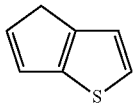

(T1-5-3)

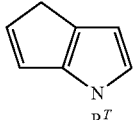

(T1-5-4)

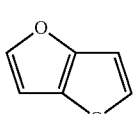

(T1-5-5)

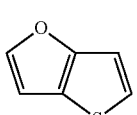

(T1-5-6)

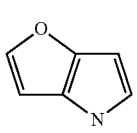

(T1-5-7)

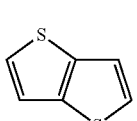

(T1-5-8)

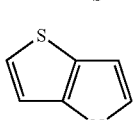

(T1-5-9)

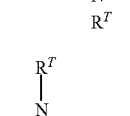

(in the formulae, each of these groups may have a bond at any position, and $R^T$ represents a hydrogen atom or an alkyl group having 1 to 20 carbon atoms. Further, each of these groups may be unsubstituted or may be substituted with one or more of the aforementioned substituent groups $L^G$). The group represented by Formula (T1-6) represents preferably a group selected from Formulae (T1-6-1) to (T1-6-7) below:

(T1-6-1)

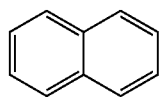

(T1-6-2)

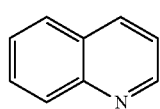

(T1-6-3)

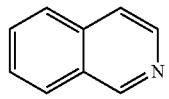

(T1-6-4)

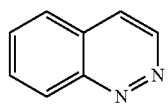

(T1-6-5)

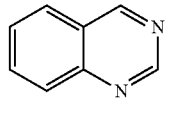

(T1-6-6)

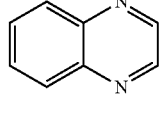

(T1-6-7)

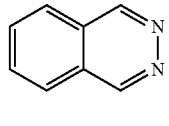

(in the formulae, each of these groups may have a bond at any position. Further, each of these groups may be unsubstituted or may be substituted with one or more of the aforementioned substituent groups $L^G$).

In Formula (I), $L^G$ represents a fluorine atom, a chlorine atom, a bromine atom, an iodine atom, a pentafluorosulfuranyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms, in which one —CH$_2$— or two or more non-adjacent —CH$_2$—'s may be each independently substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, and any hydrogen atom in the alkyl group may be substituted with a fluorine atom, or $L^u$ may represent a group represented by $P^{LG}$—(Sp$^{LG}$-X$^{LG}$)$_{kLG}$—, where $P^{LG}$ represents a polymerizable group, and a preferable polymerizable group represents the same group as that defined for $P^0$ above, and $Sp^{LG}$ represents a spacer group or single bond, and a preferable spacer group represents the same group as that defined for $Sp^0$ above, and if a plurality of $Sp^{LG}$'s exist, they may be different from or identical to each other, $X^{LG}$ represents —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—N=CH—, —CF=CF—, —C≡C—, or a single bond, and if a plurality of $X^{LG}$'s exist, they may be different from or identical to each other (provided that, $P^{LG}$— $(Sp^{LG}$-$X^{LG})_{kLG}$— does not contain a —O—O— bond), and kLG represents an integer of 0 to 10, and if a plurality of $L^G$'s exist in the compound, they may be different from or identical to each other, m1 and m2 each independently represent an integer of 0 to 6, and m1+m2 represents an integer of 0 to 6. From the viewpoint of liquid crystallinity and easiness of synthesis, $L^G$ represents preferably a fluorine atom, a chlorine atom, a pentafluorosulfuranyl group, a nitro group, a methylamino group, a dimethylamino group, a diethylamino group, a diisopropylamino group, or a linear or branched alkyl group having 1 to 20 carbon atoms, in which any hydrogen atom may be substituted with a fluorine atom and one —CH$_2$— or two or more non-adjacent —CH$_2$—'s may be each independently substituted with a group selected from —O—, —S—, —CO—, —COO—, —OCO—, —O—CO—O—, —CH=CH—, —CF=CF—, and —C≡C—, represents more preferably a fluorine atom, a chlorine atom, or a linear or branched alkyl group having 1 to 12 carbon atoms, in which any hydrogen atom may be substituted with a fluorine atom and one —CH$_2$— or two or more non-adjacent —CH$_2$—'s may be each independently substituted with a group selected from —O—, —COO—, and —OCO—, represents further preferably a fluorine atom, a chlorine atom, or a linear or branched alkyl group or alkoxy group having 1 to 12 carbon atoms, in which any hydrogen atom may be substituted with a fluorine atom, and represents particularly preferably a fluorine atom, a chlorine atom, or a linear alkyl group or linear alkoxy group having 1 to 8 carbon atoms.

In Formulae (T2-1) or (T2-2), from the viewpoint of liquid crystallinity and easiness of synthesis, preferably, Y represents a hydrogen atom, a fluorine atom, a chlorine atom, a nitro group, a cyano group, a linear or branched alkyl group having 1 to 20 carbon atoms, in which any hydrogen atom in the group may be substituted with a fluorine atom and one —CH$_2$— or two or more non-adjacent —CH$_2$—'s may be each independently substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, or a group represented by $P^Y$—$(Sp^Y$-$X^Y)_{kY}$—, more preferably, Y represents a hydrogen atom or a linear or branched alkyl group having 1 to 12 carbon atoms, in which any hydrogen atom in the group may be substituted with a fluorine atom and one —CH$_2$— or two or more non-adjacent —CH$_2$—'s may be each independently substituted with —O—, —COO—, or —OCO—, further preferably, Y represents a hydrogen atom or a linear or branched alkyl group having 1 to 12 carbon atoms, in which any hydrogen atom in the group may be substituted with a fluorine atom, and particularly preferably, Y represents a hydrogen atom or a linear alkyl group having 1 to 12 carbon atoms.

In Formulae (T2-1) or (T2-2), from the viewpoint of liquid crystallinity and easiness of synthesis, $W^1$ represents a group containing a carbon ring or a heterocyclic ring of an aromatic group and/or non-aromatic group having 1 to 80 carbon atoms, which may be substituted, and any carbon atom of the carbon ring or heterocyclic ring may be substituted with a heteroatom. From the viewpoint of easiness of raw material availability and easiness of synthesis, the aromatic group contained in $W^1$ represents preferably a group selected from Formulae (W-1) to (W-18) below (each of which may be unsubstituted or substituted with one or more of substituent groups $L^W$):

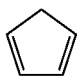 (W-1)

 (W-2)

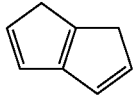 (W-3)

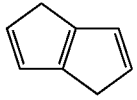 (W-4)

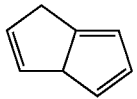 (W-5)

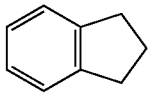 (W-6)

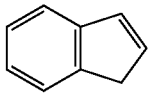 (W-7)

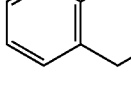 (W-8)

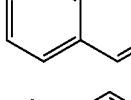 (W-9)

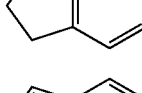 (W-10)

(W-11)

-continued

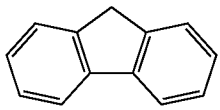 (W-12)

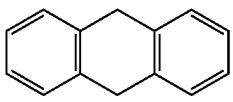 (W-13)

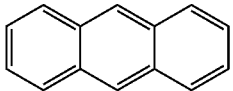 (W-14)

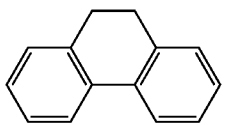 (W-15)

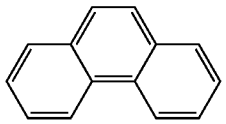 (W-16)

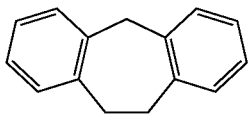 (W-17)

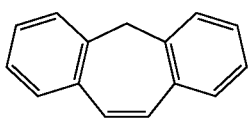 (W-18)

(in the formulae, the ring structure may have a bond at any position thereof, a group in which two or more aromatic groups selected from these groups are linked by a single bond may be formed, any —CH═'s may be each independently substituted with —N═, and —CH²-'s may be each independently substituted with —O—, —S—, —NR$^T$— (in the formulae, R$^T$ represents a hydrogen atom or an alkyl group having 1 to 20 carbon atoms), —CS—, or —CO—, provided that these groups do not contain a —O—O— bond. Further, these groups may be unsubstituted or may be substituted with one or more of the aforementioned substituent groups L$^W$). The group represented by Formula (W-1) represents preferably a group selected from Formulae (W-1-1) to (W-1-7) below (each of which may be unsubstituted or may be substituted with one or more of the aforementioned substituent groups L$^W$):

 (W-1-1)

 (W-1-2)

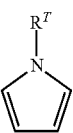 (W-1-3)

 (W-1-4)

 (W-1-5)

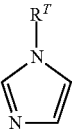 (W-1-6)

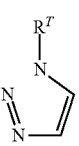 (W-1-7)

(in the formulae, these groups may have a bond at any position, and R$^T$ represents a hydrogen atom or an alkyl group having 1 to 8 carbon atoms). The group represented by Formula (W-2) represents preferably a group selected from Formulae (W-2-1) to (W-2-8) below (each of which may be unsubstituted or may be substituted with one or more of the aforementioned substituent groups L$^W$):

 (W-2-1)

 (W-2-2)

 (W-2-3)

 (W-2-4)

 (W-2-5)

 (W-2-6)

(W-2-7)
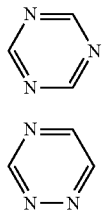

(W-2-8)

(in the formulae, these groups may have a bond at any position). The group represented by Formula (W-3) represents preferably a group selected from Formulae (W-3-1) to (W-3-6) below (each of which may be unsubstituted or may be substituted with one or more of the aforementioned substituent groups $L^W$):

(W-3-1)
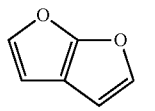

(W-3-2)
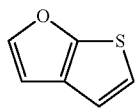

(W-3-3)
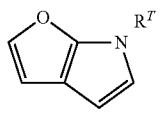

(W-3-4)
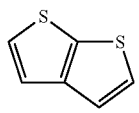

(W-3-5)
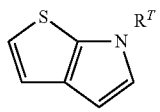

(W-3-6)
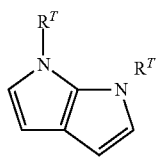

(in the formulae, these groups may have a bond at any position, and $R^T$ represents a hydrogen atom or an alkyl group having 1 to 8 carbon atoms). The group represented by Formula (W-4) represents preferably a group selected from Formulae (W-4-1) to (W-4-9) below (each of which may be unsubstituted or may be substituted with one or more of the aforementioned substituent groups $L^W$):

(W-4-1)
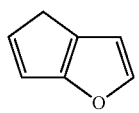

(W-4-2)
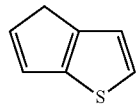

(W-4-3)
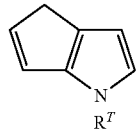

(W-4-4)
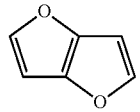

(W-4-5)
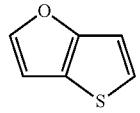

(W-4-6)
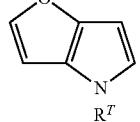

(W-4-7)
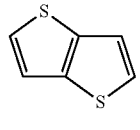

(W-4-8)
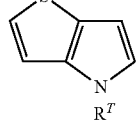

(W-4-9)
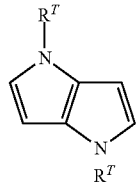

(in the formulae, these groups may have a bond at any position, and $R^T$ represents a hydrogen atom or an alkyl group having 1 to 8 carbon atoms). The group represented by Formula (W-5) represents preferably a group selected from Formulae (W-5-1) to (W-5-13) below (each of which may be unsubstituted or may be substituted with one or more of the aforementioned substituent groups $L^W$):

(W-5-1)
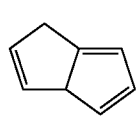

(W-5-2)
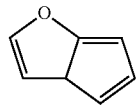

-continued (W-5-3) 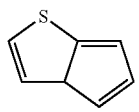

(W-5-4) 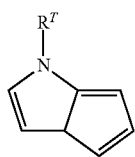

(W-5-5) 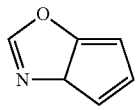

(W-5-6) 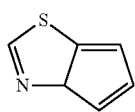

(W-5-7) 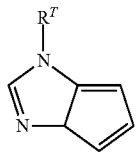

(W-5-8) 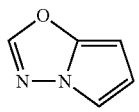

(W-5-9) 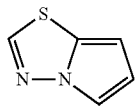

(W-5-10) 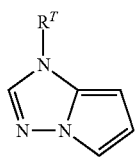

(W-5-11) 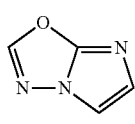

(W-5-12) 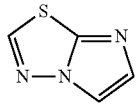

(W-5-13) 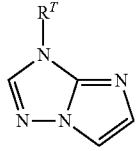

(in the formulae, these groups may have a bond at any position, and $R^T$ represents a hydrogen atom or an alkyl group having 1 to 8 carbon atoms). The group represented by Formula (W-6) represents preferably a group selected from Formulae (W-6-1) to (W-6-12) below (each of which may be unsubstituted or may be substituted with one or more of the aforementioned substituent groups $L^W$):

(W-6-1) 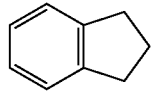

(W-6-2) 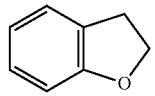

(W-6-3) 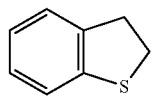

(W-6-4) 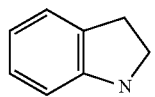

(W-6-5) 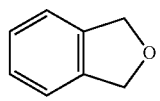

(W-6-6) 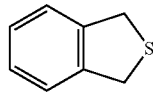

(W-6-7) 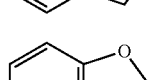

(W-6-8) 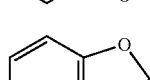

(W-6-9) 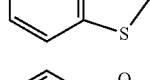

(W-6-10) 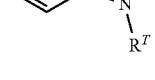

(W-6-11) 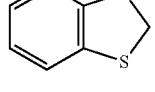

(W-6-12) 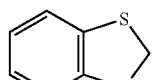

(in the formulae, these groups may have a bond at any position, and $R^T$ represents a hydrogen atom or an alkyl group having 1 to 8 carbon atoms). The group represented by Formula (W-7) represents preferably a group selected from Formulae (W-7-1) to (W-7-8) below (each of which may be unsubstituted or may be substituted with one or more of the aforementioned substituent groups $L^W$):

(W-7-1)
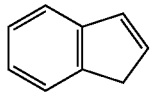

(W-7-2)
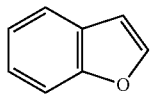

(W-7-3)
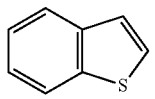

(W-7-4)
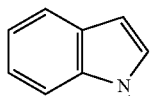

(W-7-5)
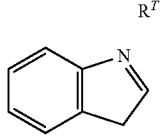

(W-7-6)
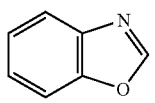

(W-7-7)
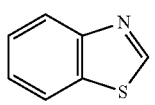

(W-7-8)
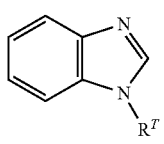

(in the formulae, these groups may have a bond at any position, and $R^T$ represents a hydrogen atom or an alkyl group having 1 to 8 carbon atoms). The group represented by Formula (W-8) represents preferably a group selected from Formulae (W-8-1) to (W-8-19) below (each of which may be unsubstituted or may be substituted with one or more of the aforementioned substituent groups $L^W$):

(W-8-1)
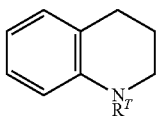

(W-8-2)
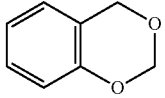

(W-8-3)
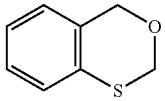

(W-8-4)
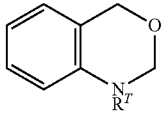

(W-8-5)
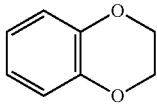

(W-8-6)
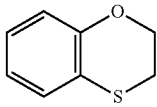

(W-8-7)
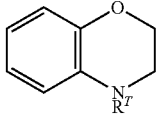

(W-8-8)
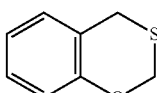

(W-8-9)
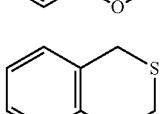

(W-8-10)
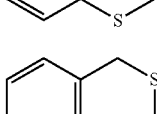

(W-8-11)
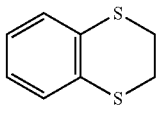

(W-8-12)
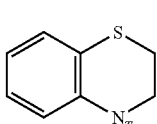

(W-8-13)

(W-8-14)

(W-8-15)
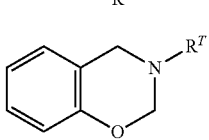

(W-8-16)

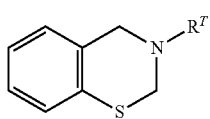 (W-8-17)

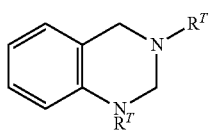 (W-8-18)

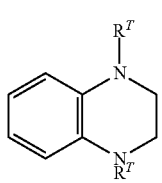 (W-8-19)

(in the formulae, these groups may have a bond at any position, and $R^T$ represents a hydrogen atom or an alkyl group having 1 to 8 carbon atoms). The group represented by Formula (W-9) represents preferably a group selected from Formulae (W-9-1) to (W-9-7) below (each of which may be unsubstituted or may be substituted with one or more of the aforementioned substituent groups $L^W$):

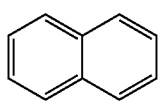 (W-9-1)

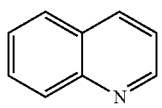 (W-9-2)

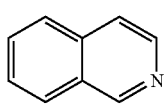 (W-9-3)

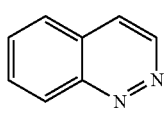 (W-9-4)

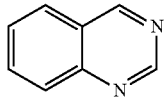 (W-9-5)

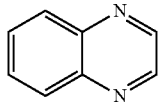 (W-9-6)

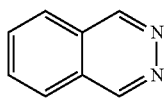 (W-9-7)

(in the formulae, these groups may have a bond at any position). The group represented by Formula (W-10) represents preferably a group selected from Formulae (W-10-1) to (W-10-16) below (each of which may be unsubstituted or may be substituted with one or more of the aforementioned substituent groups $L^W$):

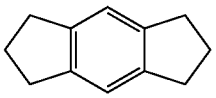 (W-10-1)

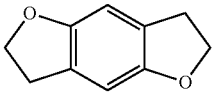 (W-10-2)

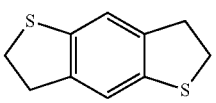 (W-10-3)

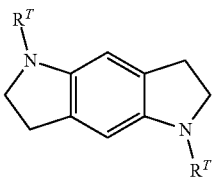 (W-10-4)

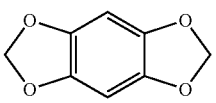 (W-10-5)

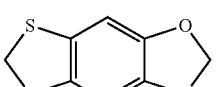 (W-10-6)

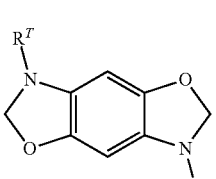 (W-10-7)

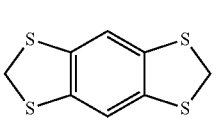 (W-10-8)

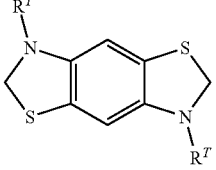 (W-10-9)

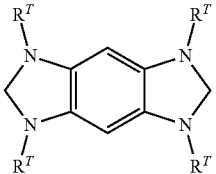 (W-10-10)

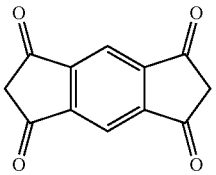 (W-10-11)

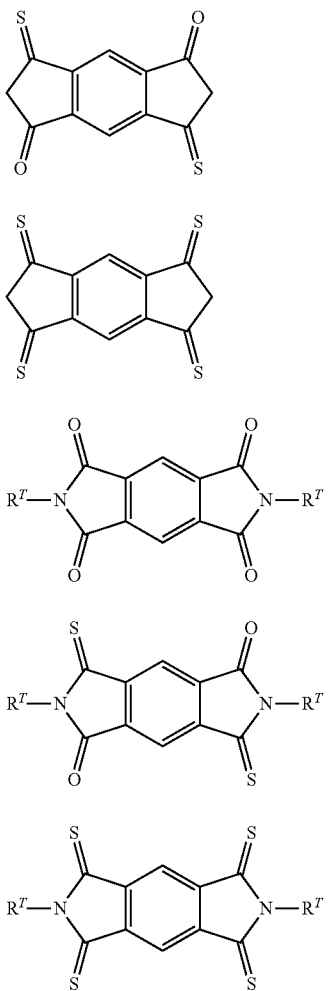

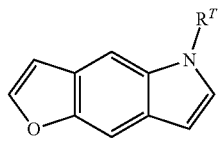
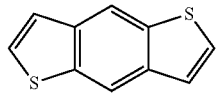
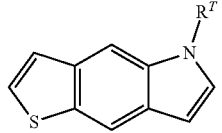
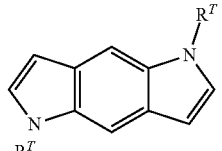
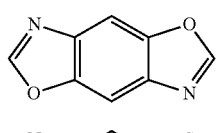
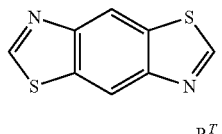
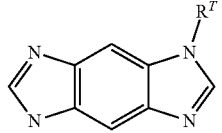

(in the formulae, these groups may have a bond at any position, and $R^T$ represents a hydrogen atom or an alkyl group having 1 to 8 carbon atoms). The group represented by Formula (W-11) represents preferably a group selected from Formulae (W-11-1) to (W-11-10) below (each of which may be unsubstituted or may be substituted with one or more of the aforementioned substituent groups $L^W$):

(in the formulae, these groups may have a bond at any position, and $R^T$ represents a hydrogen atom or an alkyl group having 1 to 8 carbon atoms). The group represented by Formula (W-12) represents preferably a group selected from Formulae (W-12-1) to (W-12-4) below (each of which may be unsubstituted or may be substituted with one or more of the aforementioned substituent groups $L^W$):

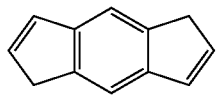
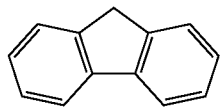
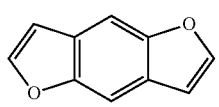
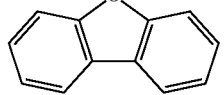
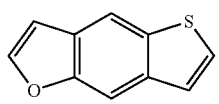
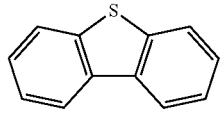

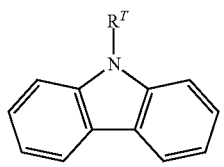
(W-12-4)

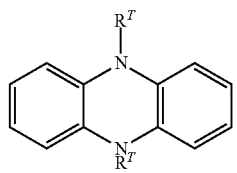
(W-13-10)

(in the formulae, these groups may have a bond at any position, and $R^T$ represents a hydrogen atom or an alkyl group having 1 to 8 carbon atoms). The group represented by Formula (W-13) represents preferably a group selected from Formulae (W-13-1) to (W-13-10) below (each of which may be unsubstituted or may be substituted with one or more of the aforementioned substituent groups $L^W$):

(in the formulae, these groups may have a bond at any position, and $R^T$ represents a hydrogen atom or an alkyl group having 1 to 8 carbon atoms). The group represented by Formula (W-17) represents preferably a group selected from Formulae (W-17-1) to (W-17-18) below (each of which may be unsubstituted or may be substituted with one or more of the aforementioned substituent groups $L^W$):

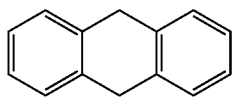
(W-13-1)

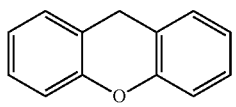
(W-13-2)

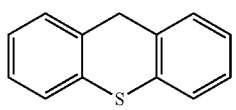
(W-13-3)

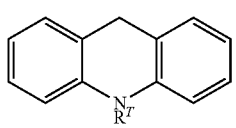
(W-13-4)

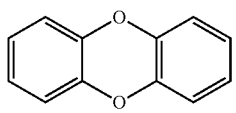
(W-13-5)

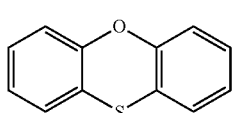
(W-13-6)

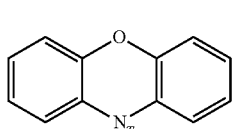
(W-13-7)

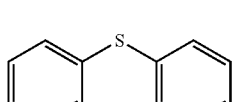
(W-13-8)

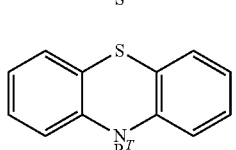
(W-13-9)

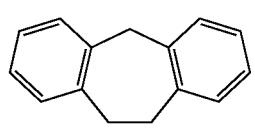
(W-17-1)

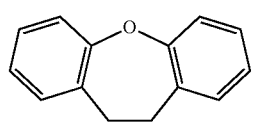
(W-17-2)

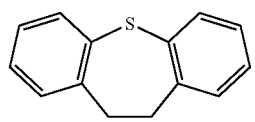
(W-17-3)

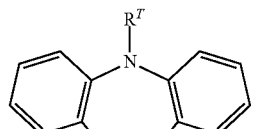
(W-17-4)

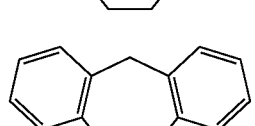
(W-17-5)

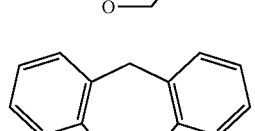
(W-17-6)

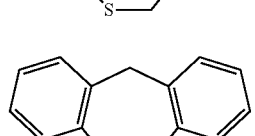
(W-17-7)

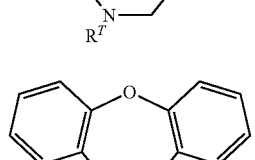
(W-17-8)

(W-17-11) 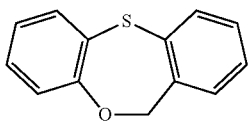

(W-17-12) 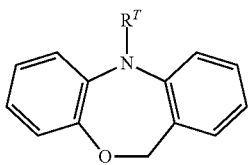

(W-17-13) 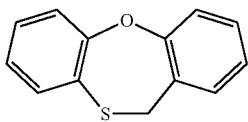

(W-17-14) 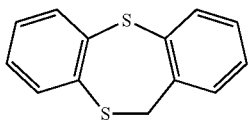

(W-17-15) 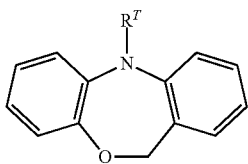

(W-17-16) 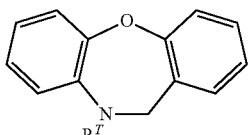

(W-17-17) 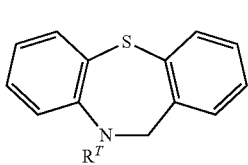

(W-17-18) 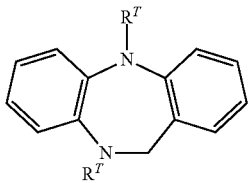

(in the formulae, these groups may have a bond at any position, and $R^T$ represents a hydrogen atom or an alkyl group having 1 to 8 carbon atoms). The group represented by Formula (W-18) represents preferably a group selected from Formulae (W-18-1) to (W-18-4) below (each of which may be unsubstituted or may be substituted with one or more of the aforementioned substituent groups $L^W$):

(W-18-1) 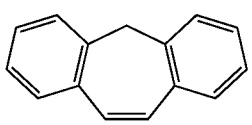

(W-18-2) 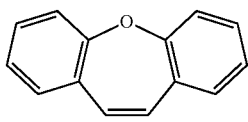

(W-18-3) 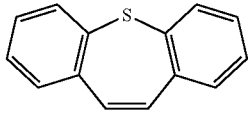

(W-18-4) 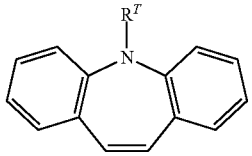

(in the formulae, these groups may have a bond at any position, and $R^T$ represents a hydrogen atom or an alkyl group having 1 to 8 carbon atoms).

The group containing the carbon ring or heterocyclic ring contained in $W^1$ represents preferably a group selected from Formulae (W-1-1), (W-1-2), (W-1-3), (W-1-4), (W-1-5), (W-1-6), (W-2-1), (W-6-9), (W-6-11), (W-6-12), (W-7-2), (W-7-3), (W-7-4), (W-7-6), (W-7-7), (W-7-8), (W-9-1), (W-12-1), (W-12-2), (W-12-3), (W-12-4), (W-13-7), (W-13-9), (W-13-10), (W-14), (W-18-1), and (W-18-4), each of which may be unsubstituted or may be substituted with one or more of the aforementioned substituent groups $L^W$, represents more preferably a group selected from Formulae (W-2-1), (W-7-3), (W-7-7), and (W-14), each of which may be unsubstituted or may be substituted with one or more of the aforementioned substituent groups $L^W$, represents further preferably a group selected from Formulae (W-7-3), (W-7-7), and (W-14), each of which may be unsubstituted or may be substituted with one or more of the aforementioned substituent groups $L^W$, represents still further preferably a group represented by Formula (W-7-7), which may be unsubstituted or may be substituted with one or more of the aforementioned substituent groups $L^W$, and represents particularly preferably a group represented by Formula (W-7-7-1) which may be unsubstituted or may be substituted with one or more of the aforementioned substituent groups $L^W$.

(W-7-7-1) 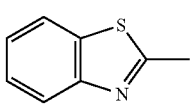

In Formulae (T-1) or (T-2), from the viewpoint of easiness of raw material availability and easiness of synthesis, more preferably, $W^2$ represents a hydrogen atom, a linear or branched alkyl group having 1 to 20 carbon atoms, in which any hydrogen atom in the group may be substituted with a fluorine atom and one —CH$_2$— or two or more non-adjacent —CH$_2$—'s may be each independently substituted with —O—, —CO—, —COO—, —OCO—, —O—CO—O—, —CH=CH—COO—, —CH=CH—OCO—, —COO—CH=CH—, —OCO—CH=CH—, —CH=CH—, —CF=CF—, or —C≡C—, or a group represented by $P^W$-(Sp$^W$-X$^W$)$_{kW}$—, further preferably, $W^2$ represents a hydrogen atom or a linear or branched alkyl group having 1 to 20 carbon atoms, in which any hydrogen atom in the group may be substituted with a fluorine atom and one —CH$_2$— or two or more non-adjacent —CH$_2$—'s may be each independently substituted with —O—, —CO—, —COO—, or —OCO—, or a group represented by P$^W$-(Sp$^W$-X$^W$)$_{kW}$—, and still further preferably, W$^2$ represents a hydrogen atom or a linear alkyl group having 1 to 12 carbon atoms, in which one —CH$_2$— or two or more non-adjacent —CH$_2$—'s may be each independently substituted with —O—, or a group represented by P$^W$-(Sp$^W$-X$^W$)$_{kW}$—. Further, when W$^2$ represents a group having 2 to 30 carbon atoms, having at least one aromatic group which may be unsubstituted or may be substituted with one or more of the aforementioned substituent groups L$^W$, W$^2$ represents preferably a group selected from Formulae (W-1) to (W-18), each of which may be unsubstituted or may be substituted with one or more of the aforementioned substituent groups L$^W$. In this case, the more preferable structure thereof is the same as above.

Further, when W$^2$ represents a group represented by P$^W$-(Sp$^W$-X$^W$)$_{kW}$—, the preferable structure of the group represented by P$^W$, Sp$^W$, X$^W$, and kW is the same as the preferable structure of the group represented by P$^O$, Sp$^O$, X$^O$, and k0.

Further, W$^1$ and W$^2$ may form a ring structure together. However, in this case, the cyclic group represented by —NW$^1$W$^2$ represents preferably a group selected from Formulae (W-19) to (W-40) below (each of which may be unsubstituted or may be substituted with one or more of the aforementioned substituent groups L$^W$):

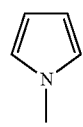
(W-19)

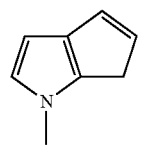
(W-20)

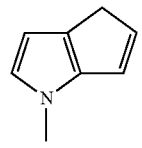
(W-21)

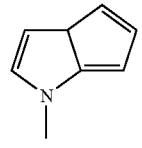
(W-22)

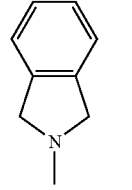
(W-23)

-continued

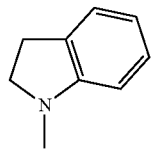
(W-24)

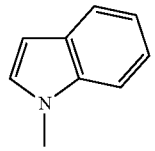
(W-25)

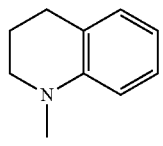
(W-26)

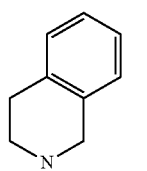
(W-27)

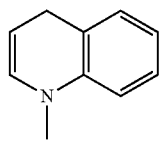
(W-28)

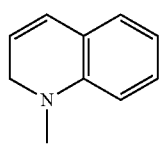
(W-29)

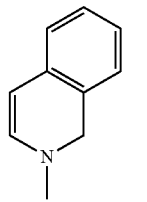
(W-30)

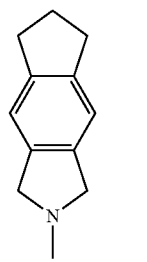
(W-31)

-continued (W-32) 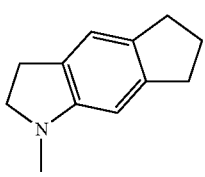

(W-33) 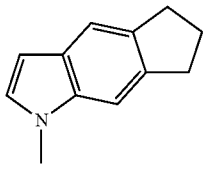

(W-34) 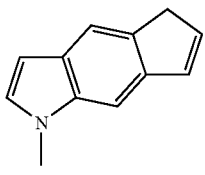

(W-35) 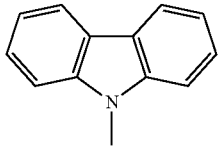

(W-36) 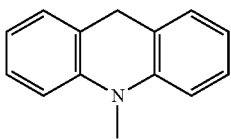

(W-37) 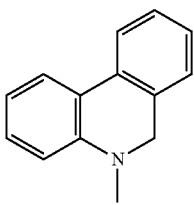

(W-38) 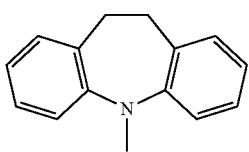

(W-39) 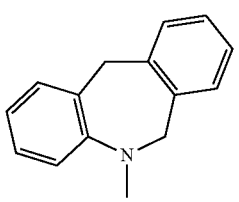

(W-40) 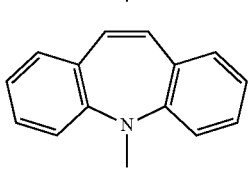

(in the formulae, any —CH═'s may be each independently substituted with —N═, and —CH²—'s may be each independently substituted with —O—, —S—, —NR$^T$— (in the formula, R$^T$ represents a hydrogen atom or an alkyl group having 1 to 20 carbon atoms), —CS—, or —CO—, provided that these groups do not contain a —O—O— bond. Further, these groups may be unsubstituted or may be substituted with one or more of the aforementioned substituent groups L$^W$). The group represented by Formula (W-19) represents preferably a group selected from Formulae (W-19-1) to (W-19-3) below (each of which may be unsubstituted or may be substituted with one or more of the aforementioned substituent groups L$^W$).

(W-19-1) 

(W-19-2) 

(W-19-3) 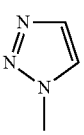

The group represented by Formula (W-20) represents preferably a group selected from Formulae (W-20-1) to (W-20-4) below (each of which may be unsubstituted or may be substituted with one or more of the aforementioned substituent groups L$^W$):

(W-20-1) 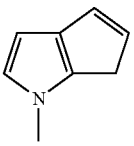

(W-20-2) 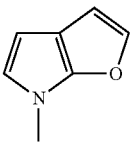

(W-20-3) 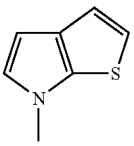

(W-20-4) 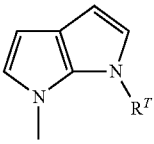

(in the formulae, R$^T$ represents a hydrogen atom or an alkyl group having 1 to 8 carbon atoms). The group represented by Formula (W-21) represents preferably a group selected from Formulae (W-21-1) to (W-21-4) below (each of which may be unsubstituted or may be substituted with one or more of the aforementioned substituent groups L$^W$):

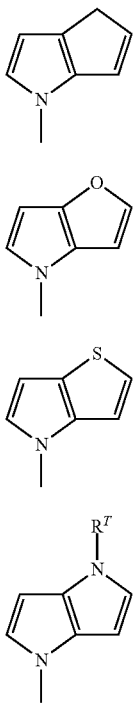

(W-21-1)

(W-21-2)

(W-21-3)

(W-21-4)

(in the formulae, $R^T$ represents a hydrogen atom or an alkyl group having 1 to 8 carbon atoms). The group represented by Formula (W-22) represents preferably a group selected from Formulae (W-22-1) to (W-22-4) below (each of which may be unsubstituted or may be substituted with one or more of the aforementioned substituent groups $L^W$).

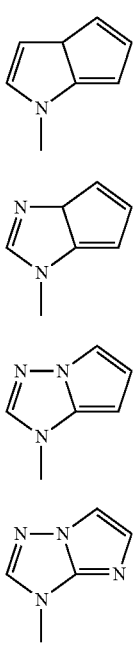

(W-22-1)

(W-22-2)

(W-22-3)

(W-22-4)

The group represented by Formula (W-23) represents preferably a group selected from Formulae (W-23-1) to (W-23-3) below (each of which may be unsubstituted or may be substituted with one or more of the aforementioned substituent groups $L^W$).

(W-23-1)

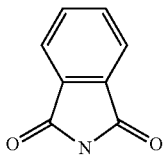

(W-23-2)

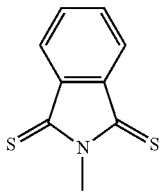

(W-23-3)

The group represented by Formula (W-24) represents preferably a group selected from Formulae (W-24-1) to (W-24-4) below (each of which may be unsubstituted or may be substituted with one or more of the aforementioned substituent groups $L^W$):

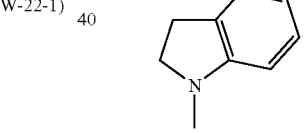

(W-24-1)

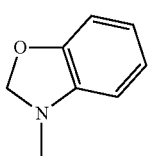

(W-24-2)

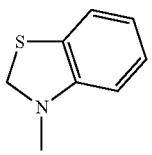

(W-24-3)

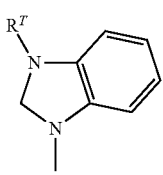

(W-24-4)

(in the formulae, $R^T$ represents a hydrogen atom or an alkyl group having 1 to 8 carbon atoms). The group represented by Formula (W-25) represents preferably a group selected from Formulae (W-25-1) to (W-25-3) below (each of which may be unsubstituted or may be substituted with one or more of the aforementioned substituent groups $L^W$):

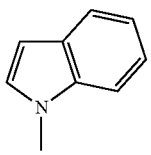
(W-25-1)

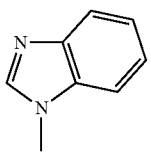
(W-25-2)

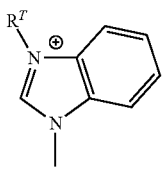
(W-25-3)

(in the formulae, $R^T$ represents a hydrogen atom or an alkyl group having 1 to 8 carbon atoms). The group represented by Formula (W-26) represents preferably a group selected from Formulae (W-26-1) to (W-26-7) below (each of which may be unsubstituted or may be substituted with one or more of the aforementioned substituent groups $L^W$):

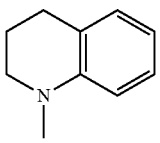
(W-26-1)

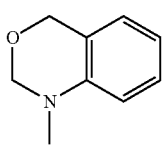
(W-26-2)

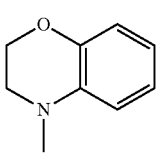
(W-26-3)

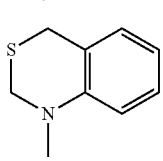
(W-26-4)

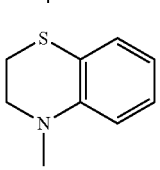
(W-26-5)

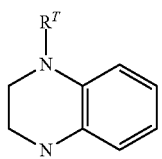
(W-26-6)

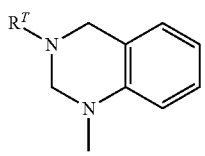
(W-26-7)

(in the formulae, $R^T$ represents a hydrogen atom or an alkyl group having 1 to 8 carbon atoms). The group represented by Formula (W-27) represents preferably a group selected from Formulae (W-27-1) to (W-27-4) below (each of which may be unsubstituted or may be substituted with one or more of the aforementioned substituent groups $L^W$):

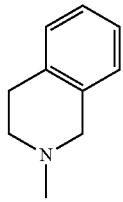
(W-27-1)

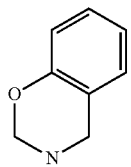
(W-27-2)

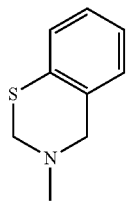
(W-27-3)

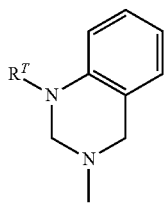
(W-27-4)

(in the formulae, $R^T$ represents a hydrogen atom or an alkyl group having 1 to 8 carbon atoms). The group represented by Formula (W-28) represents preferably a group selected from Formulae (W-28-1) to (W-28-6) below (each of which may be unsubstituted or may be substituted with one or more of the aforementioned substituent groups $L^W$):

(W-28-1)
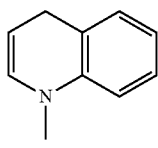

(W-28-2)
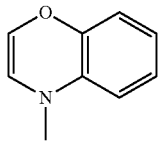

(W-28-3)
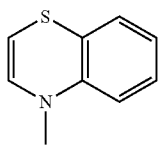

(W-28-4)
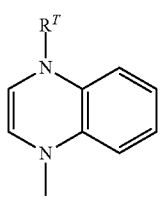

(W-28-5)
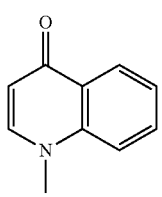

(W-28-6)
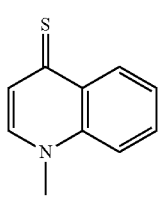

(in the formulae, $R^T$ represents a hydrogen atom or an alkyl group having 1 to 8 carbon atoms). The group represented by Formula (W-29) represents preferably a group selected from Formulae (W-29-1) to (W-29-3) below (each of which may be unsubstituted or may be substituted with one or more of the aforementioned substituent groups $L^W$).

(W-29-1)
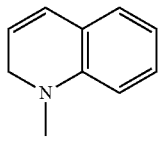

(W-29-2)
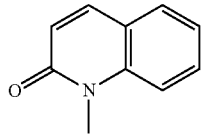

(W-29-3)
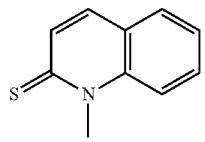

The group represented by Formula (W-30) represents preferably a group selected from Formulae (W-30-1) to (W-30-3) below (each of which may be unsubstituted or may be substituted with one or more of the aforementioned substituent groups $L^W$).

(W-30-1)
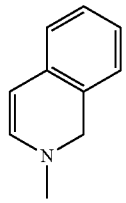

(W-30-2)
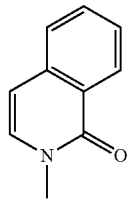

(W-30-3)
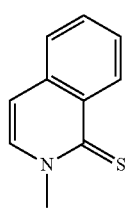

The group represented by Formula (W-31) represents preferably a group selected from Formulae (W-31-1) to (W-31-4) below (each of which may be unsubstituted or may be substituted with one or more of the aforementioned substituent groups $L^W$):

(W-31-1)
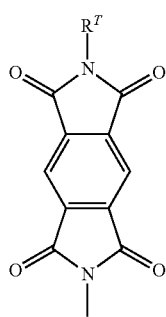

(W-31-2)

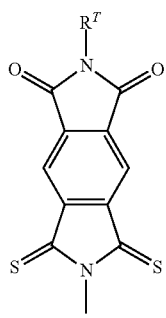

(W-31-3)

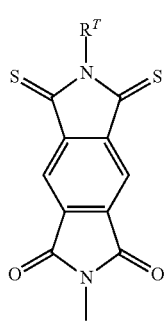

(W-31-4)

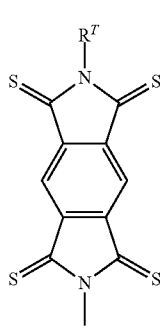

(in the formulae, $R^T$ represents a hydrogen atom or an alkyl group having 1 to 8 carbon atoms). The group represented by Formula (W-32) represents preferably a group selected from Formulae (W-32-1) to (W-32-5) below (each of which may be unsubstituted or may be substituted with one or more of the aforementioned substituent groups $L^W$):

(W-32-1)

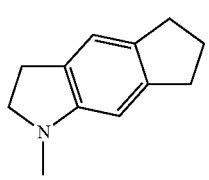

(W-32-2)

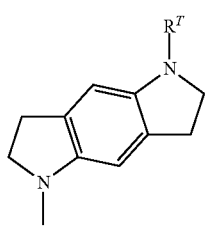

(W-32-3)

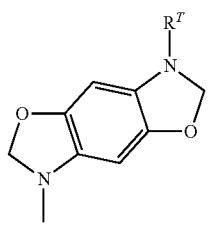

(W-32-4)

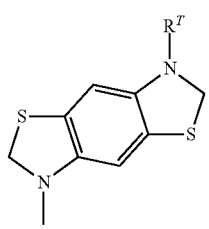

(W-32-5)

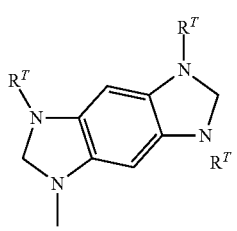

(in the formulae, R represents a hydrogen atom or an alkyl group having 1 to 8 carbon atoms). The group represented by Formula (W-33) represents preferably a group selected from Formulae (W-33-1) to (W-33-3) below (each of which may be unsubstituted or may be substituted with one or more of the aforementioned substituent groups $L^W$).

(W-33-1)

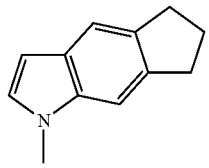

(W-33-2)

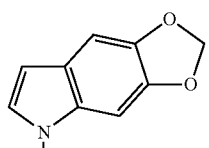

(W-33-3)

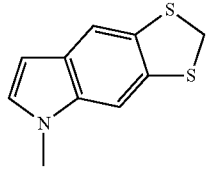

The group represented by Formula (W-34) represents preferably a group selected from Formulae (W-34-1) to (W-34-5) below (each of which may be unsubstituted or may be substituted with one or more of the aforementioned substituent groups $L^W$):

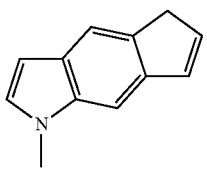
(W-34-1)

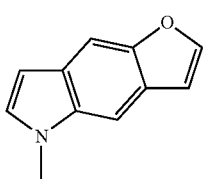
(W-34-2)

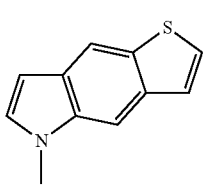
(W-34-3)

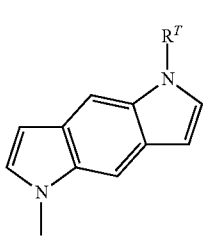
(W-34-4)

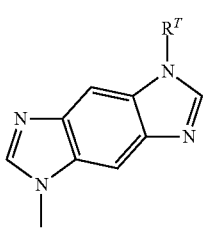
(W-34-5)

(in the formulae, $R^T$ represents a hydrogen atom or an alkyl group having 1 to 8 carbon atoms). The group represented by Formula (W-35) represents preferably a group represented by Formula (W-35-1) below (which may be unsubstituted or may be substituted with one or more of the aforementioned substituent groups $L^W$).

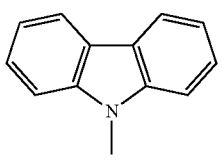
(W-35-1)

The group represented by Formula (W-36) represents preferably a group selected from Formulae (W-36-1) to (W-36-6) below (each of which may be unsubstituted or may be substituted with one or more of the aforementioned substituent groups $L^W$):

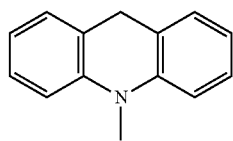
(W-36-1)

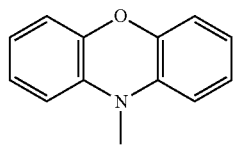
(W-36-2)

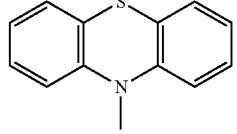
(W-36-3)

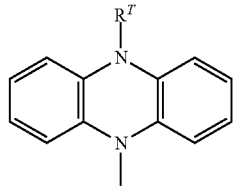
(W-36-4)

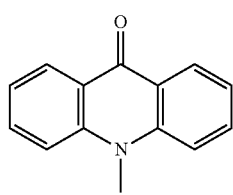
(W-36-5)

(W-36-6)

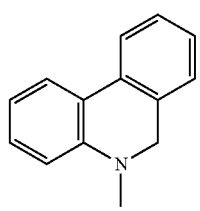

(in the formulae, $R^T$ represents a hydrogen atom or an alkyl group having 1 to 8 carbon atoms). The group represented by Formula (W-37) represents preferably a group selected from Formulae (W-37-1) to (W-37-3) below (each of which may be unsubstituted or may be substituted with one or more of the aforementioned substituent groups $L^W$).

(W-37-1)

(W-37-2)

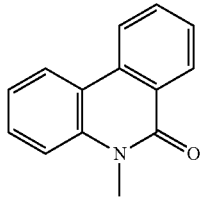

(W-37-3)

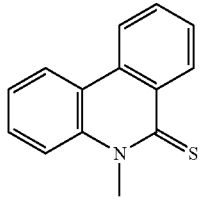

The group represented by Formula (W-38) represents preferably a group selected from Formulae (W-38-1) to (W-38-4) below (each of which may be unsubstituted or may be substituted with one or more of the aforementioned substituent groups $L^W$):

(W-38-1)

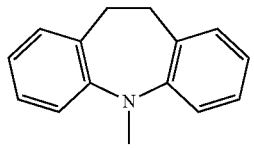

(W-38-2)

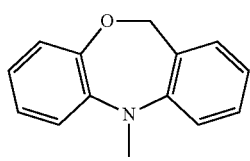

(W-38-3)

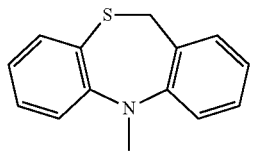

(W-38-4)

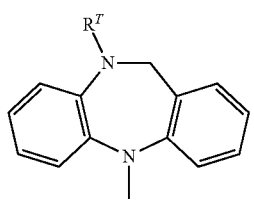

(in the formulae, $R^T$ represents a hydrogen atom or an alkyl group having 1 to 8 carbon atoms). The group represented by Formula (W-39) represents preferably a group selected from Formulae (W-39-1) to (W-39-4) below (each of which may be unsubstituted or may be substituted with one or more of the aforementioned substituent groups $L^W$):

(W-39-1)

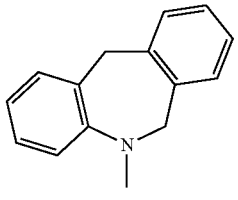

(W-39-2)

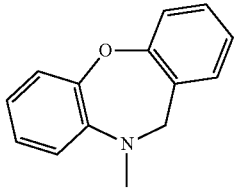

(W-39-3)

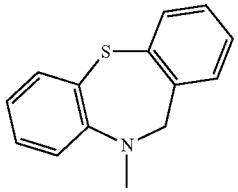

(W-39-4)

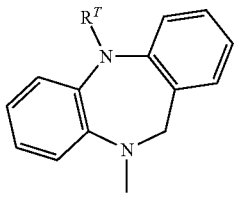

(in the formulae, $R^T$ represents a hydrogen atom or an alkyl group having 1 to 8 carbon atoms). The group represented by Formula (W-40) represents preferably a group represented by Formula (W-40-1) below (which may be unsubstituted or may be substituted with one or more of the aforementioned substituent groups $L^W$).

(W-40-1)

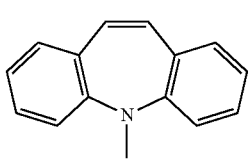

From the viewpoint of easiness of raw material availability and easiness of synthesis, more preferably, the cyclic group represented by —$NW^1W^2$ represents a group selected from Formulae (W-19-1), (W-21-2), (W-21-3), (W-21-4), (W-23-2), (W-23-3), (W-25-1), (W-25-2), (W-25-3), (W-30-2), (W-30-3), (W-35-1), (W-36-2), (W-36-3), (W-36-4), and (W-40-1), each of which may be unsubstituted or may be substituted with one or more of the aforementioned substituent groups $L^W$.

Further, $W^1$ and $W^2$ may form a ring structure together. However, in this case, the cyclic group represented by =$CW^1W^2$ represents preferably a group selected from Formulae (W-41) to (W-62) below (each of which may be unsubstituted or may be substituted with one or more of the aforementioned substituent groups $L^W$):

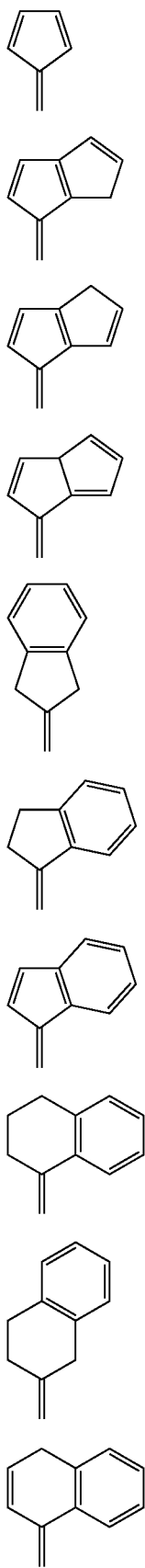
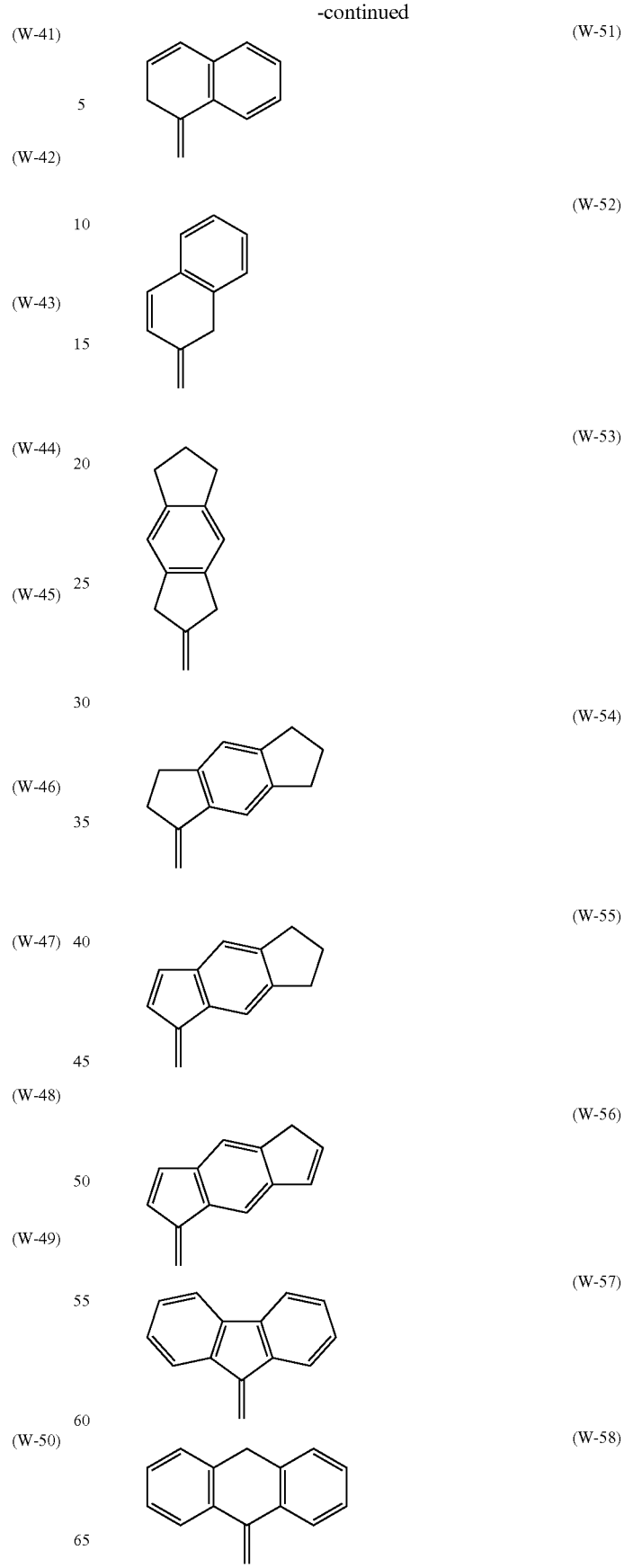

-continued (W-59)

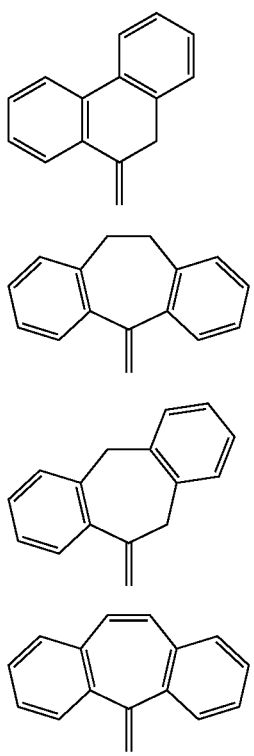

(W-60)

(W-61)

(W-62)

(in the formulae, any —CH═'s may be each independently substituted with —N═, and —CH²—'s may be each independently substituted with —O—, —S—, —NR$^T$— (in the formulae, R$^T$ represents a hydrogen atom or an alkyl group having 1 to 20 carbon atoms), —CS—, or —CO—, provided that these groups do not contain a —O—O— bond. Further, these groups may be unsubstituted or may be substituted with one or more of the aforementioned substituent groups L$^W$). The group represented by Formula (W-41) represents preferably a group selected from Formulae (W-41-1) to (W-41-3) below (each of which may be unsubstituted or may be substituted with one or more of the aforementioned substituent groups L$^W$).

(W-41-1)

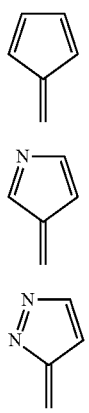

(W-41-2)

(W-41-3)

The group represented by Formula (W-42) represents preferably a group selected from Formulae (W-42-1) to (W-42-4) below (each of which may be unsubstituted or may be substituted with one or more of the aforementioned substituent groups L$^W$):

(W-42-1)

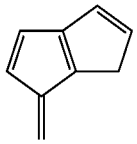

(W-42-2)

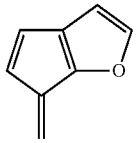

(W-42-3)

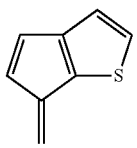

(W-42-4)

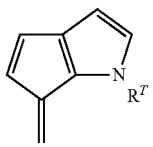

(in the formulae, R$^T$ represents a hydrogen atom or an alkyl group having 1 to 8 carbon atoms). The group represented by Formula (W-43) represents preferably a group selected from Formulae (W-43-1) to (W-43-4) below (each of which may be unsubstituted or may be substituted with one or more of the aforementioned substituent groups L$^W$):

(W-43-1)

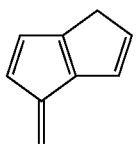

(W-43-2)

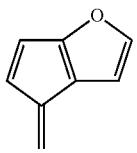

(W-43-3)

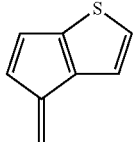

(W-43-4)

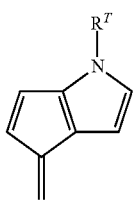

(in the formulae, R$^T$ represents a hydrogen atom or an alkyl group having 1 to 8 carbon atoms). The group represented by Formula (W-44) represents preferably a group selected from Formulae (W-44-1) to (W-44-4) below (each of which may be unsubstituted or may be substituted with one or more of the aforementioned substituent groups L$^W$).

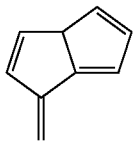
(W-44-1)

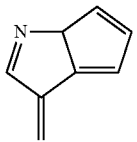
(W-44-2)

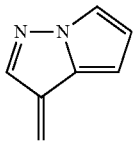
(W-44-3)

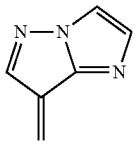
(W-44-4)

The group represented by Formula (W-45) represents preferably a group selected from Formulae (W-45-1) to (W-45-4) below (each of which may be unsubstituted or may be substituted with one or more of the aforementioned substituent groups $L^W$):

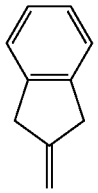
(W-45-1)

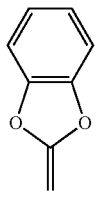
(W-45-2)

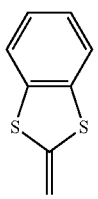
(W-45-3)

(W-45-4)

(in the formulae, $R^{1'}$ represents a hydrogen atom or an alkyl group having 1 to 8 carbon atoms). The group represented by Formula (W-46) represents preferably a group selected from Formulae (W-46-1) to (W-46-4) below (each of which may be unsubstituted or may be substituted with one or more of the aforementioned substituent groups $L^W$):

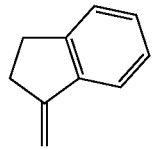
(W-46-1)

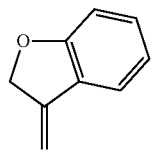
(W-46-2)

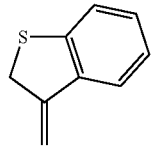
(W-46-3)

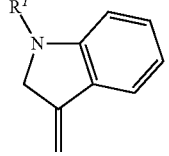
(W-46-4)

(in the formulae, $R^T$ represents a hydrogen atom or an alkyl group having 1 to 8 carbon atoms). The group represented by Formula (W-47) represents preferably a group selected from Formulae (W-47-1) to (W-47-3) below (each of which may be unsubstituted or may be substituted with one or more of the aforementioned substituent groups $L^W$):

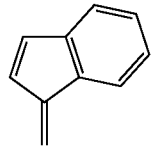
(W-47-1)

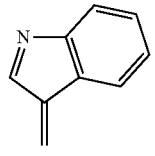
(W-47-2)

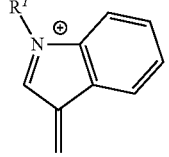
(W-47-3)

(in the formulae, $R^T$ represents a hydrogen atom or an alkyl group having 1 to 8 carbon atoms). The group represented by Formula (W-48) represents preferably a group selected from Formulae (W-48-1) to (W-48-7) below (each of which may be unsubstituted or may be substituted with one or more of the aforementioned substituent groups $L^W$):

(W-48-1)
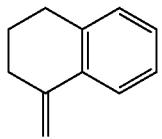

(W-48-2)
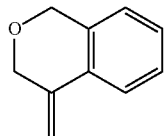

(W-48-3)
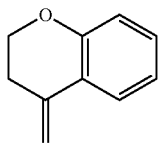

(W-48-4)
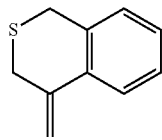

(W-48-5)
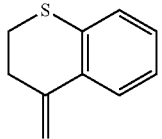

(W-48-6)
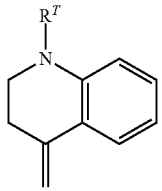

(W-48-7)
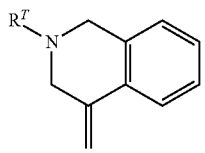

(in the formulae, $R^T$ represents a hydrogen atom or an alkyl group having 1 to 8 carbon atoms). The group represented by Formula (W-49) represents preferably a group selected from Formulae (W-49-1) to (W-49-4) below (each of which may be unsubstituted or may be substituted with one or more of the aforementioned substituent groups $L^W$):

(W-49-1)
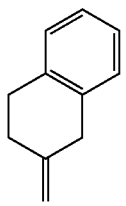

(W-49-2)
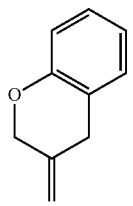

(W-49-3)
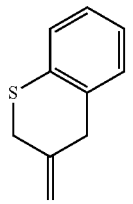

(W-49-4)
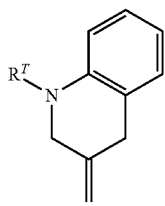

(in the formulae, $R^T$ represents a hydrogen atom or an alkyl group having 1 to 8 carbon atoms). The group represented by Formula (W-50) represents preferably a group selected from Formulae (W-50-1) to (W-50-6) below (each of which may be unsubstituted or may be substituted with one or more of the aforementioned substituent groups $L^W$):

(W-50-1)
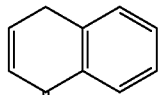

(W-50-2)
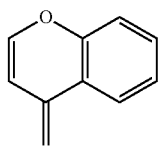

(W-50-3)
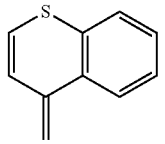

(W-50-4)
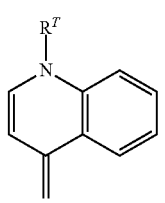

(W-50-5)

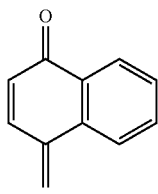

(W-50-6)

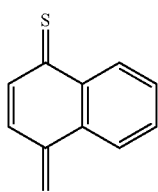

(in the formulae, $R^T$ represents a hydrogen atom or an alkyl group having 1 to 8 carbon atoms). The group represented by Formula (W-51) represents preferably a group selected from Formulae (W-51-1) to (W-51-3) below (each of which may be unsubstituted or may be substituted with one or more of the aforementioned substituent groups $L^W$).

(W-51-1)

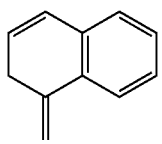

(W-51-2)

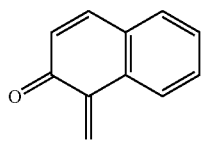

(W-51-3)

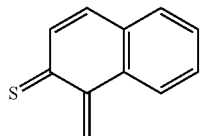

The group represented by Formula (W-52) represents preferably a group selected from Formulae (W-52-1) to (W-52-3) below (each of which may be unsubstituted or may be substituted with one or more of the aforementioned substituent groups $L^W$).

(W-52-1)

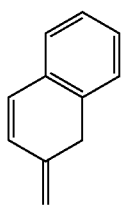

(W-52-2)

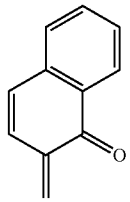

(W-52-3)

The group represented by Formula (W-53) represents preferably a group selected from Formulae (W-53-1) to (W-53-8) below (each of which may be unsubstituted or may be substituted with one or more of the aforementioned substituent groups $L^W$):

(W-53-1)


(W-53-2)

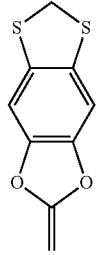

(W-53-3)

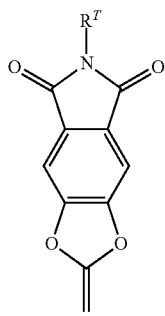

-continued (W-53-4)
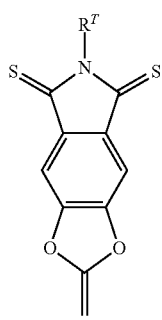

(W-53-5)
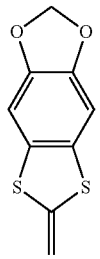

(W-53-6)
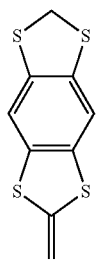

(W-53-7)
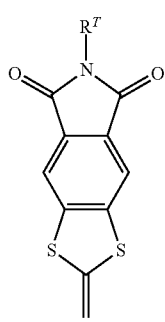

(W-53-8)
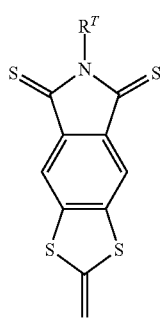

(in the formulae, $R^T$ represents a hydrogen atom or an alkyl group having 1 to 8 carbon atoms). The group represented by Formula (W-54) represents preferably a group selected from Formulae (W-54-1) to (W-54-5) below (each of which may be unsubstituted or may be substituted with one or more of the aforementioned substituent groups $L^W$):

(W-54-1)
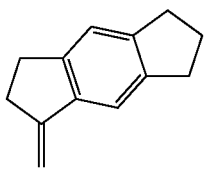

(W-54-2)
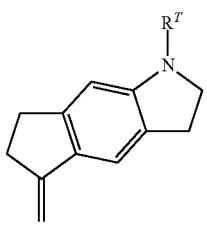

(W-54-3)
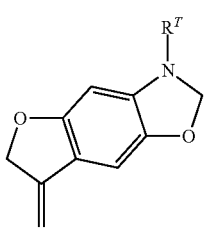

(W-54-4)
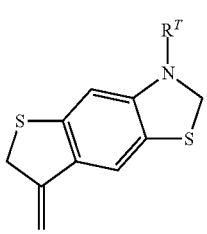

(W-54-5)
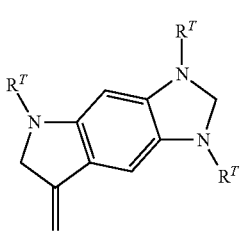

(in the formulae, R represents a hydrogen atom or an alkyl group having 1 to 8 carbon atoms). The group represented by Formula (W-55) represents preferably a group selected from Formulae (W-55-1) to (W-55-3) below (each of which may be unsubstituted or may be substituted with one or more of the aforementioned substituent groups $L^W$).

(W-55-1)
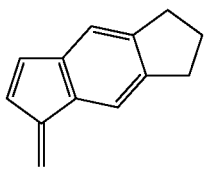

(W-55-2)

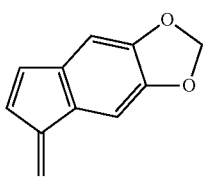

(W-55-3)

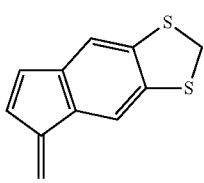

The group represented by Formula (W-56) represents preferably a group selected from Formulae (W-56-1) to (W-56-5) below (each of which may be unsubstituted or may be substituted with one or more of the aforementioned substituent groups $L^W$):

(W-56-1)

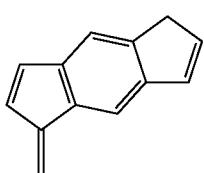

(W-56-2)

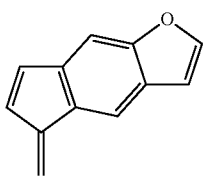

(W-56-3)

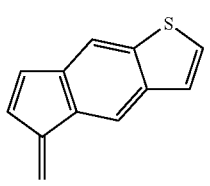

(W-56-4)

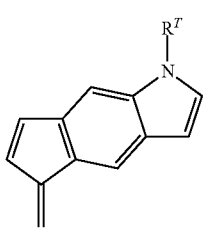

(W-56-5)

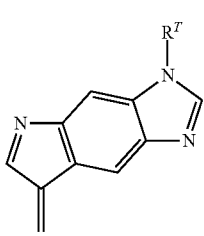

(in the formulae, $R^T$ represents a hydrogen atom or an alkyl group having 1 to 8 carbon atoms). The group represented by Formula (W-57) represents preferably a group represented by Formula (W-57-1) below (which may be unsubstituted or may be substituted with one or more of the aforementioned substituent groups $L^W$).

(W-57-1)

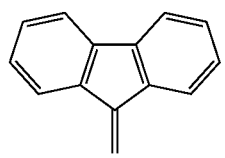

The group represented by Formula (W-58) represents preferably a group selected from Formulae (W-58-1) to (W-58-6) below (each of which may be unsubstituted or may be substituted with one or more of the aforementioned substituent groups $L^W$):

(W-58-1)

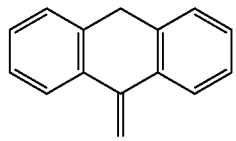

(W-58-2)

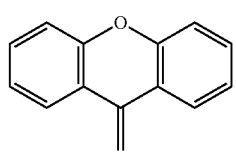

(W-58-3)

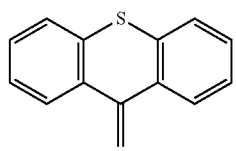

(W-58-4)

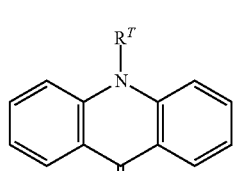

(W-58-5)

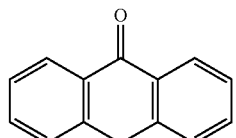

(W-58-6)

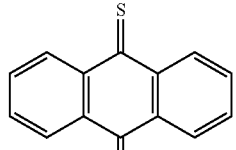

(in the formulae, $R^T$ represents a hydrogen atom or an alkyl group having 1 to 8 carbon atoms). The group represented by Formula (W-59) represents preferably a group selected from Formulae (W-59-1) to (W-59-3) below (each of which may be unsubstituted or may be substituted with one or more of the aforementioned substituent groups $L^W$).

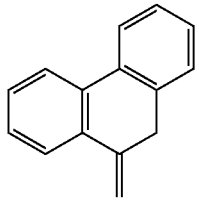
(W-59-1)

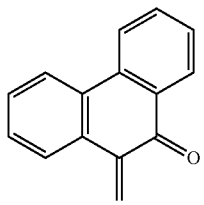
(W-59-2)

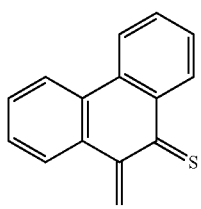
(W-59-3)

The group represented by Formula (W-60) represents preferably a group selected from Formulae (W-60-1) to (W-60-4) below (each of which may be unsubstituted or may be substituted with one or more of the aforementioned substituent groups $L^W$);

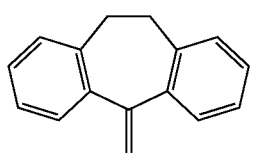
(W-60-1)

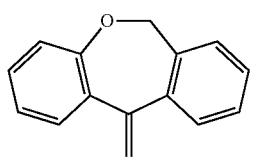
(W-60-2)

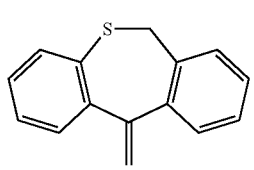
(W-60-3)

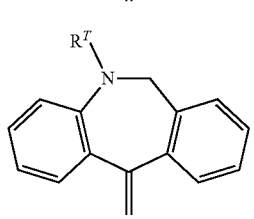
(W-60-4)

(in the formulae, $R^T$ represents a hydrogen atom or an alkyl group having 1 to 8 carbon atoms). The group represented by Formula (W-61) represents preferably a group selected from Formulae (W-61-1) to (W-61-4) below (each of which may be unsubstituted or may be substituted with one or more of the aforementioned substituent groups $L^W$):

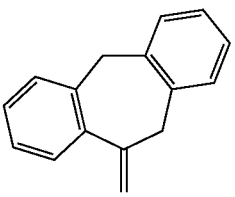
(W-61-1)

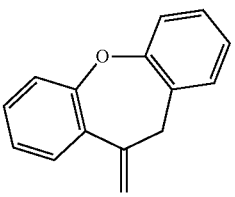
(W-61-2)

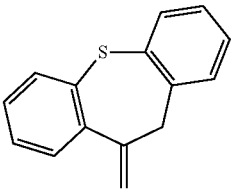
(W-61-3)

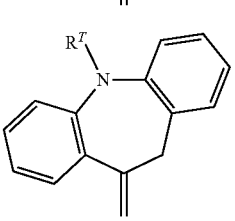
(W-61-4)

(in the formulae, $R^T$ represents a hydrogen atom or an alkyl group having 1 to 8 carbon atoms). The group represented by Formula (W-62) represents preferably a group represented by Formula (W-62-1) below (which may be unsubstituted or may be substituted with one or more of the aforementioned substituent groups $L^W$).

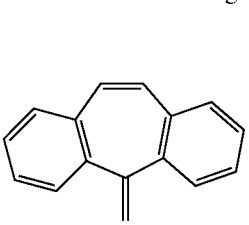
(W-62-1)

From the viewpoint of easiness of raw material availability and easiness of synthesis, more preferably, the cyclic group represented by =CW¹W² represents a group selected from Formulae (W-42-2), (W-42-3), (W-43-2), (W-43-3), (W-45-3), (W-45-4), (W-57-1), (W-58-2), (W-58-3), (W-58-4), and (W-62-1), each of which may be unsubstituted or may be substituted with one or more of the aforementioned substituent groups $L^W$, further preferably, the cyclic group represents a group selected from Formulae (W-57-1) and (W-62-1), each of which may be unsubstituted or may be substituted with one or more of the aforementioned substituent groups $L^W$, and still further preferably, the cyclic group represents a group represented by Formula (W-57-1), which may be unsubstituted or may be substituted with one or more of the aforementioned substituent groups $L^W$.

The total number of π electrons contained in $W^1$ and $W^2$ is preferably 4 to 24 from the viewpoint of wavelength dispersion properties, storage stability, liquid crystallinity, and easiness of synthesis.

From the viewpoint of liquid crystallinity and easiness of synthesis, preferably, $L^W$ represents a fluorine atom, a chlorine atom, a pentafluorosulfuranyl group, a nitro group, a methylamino group, a dimethylamino group, a diethylamino group, a diisopropylamino group, or a linear or branched alkyl group having 1 to 20 carbon atoms, in which any hydrogen atom may be substituted with a fluorine atom and one —$CH_2$— or two or more non-adjacent —$CH_2$—'s may be each independently substituted with a group selected from —O—, —S—, —CO—, —COO—, —OCO—, —O—CO—O—, —CH=CH—, —CF=CF—, and —C≡C—, more preferably, $L^W$ represents a fluorine atom, a chlorine atom, or a linear or branched alkyl group having 1 to 12 carbon atoms, in which any hydrogen atom may be substituted with a fluorine atom and one —$CH_2$— or two or more non-adjacent —$CH_7$—'s may be each independently substituted with a group selected from —O—, —COO—, and —OCO—, further preferably, $L^W$ represents a fluorine atom, a chlorine atom, or a linear or branched alkyl group or an alkoxy group having 1 to 12 carbon atoms, in which any hydrogen atom may be substituted with a fluorine atom, and particularly preferably, $L^W$ represents a fluorine atom, a chlorine atom, or a linear alkyl group or a linear alkoxy group having 1 to 8 carbon atoms. In Formula (I), more preferably, $G^1$ represents a group selected from Formulae (G-1) to (G-22) below:

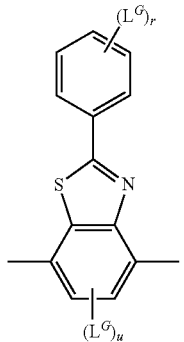

(G-1)

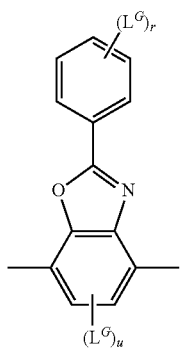

(G-2)

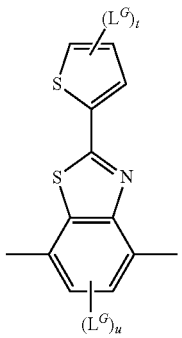

(G-3)

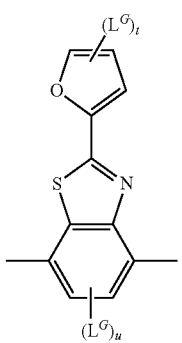

(G-4)

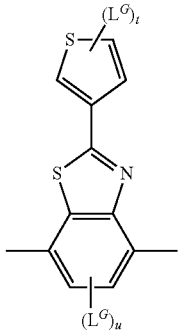

(G-5)

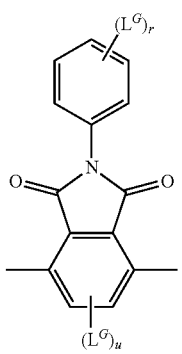

(G-6)

(G-7)
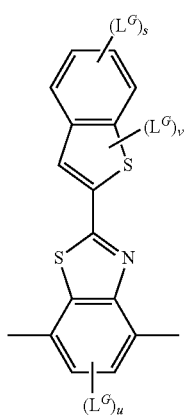
(G-8)
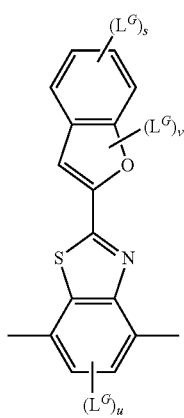
(G-9)
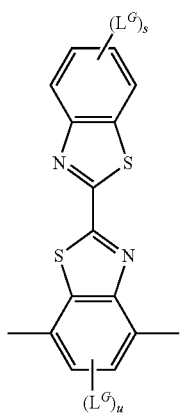
(G-10)
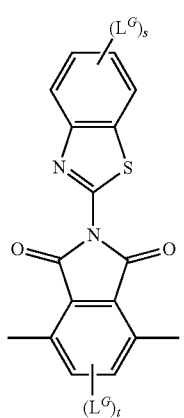
(G-11)
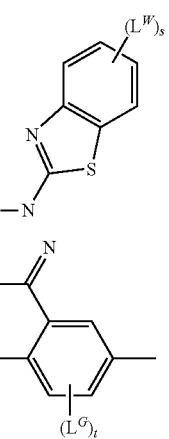
(G-12)
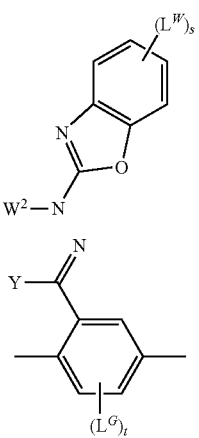
(G-13)
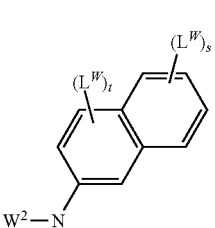

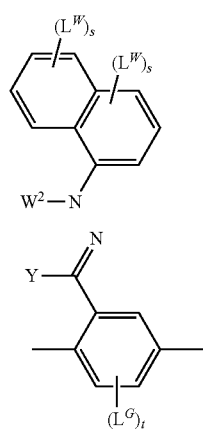 (G-14)
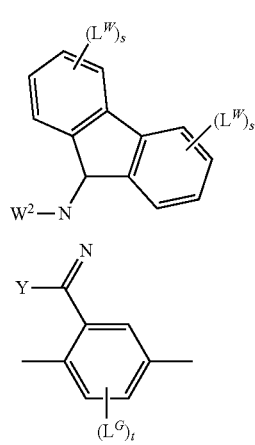 (G-15)
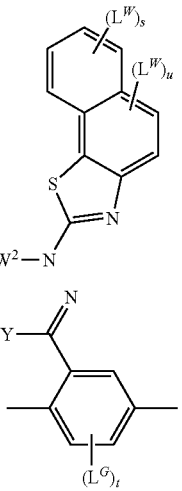 (G-17)
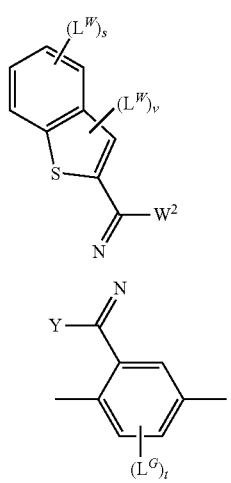 (G-18)
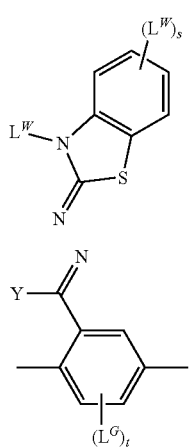 (G-19)
(G-16)

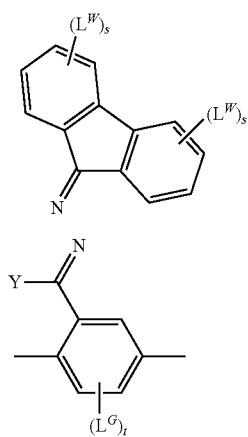
(G-20)

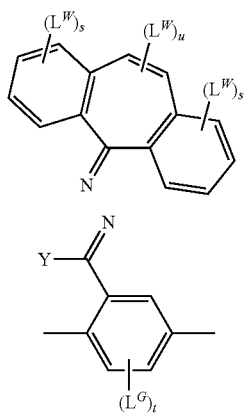
(G-21)

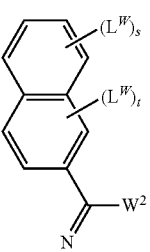
(G-22)

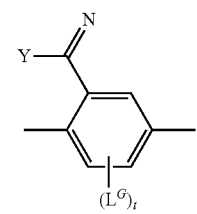

(In the formulae, $L^G$, $L^W$, Y, and $W^2$ represent the same meanings as those described above, r represents an integer of 0 to 5, s represents an integer of 0 to 4, t represents an integer of 0 to 3, u represents an integer of 0 to 2, and v represents 0 or 1. Further, these groups may be configured such that right and left thereof are reversed). In Formulae (G-1) to (G-10), a group selected from Formulae (G-1), (G-3), (G-5), (G-6), (G-7), (G-8), and (G-10) is further preferable, u is still further preferably 0, and a group selected from Formulae (G-1-1) to (G-10-1) below is particularly preferable:

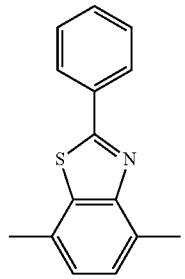
(G-1-1)

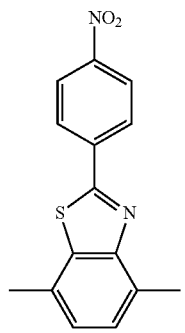
(G-1-2)

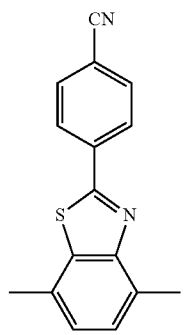
(G-1-3)

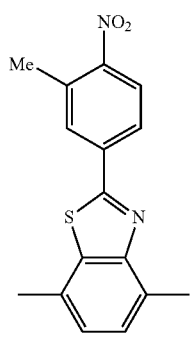
(G-1-4)

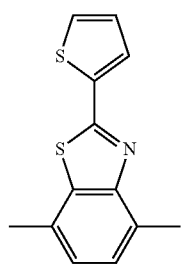
(G-3-1)

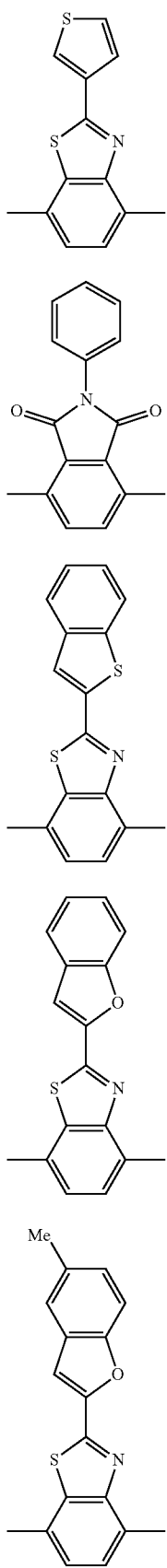
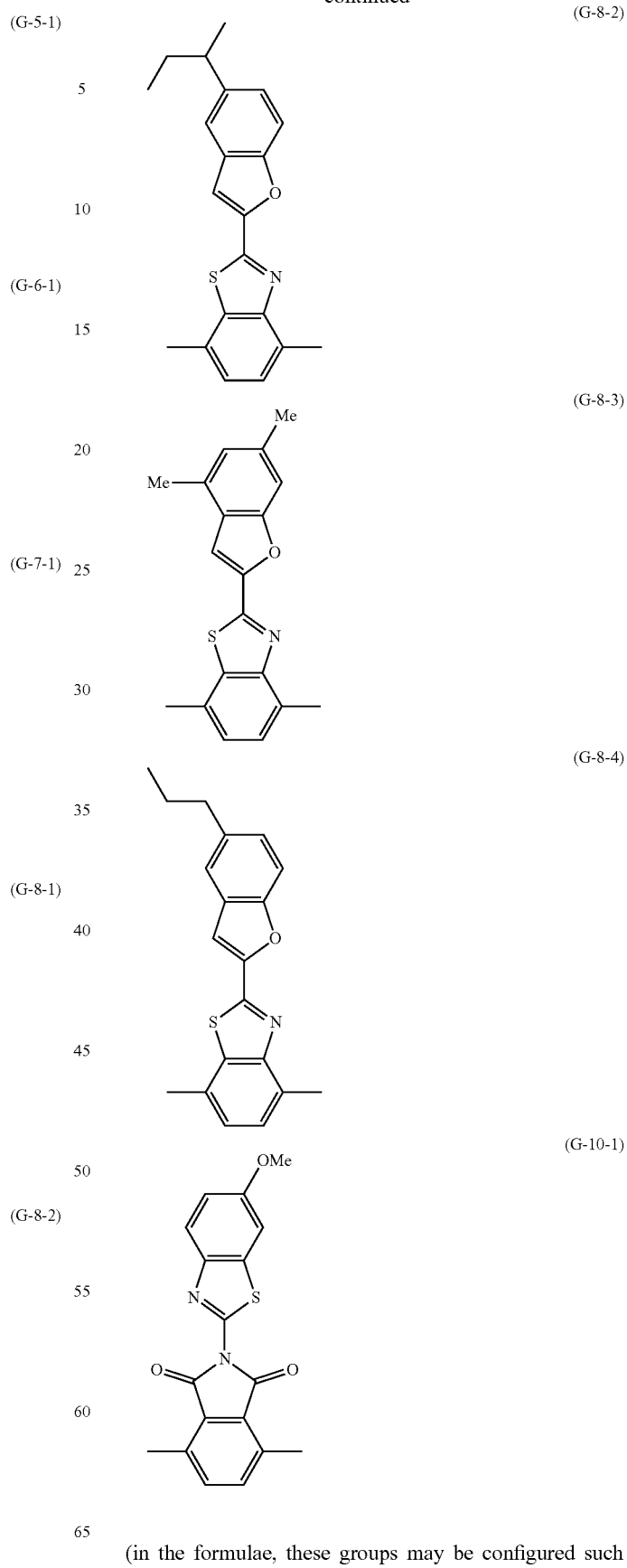
(in the formulae, these groups may be configured such that right and left thereof are reversed). Further, in Formulae (G-11) to (G-22), Y represents more preferably a hydrogen atom, each of s, t, u, and v is further preferably 0, and a group selected from Formulae (G-11-1) to (G-20-1) below is particularly preferable.
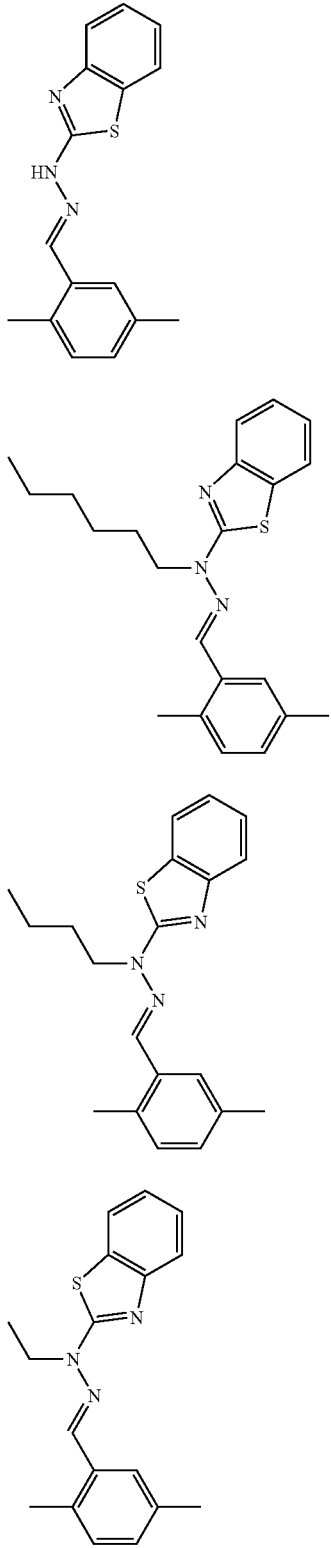
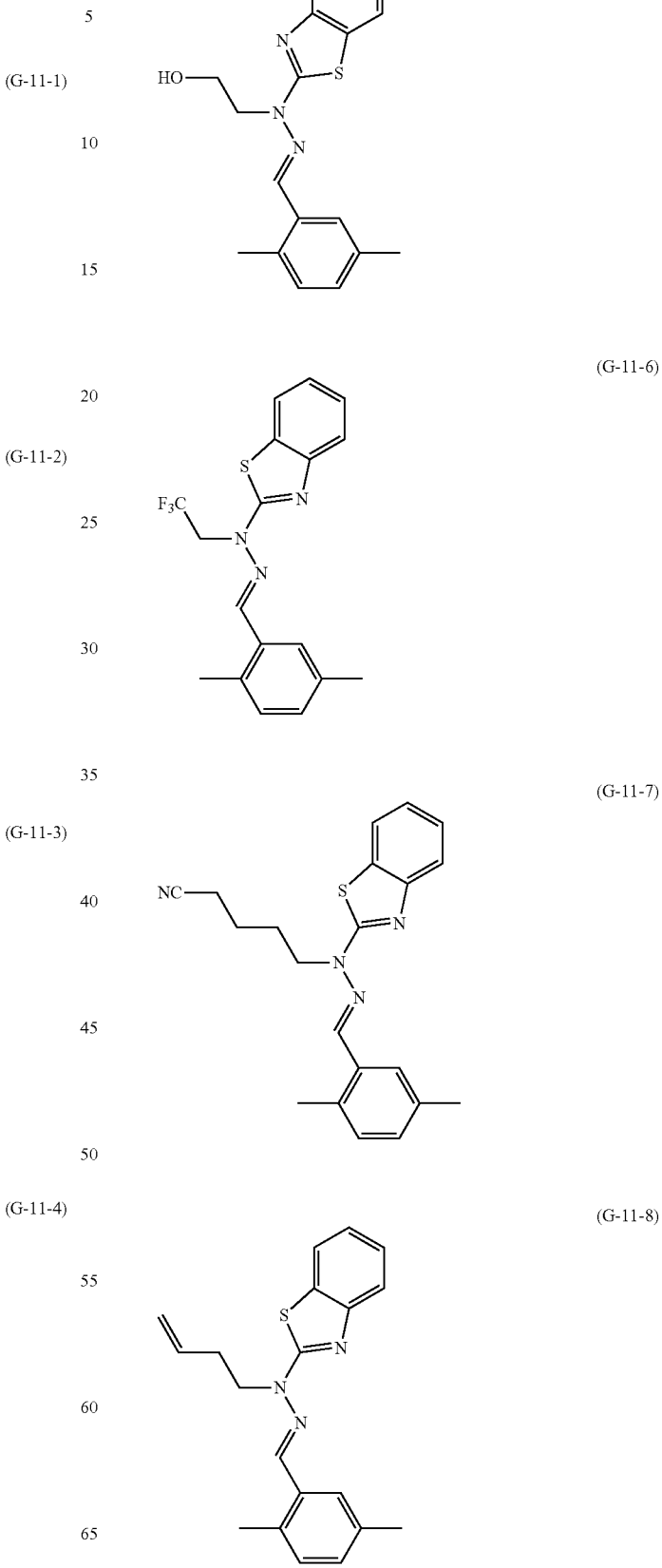

(G-11-9) 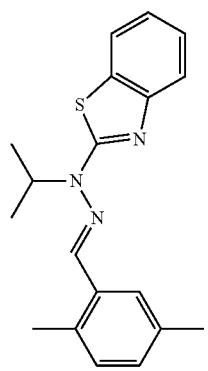
(G-11-10) 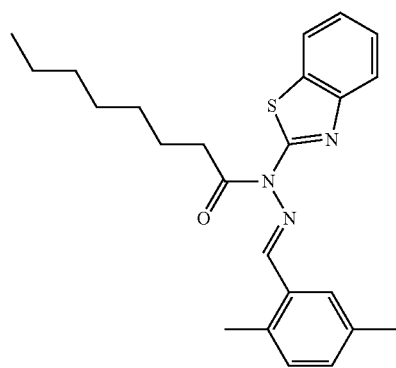
(G-11-11) 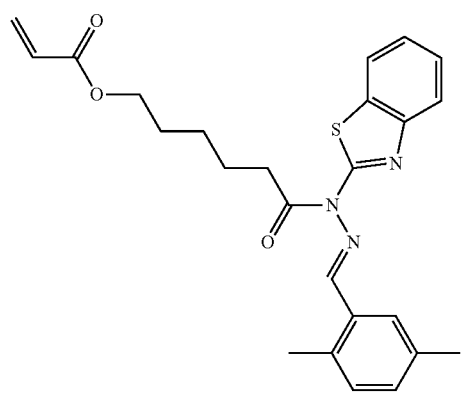
(G-11-12) 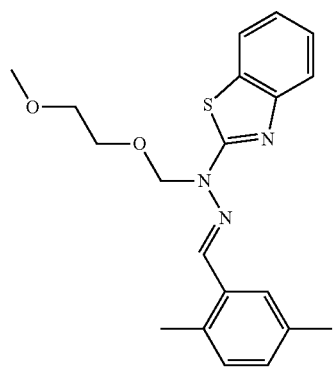
(G-11-13) 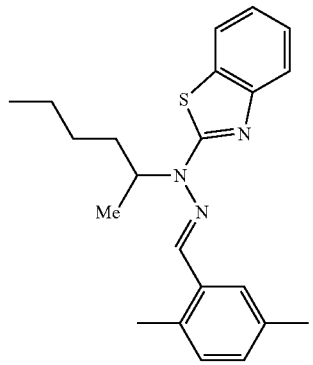
(G-11-14) 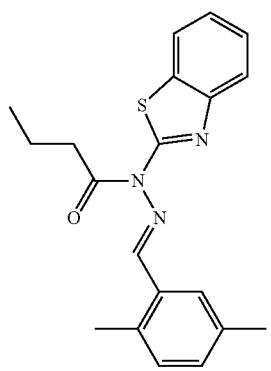
(G-11-15) 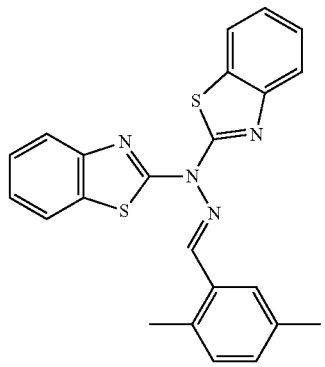
(G-11-16) 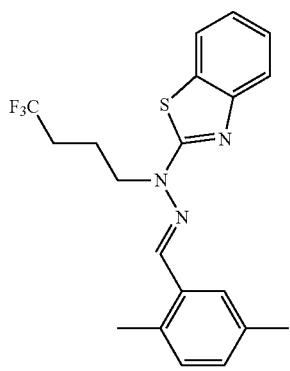

-continued
(G-11-17)
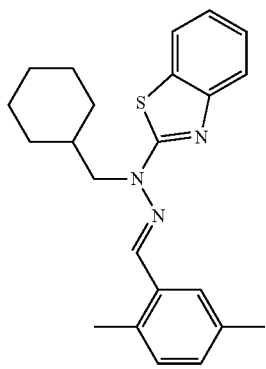
(G-11-18)
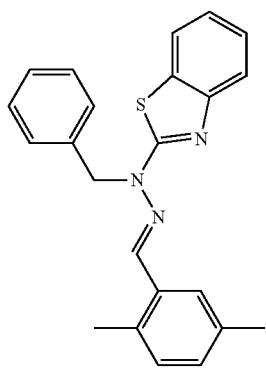
(G-11-19)
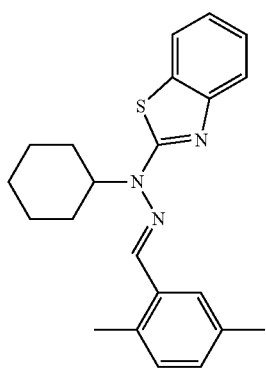
(G-11-20)
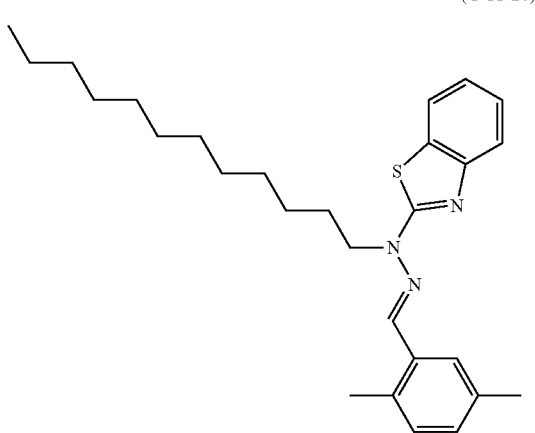
-continued
(G-11-21)
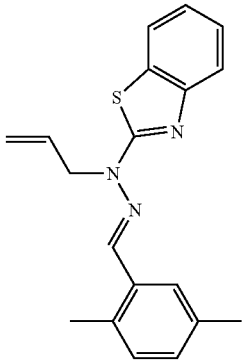
(G-11-22)
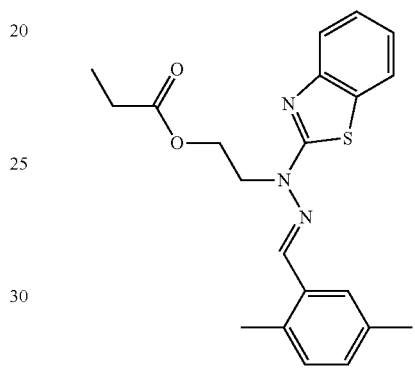
(G-11-23)
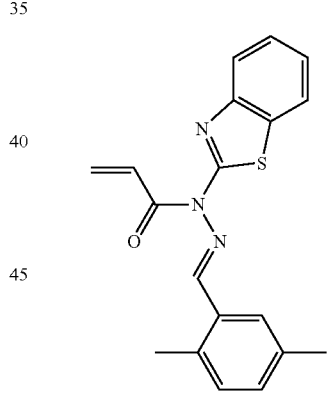
(G-11-24)
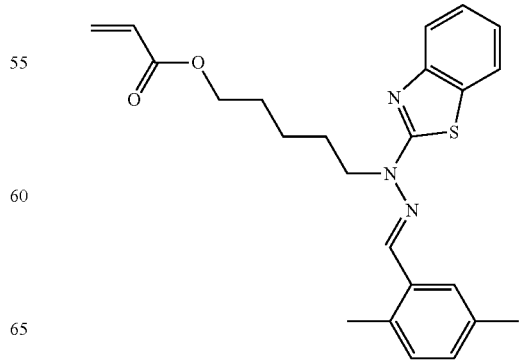

(G-11-25)

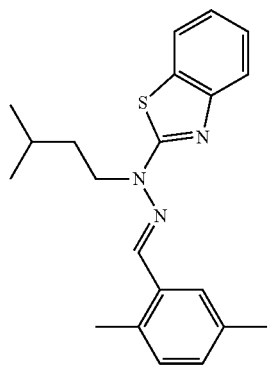

(G-11-26)

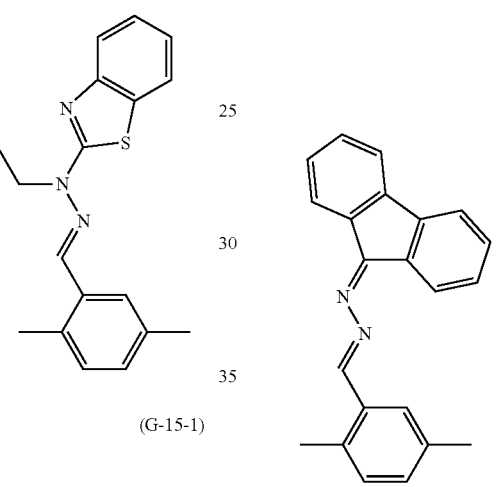

(G-15-1)

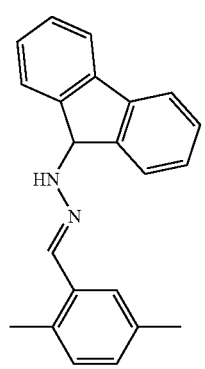

(G-16-1)

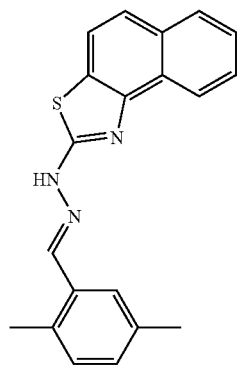

(G-17-1)

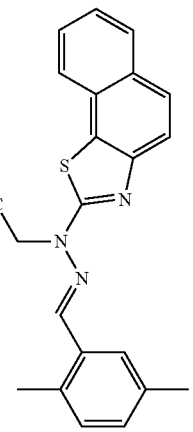

(G-20-1)

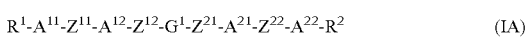

In the compound represented by Formula (I), from the viewpoint of reverse dispersibility and liquid crystallinity, a compound represented by Formula (IA) below is preferable:

$$R^1\text{-}A^{11}\text{-}Z^{11}\text{-}A^{12}\text{-}Z^{12}\text{-}G^1\text{-}Z^{21}\text{-}A^{21}\text{-}Z^{22}\text{-}A^{22}\text{-}R^2 \qquad (IA)$$

(in the formula, $R^1$, $R^2$, and $G^1$ represent the same meanings as those in Formula (I), $A^{11}$ and $A^{22}$ represent the same meanings as $A^1$ and $A^2$ in Formula (I), $Z^{11}$ and $Z^{22}$ represent the same meanings as $Z^1$ and $Z^2$ in Formula (I), $A^{12}$ and $A^{21}$ each independently represent a 1,4-cyclohexylene group which may be unsubstituted or may be substituted with one or more of substituent groups L, and $Z^{12}$ and $Z^{21}$ each independently represent a group represented by Formula (Z0-1) or (Z0-2)). Preferable forms of each of the groups are the same as those in Formula (I).

Preferably, specific examples of the compound represented by Formula (I) include compounds represented by Formulae (I-1) to (I-125) below.

(I-1)
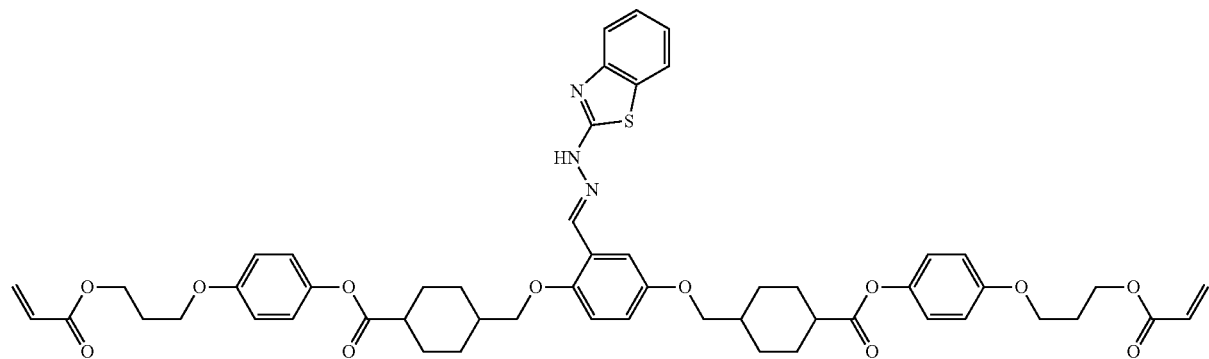
(I-2)
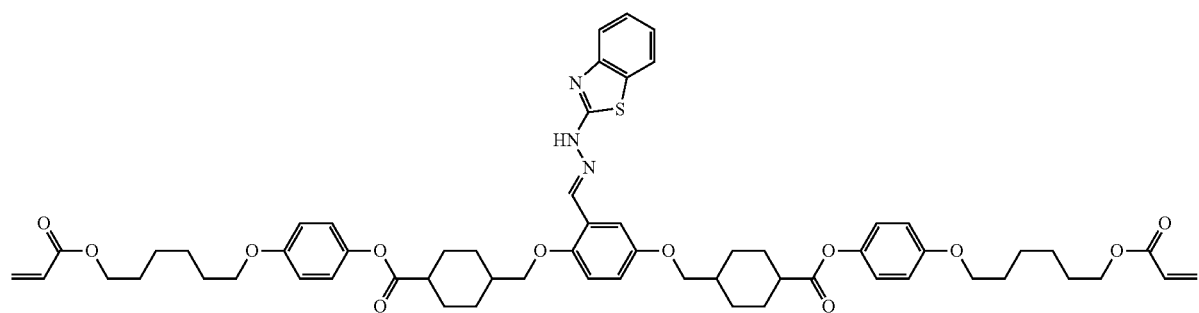
(I-3)
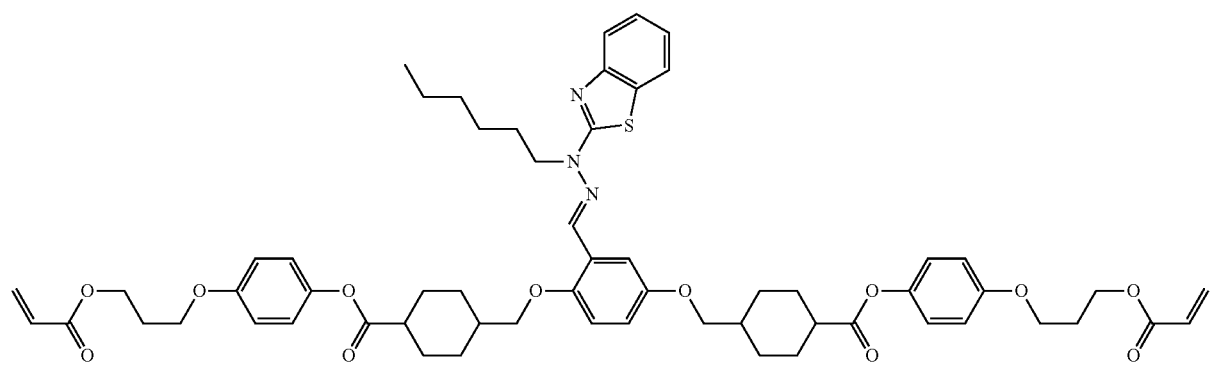
(I-4)
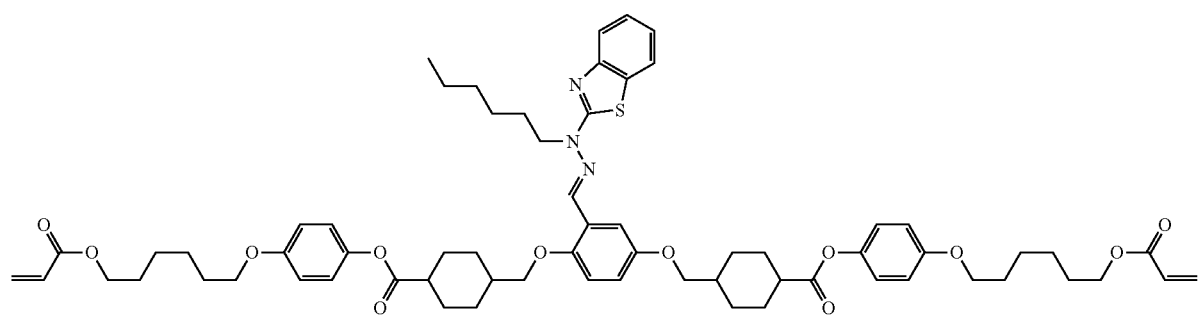

-continued
(I-5)
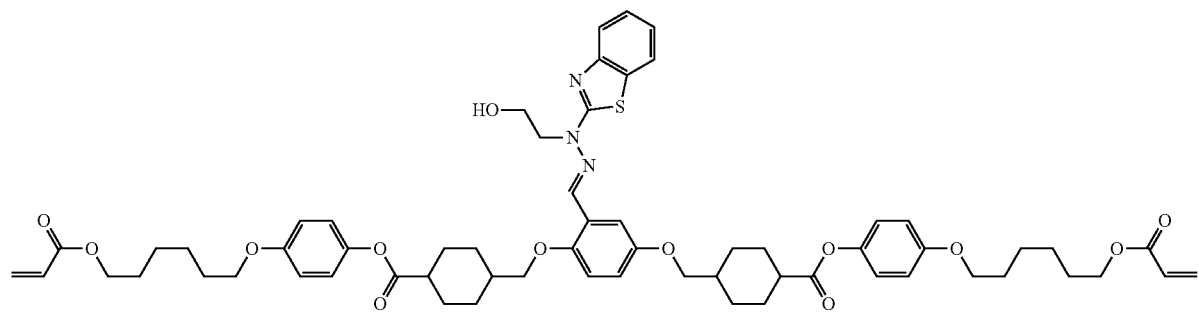
(I-6)
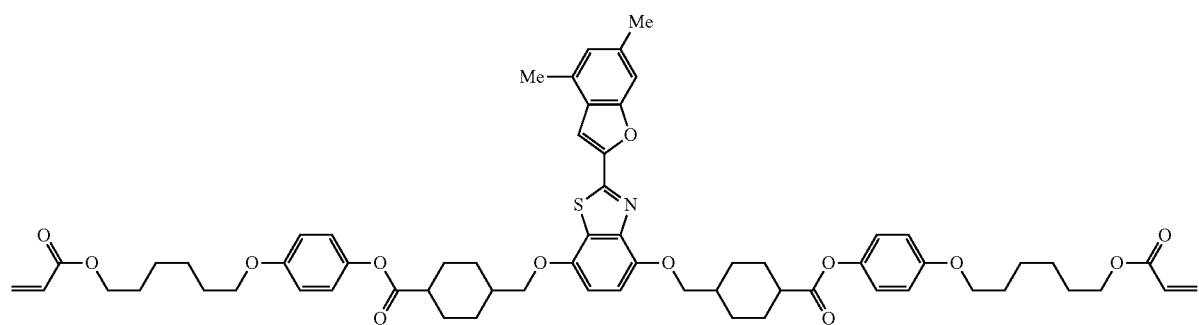
(I-7)
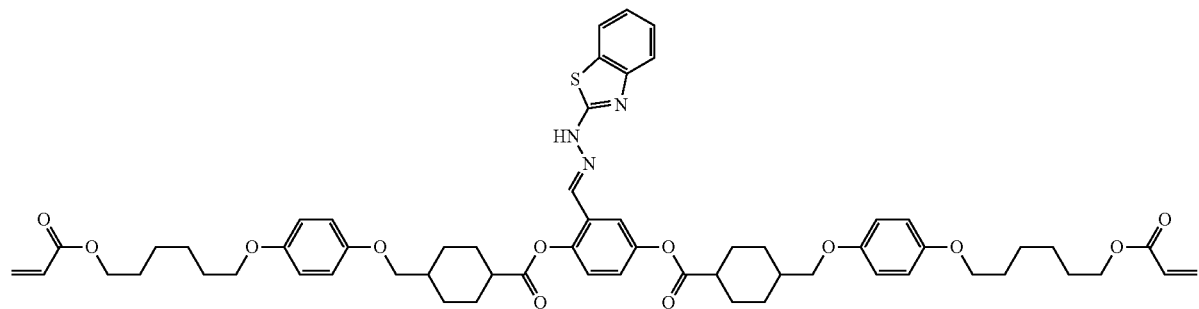
(I-8)
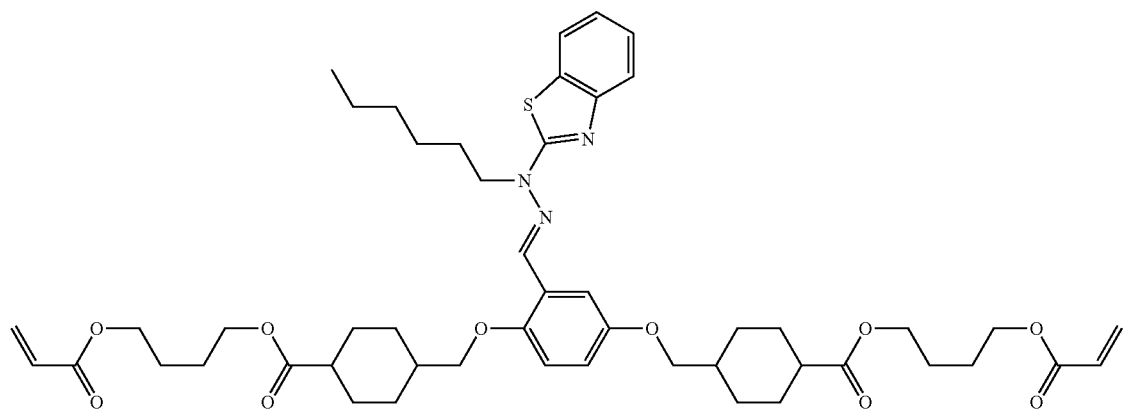

-continued
(I-9)
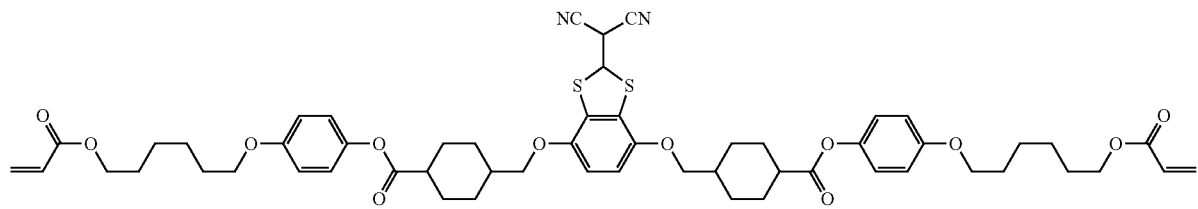
(I-10)
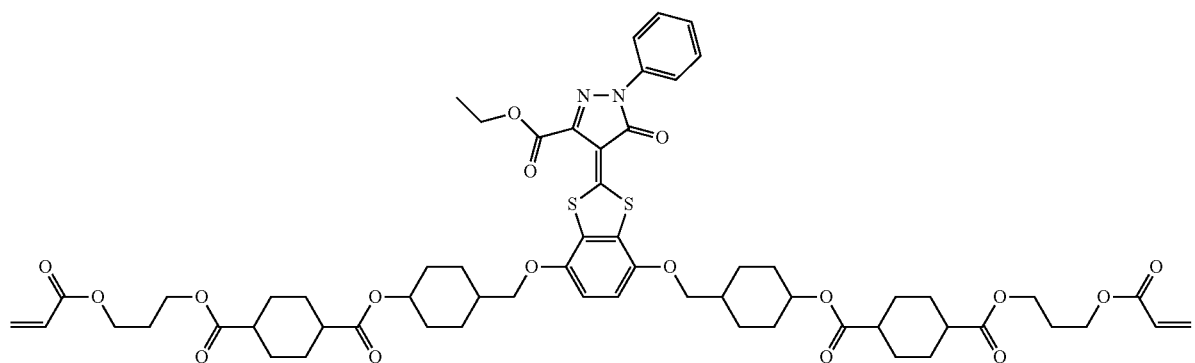
(I-11)
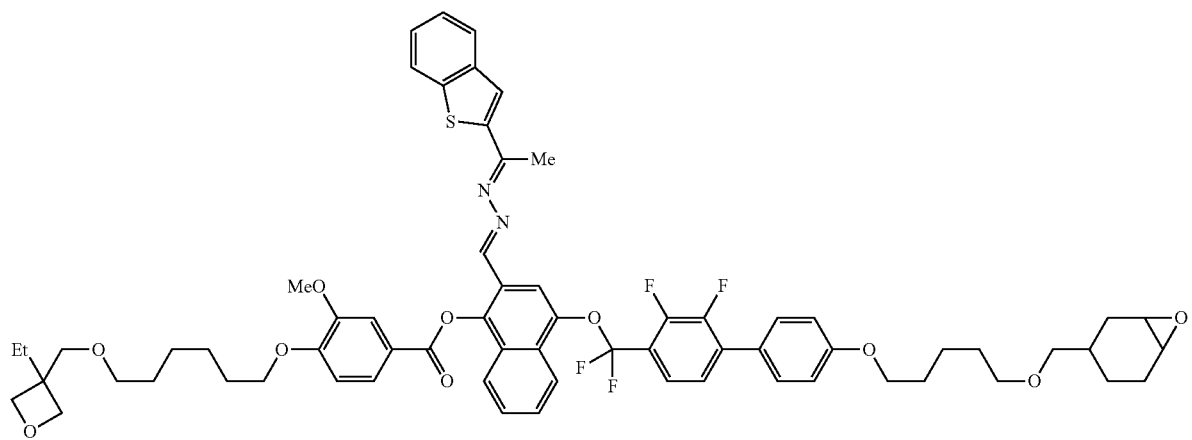
(I-12)
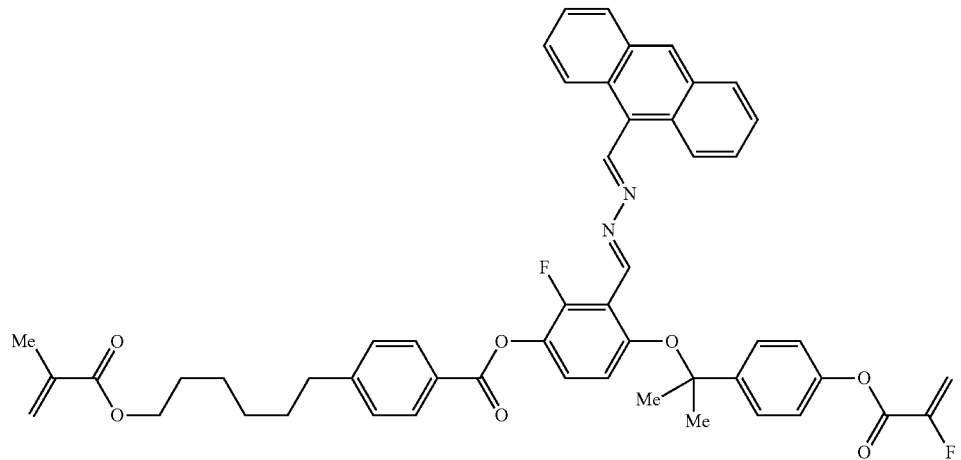

-continued
(I-13)
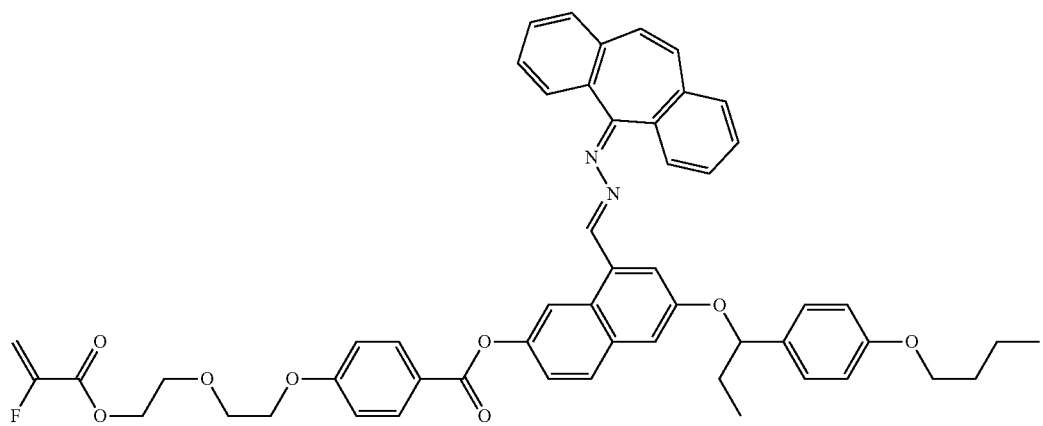
(I-14)
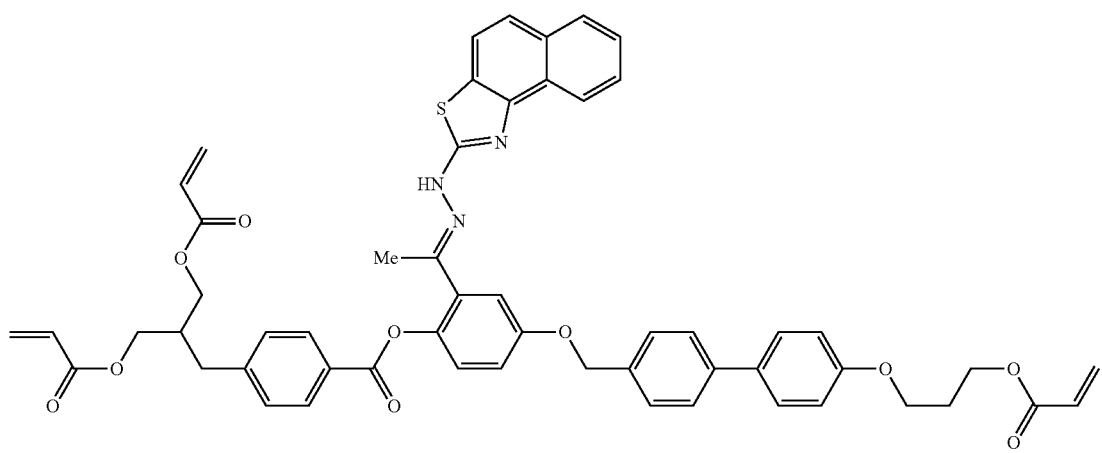
(I-15)
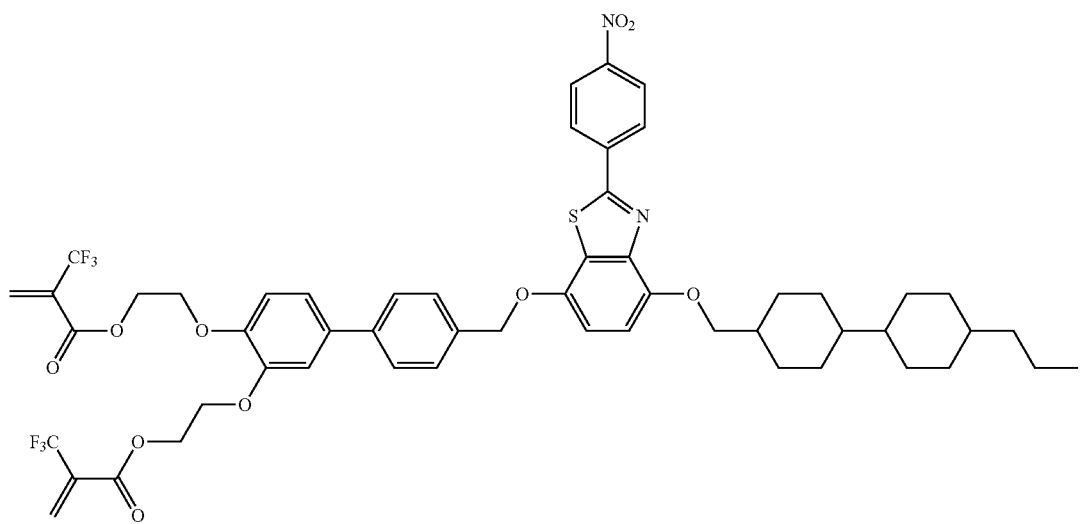

(I-16)
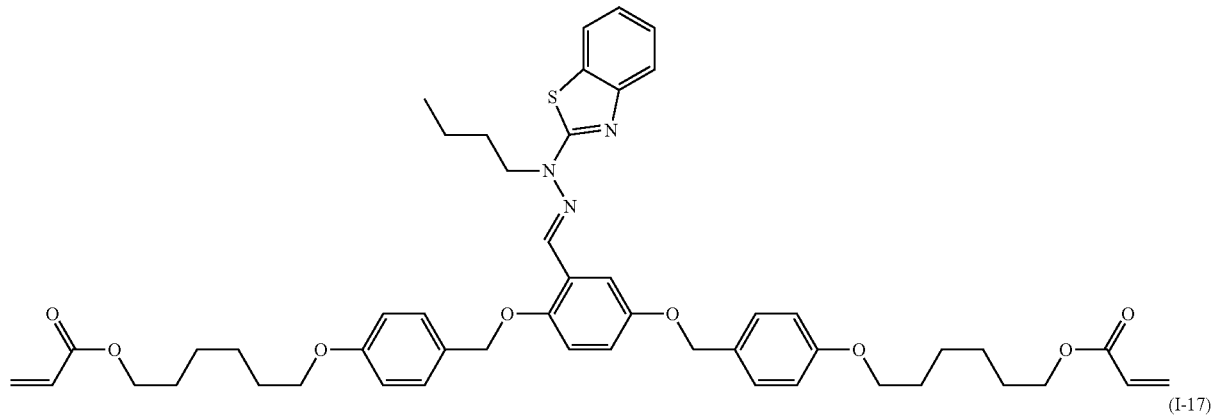
(I-17)
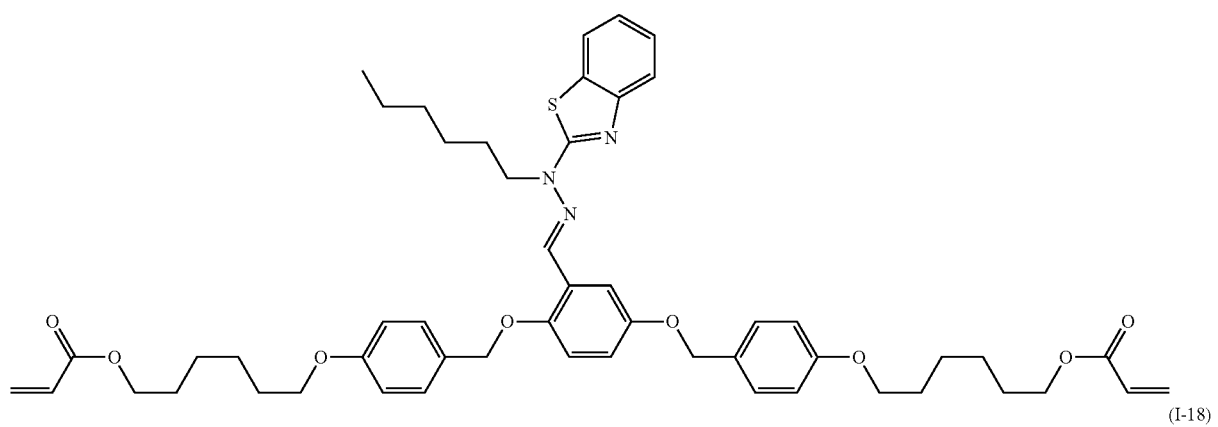
(I-18)
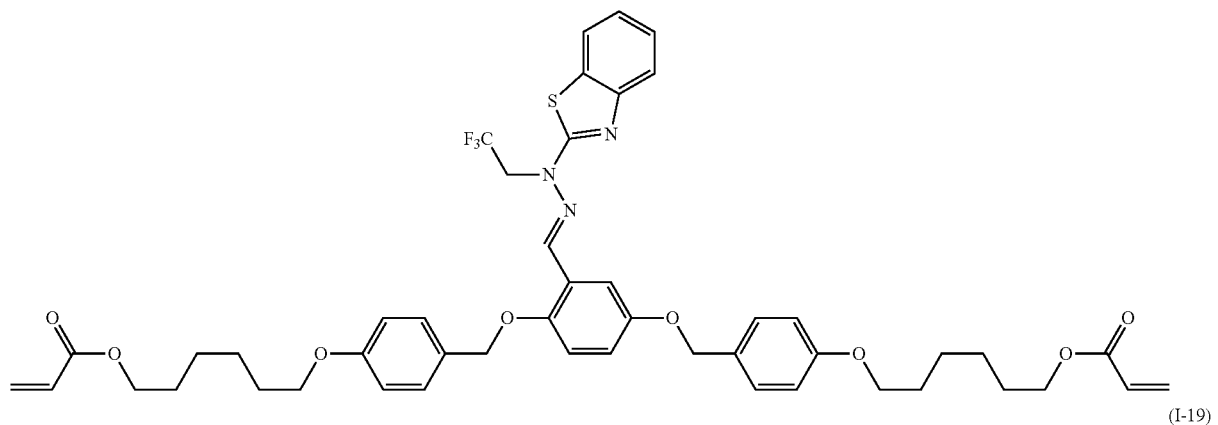
(I-19)
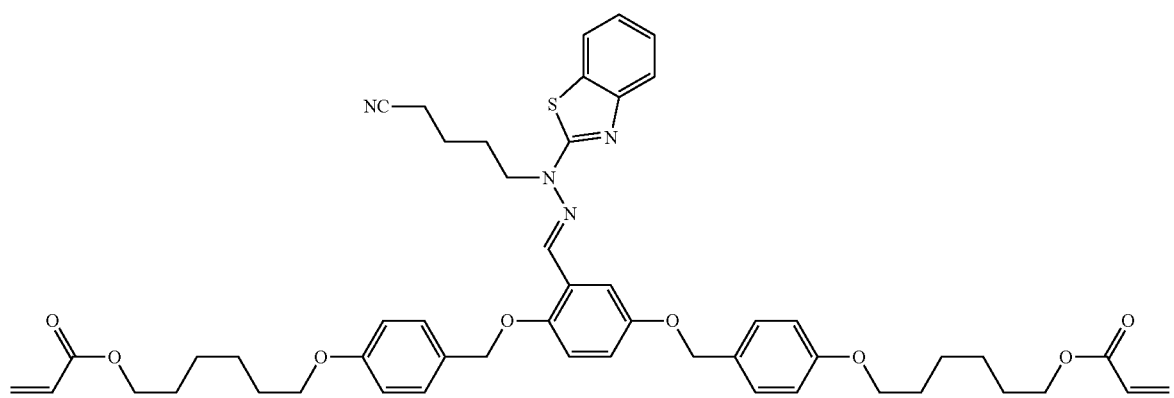

-continued
(I-20)
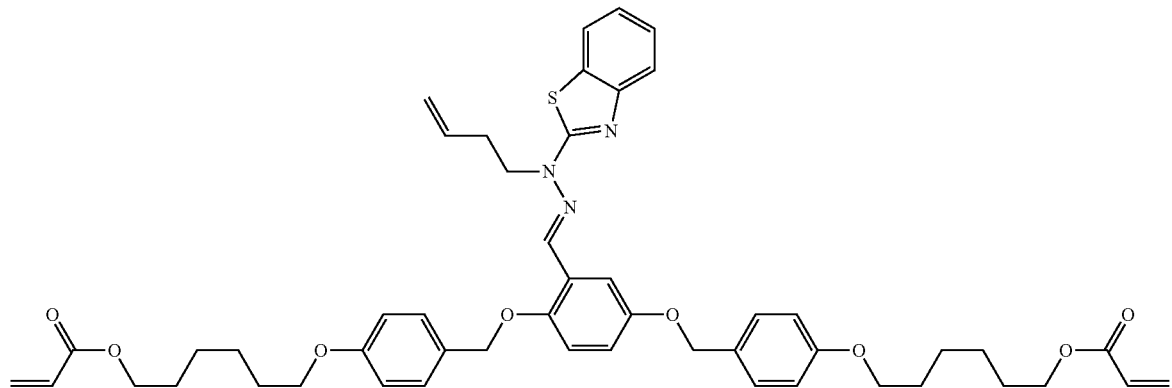
(I-21)
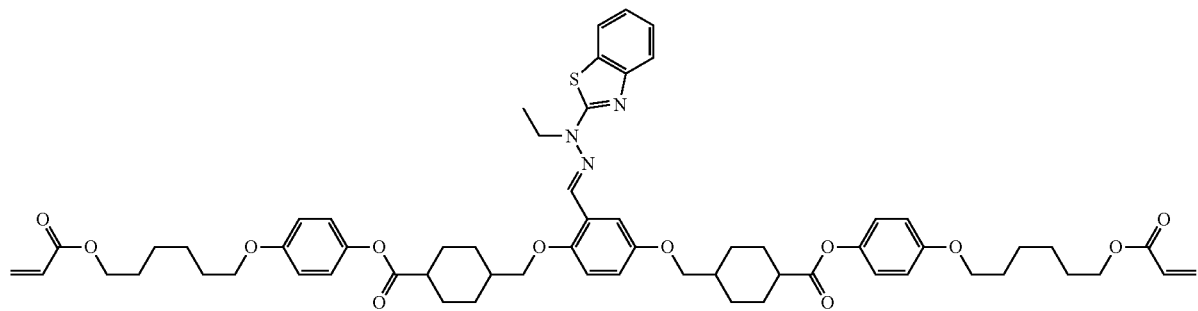
(I-22)
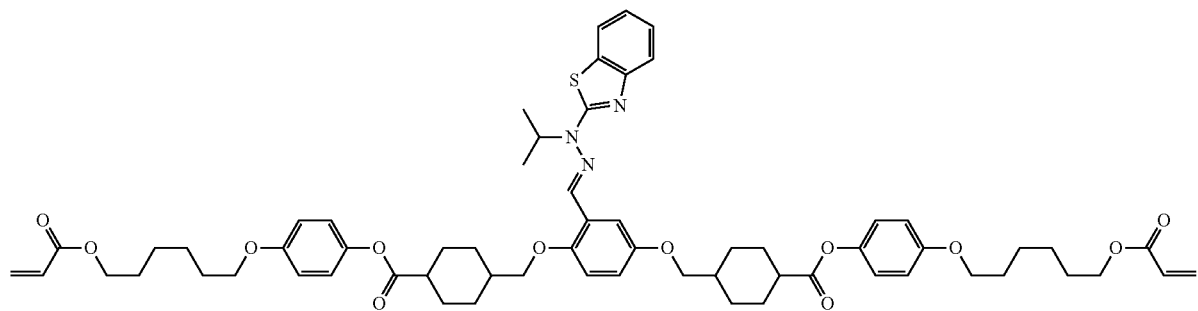
(I-23)
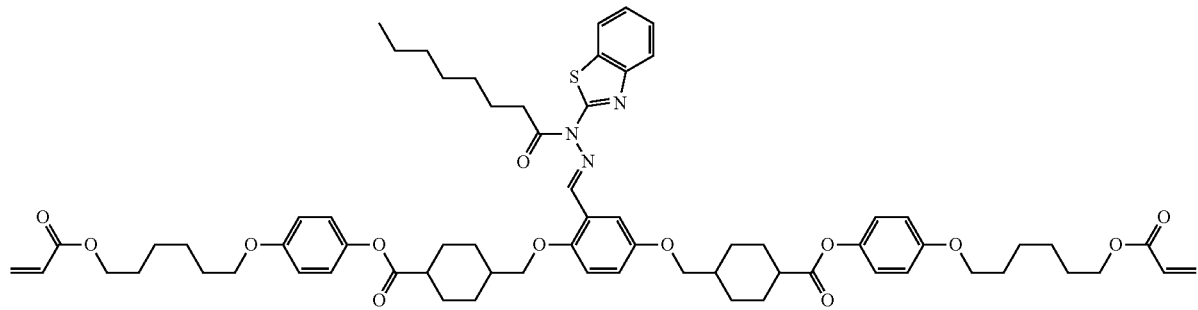

(I-24)
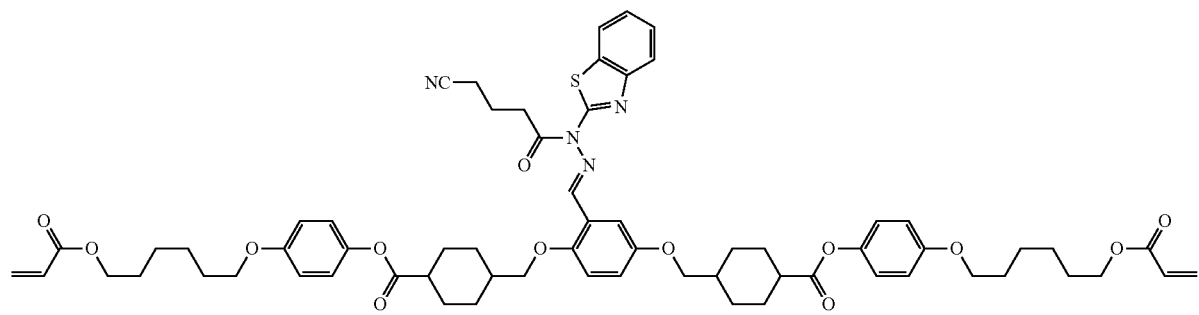
(I-25)
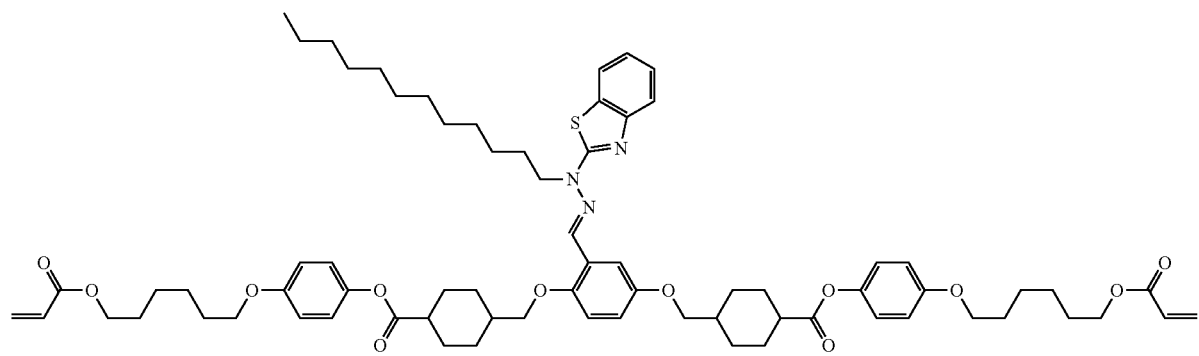
(I-26)
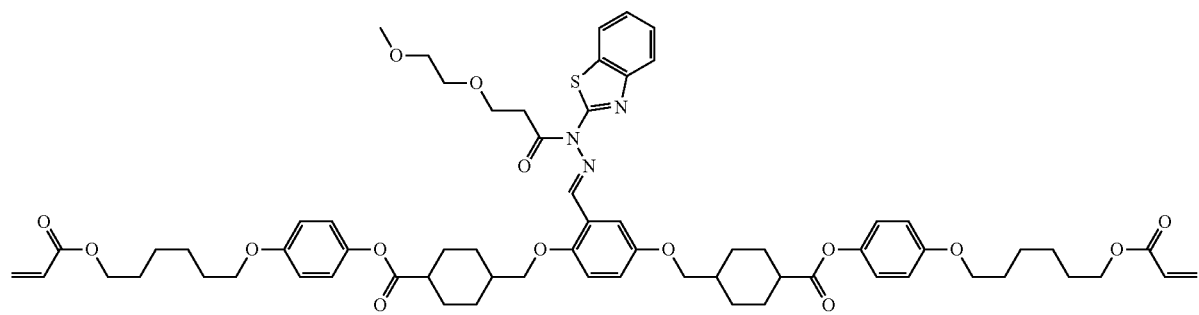
(I-27)
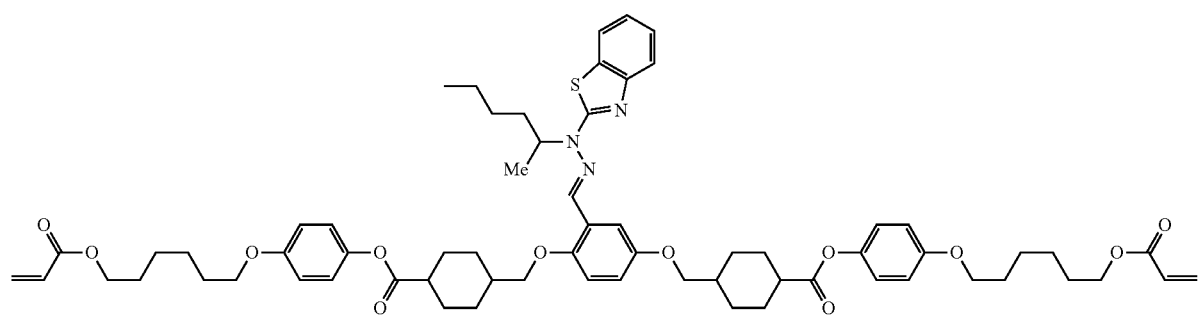

-continued
(I-28)
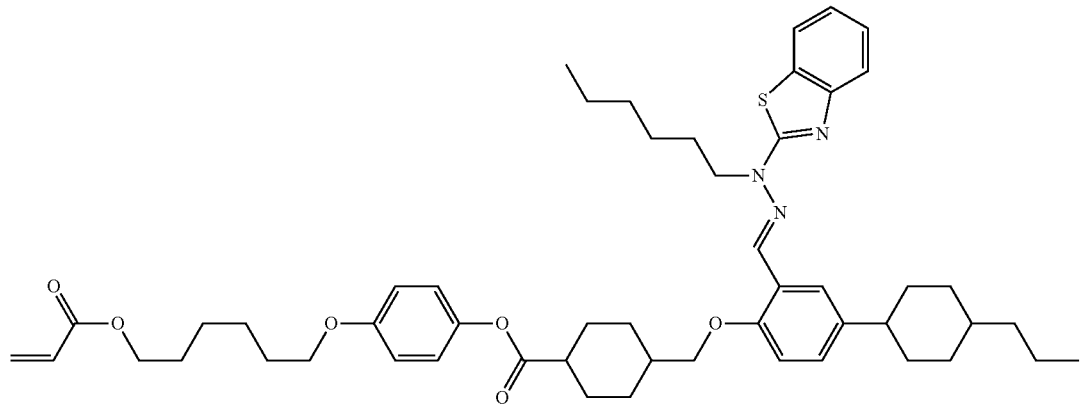
(I-29)
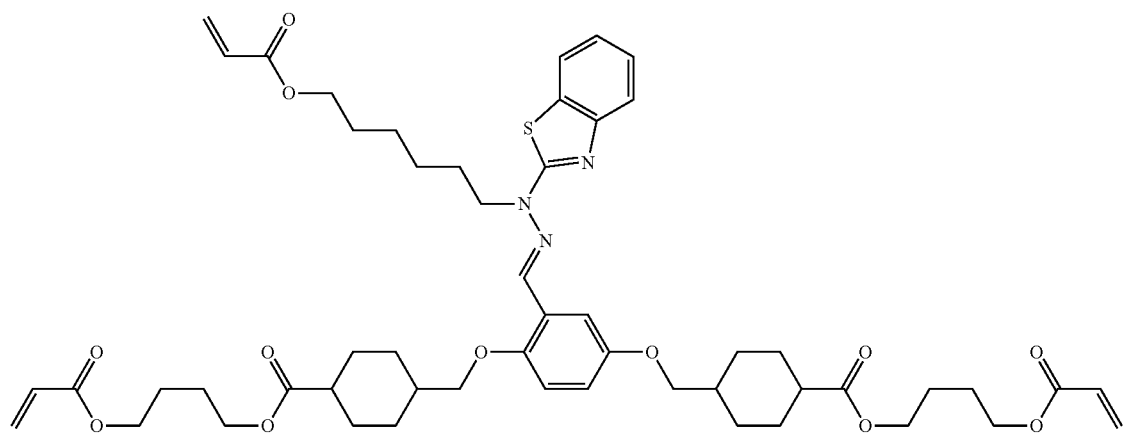
(I-30)
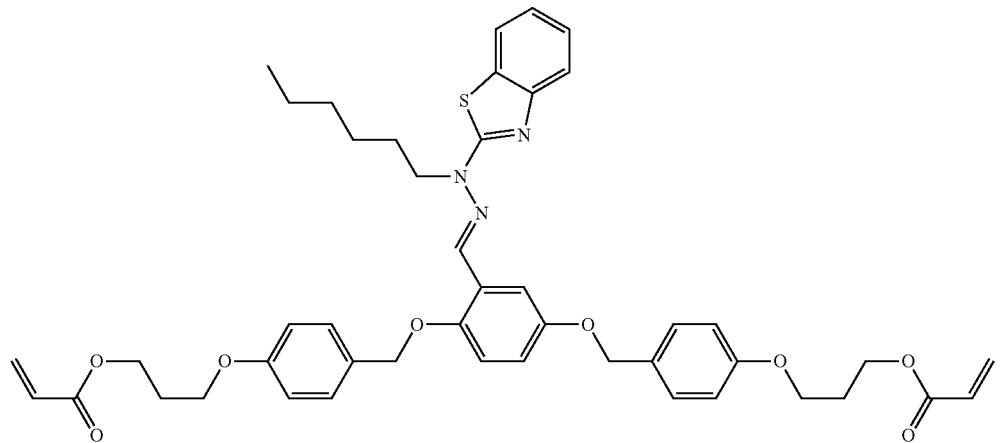

(I-31)
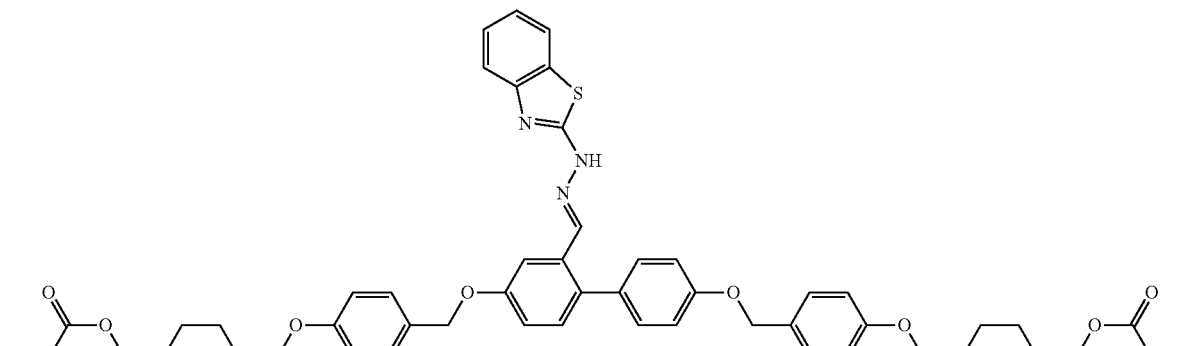
(I-32)
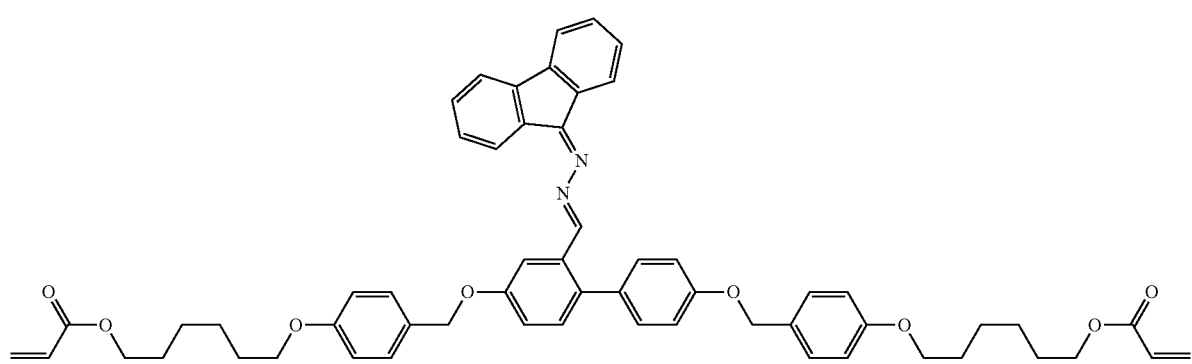
(I-33)
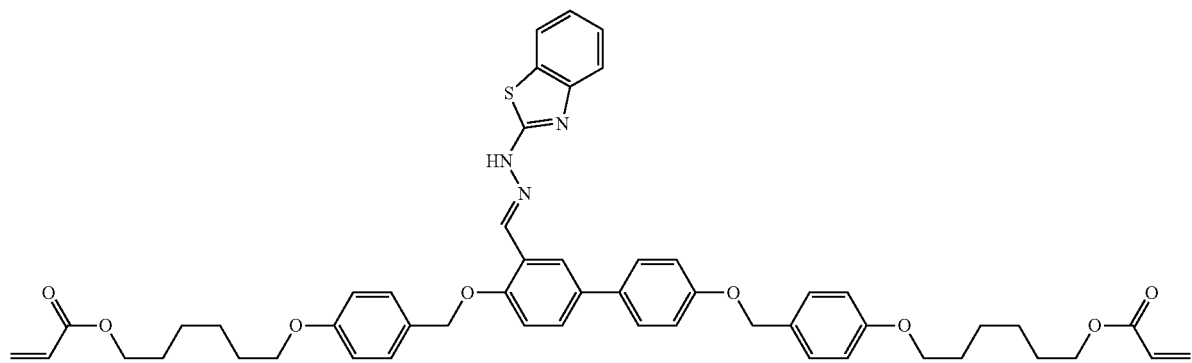
(I-34)
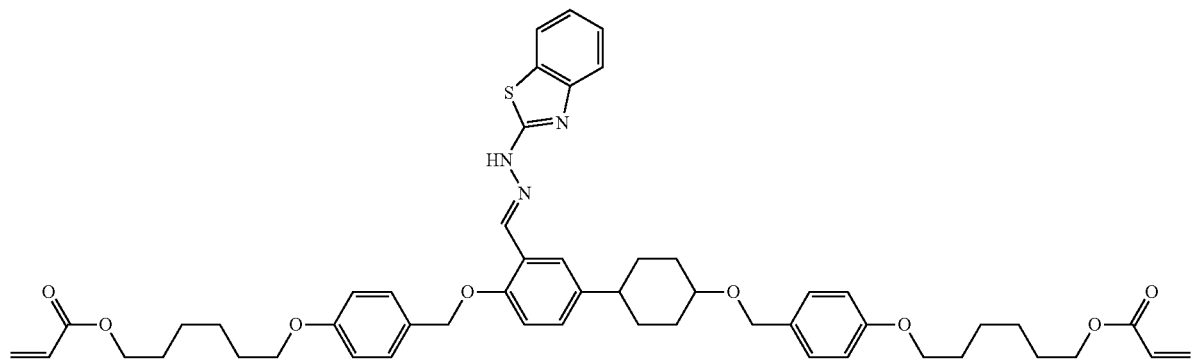

(I-35)
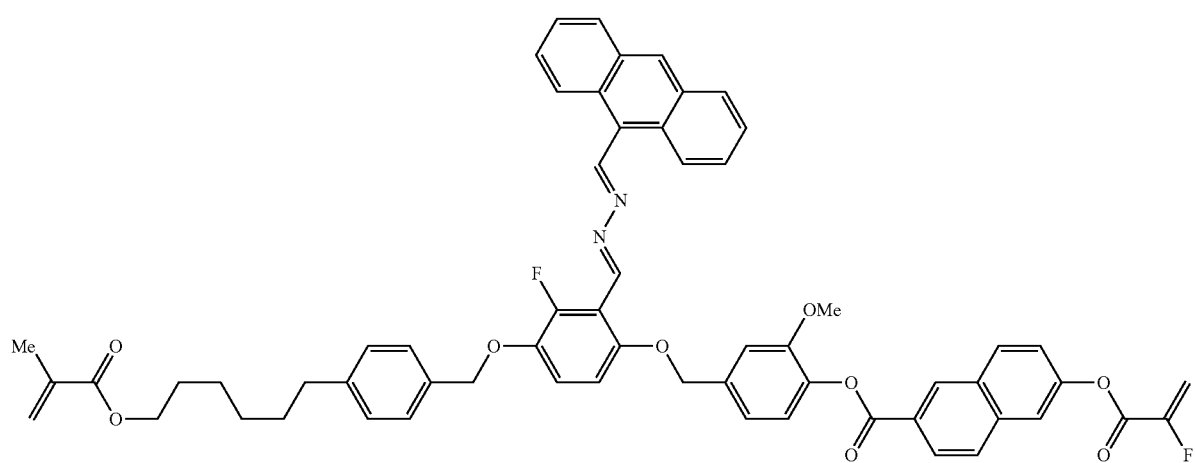
(I-36)
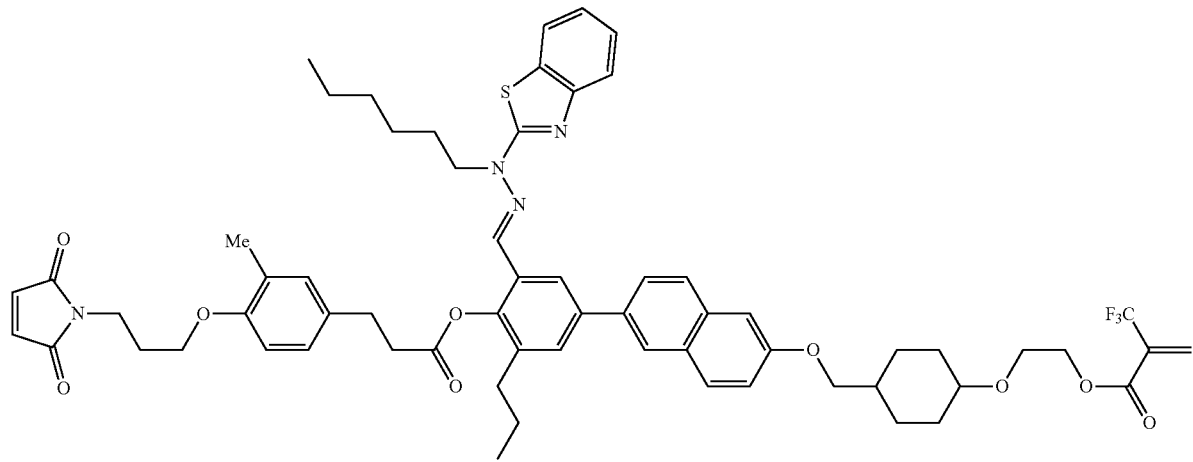
(I-37)
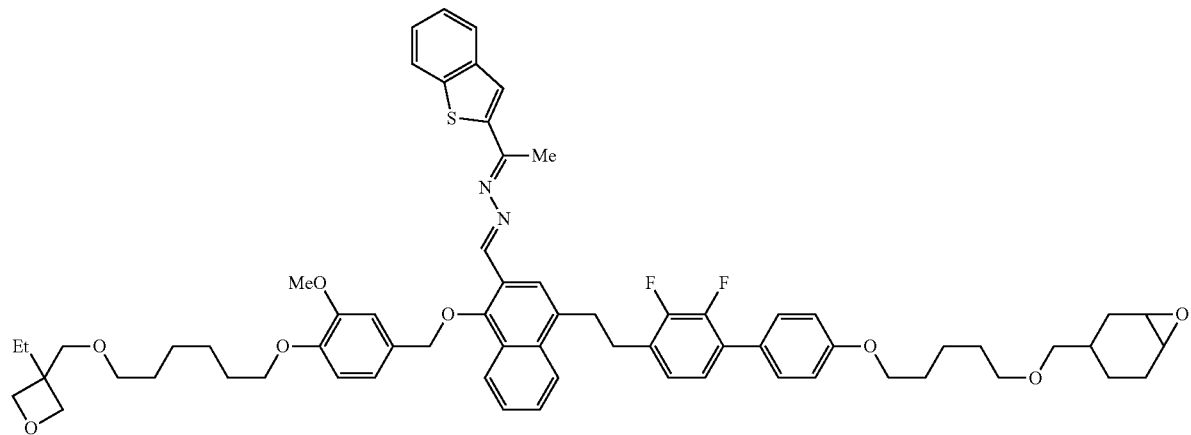

-continued
(I-38)
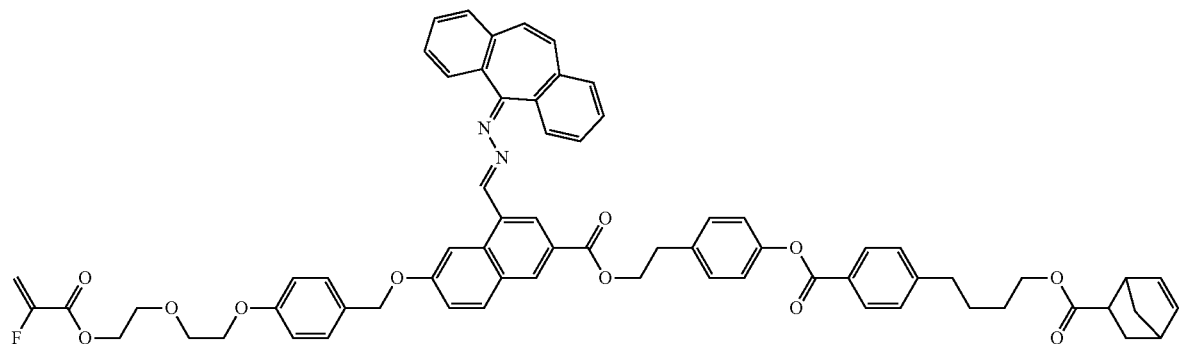
(I-39)
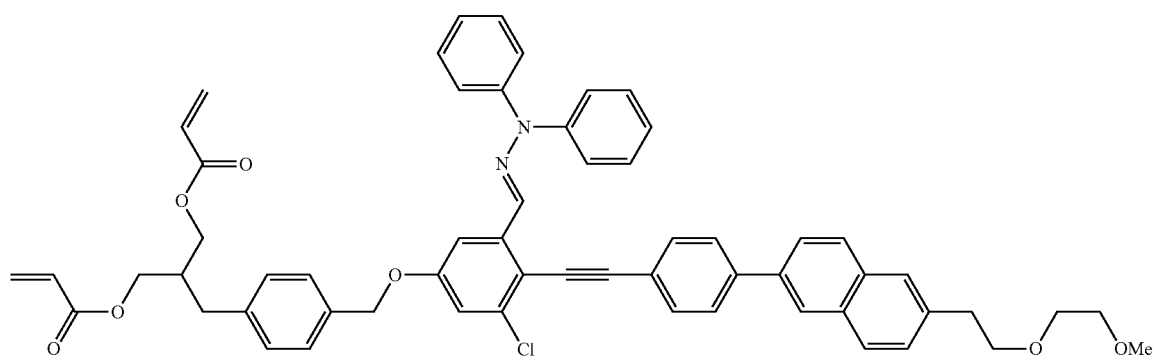
(I-40)
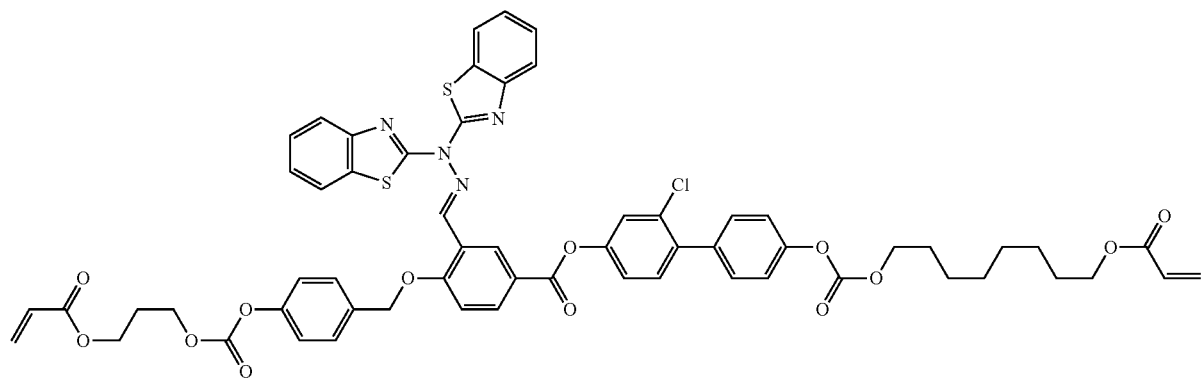
(I-41)
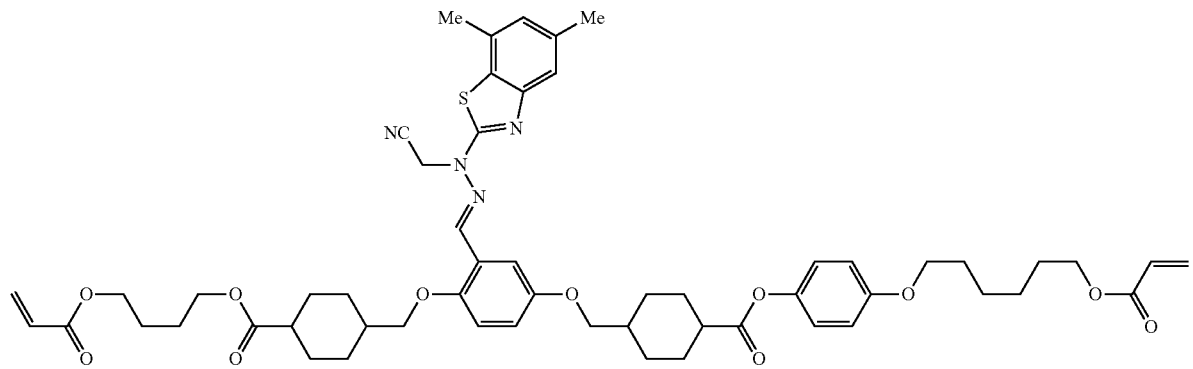

(I-42)
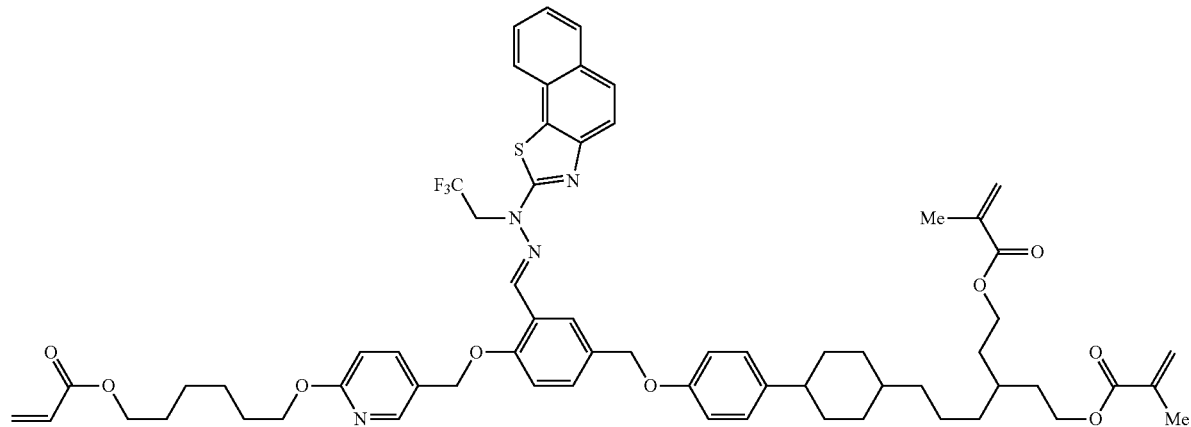
(I-43)
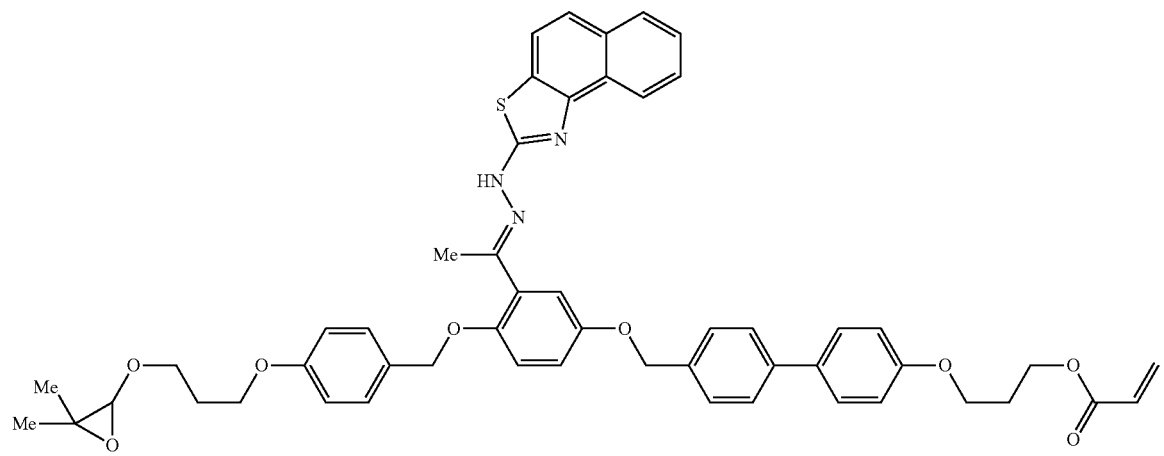
(I-44)
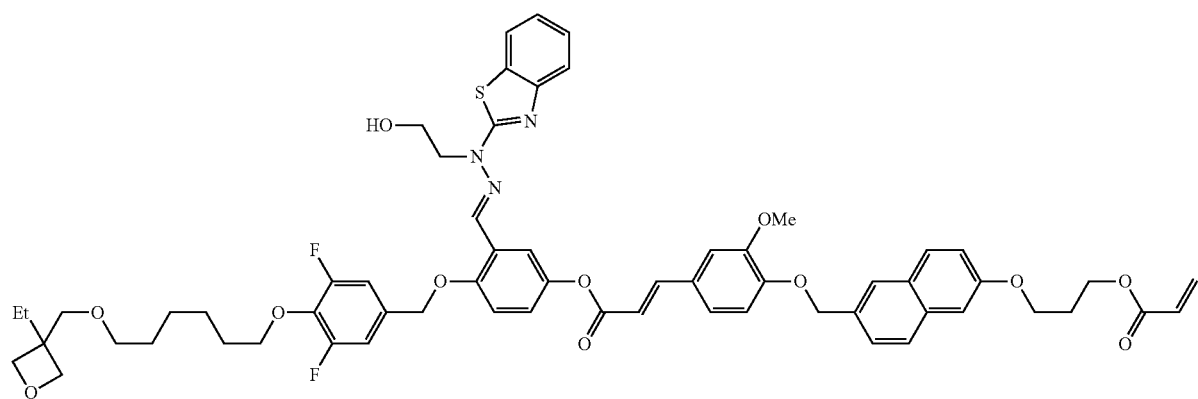

(I-45)
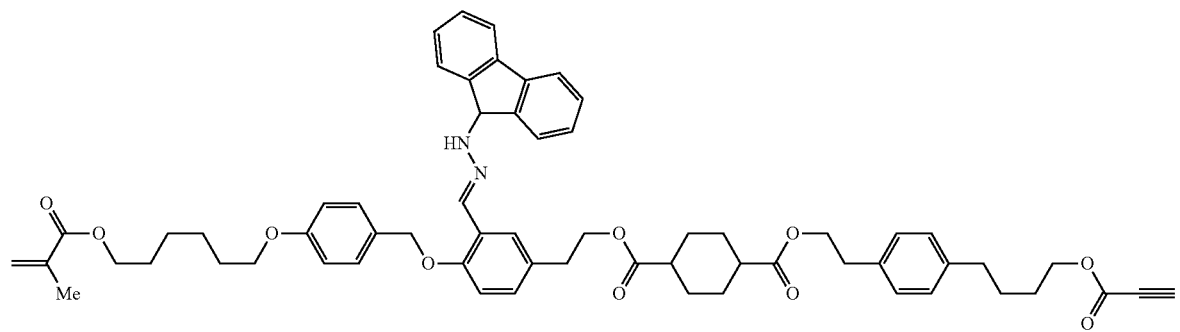
(I-46)
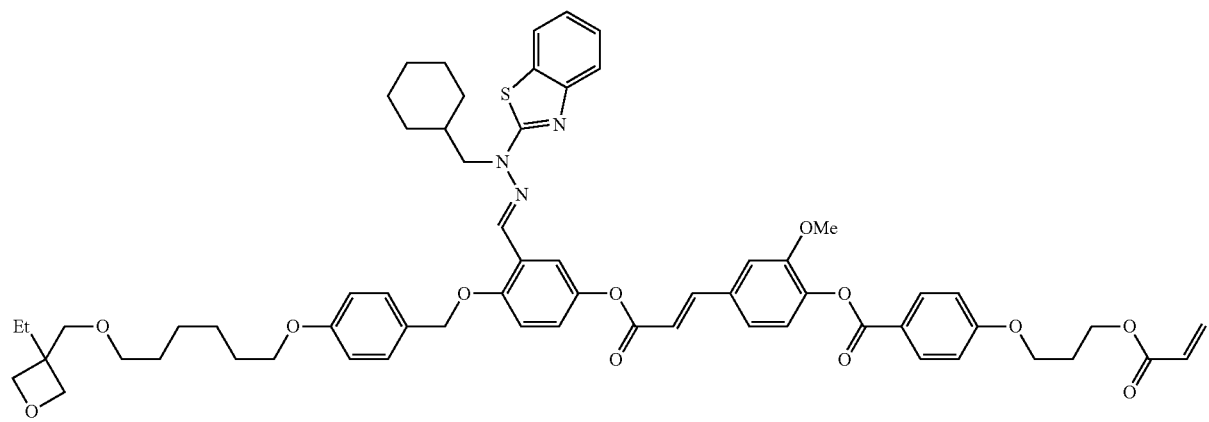
(I-47)
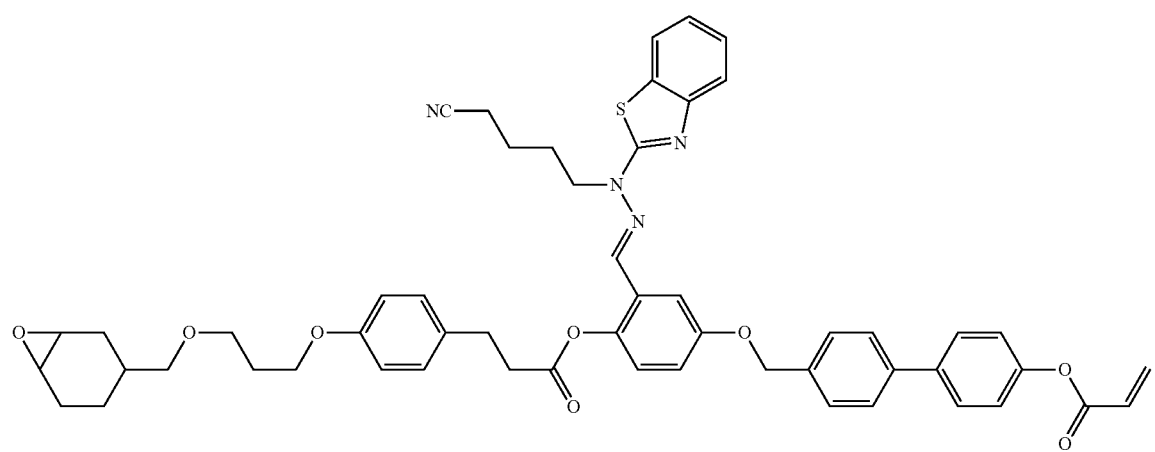

-continued
(I-48)
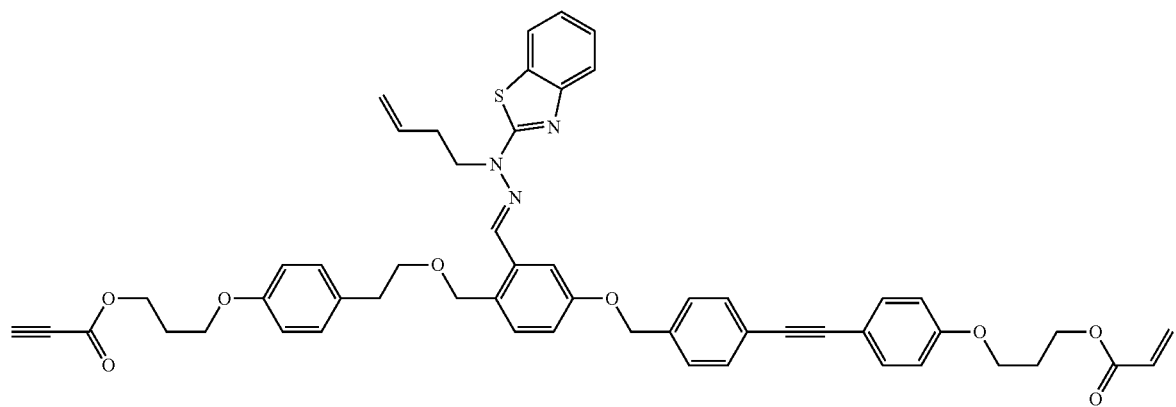
(I-49)
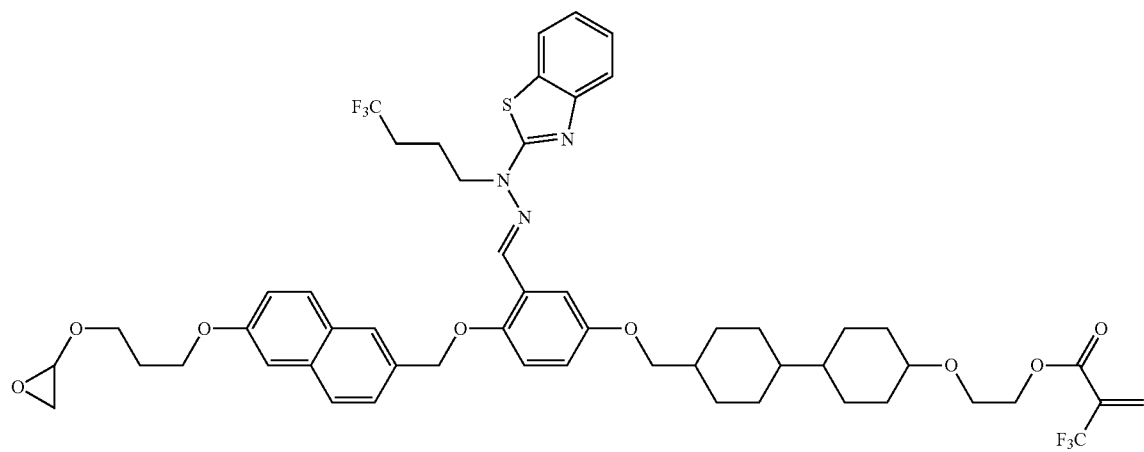
(I-50)
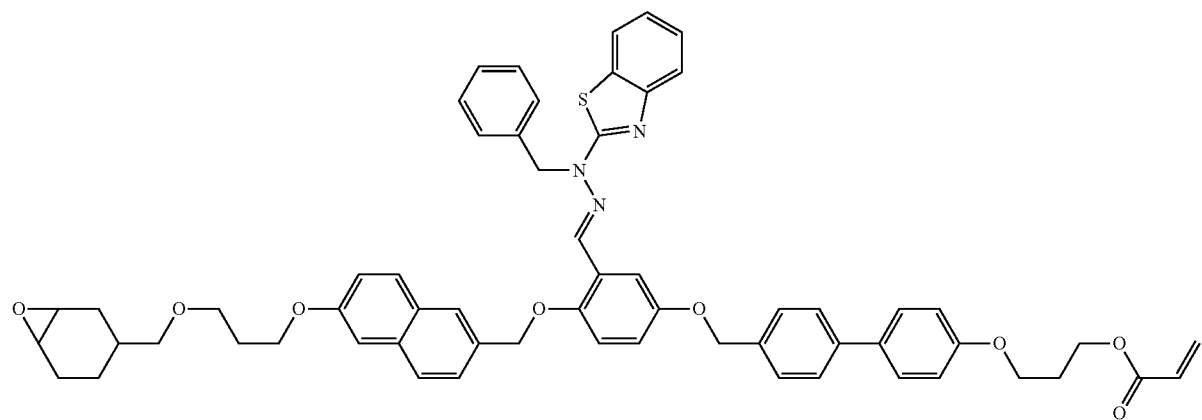

-continued
(I-51)
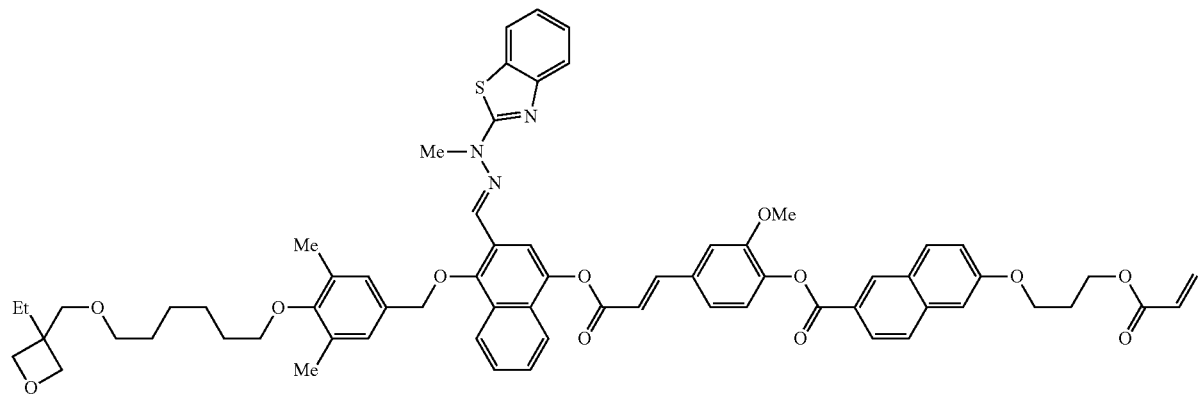
(I-52)
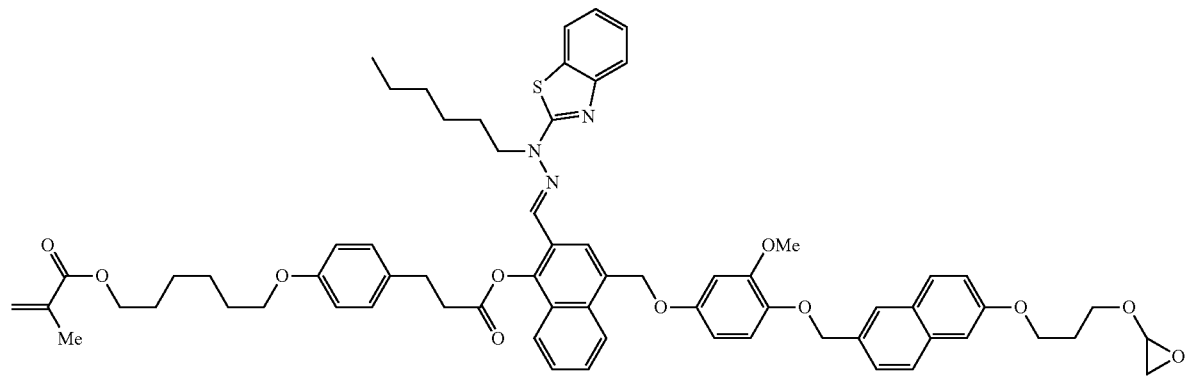
(I-53)
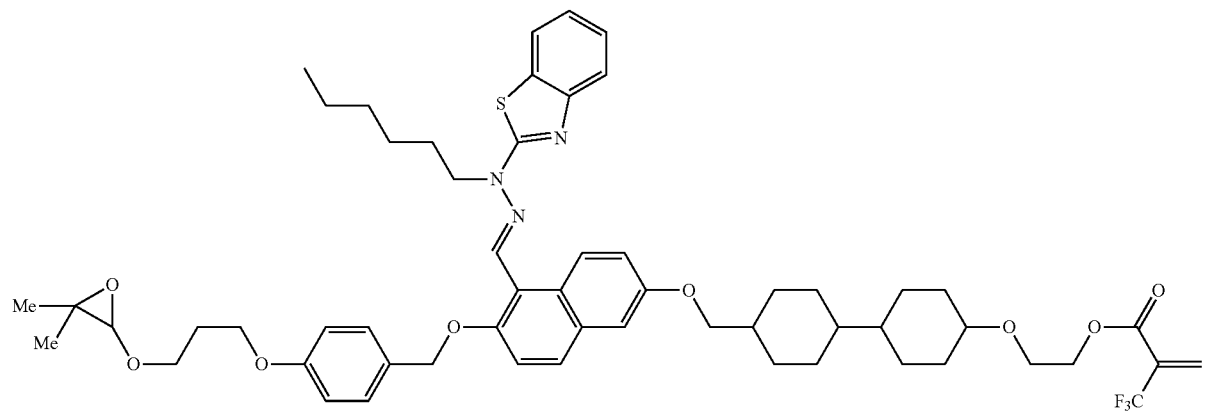

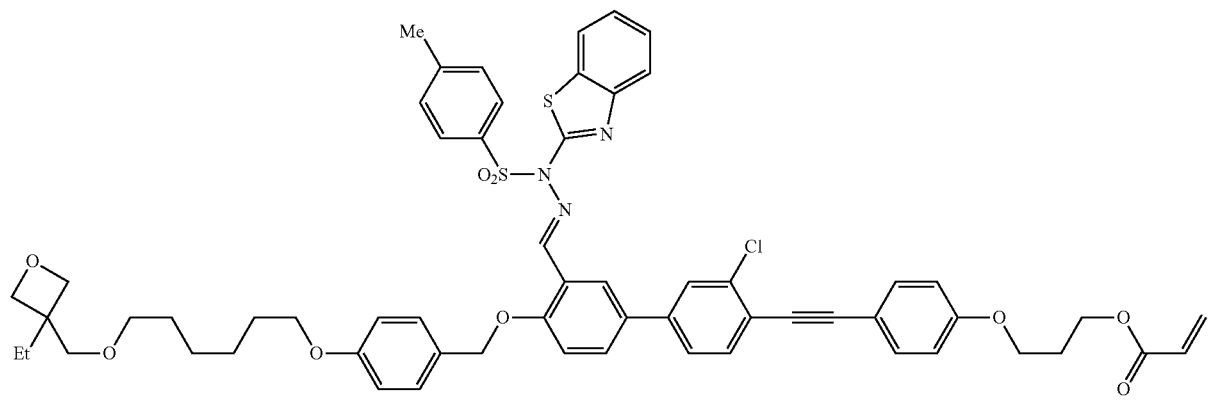
(I-54)
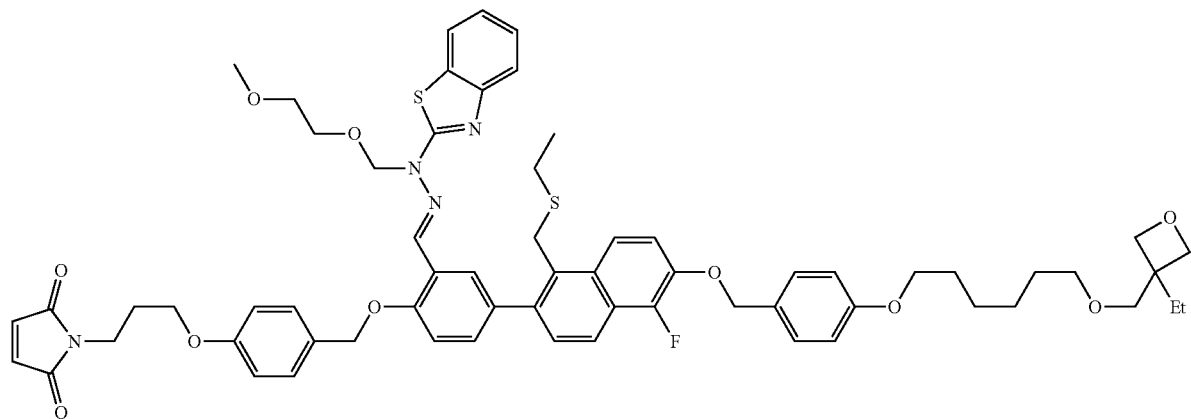
(I-55)
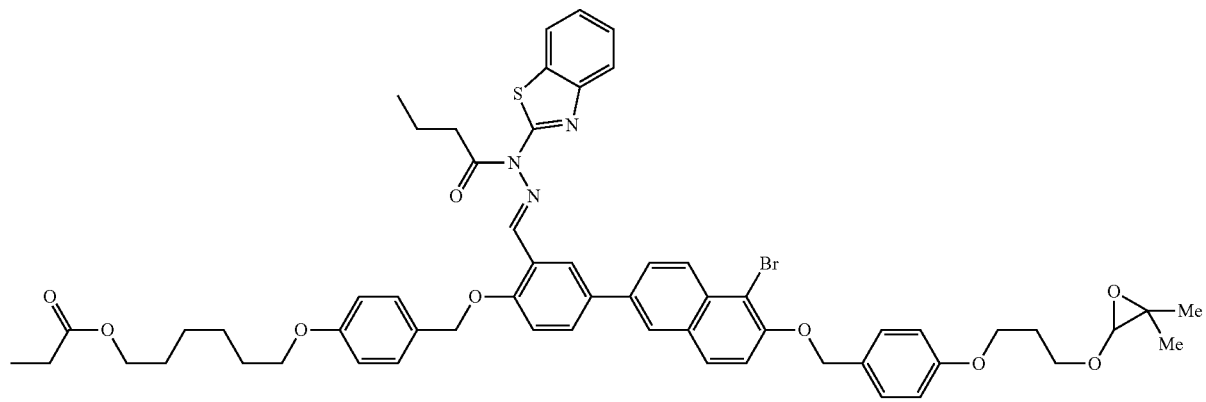
(I-56)

(I-57)
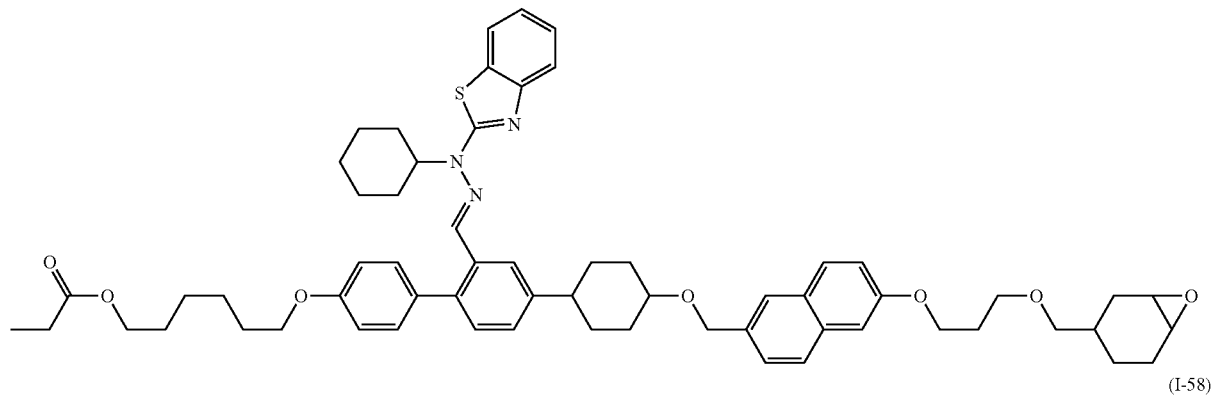
(I-58)
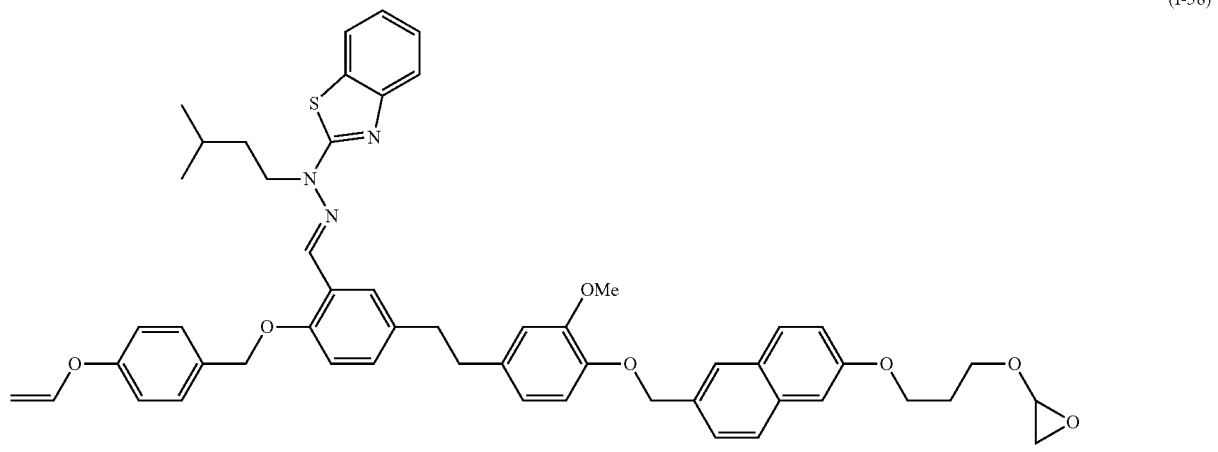
(I-59)
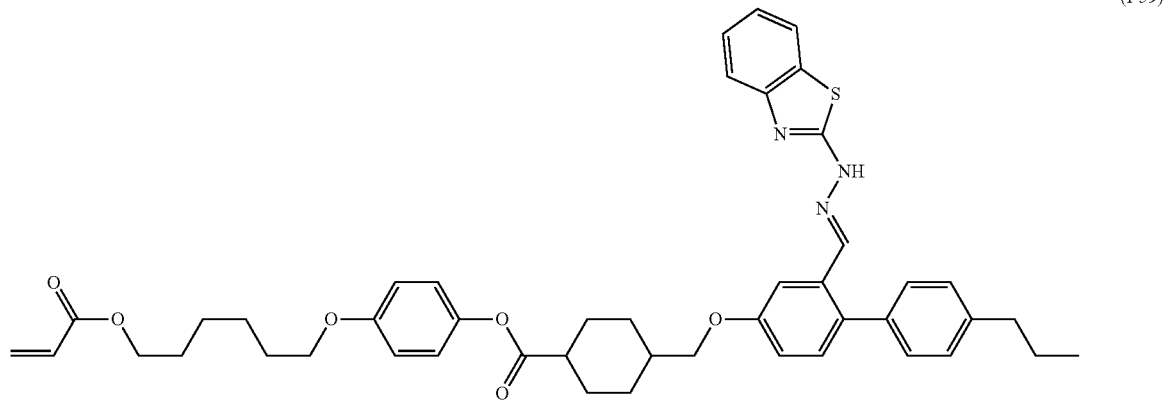
(I-60)
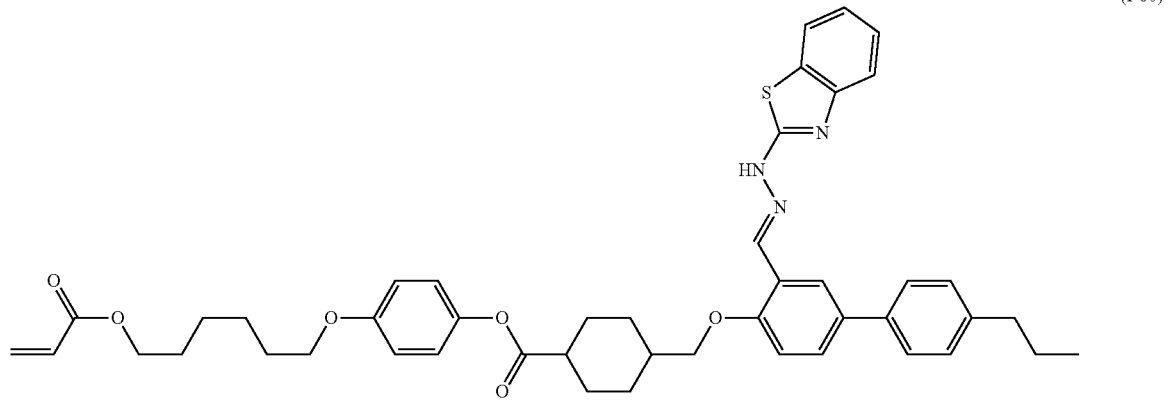

-continued
(I-61)
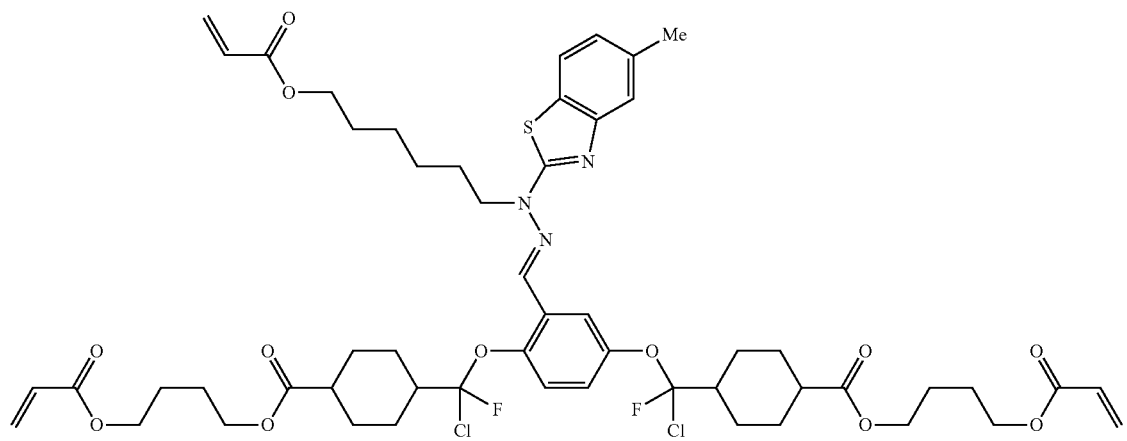
(I-62)
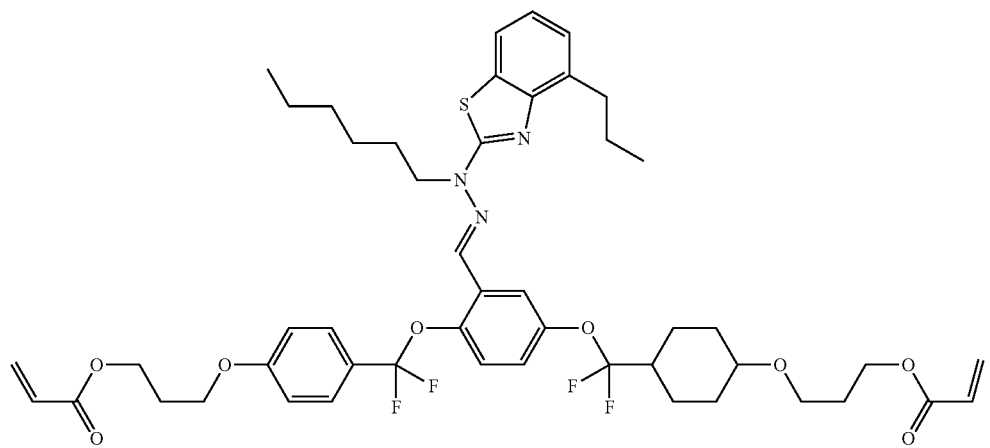
(I-63)
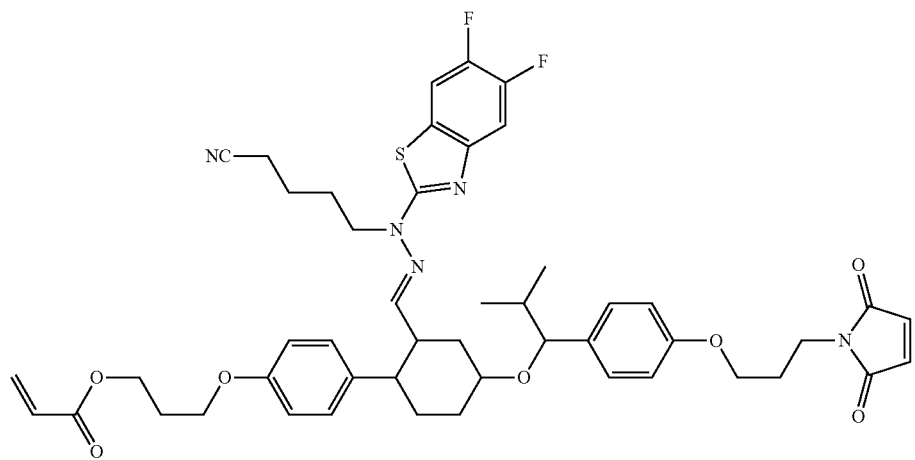

-continued
(I-64)
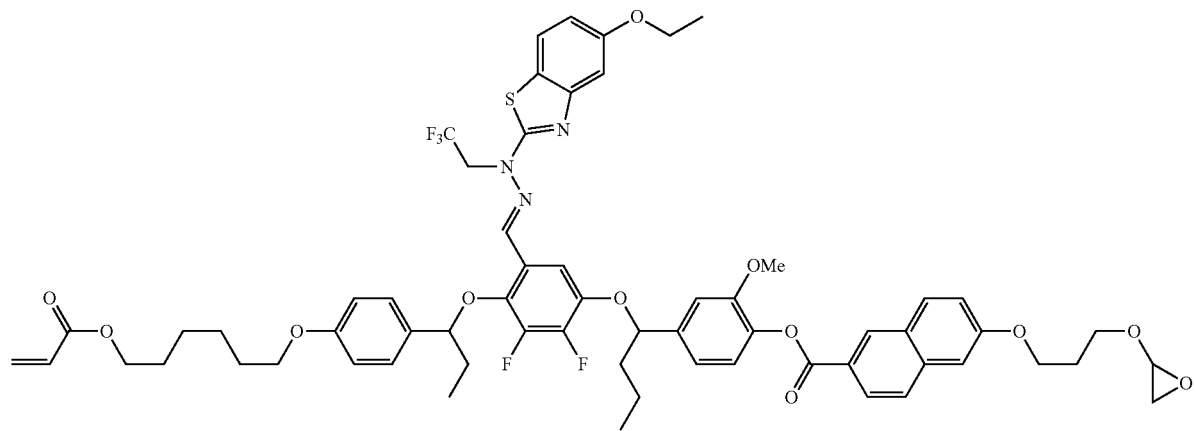
(I-65)
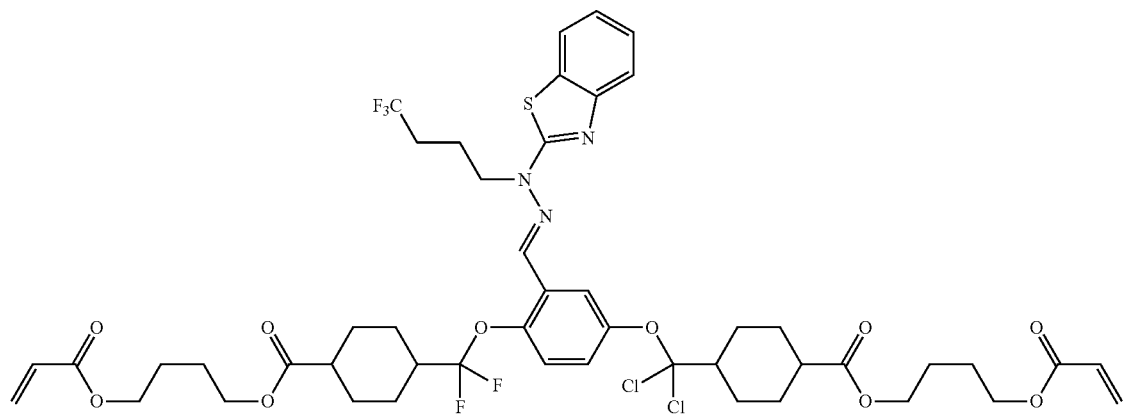
(I-66)
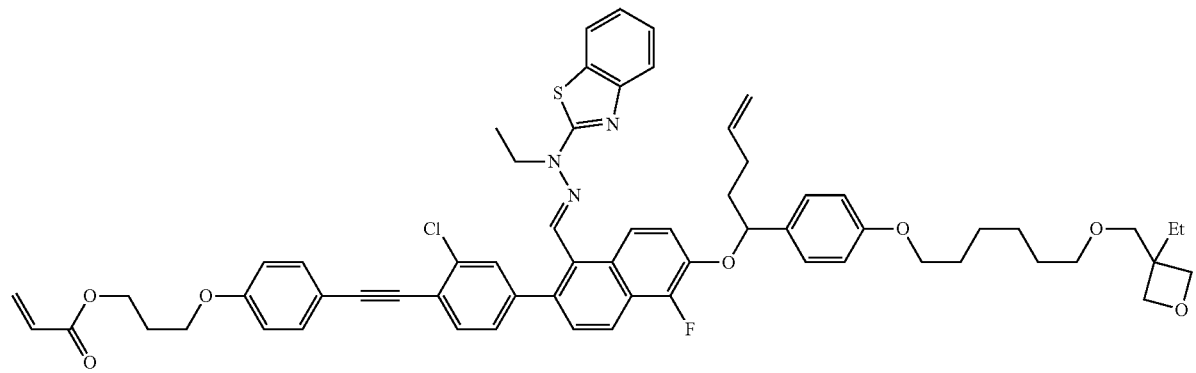

-continued
(I-67)
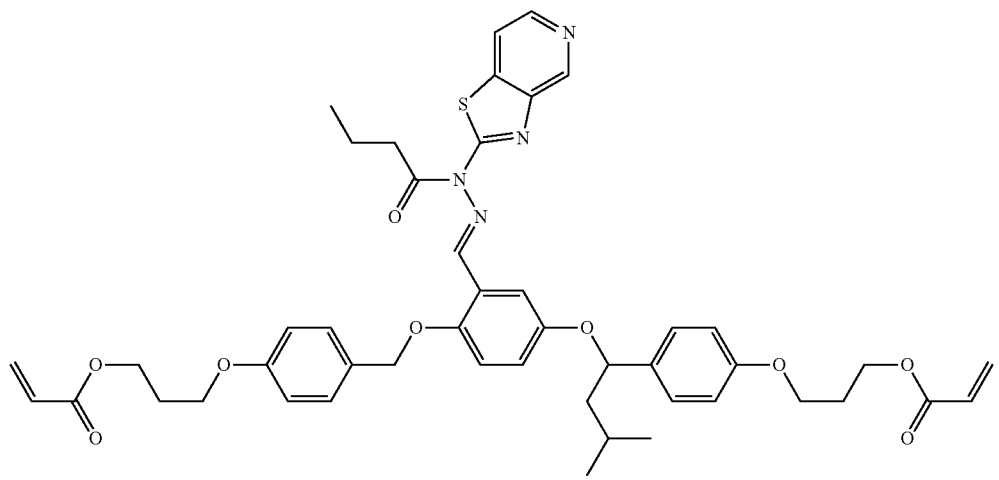
(I-68)
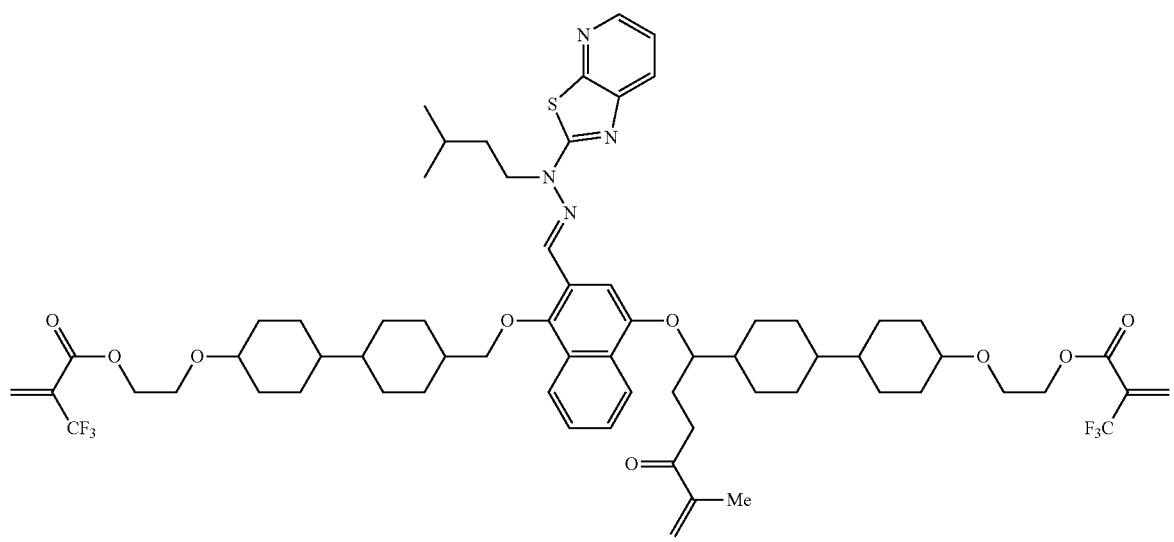
(I-69)
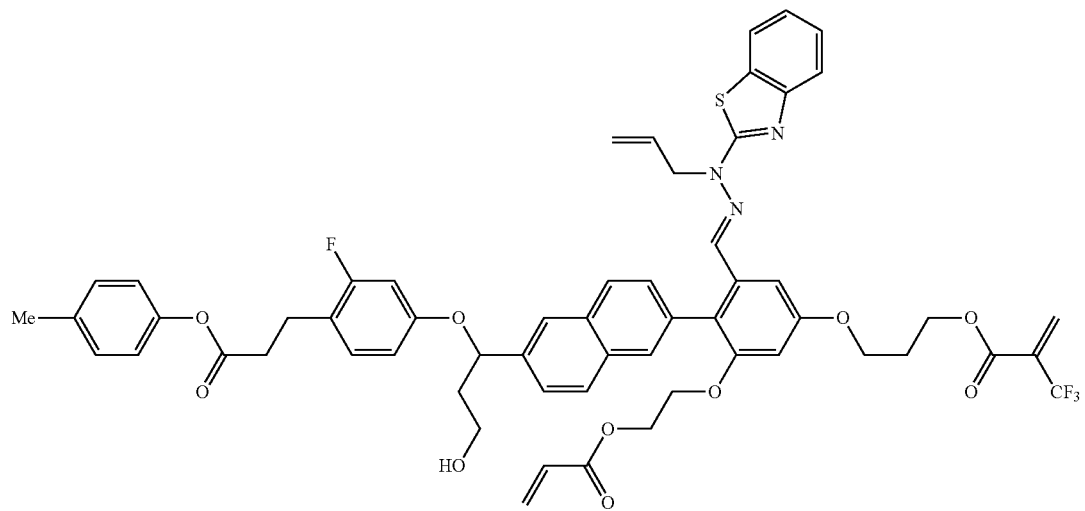

(I-70)
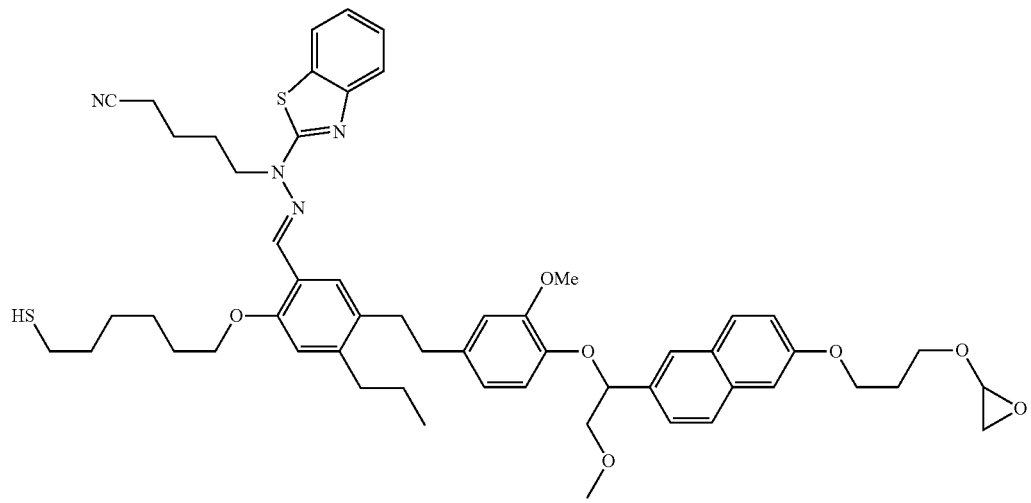
(I-71)
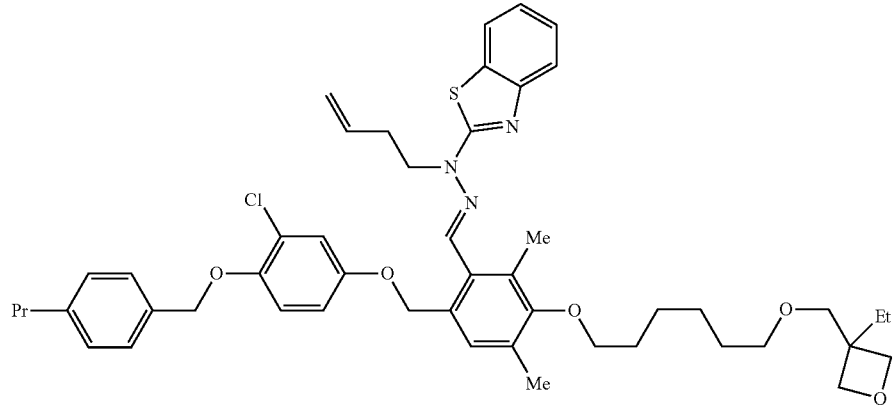
(I-72)
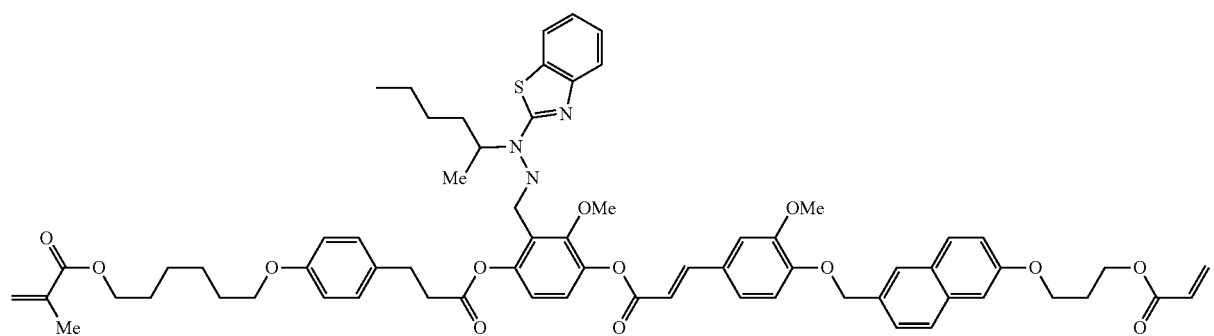

-continued
(I-73)
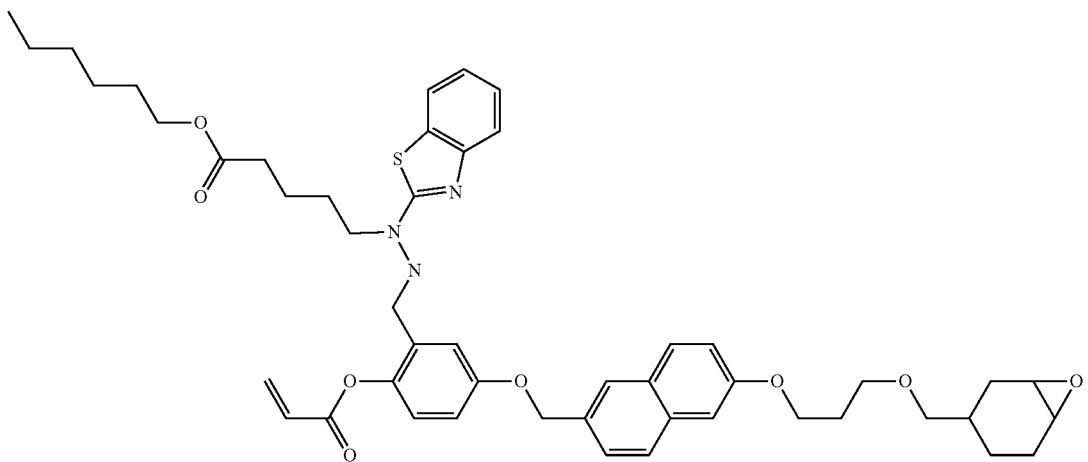
(I-74)
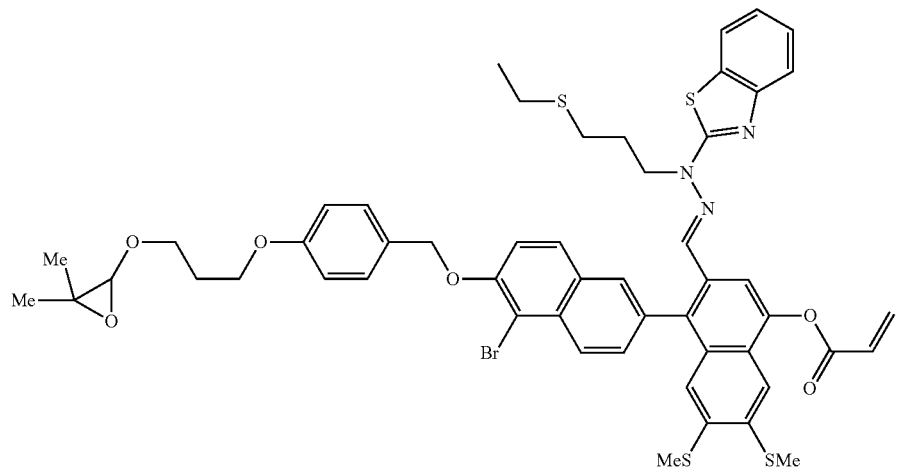
(I-75)
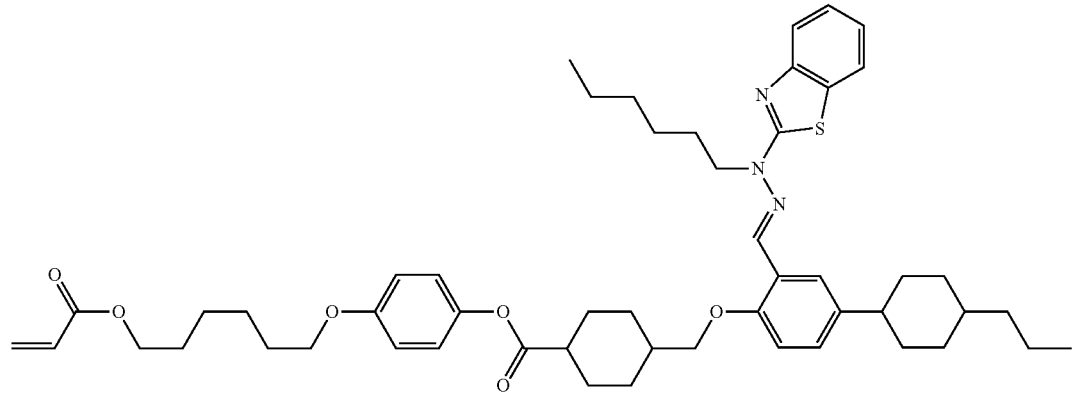

(I-76)
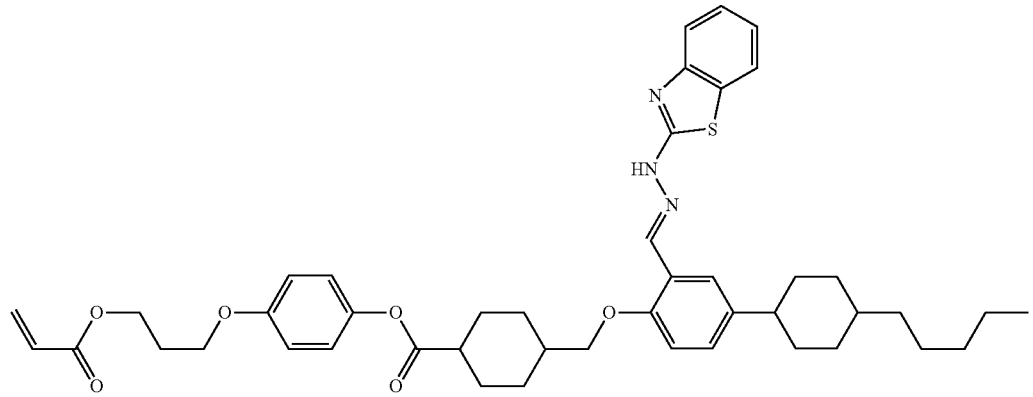
(I-77)
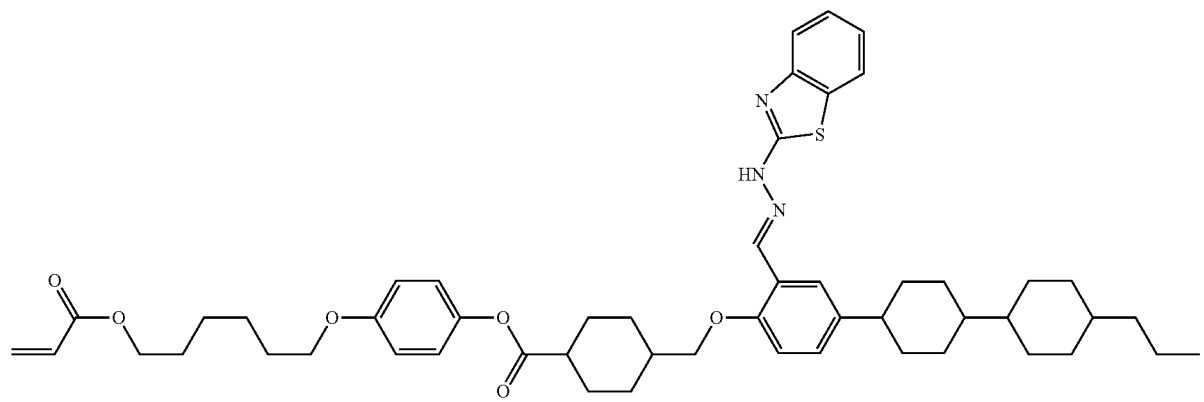
(I-78)
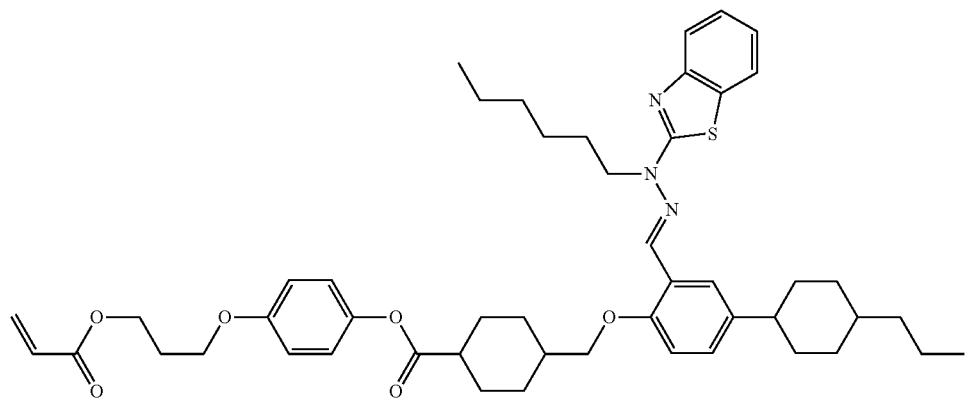
(I-79)
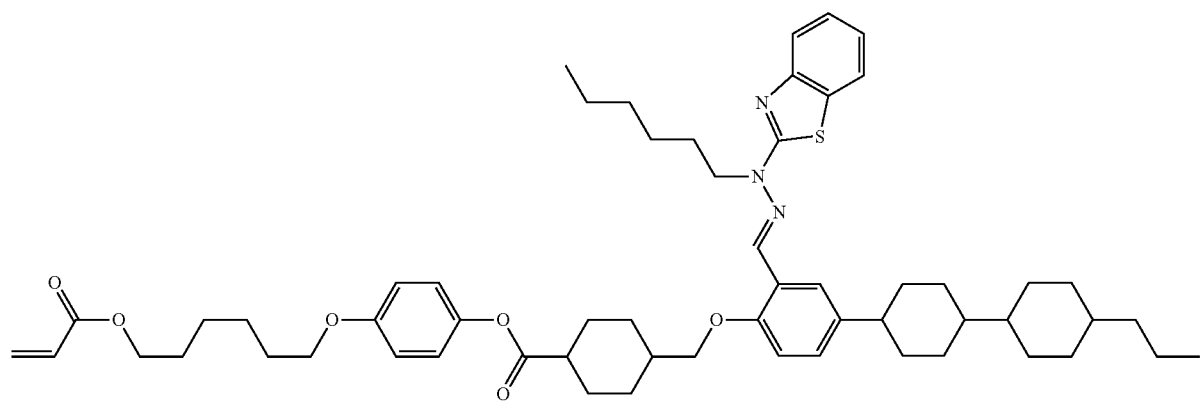

(I-80)
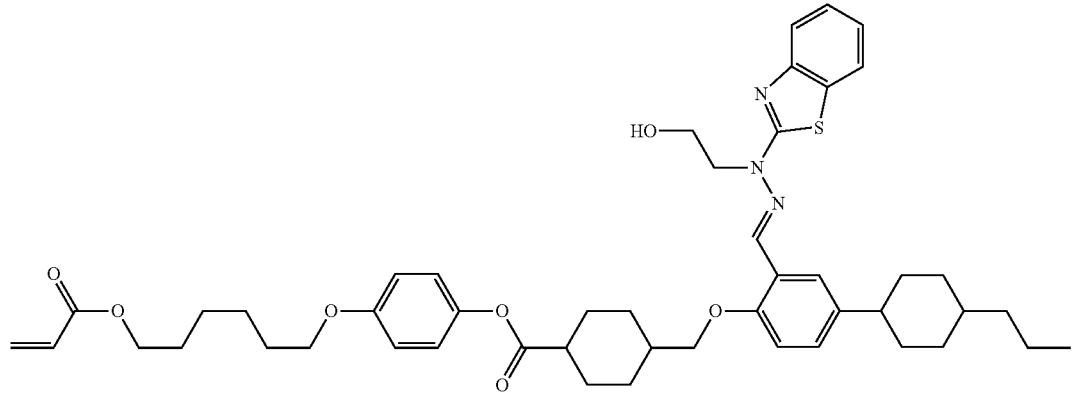
(I-81)
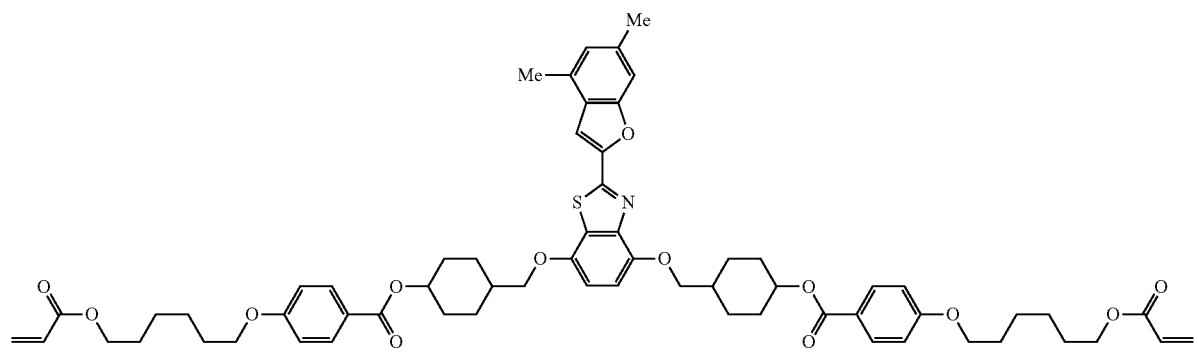
(I-82)
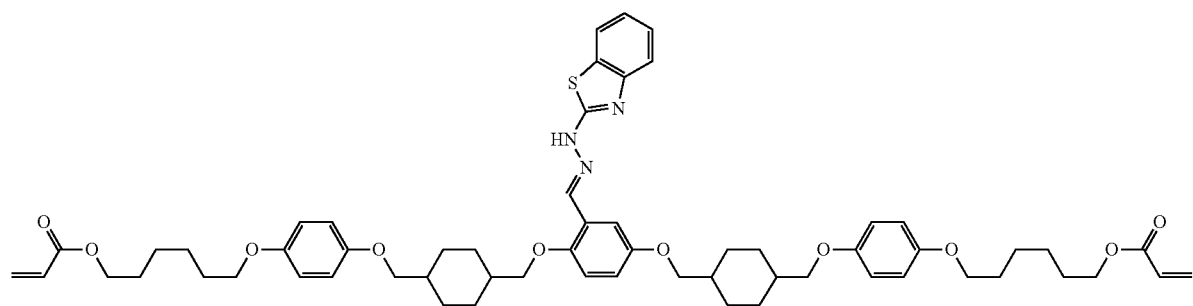
(I-83)
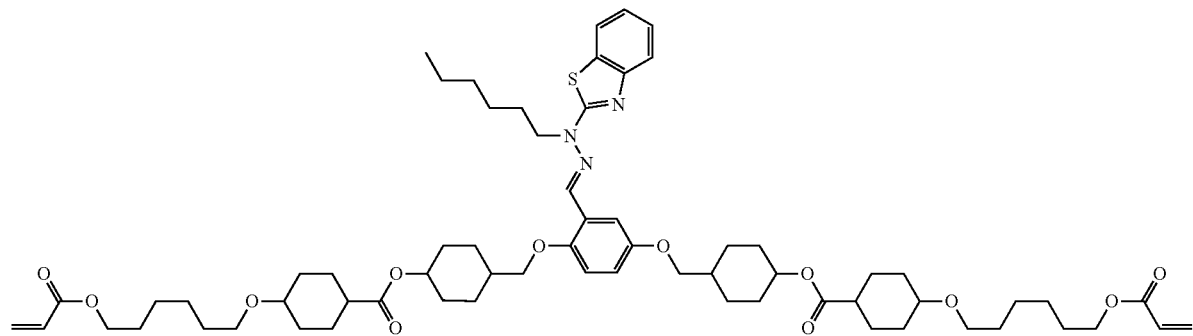

-continued
(I-84)
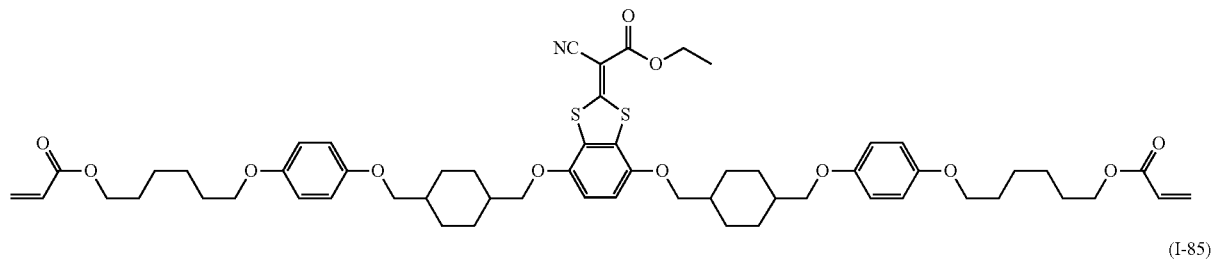
(I-85)
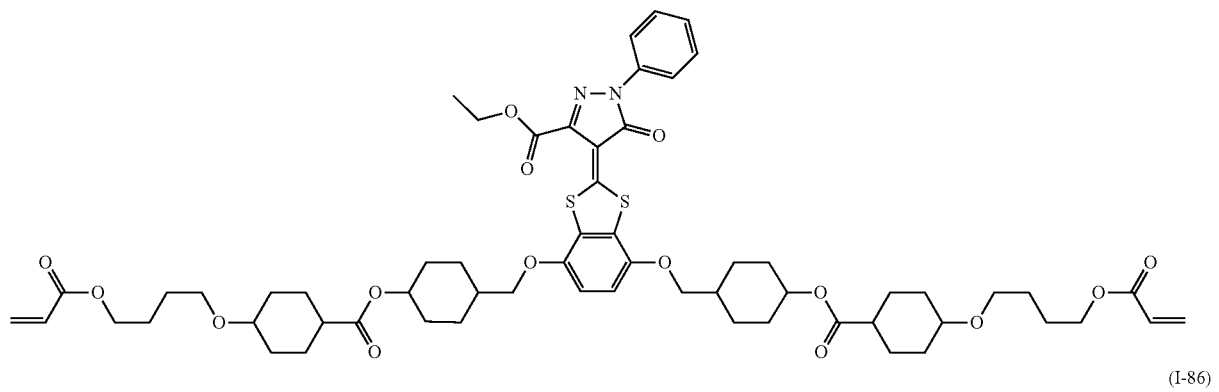
(I-86)
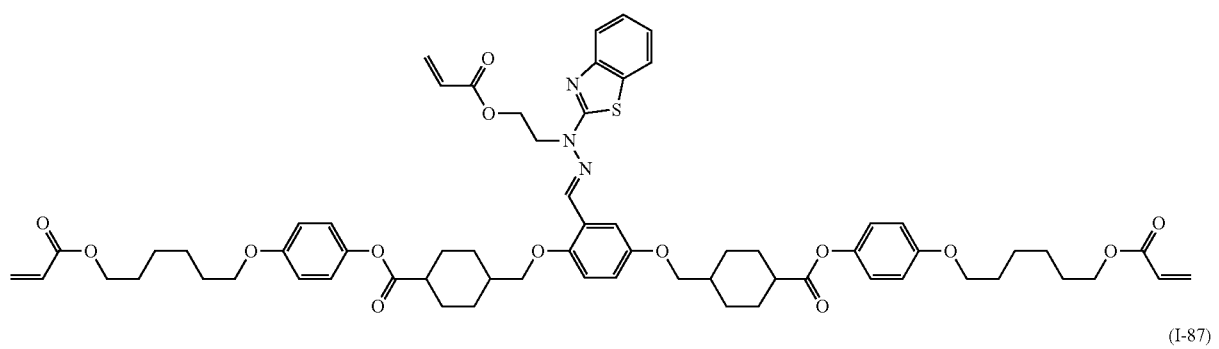
(I-87)
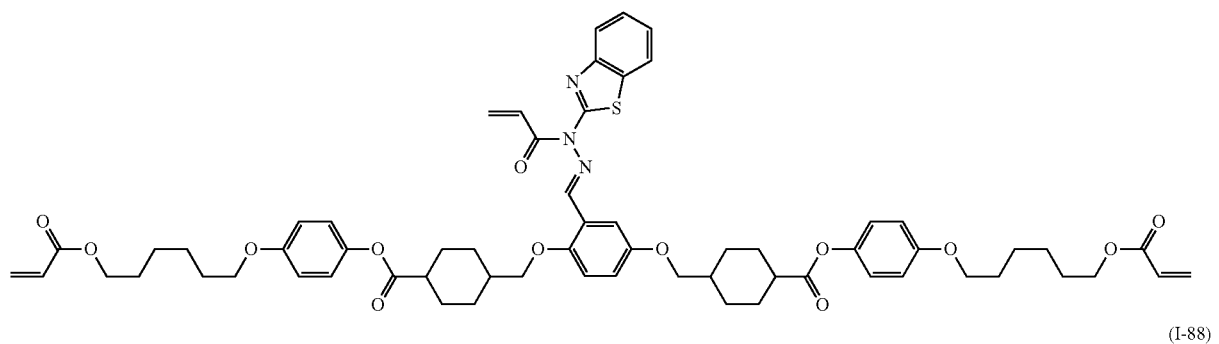
(I-88)
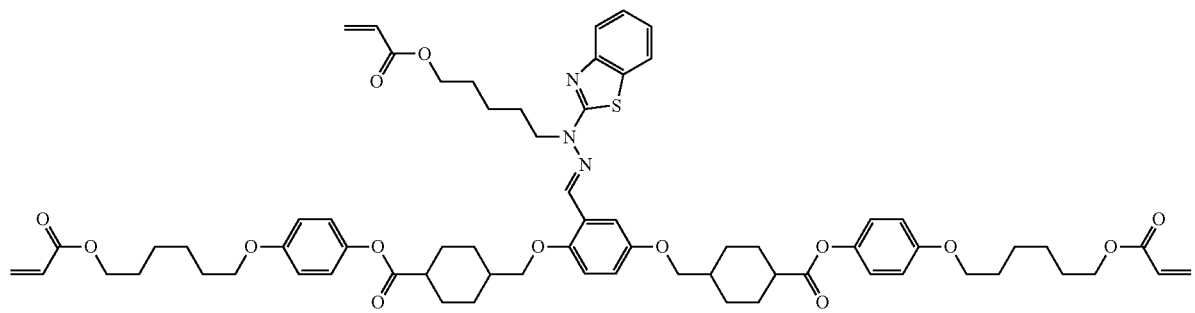

-continued
(I-89)
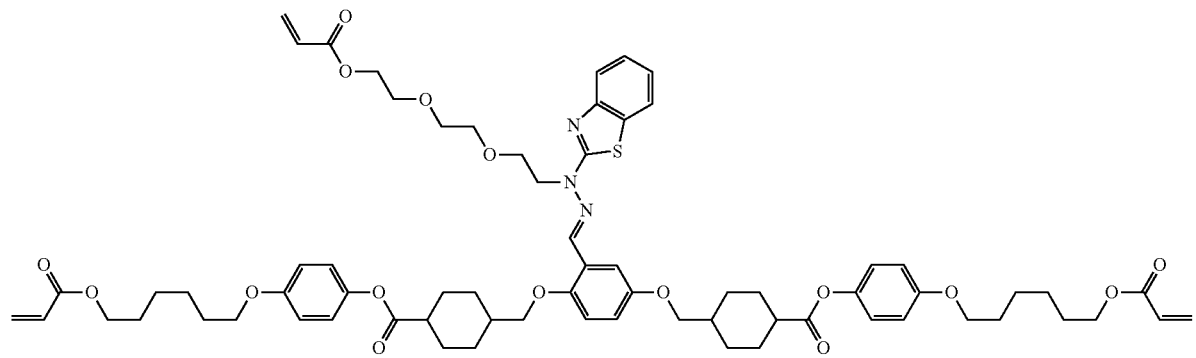
(I-90)
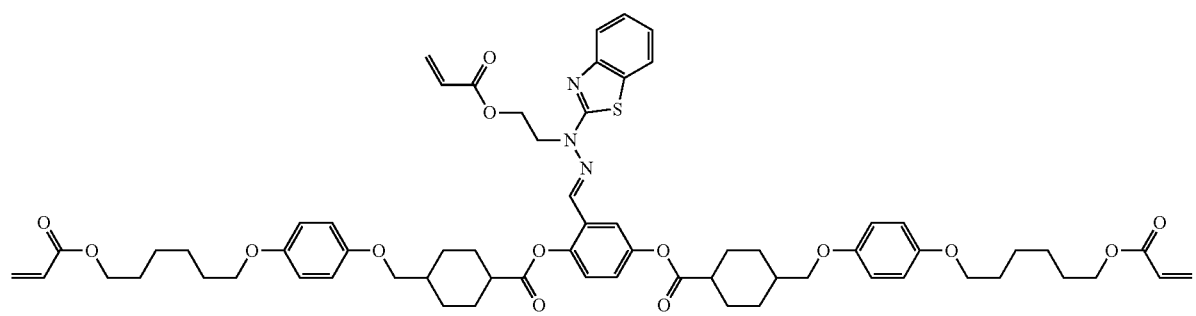
(I-91)
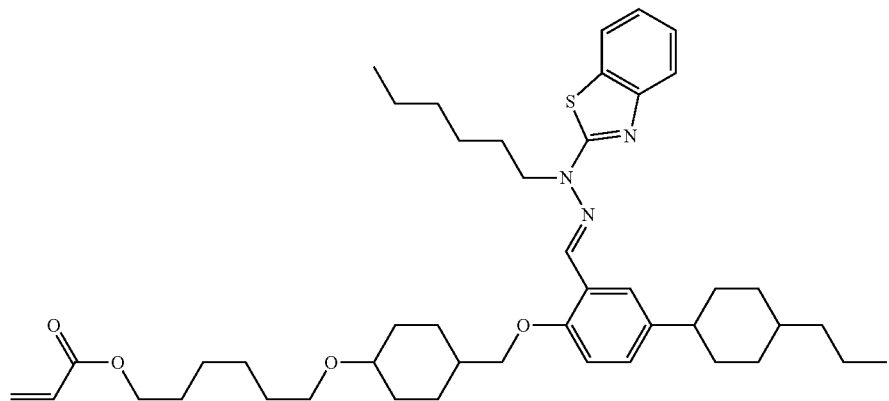
(I-92)
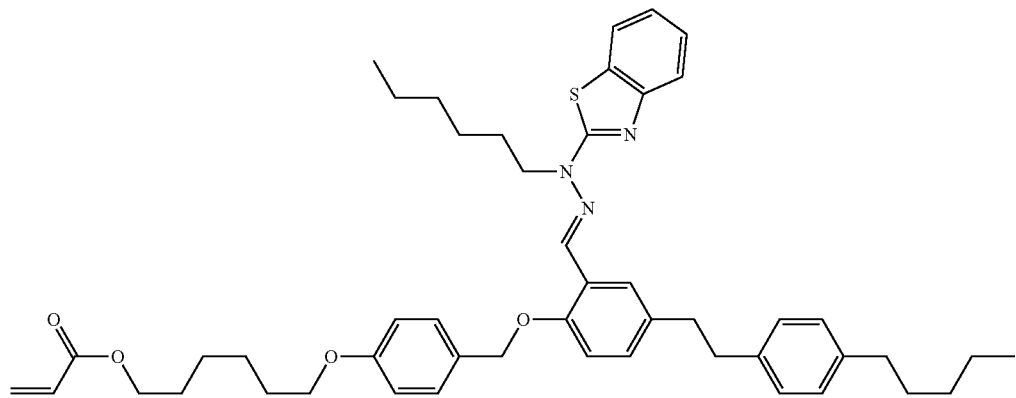

-continued
(I-93)
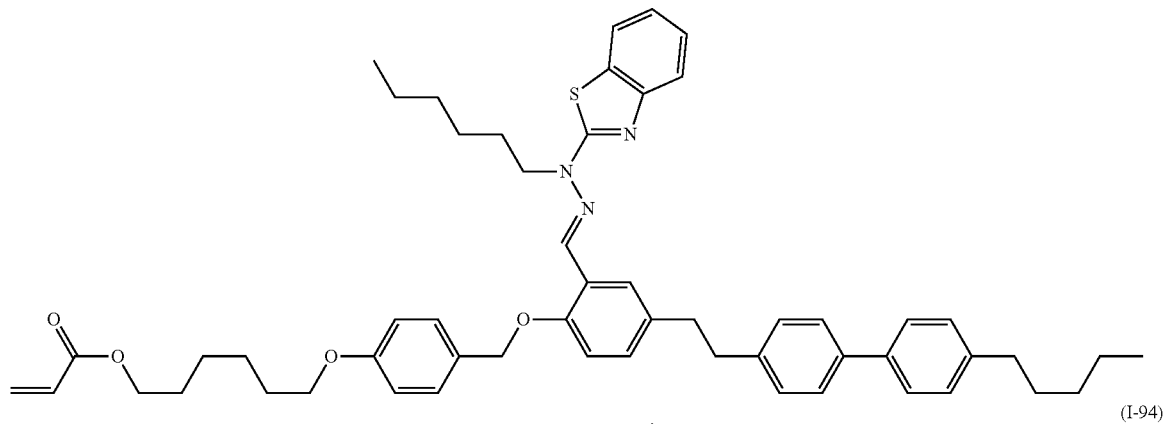
(I-94)
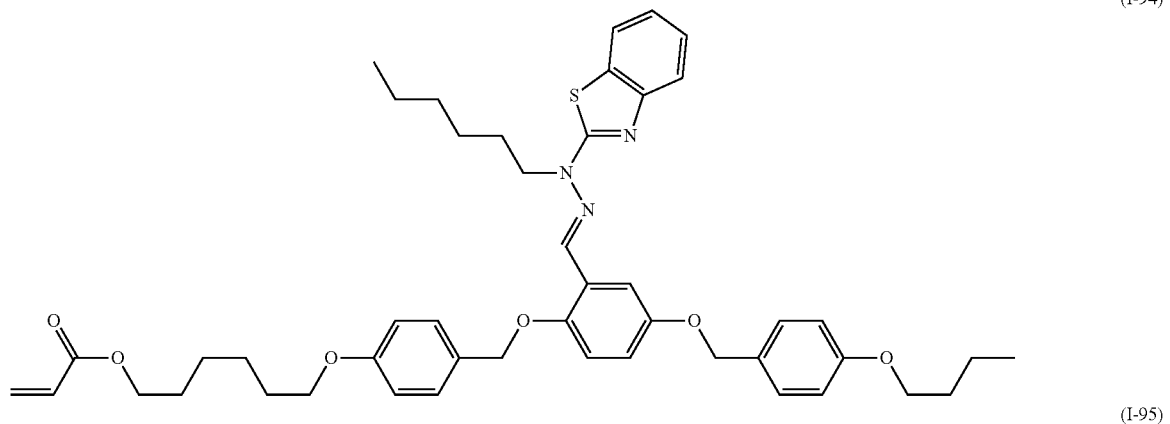
(I-95)
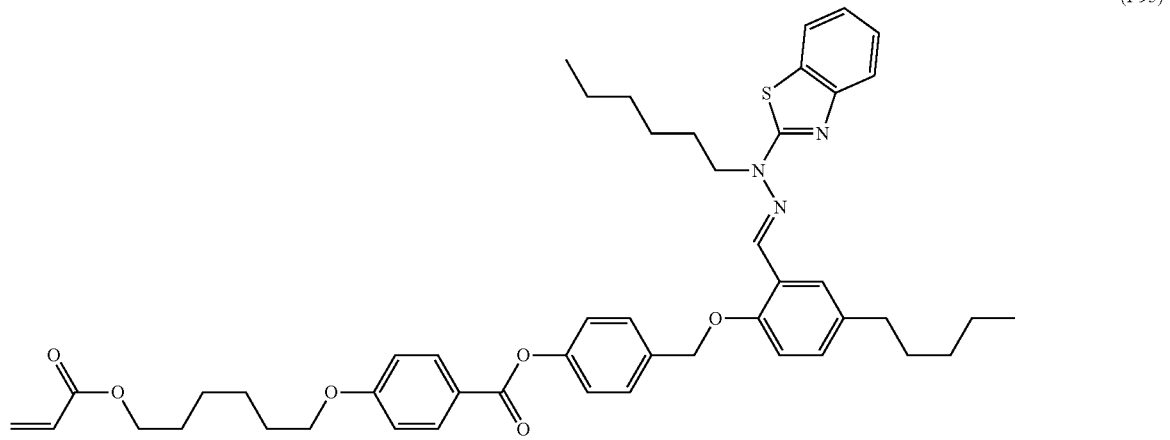
(I-96)
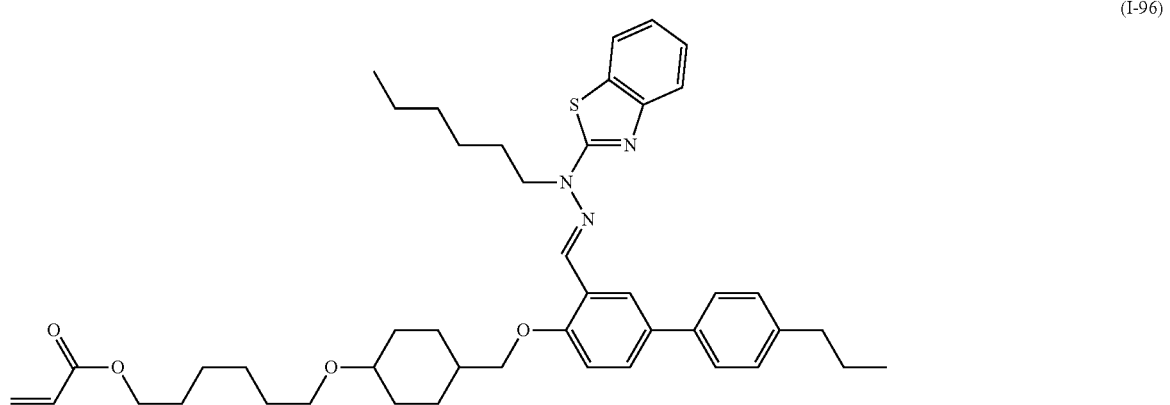

-continued
(I-97)
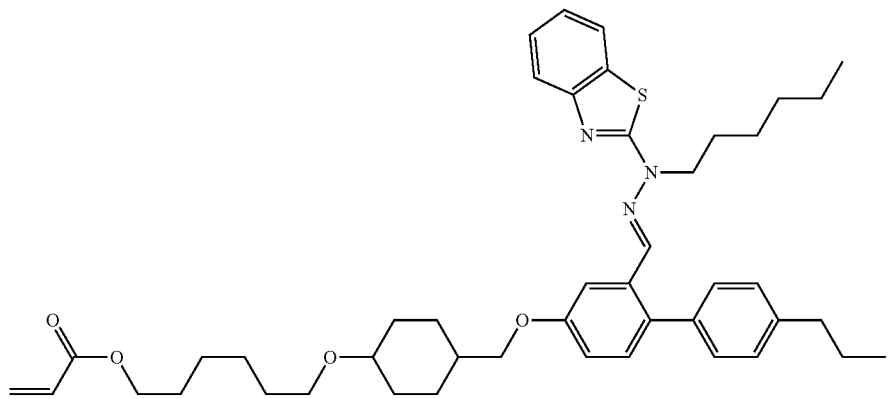
(I-98)
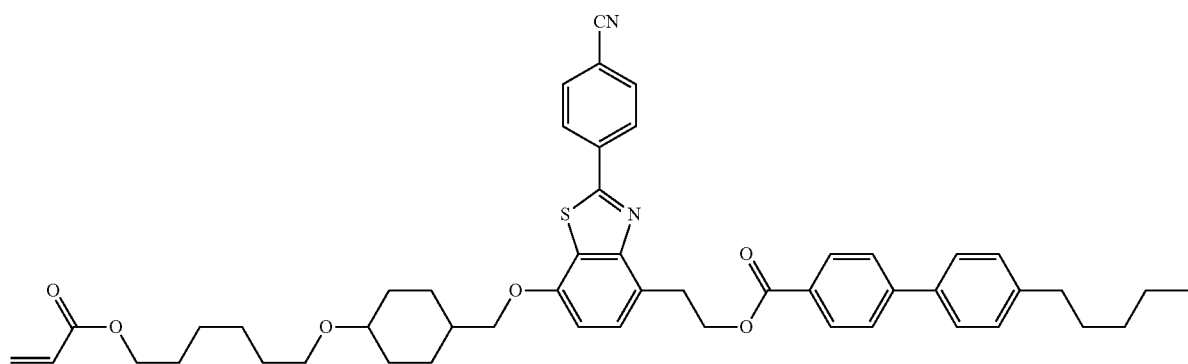
(I-99)
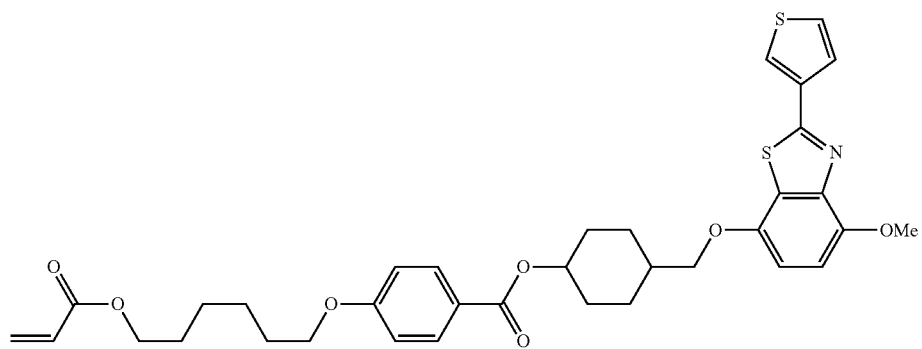
(I-100)
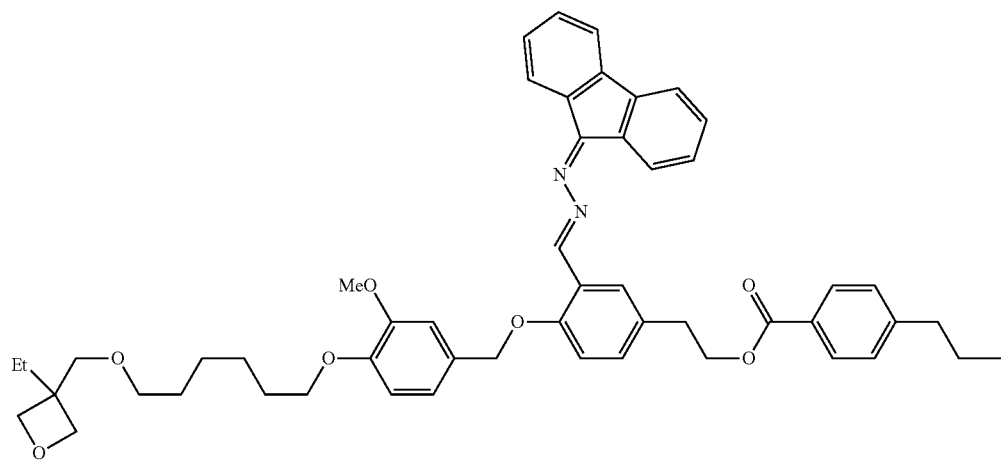

(I-101)
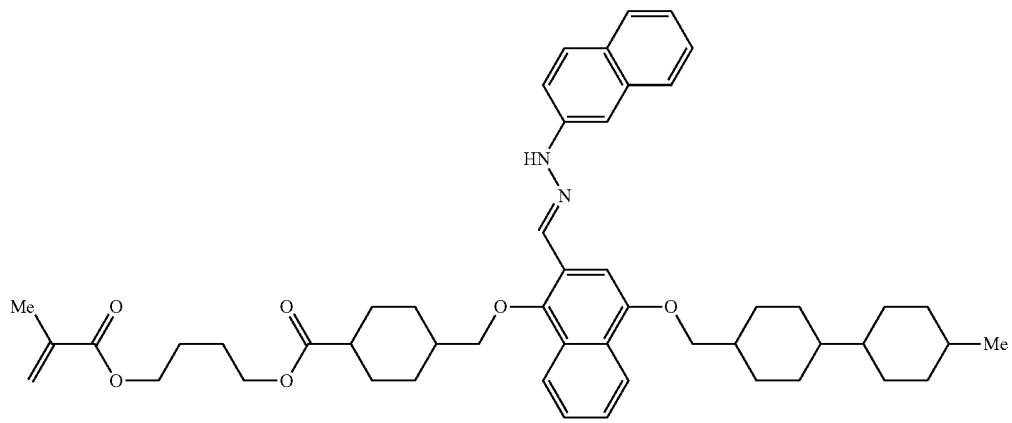
(I-102)
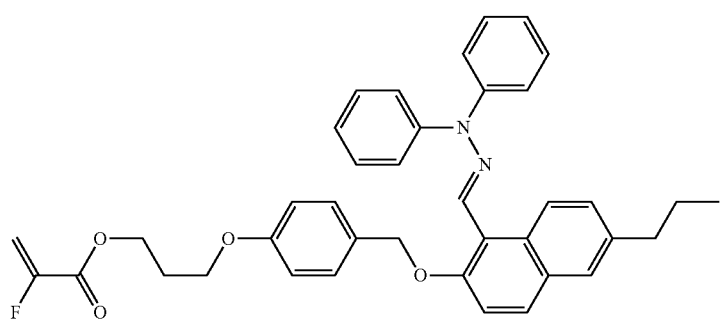
(I-103)
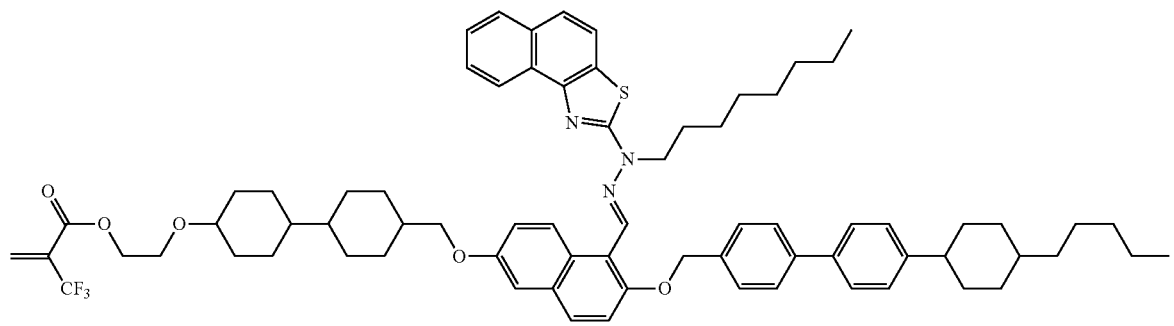
(I-104)
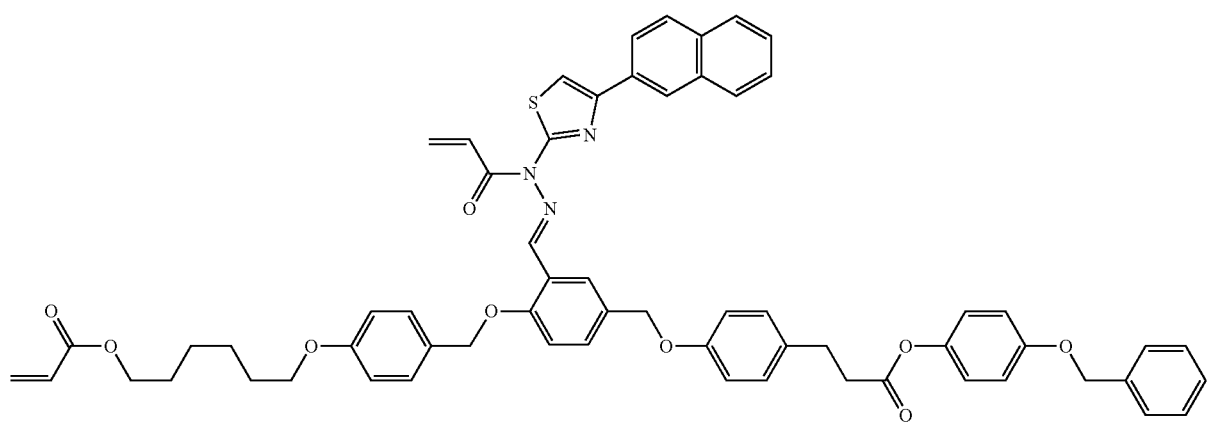

(I-105)
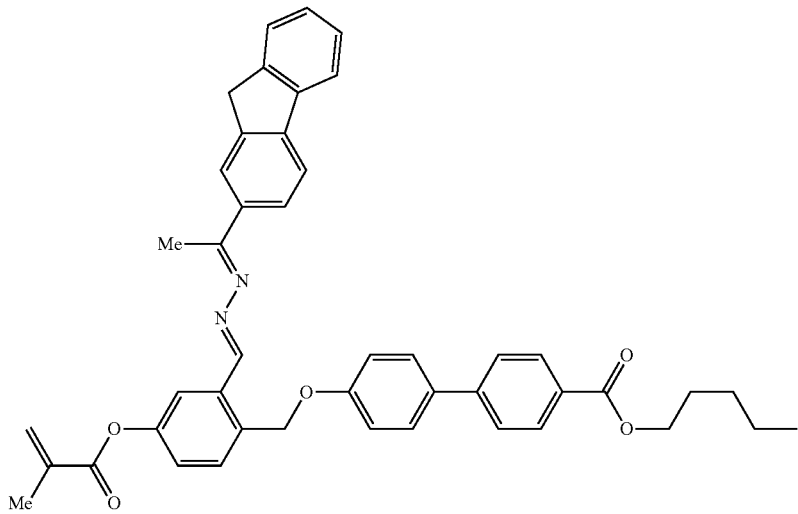
(I-106)
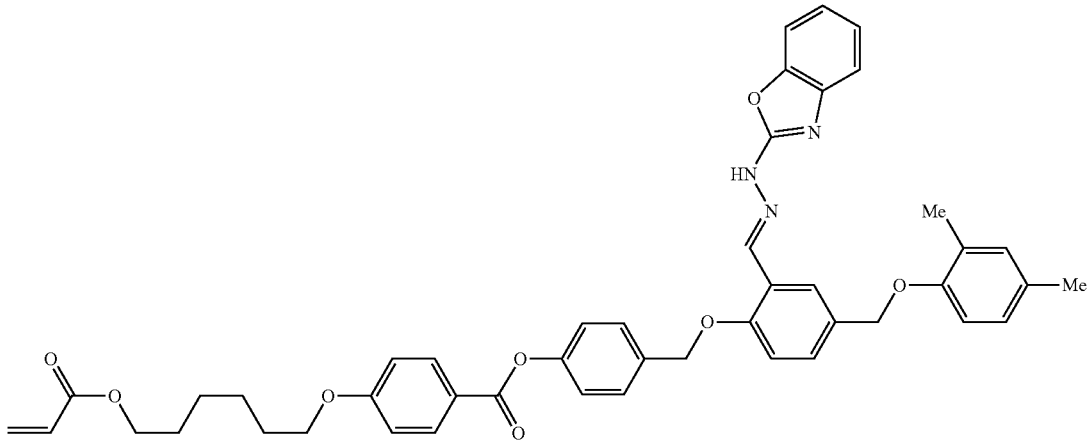
(I-107)
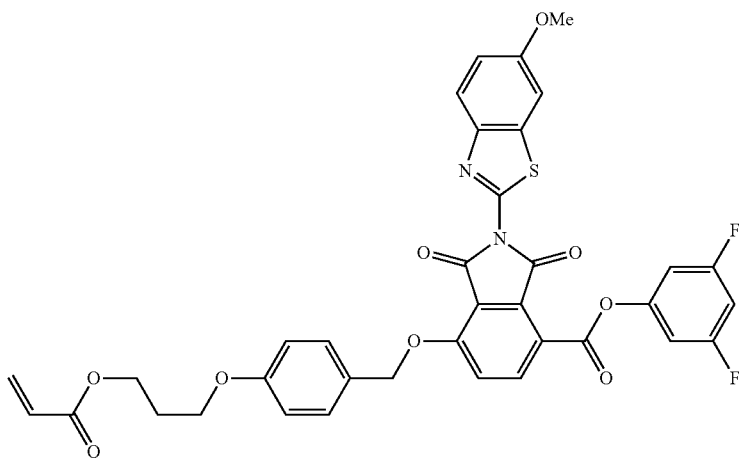

-continued
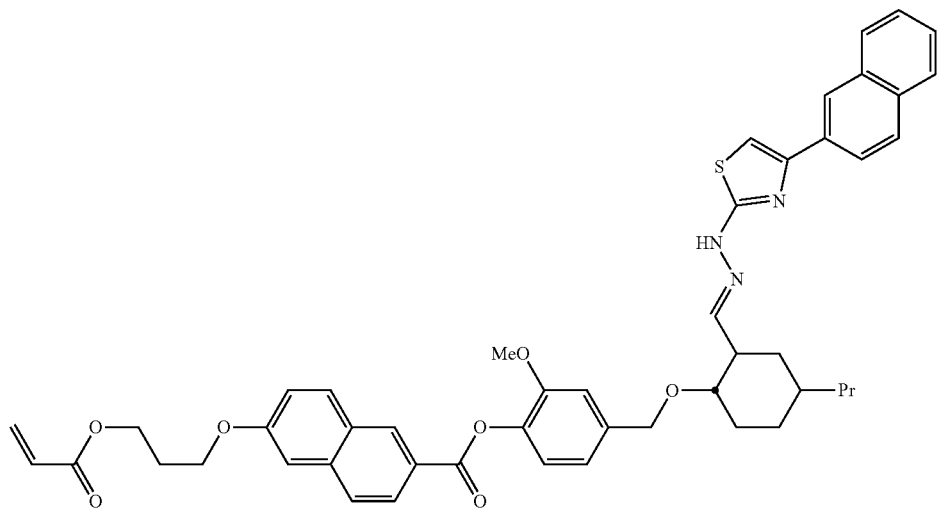
(I-108)
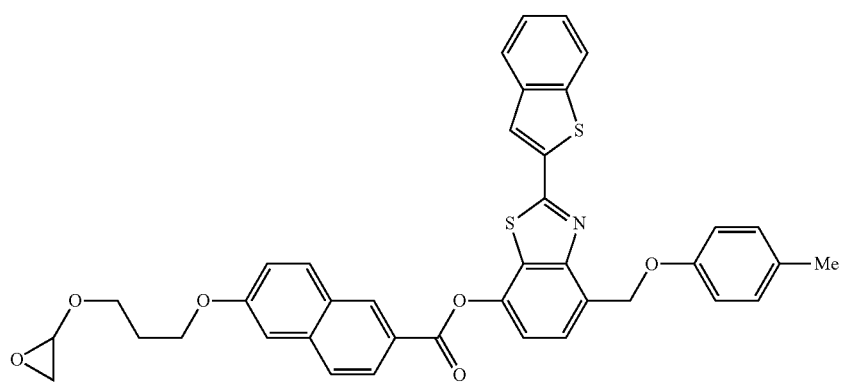
(I-109)
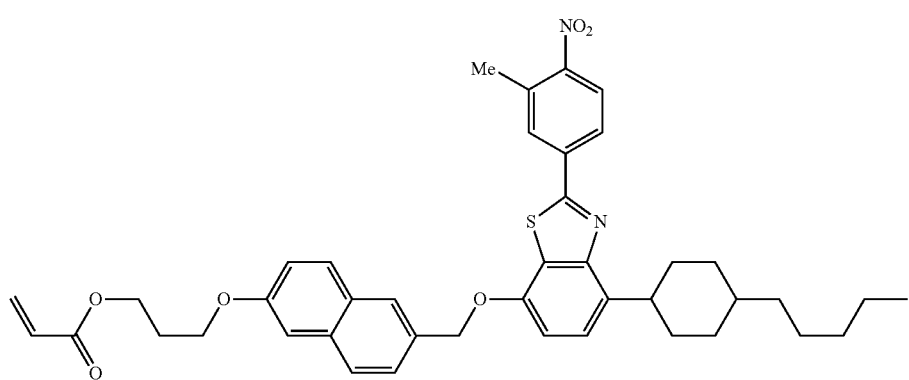
(I-110)

-continued
(I-111)
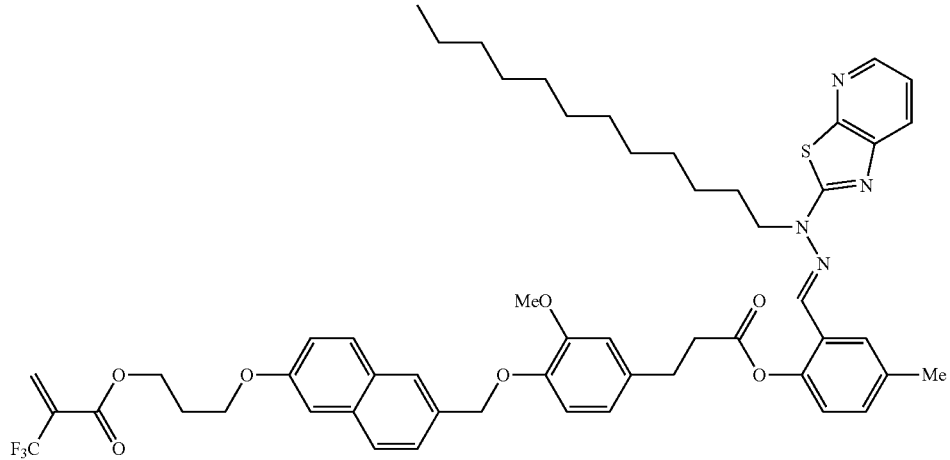
(I-112)
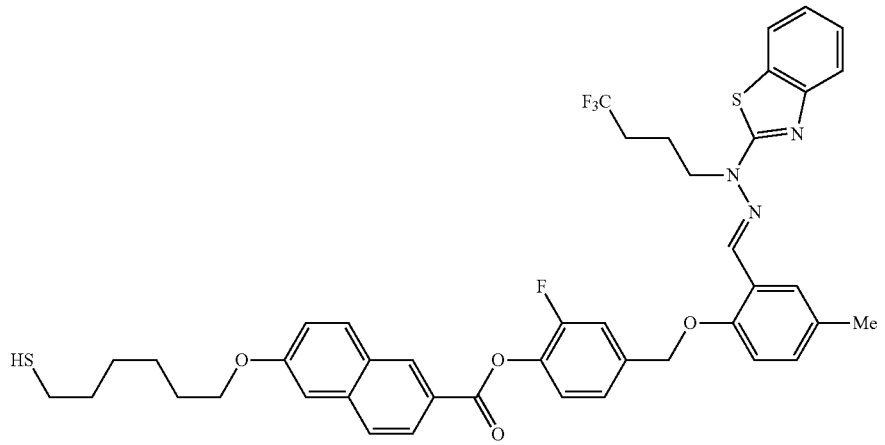
(I-113)
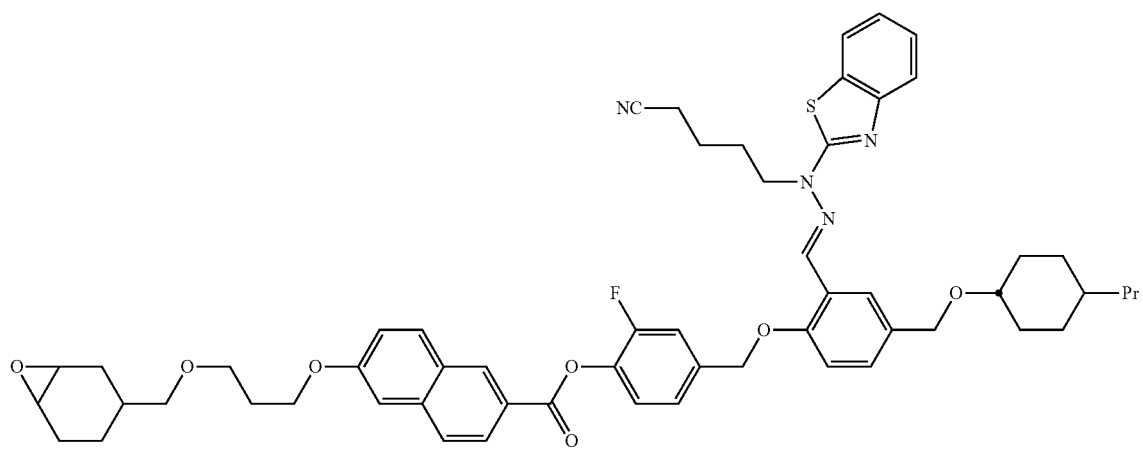

-continued
(I-114)
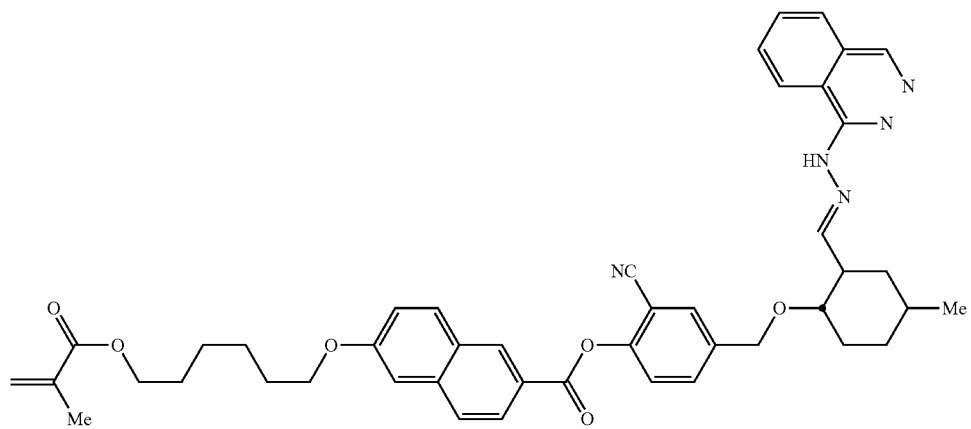
(I-115)
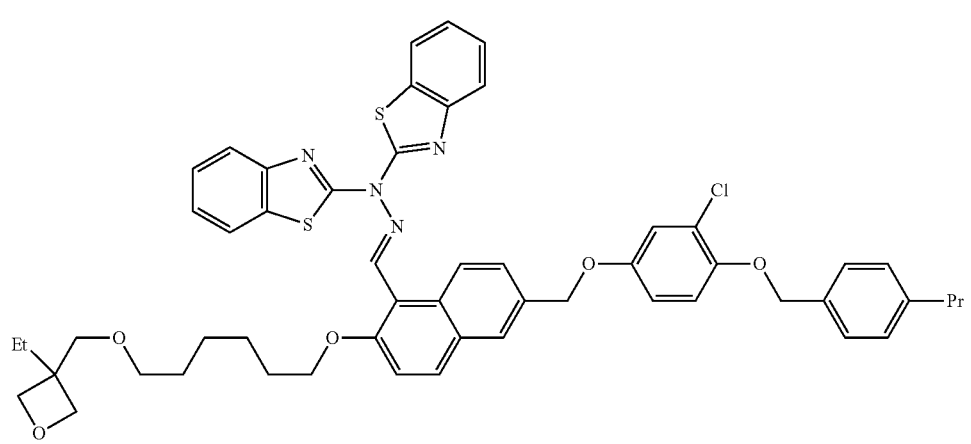
(I-116)
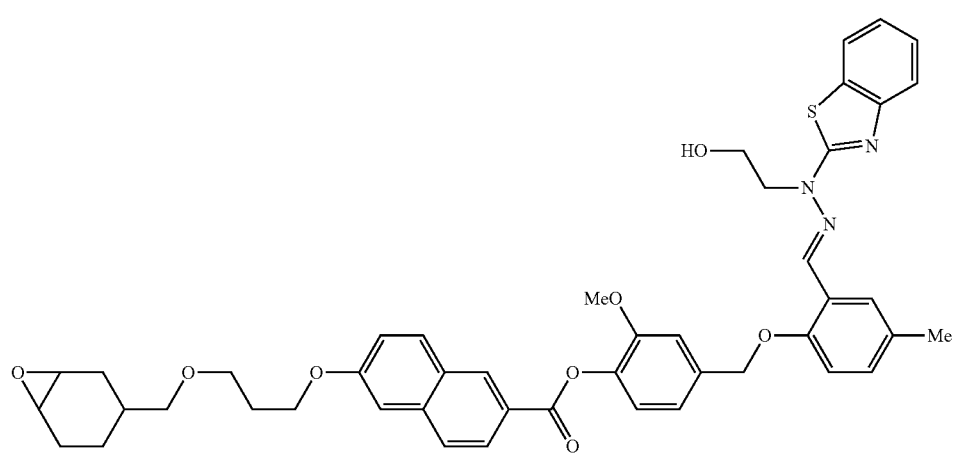

-continued
(I-117)
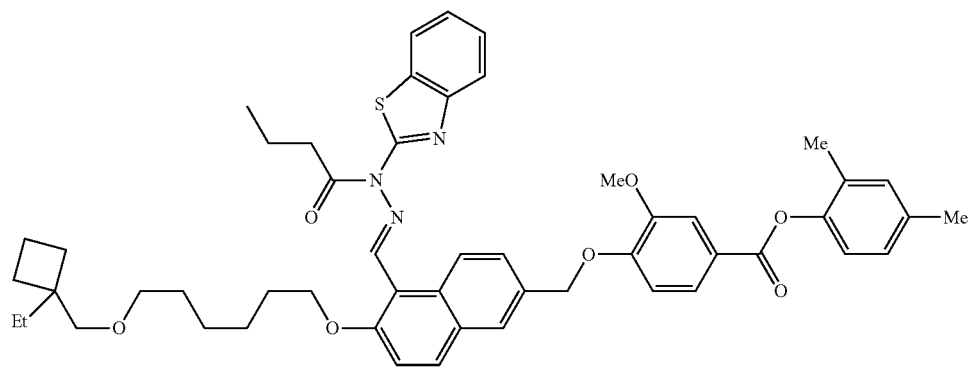
(I-118)
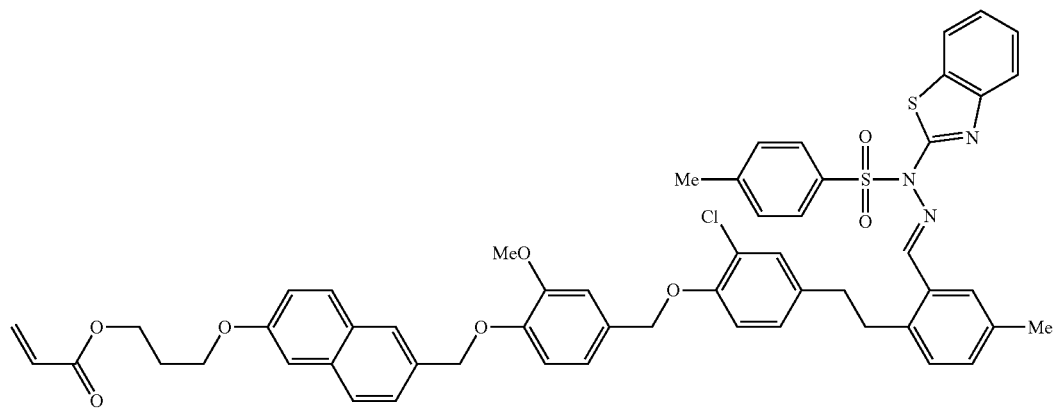
(I-119)
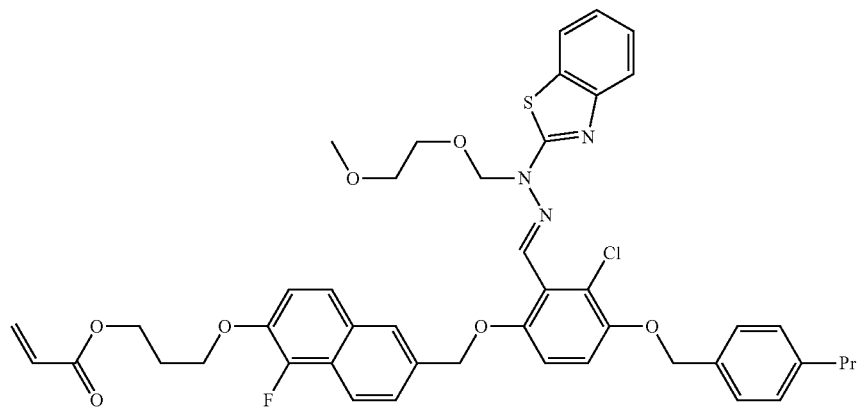
(I-120)
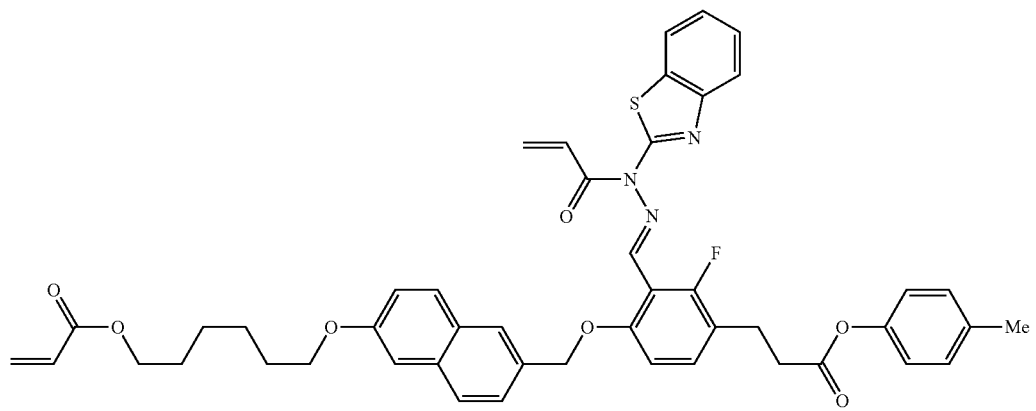

(I-121)
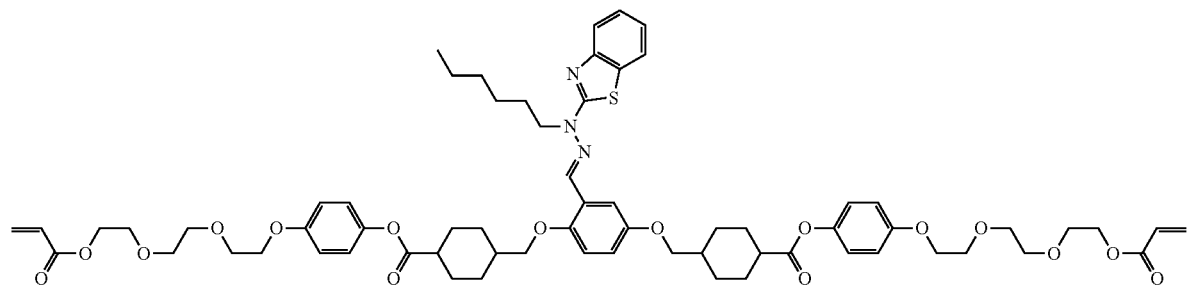
(I-122)
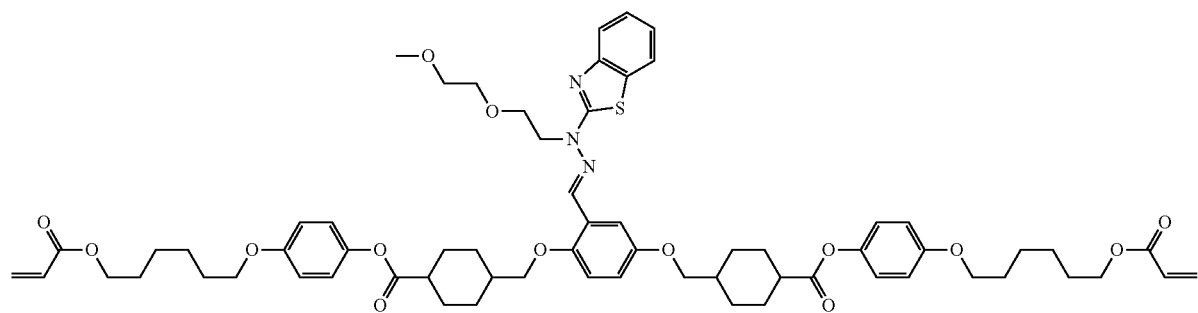
(I-123)
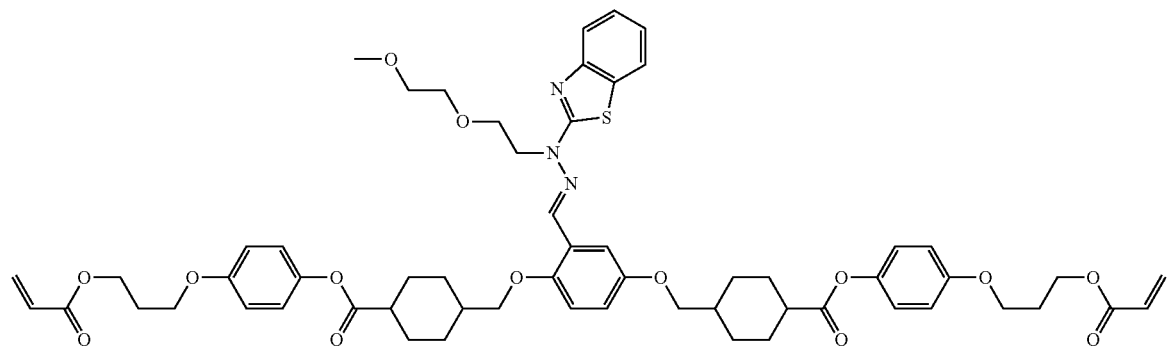
(I-124)
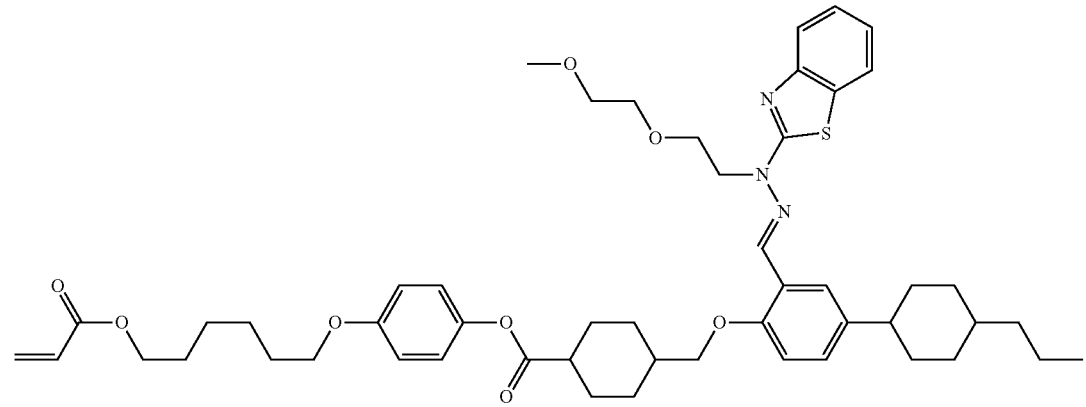

-continued
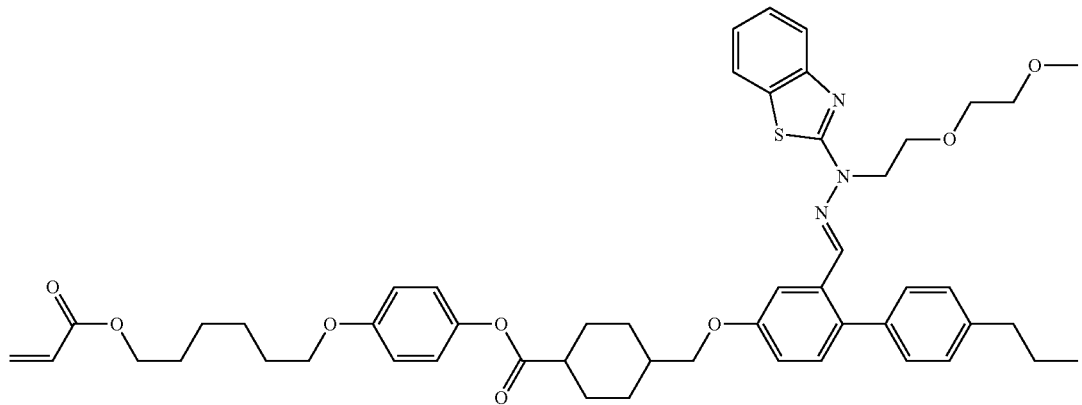
(I-125)
The compound of the present invention can be prepared by the following preparation processes.
(Preparation Process 1) Preparation of a Compound Represented by Formula (S-9) Below
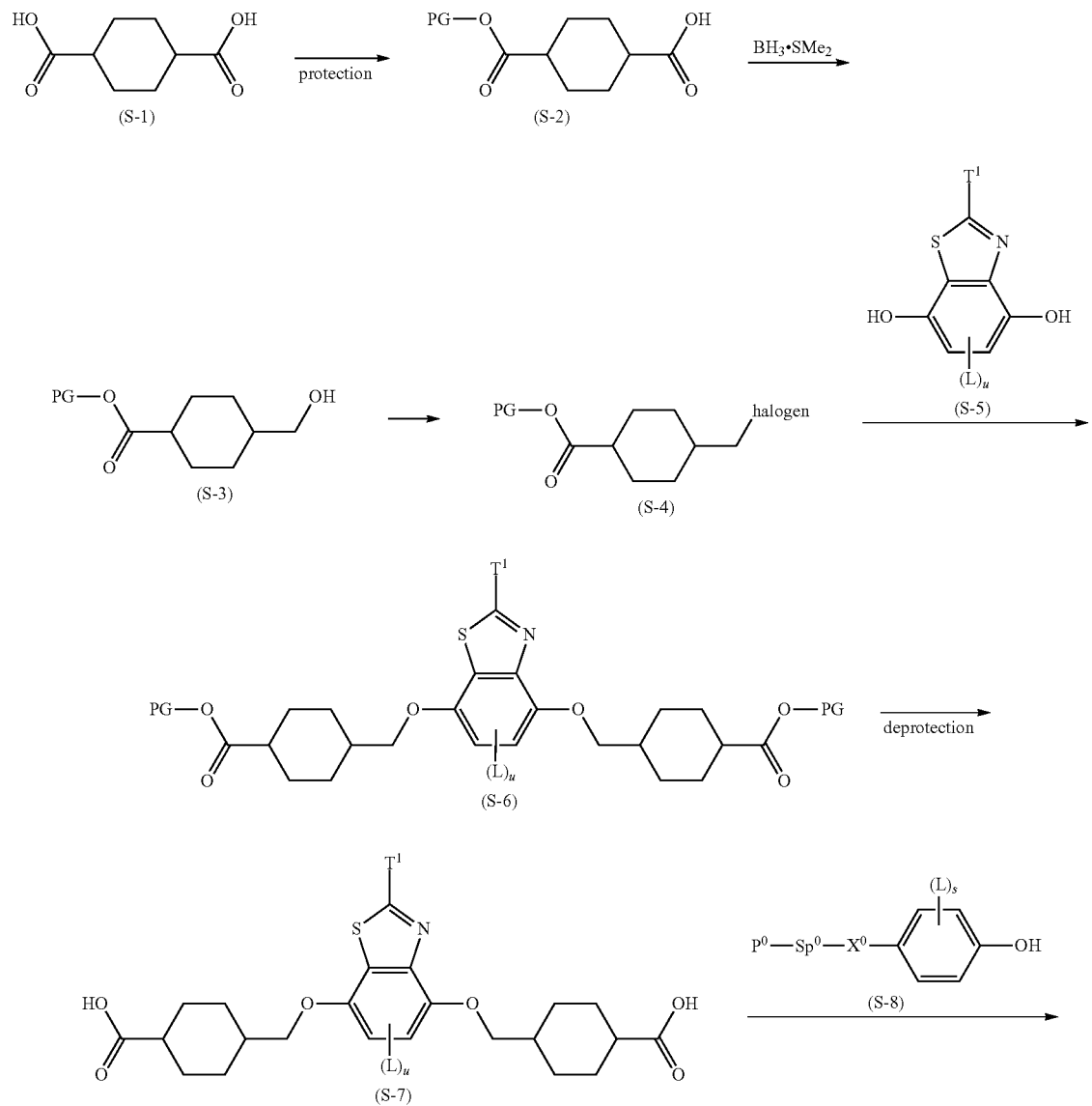

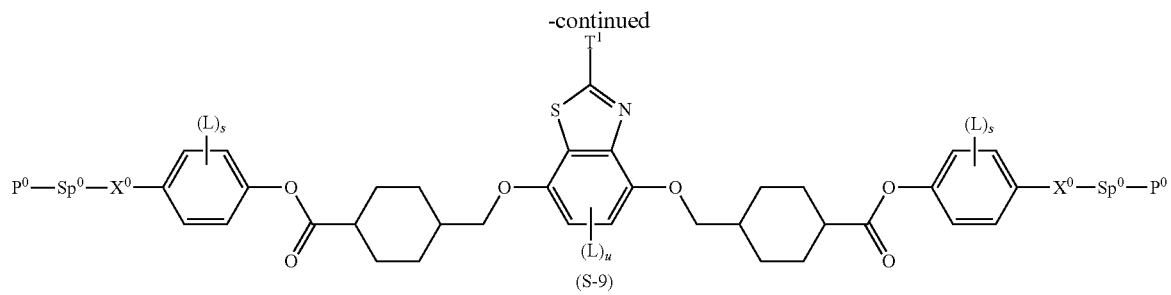

(S-9)

(in the formula, $P^0$, $Sp^0$, $X^0$, L, and $T^1$ each independently represent the same as those defined in Formula (Z-0), Formula (I-0-R), and Formula (I), s's each independently represent an integer of 0 to 4, u represents an integer of 0 to 2, PG represents a protective group, and halogen represents a halogen atom or a halogen equivalent.)

The carboxyl group of a compound represented by Formula (S-1) is protected by a protective group (PG). The protective group (PG) is not particularly limited as long as it can provide stable protection up to a deprotecting step, but, for example, protective groups (PG), cited in the GREENE'S PROTECTIVE GROUPS IN ORGANIC SYNTHESIS ((Fourth Edition), PETER G. M. WUTS, THEODORA W. GREENE co-authored, John Wiley & Sons, Inc., Publication), are preferable. Specific examples of the protective group include a tetrahydropyranyl group, a tert-butyl group, and a methoxymethyl group.

A compound represented by Formula (S-3) can be obtained by reducing a compound represented by Formula (S-2). Examples of the reductant include borane complexes, such as a borane-tetrahydrofuran complex and a borane-dimethyl sulfide complex, and diborane.

A compound represented by Formula (S-4) can be obtained by halogenating the compound represented by Formula (S-3). As the conditions of the halogenation, a method of reacting with iodine in the presence of triphenylphosphine and imidazole, a method of reacting with carbon tetrabromide or N-bromosuccinimide in the presence of triphenylphosphine, and a method of reacting with lithium chloride in the presence of a base are exemplified. Further, a method of deriving into a halogen equivalent by reacting with methanesulfonyl chloride or p-toluenesulphonyl chloride in the presence of a base is exemplified.

A compound represented by Formula (S-6) can be obtained by reacting the compound represented by Formula (S-4) with a compound represented by Formula (S-5) in the presence of a base. Examples of the base include potassium carbonate, cesium carbonate, and triethylamine. Further, the compound represented by Formula (S-6) can also be obtained by reacting the compound represented by Formula (S-3) with the compound represented by Formula (S-5) through Mitsunobu reaction. As the azodicarboxylic acid ester used at that time, diethylazodicarboxylate, diisopropylazodicarboxylate, and the like are exemplified.

The protective group (PG) of the compound represented by Formula (S-6) is deprotected. The reaction conditions of the deprotection are not particularly limited as long as a compound represented by Formula (S-7) is provided, but those cited in the literature are preferable.

A compound represented by Formula (S-9) can be obtained by reacting the compound represented by Formula (S-7) with a compound represented by Formula (S-8). As the reaction condition, a method of using a condensing agent or a method of reacting an acid chloride, a mixed acid anhydride, or a carboxylic acid anhydride, derived from the compound represented by Formula (S-7), with the compound represented by Formula (S-8) is exemplified. When a condensing agent is used in this reaction, examples of the condensing agent include N,N'-dicyclohexylcarbodiimide, N,N'-diisopropylcarbodiimide, and 1-ethyl-3-(3-dimethylaminopropyl)carbodiimide hydrochloride.

Examples of the base include triethylamine and diisopropylethylamine.

(Preparation Process 2) Preparation of a Compound Represented by Formula (S-18) Below

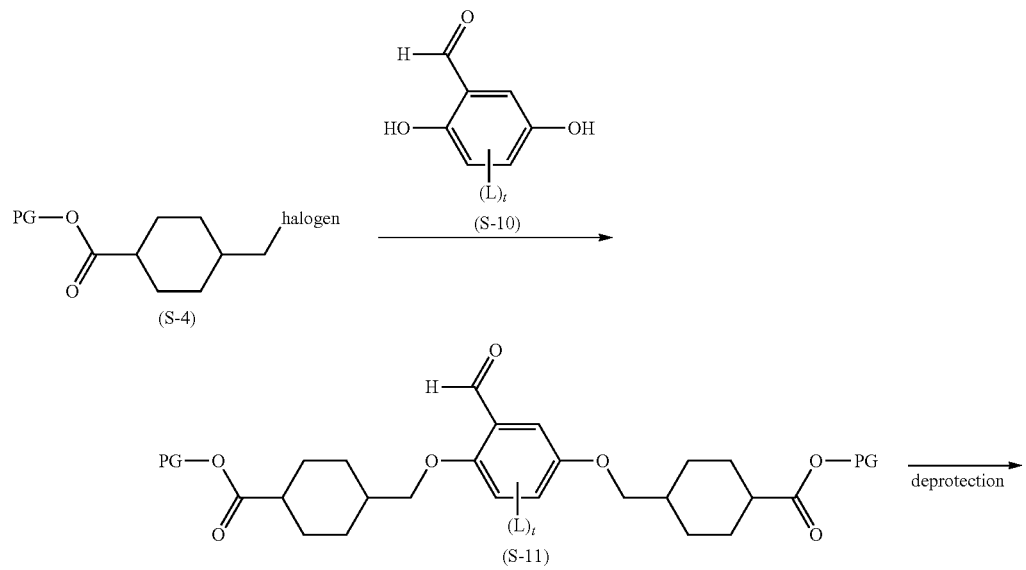

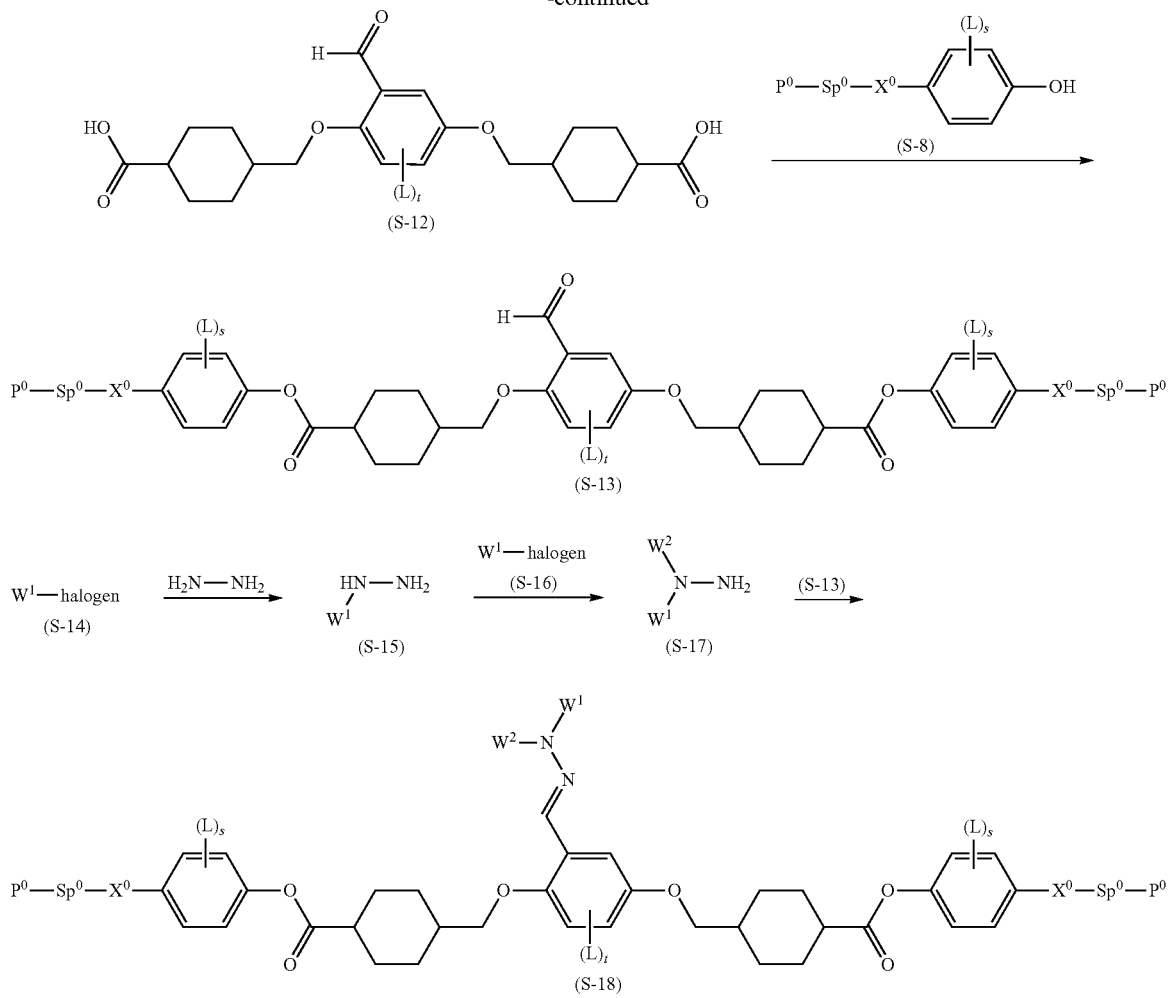

(In the formula, $P^0$, $Sp^0$, $X^0$, L, $W^1$, and $W^2$ each independently represent the same as those defined in Formula (Z-0), Formula (I-0-R), and Formula (I), s's each independently represent an integer of 0 to 4, t represents an integer of 0 to 3, PG represents a protective group, and halogen represents a halogen atom or a halogen equivalent.)

A compound represented by Formula (S-11) can be obtained by reacting the compound represented by Formula (S-4) with a compound represented by Formula (S-10) in the presence of a base. Examples of the base are the same as those described in the preparation process 1.

The protective group (PG) of the compound represented by Formula (S-11) is deprotected. The reaction conditions of the deprotection are not particularly limited as long as a compound represented by Formula (S-12) is provided, but those cited in the literature are preferable.

A compound represented by Formula (S-13) can be obtained by reacting the compound represented by Formula (S-12) with a compound represented by Formula (S-8). Examples of the reaction conditions include those described in the preparation process 1.

A compound represented by Formula (S-15) can be obtained by reacting a compound represented by Formula (S-14), for example, with hydrazine monohydrate.

A compound represented by Formula (S-17) can be obtained by reacting the compound represented by Formula (S-15) with a compound represented by Formula (S-16) in the presence of a base. Examples of the base include potassium carbonate, cesium carbonate, and triethylamine.

A compound represented by Formula (S-18) can be obtained by reacting the compound represented by Formula (S-17) with the compound represented by Formula (S-13) in the presence of an acid catalyst. Examples of the acid include p-toluenesulfonic acid, pyridinium p-toluenesulfonate, and 10-camphorsulfonic acid.

Examples of the reaction conditions other than those described in each step of the preparation processes 1 and 2 include conditions described in literatures such as Experimental Chemistry Course (edited by the Chemical Society of Japan, published by Maruzen Co., Ltd.), Organic Syntheses (John Wiley & Sons, Inc., Publication), Beilstein Handbook of Organic Chemistry (Beilstein-Institut fuer Literatur der Organischen Chemie, Springer-Verlag Berlin and Heidelberg GmbH & Co. K), and Fiesers' Reagents for Organic Synthesis (John Wiley & Sons, Inc.) and conditions provided by online search services such as SciFinder (Chemical Abstracts Service, American Chemical Society) and Reaxys (Elsevier Ltd.).

Further, an appropriate reaction solvent can be used in each step. The solvent is not particularly limited as long as a desired compound is provided, and examples thereof include isopropyl alcohol, ethylene glycol, diethylene glycol, methanol, ethanol, propanol, chloroform, dichloromethane, 1,2-dichloroethane, acetone, acetonitrile, N,N-dimethylformamide, N,N-dimethylacetamide, dimethyl sulfoxide, diethylether, ethylene glycol monoethyl ether, xylene, ethyl acetate, butyl acetate, propyl acetate, methyl acetate, cyclohexanone, 1,4-dioxane, dichloromethane, styrene, tetrahydrofuran, pyridine, 1-methyl-2-pyrrolidinone, toluene, hexane, cyclohexane, heptane, benzene, methyl isobutyl ketone, tert-butyl methyl ether, and methyl ethyl ketone. When the reaction is performed in a two-phase system of an organic solvent and water, it is also possible to add a phase transfer catalyst. Examples of the phase transfer catalyst include benzyltrimethylammonium chloride, polyoxyethylene (20) sorbitan monolaurate [Tween 20], and sorbitan monooleate [Span 80].

If necessary, purification can be performed in each step. Examples of the purification method include chromatography, recrystallization, distillation, sublimation, re-precipitation, adsorption, and liquid separation treatment. When a purifying agent is used, examples of the purifying agent include silica gel, alumina, activated carbon, activated clay, celite, zeolite, mesoporous silica, carbon nanotubes, carbon nanohorns, Bincho charcoal, wood charcoal, graphene, ion exchange resins, acidic clay, silicon dioxide, diatomaceous earth, perlite, cellulose, organic polymers, and porous gel.

Preferably, the compound of the present invention is used for a nematic liquid crystal composition, a smectic liquid crystal composition, a chiral smectic liquid crystal composition, and a cholesteric liquid crystal composition. In the liquid crystal composition using the reactive compound of the present invention, compounds other than those of the present invention may be added. As other polymerizable compounds used in a mixture with the polymerizable compound of the present invention, specifically, compounds represented by Formula (X-11) and/or Formula (X-12):

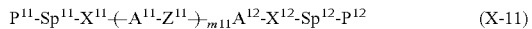     (X-11)

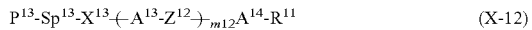     (X-12)

(in the formulae, $P^{11}$, $P^{12}$, and $P^{11}$ each independently represent a polymerizable group; $Sp^{11}$, $Sp^{12}$, and $Sp^{13}$ each independently represent a single bond or an alkylene group having 1 to 20 carbon atoms, in which one —$CH_2$— or two or more non-adjacent —$CH_2$—'s may be substituted with —O—, —COO—, —OCO—, —OCOO—; $X^{11}$, $X^{12}$, and $X^{13}$ each independently represent -O—, —S—, —$OCH_2$—, —$CH_2O$—, —CO—, —COO—, —OCO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —$SCF_2$—, —CH=CH—COO—, —CH=CH—OCO—, —COO—CH=CH—, —OCO—CH=CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH=CH—, —CF=CF—, —C≡C—, or a single bond; $Z^{11}$ and $Z^{12}$ each independently represent —O—, —S—, —$OCH_2$—, —$CH_2O$—, —COO—, —OCO—, —CO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —$SCF_2$—, —$CH_2CH_2$—, —$CH_2CF_2$—, —$CF_2CH_2$—, —$CF_2CF_2$—, —CH=CH—COO—, —CH=CH—OCO—, —COO—CH=CH—, —OCO—CH=CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH=CH—, —CF=CF—, —C≡C—, or a single bond; $A^{11}$, $A^{12}$, $A^{13}$, and $A^{14}$ each independently represent a 1,4-phenylene group, a 1,4-cyclohexylene group, a pyridine-2,5-diyl group, a pyrimidine-2,5-diyl group, a naphthalene-2,6-diyl group, a naphthalene-1,4-diyl group, a tetrahydronaphthalene-2,6-diyl group, or a 1,3-dioxane-2,5-diyl group, and $A^{11}$, $A^{12}$, $A^{13}$, and $A^{14}$ may be each independently unsubstituted or may be substituted with an alkyl group, a halogenated alkyl group, an alkoxy group, a halogenated alkoxy group, a halogen atom, a cyano group, or a nitro group; $R''$ represents a hydrogen atom, a fluorine atom, a chlorine atom, a bromine atom, an iodine atom, a pentafluorosulfuranyl group, a cyano group, a nitro group, an isocyano group, a thioisocyano group, or a linear or branched alkyl group having 1 to 20 carbon atoms, in which one —$CH_2$— or two or more non-adjacent —$CH_2$—'s may be each independently substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—; and m11 and m12 represent 0, 1, 2, or 3, and when m11 and/or m12 represent 2 or 3, two or three $A^{11}$, $A^{13}$, $Z^{11}$, and/or $z^{12}$ may be identical to or different from each other) are preferable, and compounds represented by Formula (X-11) and/or Formula (X-12), in each of which $P^{11}$, $P^{12}$, and $P^{13}$ represent an acryl group or a methacryl group, are particularly preferable. As the compound represented by Formula (X-11), specifically, a compound represented by Formula (X-11a):

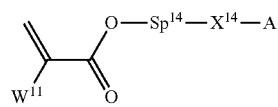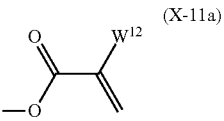     (X-11a)

(in the formula, $W^{11}$ and $W^{12}$ each independently represent a hydrogen atom or a methyl group; $Sp^{14}$ and $Sp^{13}$ each independently represent an alkylene group having 2 to 18 carbon atoms; $X^{14}$ and $X^{15}$ each independently represent —O—, —COO—, —OCO—, or a single bond; $Z^{13}$ and $Z^{14}$ each independently represent —COO— or —OCO—; $A^{15}$, $A^{16}$ and $A^{17}$ each independently represent a 1,4-phenylene group which may be unsubstituted or may be substituted with a fluorine atom, a chlorine atom, a linear or branched alkyl group having 1 to 4 carbon atoms, or a linear or branched alkoxy group having 1 to 4 carbon atoms) is preferable, and compounds represented by Formulae (X-11a-1) to (X-11a-4) below:

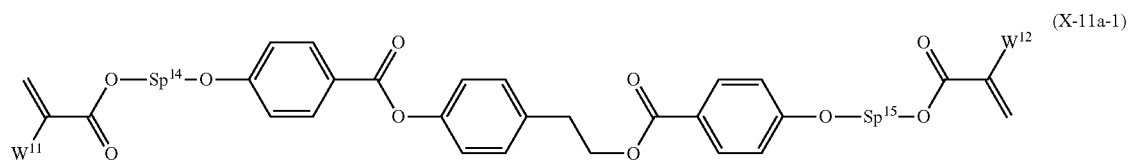

(X-11a-1)

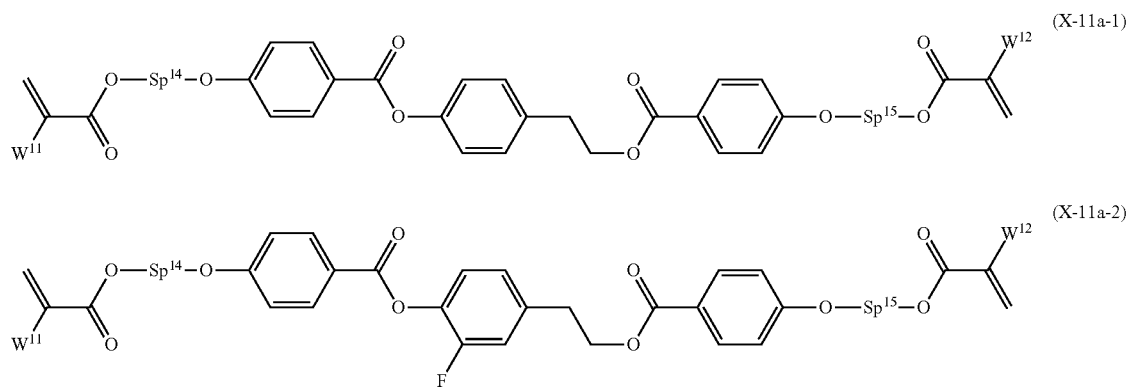

(X-11a-2)

(X-11a-3)

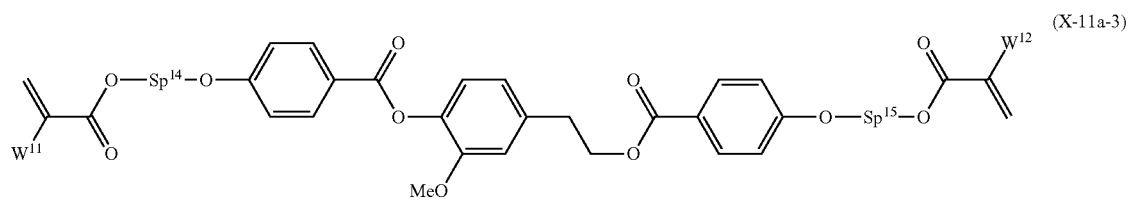

(X-11a-4)

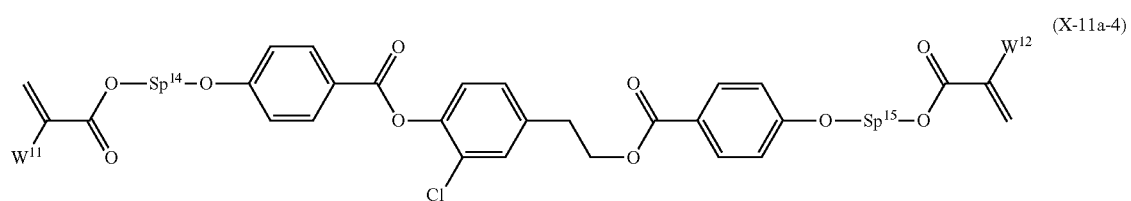

(in the formula, $W^{11}$, $W^{12}$, $Sp^{14}$, and $Sp^{15}$ represent the same meanings as those in Formula (X-11a)) are particularly preferable. In Formulae (X-11a-1) to (X-11a-4), compounds, in each of which $Sp^{14}$ and $Sp^{15}$ each independently are an alkylene group having 2 to 8 carbon atoms, are particularly preferable.

In addition, examples of preferable bifunctional polymerizable compounds include compounds represented by Formulae (X-11b-1) to (X-11b-3) below:

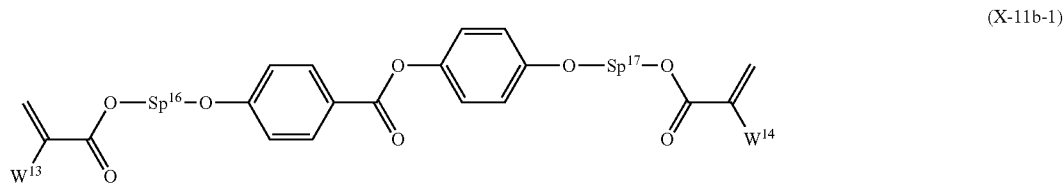

(X-11b-1)

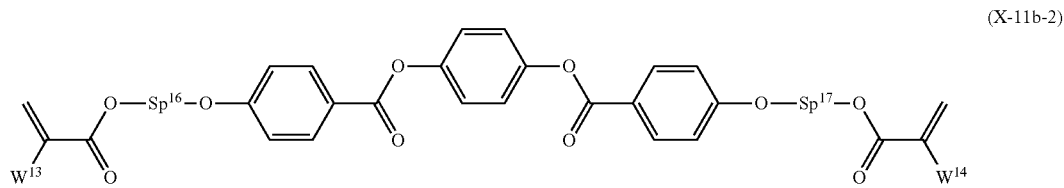

(X-11b-2)

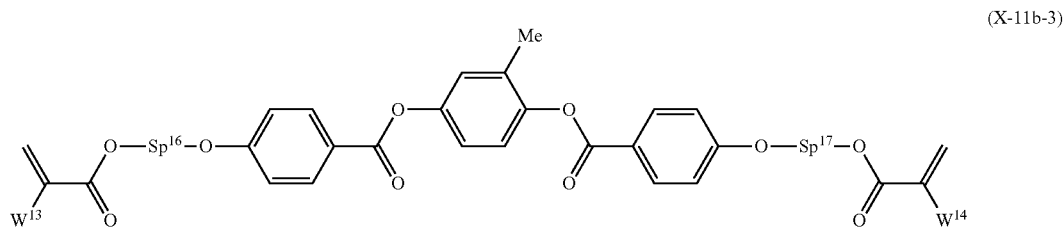

(X-11b-3)

(in the formula, $W^{13}$ and $W^{14}$ each independently represent a hydrogen atom or a methyl group; and $Sp^{16}$ and $Sp^{17}$ each independently represent an alkylene group having 2 to 18 carbon atoms). In Formulae (X-11b-1) to (X-11b-3), compounds, in each of which $Sp^{16}$ and $Sp^{17}$ each independently are an alkylene group having 2 to 8 carbon atoms, are particularly preferable.

Specific examples of the compound represented by Formula (X-12) include compounds represented by Formulae (X-12-1) to (X-12-7) below:

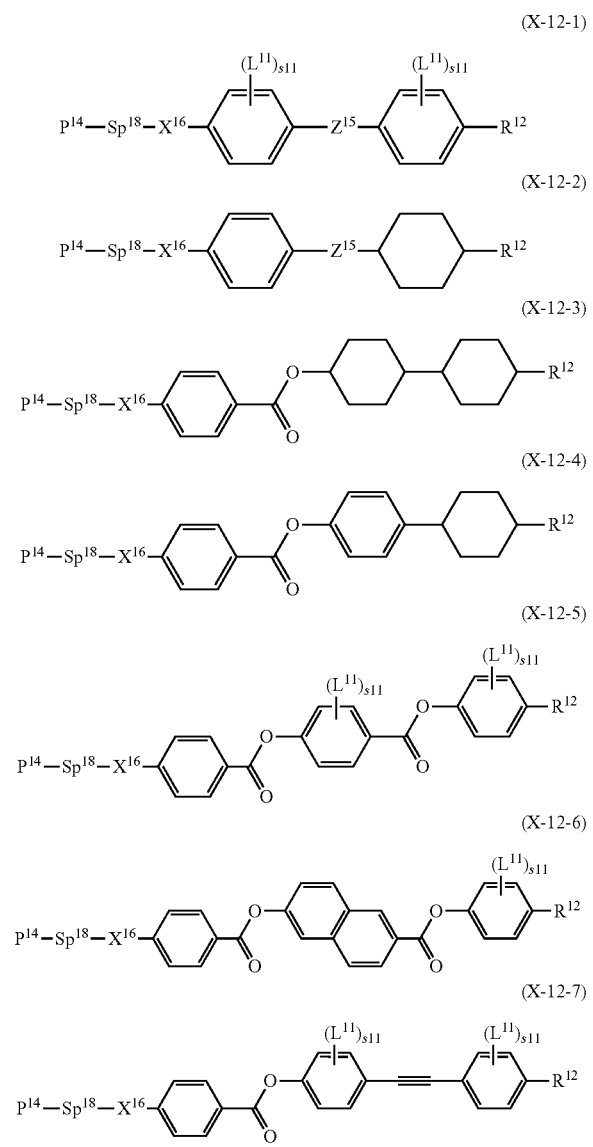

(in the formulae, $P^{14}$ represents a polymerizable group; $Sp^{18}$ represents a single bond or an alkylene group having 1 to 20 carbon atoms, in which one —$CH_2$— or two or more non-adjacent —$CH_2$—'s may be substituted with —O—, —COO—, —OCO—, —O—CO—O—; $X^{16}$ represents a single bond, —O—, —COO—, or —OCO—; $Z^{15}$ represents a single bond, —COO—, or —OCO—; $L^{11}$ represents a fluorine atom, a chlorine atom, or a linear or branched alkyl group having 1 to 10 carbon atoms, in which one —$CH_2$— or two or more non-adjacent —$CH_2$—'s may be each independently substituted with —O—, —COO—, or —OCO—; s11 represents an integer of 0 to 4; and $R^{12}$ represents a hydrogen atom, a fluorine atom, a chlorine atom, a cyano group, a nitro group, or a linear or branched alkyl group having 1 to 20 carbon atoms, in which one —$CH_2$— or two or more non-adjacent —$CH_2$—'s may be each independently substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—).

A polymerizable compound not exhibiting liquid crystallinity can also be added to the polymerizable liquid crystal composition containing the compound of the present invention to such a degree that the liquid crystallinity of the composition is not remarkably deteriorated. Specifically, if a compound is recognized as a polymer-formable monomer or a polymer-formable oligomer in the art, it can be used without particular limitation. Specific examples thereof are described in "Material edition (monomer, oligomer, photopolymerization initiator), Photocuring technology data book" (supervised by Ichimura Kunihiro and Kato Kiyomi, Techno net Co., Ltd.).

Although the compound of the present invention can also be polymerized without using a photopolymerization initiator, if necessary, the photopolymerization initiator may be added thereto. In this case, the concentration of the photopolymerization initiator to the compound of the present invention is preferably 0.1 mass % to 15 mass %, more preferably 0.2 mass % to 10 mass %, and further preferably 0.4 mass % to 8 mass %. Examples of the photopolymerization initiator include benzoin ethers, benzophenones, acetophenones, benzyl ketals, and acylphosphine oxides. Specific examples of the photopolymerization initiator include
2-methyl-1-(4-methylthiophenyl)-2-morpholinopropan-1-one (IRGACURE 907) and benzoic acid
[1-[4-(phenylthio)benzoyl]heptylidene] amino (IRGACURE OXE 01).

Examples of the thermopolymerization initiator include azo compounds and peroxides. Specific examples of the thermopolymerization initiator include
2,2'-azobis(4-methoxy-2,4-dimethylvaleronitrile) and
2,2'-azobis(isobutyronitrile). The polymerization initiators may be used alone or may be used in combination of two or more kinds thereof.

Meanwhile, a stabilizer can be added to the liquid crystal composition of the present invention in order to improve the storage stability of the composition. Examples of the stabilizer that can be used include hydroquinones, hydroquinone mono alkyl ethers, tertiary butyl catechols, pyrogallols, thiophenols, nitro compounds, β-naphthylamines, β-naphthols, and nitroso compounds. When the stabilizer is used, the amount of the stabilizer added is preferably 0.005 mass % to 1 mass %, more preferably 0.02 mass % to 0.8 mass %, further preferably 0.03 mass % to 0.5 mass %. The stabilizer may be used alone or may be used in combination of two or more kinds thereof. As the stabilizer, specifically, compounds represented by Formulae (X-13-1) to (X-13-35) below:

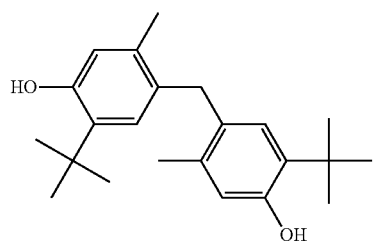 (X-13-1)
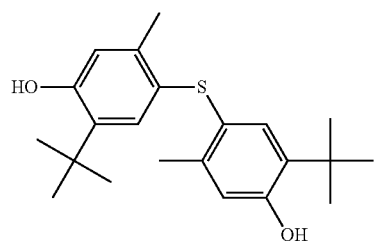 (X-13-2)
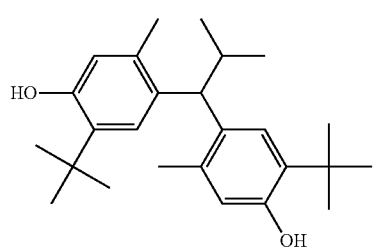 (X-13-3)
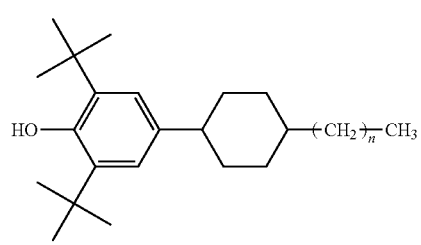 (X-13-4)
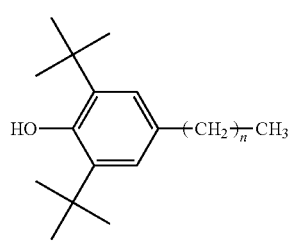 (X-13-5)
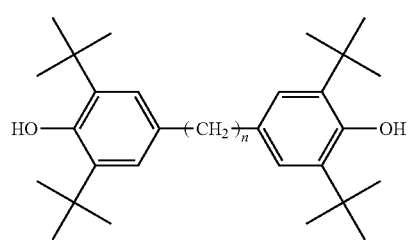 (X-13-6)
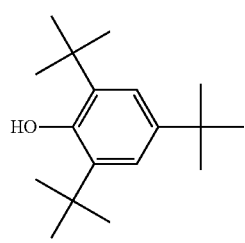 (X-13-7)
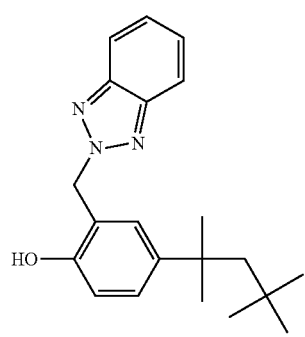 (X-13-8)
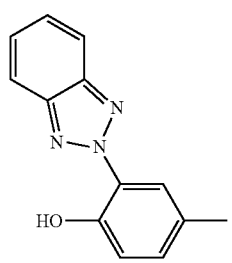 (X-13-9)
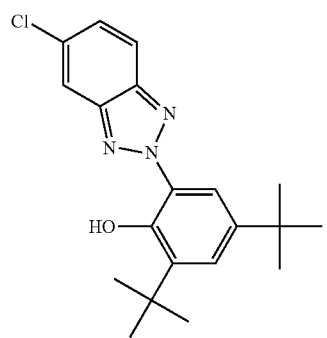 (X-13-10)

-continued
(X-13-11)
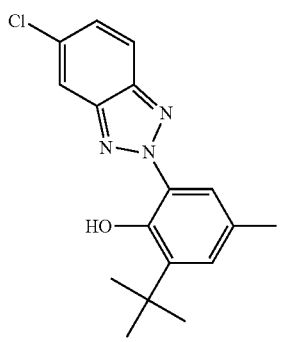
(X-13-12)
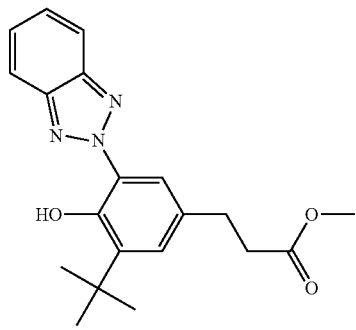
(X-13-13)
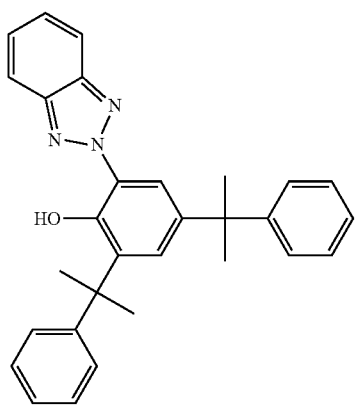
(X-13-14)
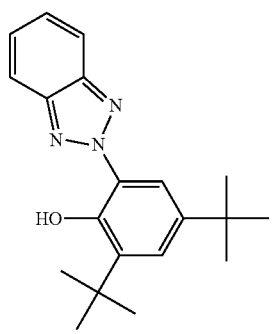
(X-13-15)
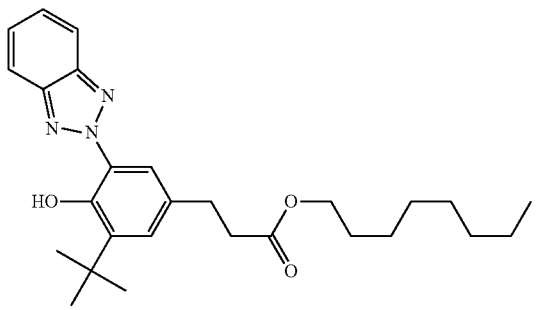
(X-13-16)
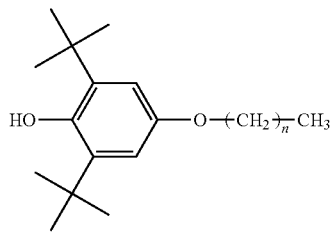
(X-13-17)
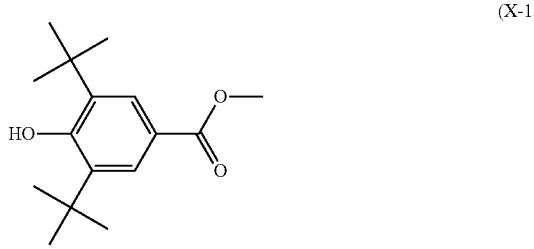
(X-13-18)
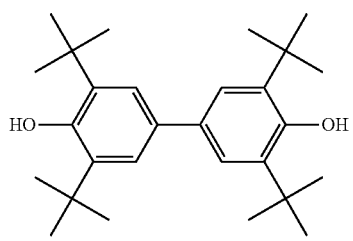
(X-13-19)
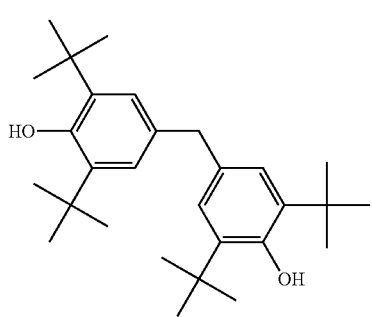
(X-13-20)
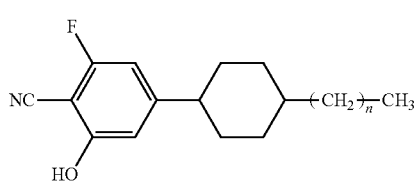

-continued
(X-13-21)
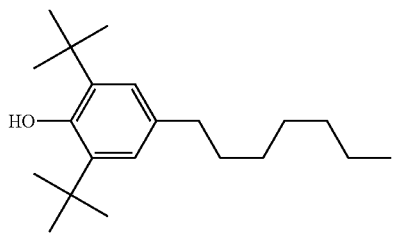
(X-13-22)
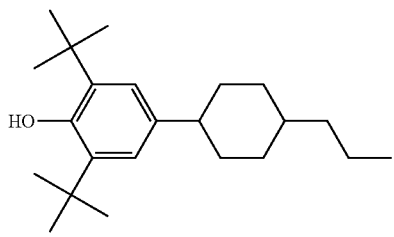
(X-13-23)
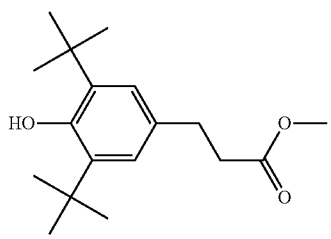
(X-13-24)
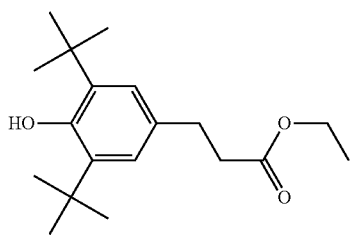
(X-13-25)
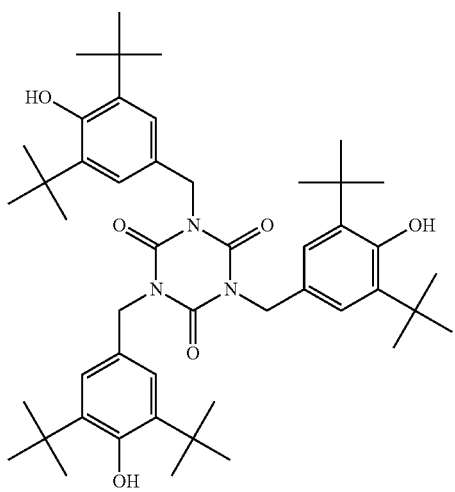
(X-13-26)
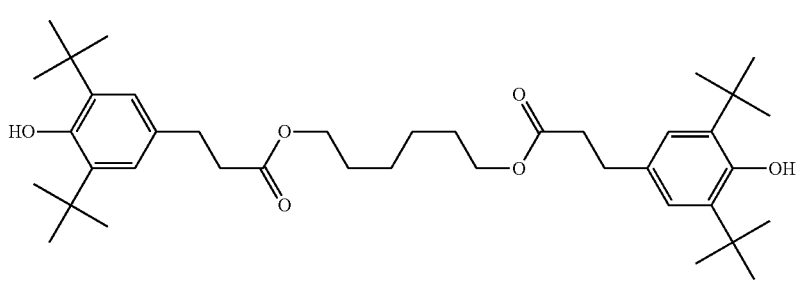
(X-13-27)
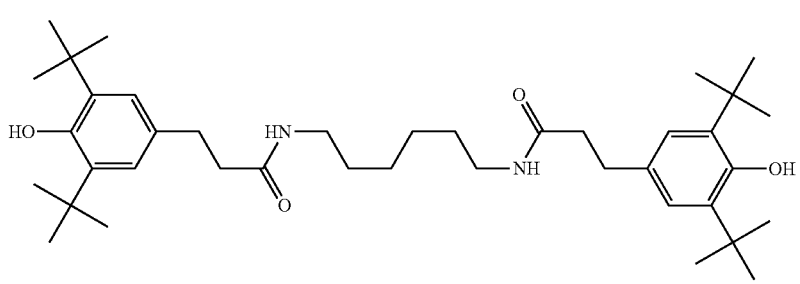

(X-13-28)
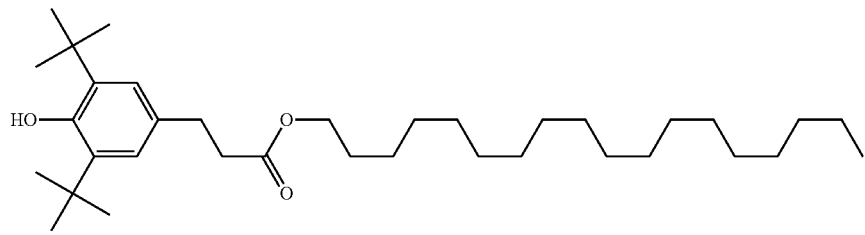
(X-13-29)
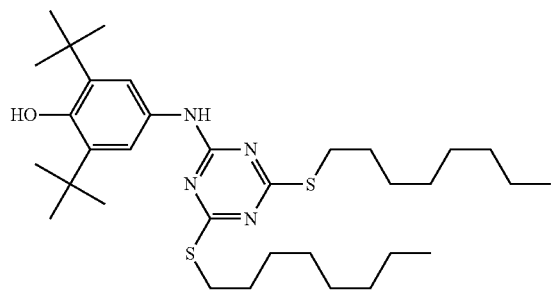
(X-13-30)
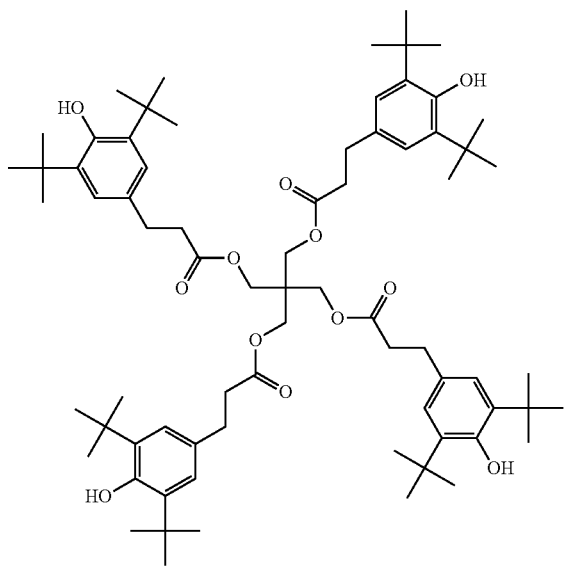
(X-13-31)
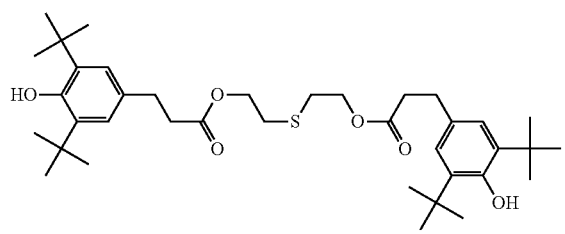
(X-13-32)
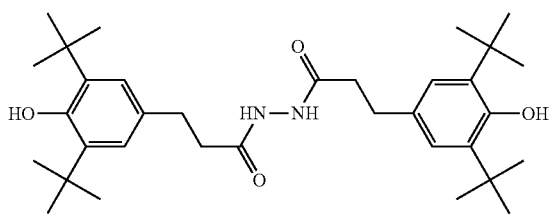
(X-13-33)
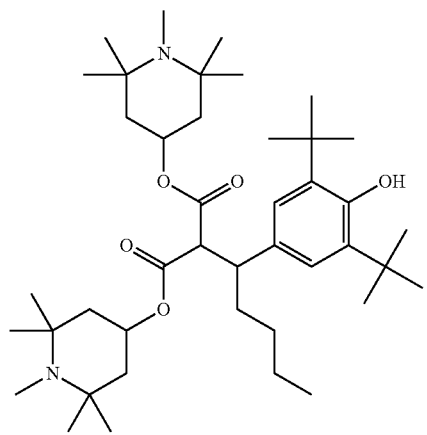
(X-13-34)
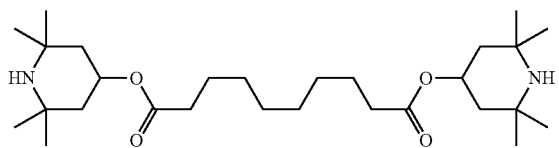

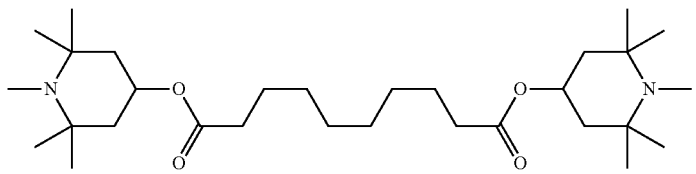

(X-13-35)

(in the formulae, n represents an integer of 0 to 20) are preferable. Meanwhile, when the polymerizable liquid crystal composition containing the compound of the present invention is used for films, optical elements, functional pigments, pharmaceutical products, cosmetics, coating agents, and synthetic resins, if necessary, a metal, a metal complex, a dye, a pigment, a colorant, a fluorescent material, a phosphorescent material, a surfactant, a leveling agent, a thixotropic agent, a gelling agent, polysaccharides, an ultraviolet absorber, an infrared absorber, an antioxidant, an ion exchange resin, or metal oxide such as titanium oxide can also be added.

Polymers obtained by polymerizing the polymerizable liquid crystal composition containing the compound of the present invention can be used for various applications. For example, polymers obtained by polymerizing the polymerizable liquid crystal composition containing the compound of the present invention without alignment can be used for a light scattering plate, a depolarizing plate, and a moire stripe preventing plate. Further, polymers obtained by aligning and then polymerizing the polymerizable liquid crystal composition are useful because they have optical anisotropy. Such an optically anisotropic body can be manufactured by supporting the polymerizable liquid crystal composition containing the compound of the present invention on a substrate rubbed with a cloth, a substrate provided with organic thin film, or a substrate having an alignment film obliquely evaporated with $SiO_2$ or interposing the polymerizable liquid crystal composition between the substrates and then polymerizing the polymerizable liquid crystal composition.

As the method of supporting the polymerizable liquid crystal composition on the substrate, spin coating, die coating, extrusion coating, roll coating, wire bar coating, gravure coating, spray coating, dipping, printing, and the like are exemplified. During coating, an organic solvent may be added to the polymerizable liquid crystal composition. As the organic solvent, a hydrocarbon solvent, a halogenated hydrocarbon solvent, an ether solvent, an alcohol solvent, a ketone solvent, an ester solvent, or a non-protic solvent can be used. For example, toluene or hexane can be used as the hydrocarbon solvent, methylene chloride can be used as the halogenated hydrocarbon solvent, tetrahydrofuran, acetoxy-2-ethoxy-ethane, or propylene glycol monomethyl ether acetate can be used as the ether solvent, methanol, ethanol, or isopropanol can be used as the alcohol solvent, acetone, methyl ethyl ketone, cyclohexanone, γ-butyrolactone or N-methylpyrrolidinones can be used as the ketone solvent, ethyl acetate or cellosolve can be used as the ester solvent, and dimethylformamide or acetonitrile can be used as the non-protic solvent. These solvents may be used alone or in combination thereof, and may be appropriately selected in consideration of the solubility of the polymerizable liquid crystal composition and the vapor pressure thereof. As the method of volatilizing the added organic solvent, natural drying, heat drying, vacuum drying, or vacuum heat drying can be used. In order to further improve the coating properties of a polymerizable liquid crystal material, it is also effective to provide an intermediate layer such as a polyimide thin film on a substrate or to add a leveling agent to a polymerizable liquid crystal material. The method of providing an intermediate layer such as a polyimide thin film on a substrate is effective for improving the adhesiveness between the substrate and the polymer obtained by polymerizing a polymerizable liquid crystal material. As the alignment treatment other than the above, the use of flow alignment of a liquid crystal material or the use of an electric field or magnetic field can be exemplified. These alignment means may be used alone or in combination thereof. Further, as the alignment treatment method instead of rubbing, a photo-alignment method can be used. As the shape of the substrate, the substrate may have a curved surface as a component in addition to a flat plate. As the material constituting the substrate, both organic materials and inorganic materials can be used. Examples of the organic materials serving as the material of the substrate include polyethylene terephthalate, polycarbonate, polyimide, polyamide, polymethyl methacrylate, polystyrene, polyvinyl chloride, polytetrafluoroethylene, polychlorotrifluoroethylene, polyarylate, polysulfone, triacetyl cellulose, cellulose, and polyether ether ketone. Further, examples of the inorganic materials include silicon, glass, and calcite.

At the time of polymerizing the polymerizable liquid crystal composition containing the compound of the present invention, it is desirable for polymerization to proceed quickly, and thus a method of polymerizing the composition by irradiation with active energy rays such as ultraviolet rays or electron beams is preferable. When ultraviolet rays are used, a polarized light source may be used, and a non-polarized light source may also be used. Further, when polymerization is performed in a state in which the liquid crystal composition is interposed between two substrates, the substrate of at least irradiated surface side should have appropriate transparency to active energy rays. Moreover, a means may be used in which only the specific portion is polymerized using a mask at the time of light irradiation and conditions such as an electric field and a magnetic field or temperature are changed, thereby changing the alignment state of the unpolymerized portion and further, active energy rays is applied for performing polymerization. Further, it is preferable that the temperature during irradiation is within a temperature range in which the liquid crystal state of the polymerizable liquid crystal composition of the present invention is maintained. In particular, when an optically anisotropic body intends to be manufactured by photopolymerization, it is preferable that polymerization is performed at a temperature as close to room temperature as possible, that is, typically at a temperature of 25° C., in order to avoid the induction of unintended thermal polymerization. The intensity of active energy rays is preferably 0.1 mW/cm² to 2 W/cm². When the intensity thereof is 0.1 mW/cm² or less, it takes a lot of time to complete the photopolymerization, and thus productivity is lowered, and when the intensity thereof is 2 W/cm² or more, there is a risk of deteriorating the polymerizable liquid crystal compound or the polymerizable liquid crystal composition.

The optically anisotropic body obtained by polymerization can also be heat-treated for the purpose of reducing the change of initial characteristics and exhibiting stable characteristics. The heat-treatment temperature is preferably 50° C. to 250° C., and the heat-treatment time is preferably 30 seconds to 12 hours. The optically anisotropic body manufactured in this way may be used alone after being peeled from the substrate, or may be used without being peeled from the substrate. Moreover, the obtained optically anisotropic body may be laminated, or may be used after being bonded to another substrate.

EXAMPLES

Hereinafter, the present invention will be described in more detail with reference to the following Examples, but the present invention is not limited to these Examples. Further, in the compositions of Examples and Comparative Examples, "%" means "mass %". When unstable substances to oxygen and/or moisture are treated in each step, it is preferable to perform an operation in inert gas such as nitrogen gas, argon gas, or the like. "Ordinary post-treatment" is an operation for obtaining the desired compound from a reaction solution, and means an operation, such as quenching of reaction, liquid separation and extract ion, neutralization, washing, drying, or concentration, which is ordinary performed by those skilled in the art.

(Example 1) Preparation of Compound Represented by Formula (I-1)

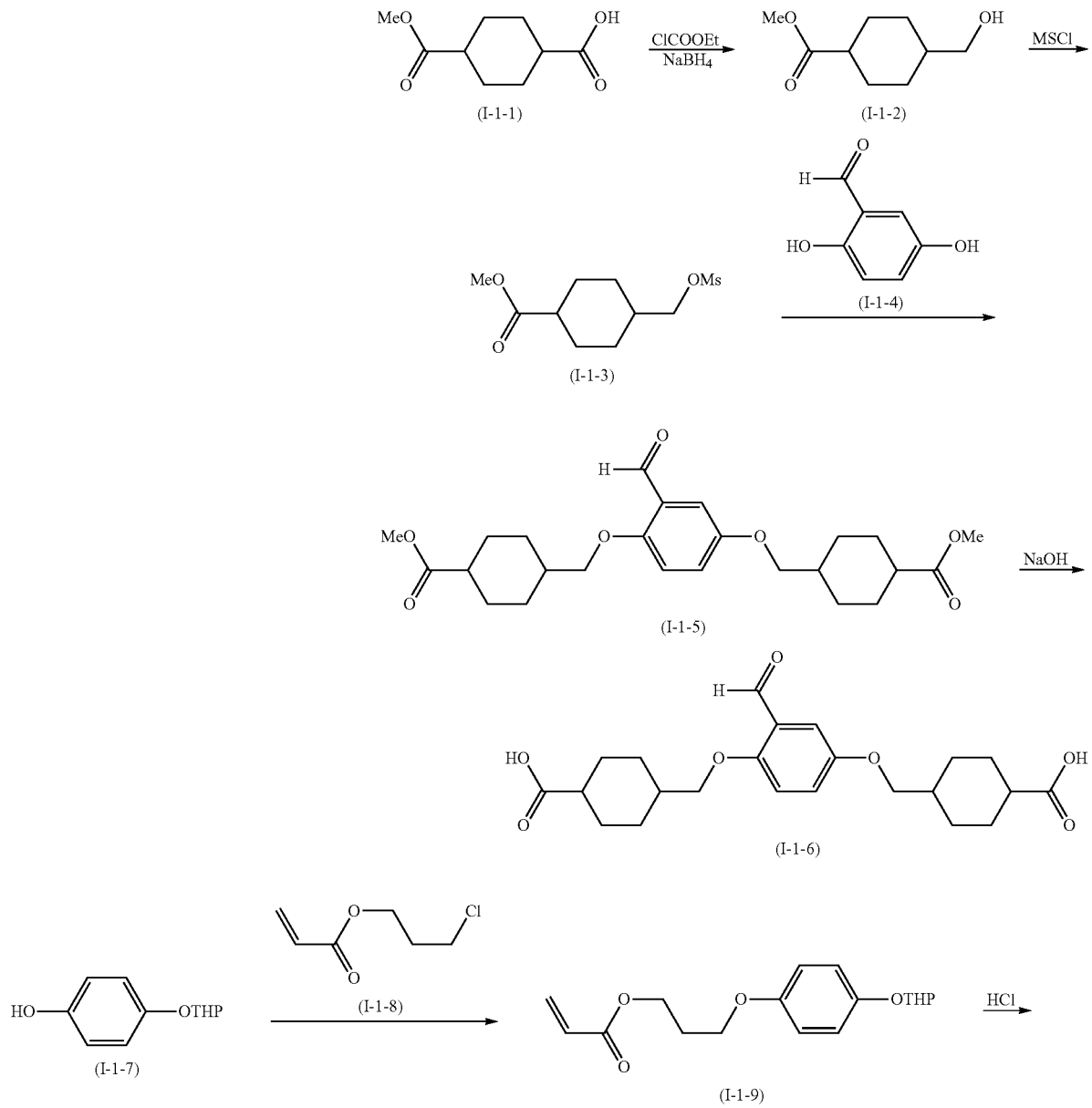

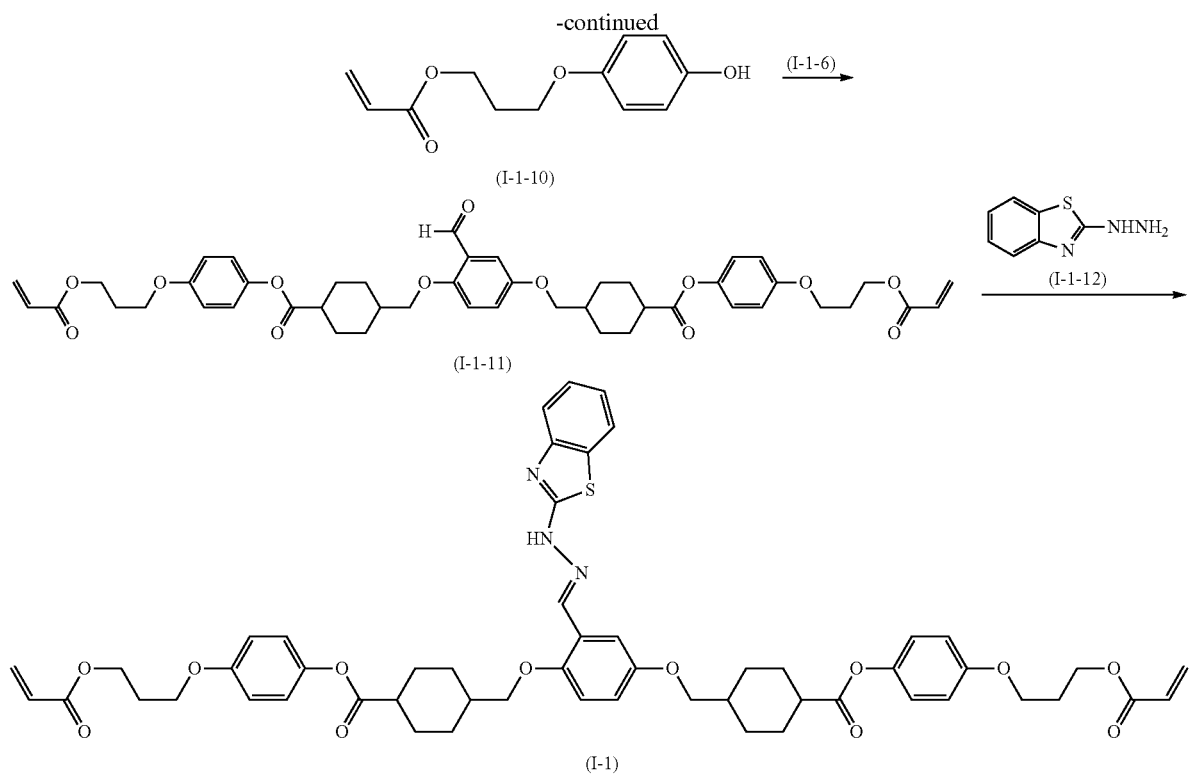

A compound represented by Formula (I-1-1), triethylamine, and tetrahydrofuran were put into a reaction container. With ice cooling, ethyl chloroformate was dropped, followed by stirring at room temperature. The precipitate was filtered to obtain a solution. Sodium borohydride and tetrahydrofuran were put into another reaction container under a nitrogen atmosphere. With ice cooling, the solution was dropped and the obtained mixture was stirred. A mixed liquid of methanol and water was dropped and the obtained mixture was further stirred. After the addition of hydrochloric acid, extraction was performed with ethyl acetate. Purification was performed by column chromatography (alumina) to obtain a compound represented by Formula (I-1-2).

The compound represented by Formula (I-1-2), pyridine, and dichloromethane were put into a reaction container under a nitrogen atmosphere. With ice cooling, methanesulfonyl chloride was dropped, followed by stirring at room temperature. After ordinary post-treatment was performed, purification was performed by column chromatography (silica gel) to obtain a compound represented by Formula (I-1-3).

The compound represented by Formula (I-1-3), a compound represented by Formula (I-1-4), potassium carbonate, and N,N-dimethylformamide were put into a reaction container, followed by heating and stirring. The resultant product was diluted with dichloromethane, and then washed with water and brine. Purification was performed by column chromatography (silica gel) to obtain a compound represented by Formula (I-1-5).

The compound represented by Formula (I-1-5), methanol, and an aqueous sodium hydroxide solution were put into a reaction container, followed by heating and stirring. The resultant product was neutralized with hydrochloric acid, diluted with ethyl acetate, and then washed with water and brine. Purification was performed by column chromatography (alumina) to obtain a compound represented by Formula (I-1-6).

A compound represented by Formula (I-1-7), a compound represented by Formula (I-1-8), potassium carbonate, and N,N-dimethylformamide were put into a reaction container, followed by heating and stirring. The resultant product was diluted with dichloromethane, and then washed with water and brine. Purification was performed by column chromatography (alumina) to obtain a compound represented by Formula (I-1-9).

The compound represented by Formula (I-1-9), tetrahydrofuran, methanol, and concentrated hydrochloric acid were put into a reaction container, followed by stirring. After ordinary post-treatment was performed, drying was performed to obtain a compound represented by Formula (I-1-10).

The compound represented by Formula (I-1-10), the compound represented by Formula (I-1-6), N,N-dimethylaminopyridine, and dichloromethane were put into a nitrogen-purged reaction container. With ice cooling, diisopropylcarbodiimide was dropped, followed by stirring at room temperature. The precipitate was filtered, and then washed with hydrochloric acid, water, and brine. Purification was performed by column chromatography (silica gel) and recrystallization to obtain a compound represented by Formula (I-1-11).

The compound represented by Formula (I-1-11), a compound represented by Formula (I-1-12), (±)-10-camphorsulfonic acid, tetrahydrofuran, and ethanol were put into a reaction container, followed by stirring. The solvent was concentrated, and purification was performed by column chromatography (silica gel) and recrystallization to obtain a compound represented by Formula (I-1).

Transition temperature (temperature rise rate 5° C./min) C 155 N>220 I $^1$H NMR (CDCl$_3$) δ 1.12 (q, 2H), 1.26 (q, 2H), 1.50 (q, 2H), 1.67 (qd, 2H), 1.91-2.27 (m, 14H), 2.43 (t, 1H), 2.56 (tt, 2H), 3.77 (d, 2H), 3.88 (d, 2H), 4.09 (t, 4H), 4.40 (t, 4H), 5.88 (d, 2H), 6.17 (ddd, 2H), 6.45 (d, 2H), 6.85 (d, 1H), 6.92 (m, 5H), 7.02 (d, 4H), 7.19 (t, 1H), 7.37 (t, 1H), 7.59 (m, 2H), 7.71 (d, 1H), 8.44 (s, 1H) ppm.

(Example 2) Preparation of Compound Represented by Formula (I-2)

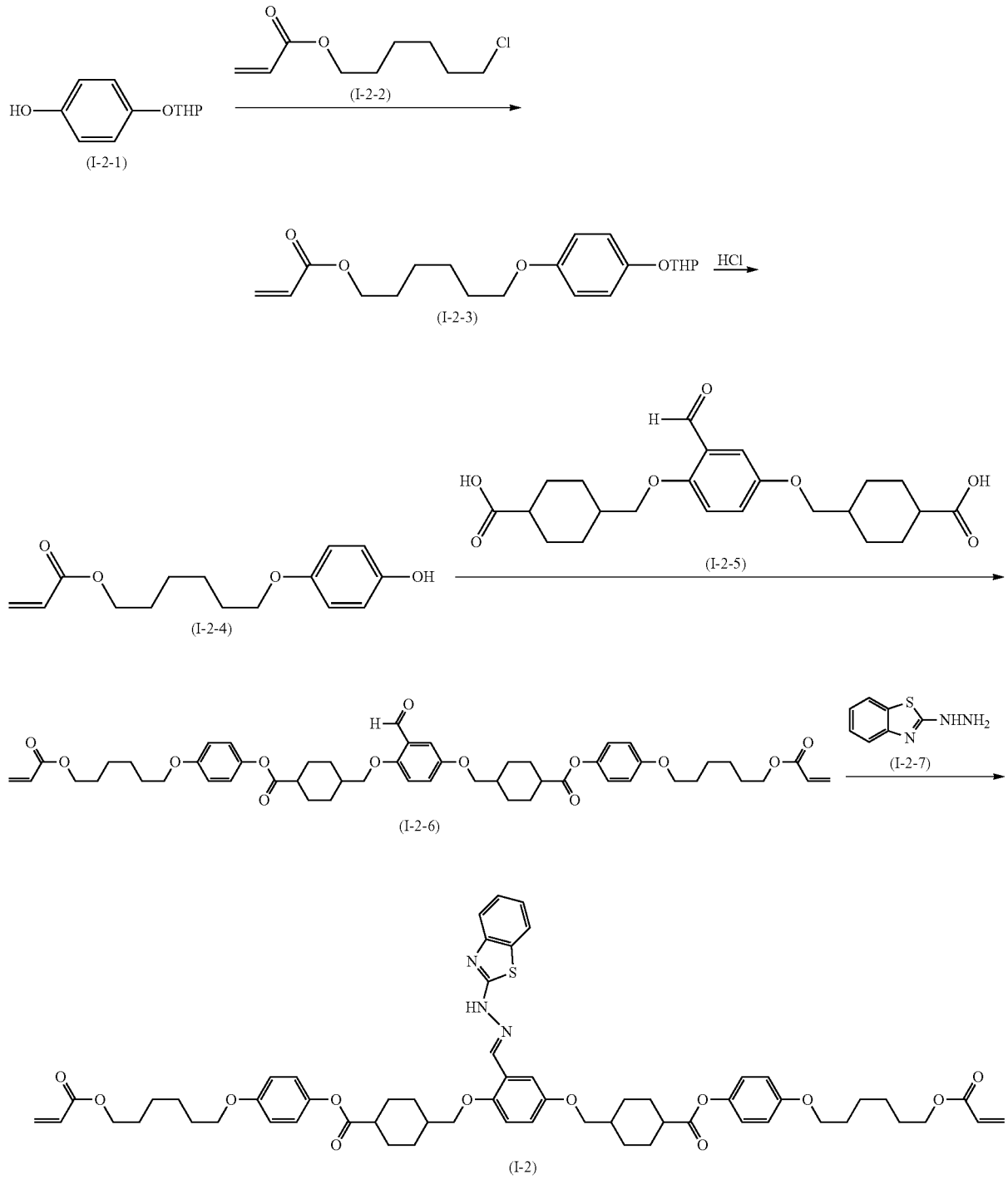

A compound represented by Formula (I-2) was obtained in the same manner as in Example 1, except that the compound represented by Formula (I-1-8) was replaced by a compound represented by Formula (I-2-2).

Transition temperature (temperature rise rate 5° C./min) C 90-110 N 182-187 I $^1$H NMR (CDCl$_3$) δ 1.07 (q, 2H), 1.24 (q, 2H), 1.47-1.90 (m, 24H), 2.09 (m, 4H), 2.22 (d, 2H), 2.39 (t, 1H), 2.53 (t, 1H), 3.74 (d, 2H), 3.85 (d, 2H), 3.94 (td, 4H), 4.17 (td, 4H), 5.82 (d, 2H), 6.13 (dd, 2H), 6.40 (d, 2H), 6.80-6.99 (m, 6H), 6.98 (d, 4H), 7.16 (t, 1H), 7.33 (t, 1H), 7.55 (m, 2H), 7.67 (d, 1H), 8.40 (s, 1H) ppm.

(Example 3) Preparation of Compound Represented by Formula (I-3)

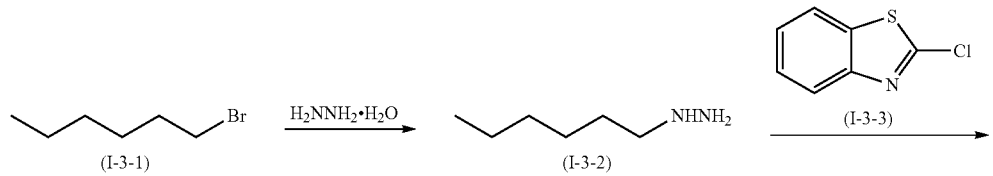

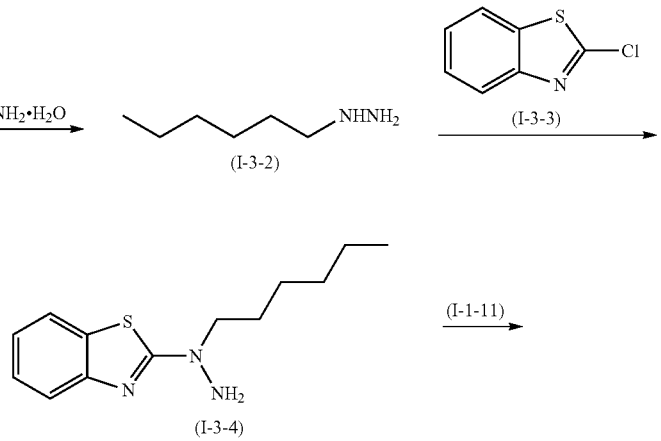

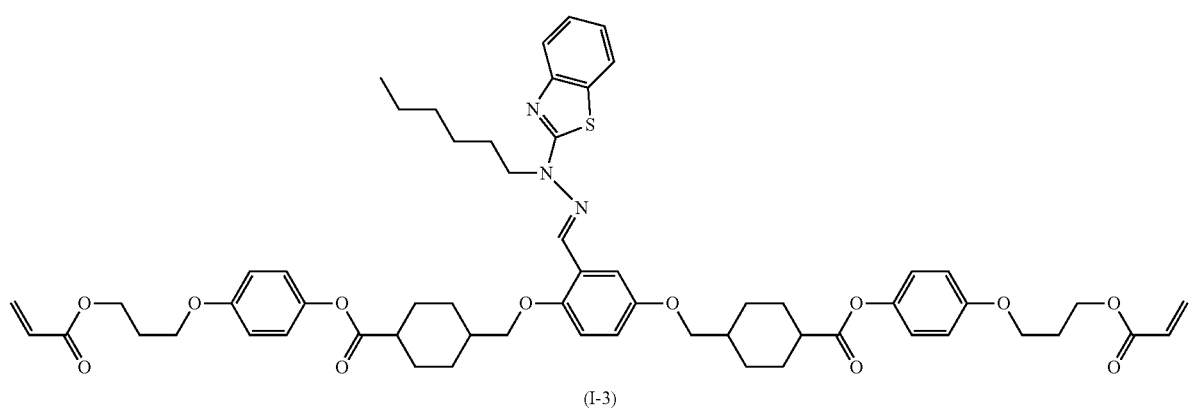

Hydrazine monohydrate and ethanol were put into a nitrogen-purged reaction container. With heating, a compound represented by Formula (I-3-1) was dropped, followed by stirring. The resultant product was concentrated to obtain a compound represented by Formula (I-3-2).

A compound represented by Formula (I-3-3), 1,2-dimethoxyethane, and triethylamine were put into a nitrogen-purged reaction container. The compound represented by Formula (I-3-2) was dropped, followed by heating and stirring. The reaction solution was poured into water, and the precipitated solid was filtered. The resultant product was washed with hexane, and then dried to obtain a compound represented by Formula (I-3-4).

The compound represented by Formula (I-1-11), the compound represented by Formula (I-3-4), (±)-10-camphorsulfonic acid, tetrahydrofuran, and ethanol were put into a reaction container, followed by heating and stirring. The solvent was concentrated, and purification was performed by column chromatography (silica gel) and recrystallization to obtain a compound represented by Formula (I-3).

LCMS: 1058 [M+1]

(Example 4) Preparation of Compound Represented by Formula (I-4)

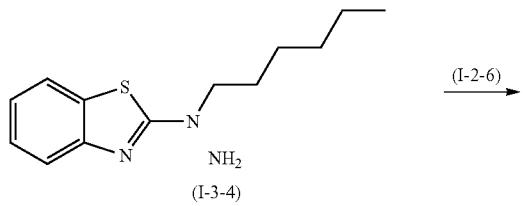

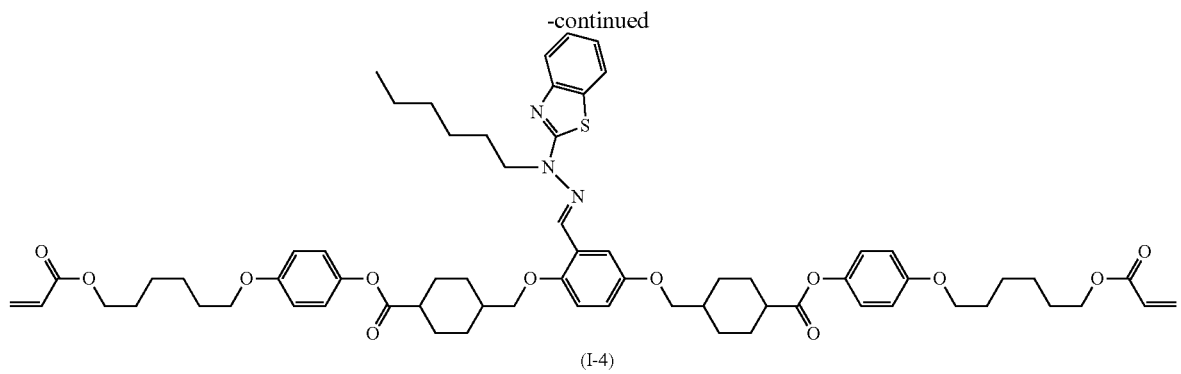

(I-4)

A compound represented by Formula (I-4) was obtained in the same manner as in Example 3.

LCMS: 1142 [M+1]

(Example 5) Preparation of Compound Represented by Formula (I-5)

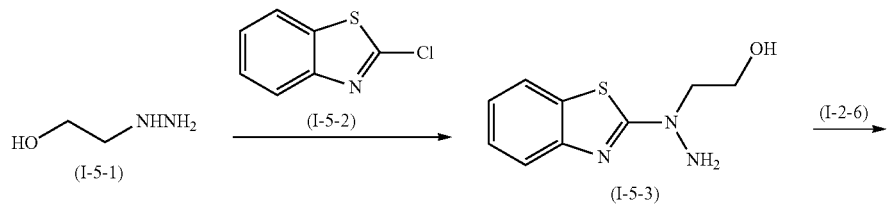

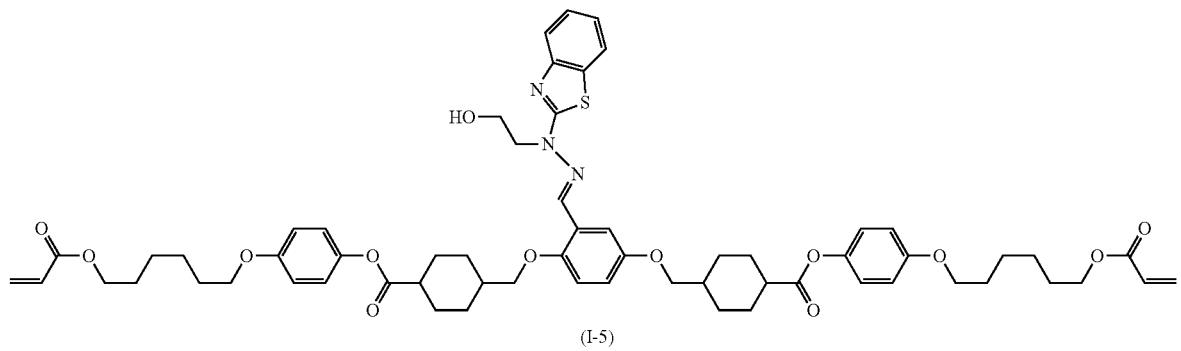

(I-5)

A compound represented by Formula (I-5) was obtained in the same manner as in Example 3.

Transition temperature (temperature rise rate 5° C./min) C 119-122 N 144 I $^1$H NMR (CDCl$_3$) δ 1.25 (m, 4H), 1.48 (m, 8H), 1.63-1.82 (m, 12H), 1.90 (m, 2H), 2.07 (dd, 4H), 2.24 (d, 4H), 2.52 (m, 2H), 3.30 (t, 1H), 3.86 (dd, 4H), 3.94 (t, 4H), 4.08 (td, 2H), 4.17 (t, 4H), 4.50 (t, 2H), 5.82 (dd, 2H), 6.12 (dd, 2H), 6.40 (dd, 2H), 6.88 (m, 6H), 6.97 (dd, 4H), 7.16 (t, 1H), 7.33 (t, 1H), 7.52 (d, 1H), 7.64 (d, 1H), 7.69 (d, 1H), 8.28 (s, 1H) ppm.

LCMS: 1102 [M+1]

(Example 6) Preparation of Compound Represented by Formula (I-6)

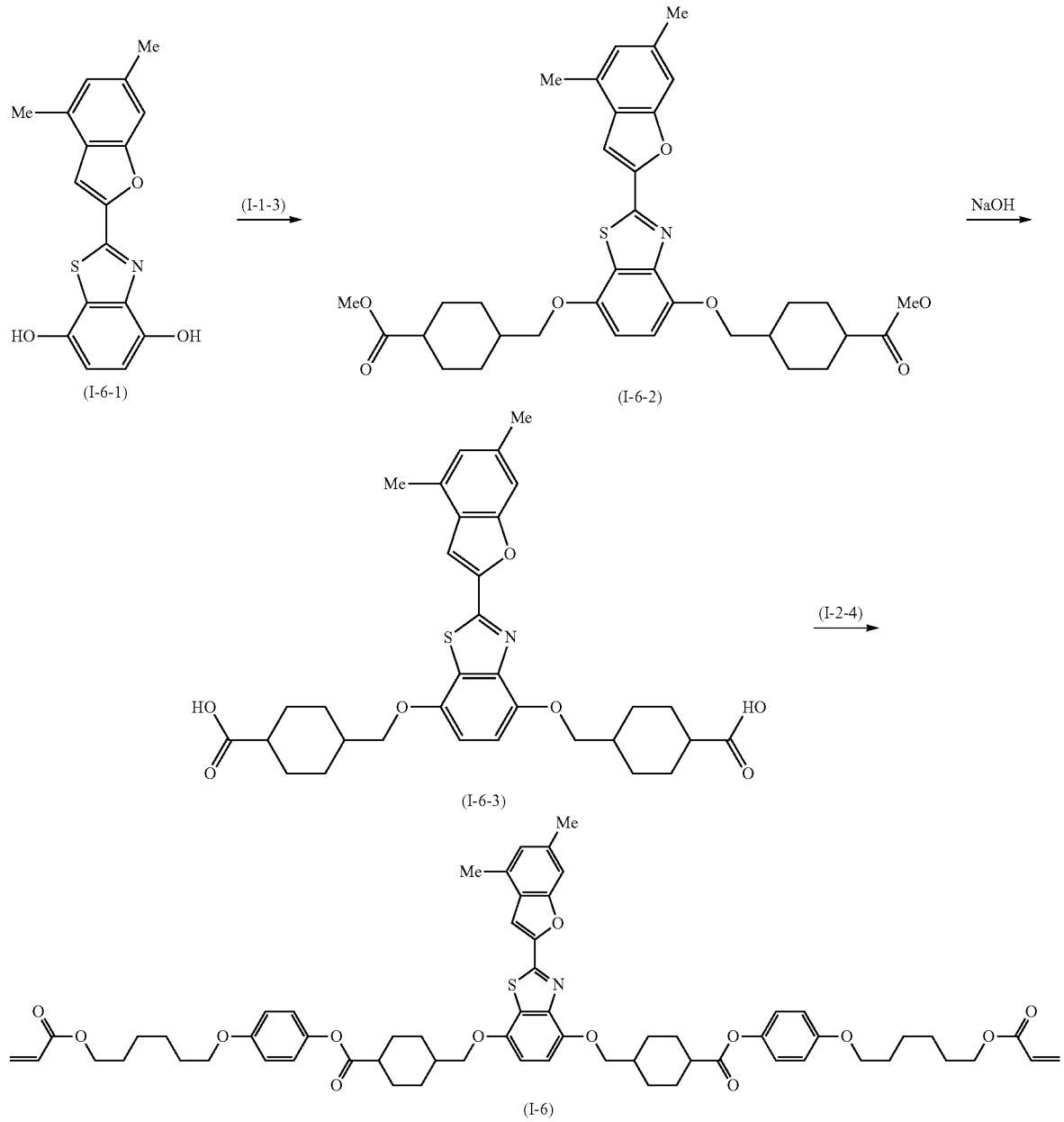

A compound represented by Formula (I-6-1) was prepared by the method described in JP-A-2011-207765. The compound represented by Formula (I-6-1), the compound represented by Formula (I-1-3), cesium carbonate, and dimethyl sulfoxide were put into a reaction container, followed by heating and stirring. After ordinary post-treatment was performed, purification was performed by column chromatography (silica gel) and recrystallization to obtain a compound represented by Formula (I-6-2).

The compound represented by Formula (I-6-2), tetrahydrofuran, methanol, and an aqueous sodium hydroxide solution were put into a reaction container, followed by heating and stirring. After the resultant product was neutralized with hydrochloric acid, ordinary post-treatment was performed to obtain a compound represented by Formula (I-6-3).

The compound represented by Formula (I-6-3), the compound represented by Formula (I-2-4), N,N-dimethylaminopyridine, and dichloromethane were put into a reaction container. With ice cooling, diisopropylcarbodiimide was dropped, followed by stirring at room temperature. The precipitate was filtered, and then washed with hydrochloric acid, water, and brine. Purification was performed by column chromatography (silica gel) and recrystallization to obtain a compound represented by Formula (I-6).

LCMS: 1084 [M+1]

(Example 7) Preparation of Compound Represented by Formula (I-7)
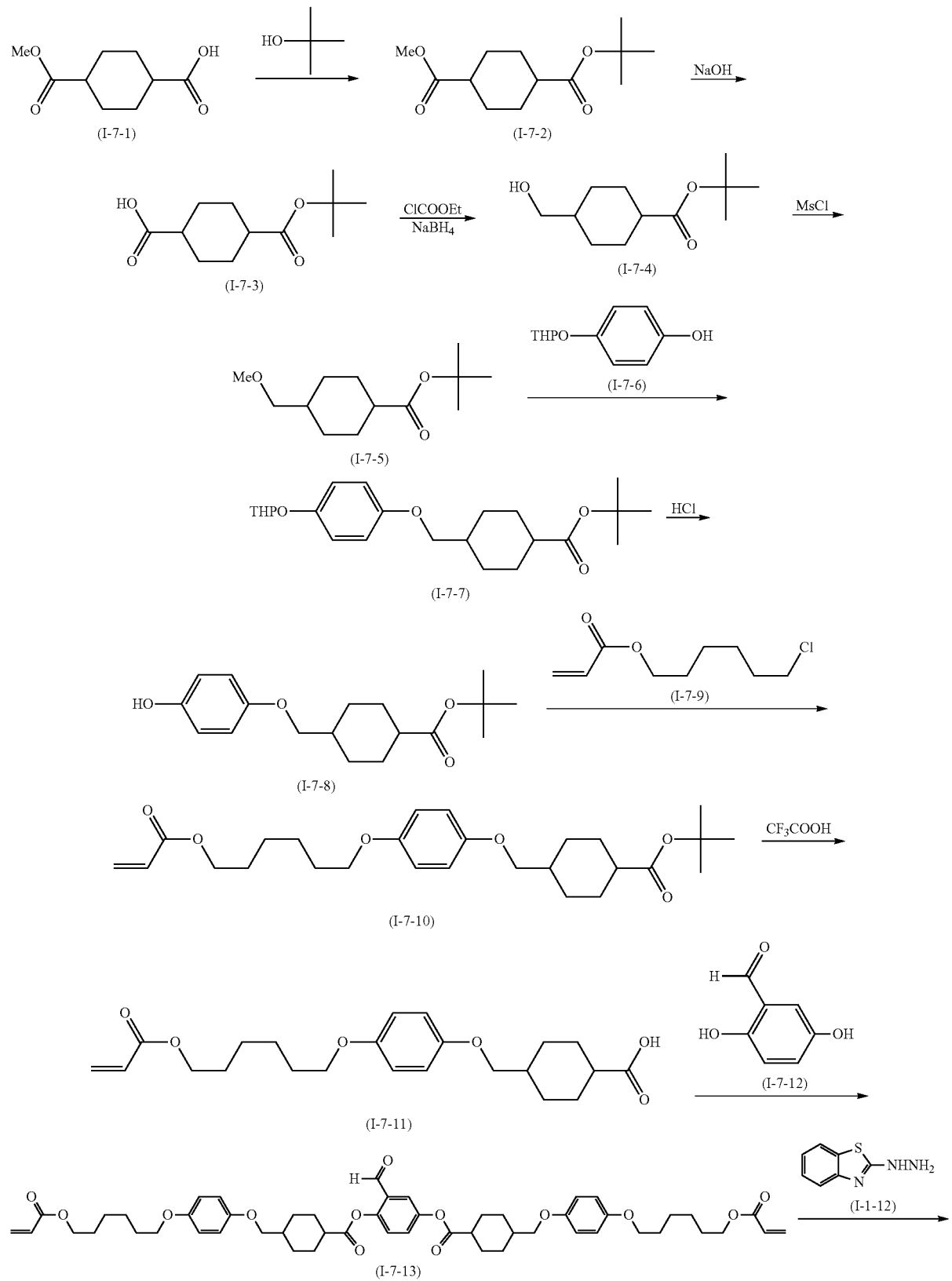

-continued

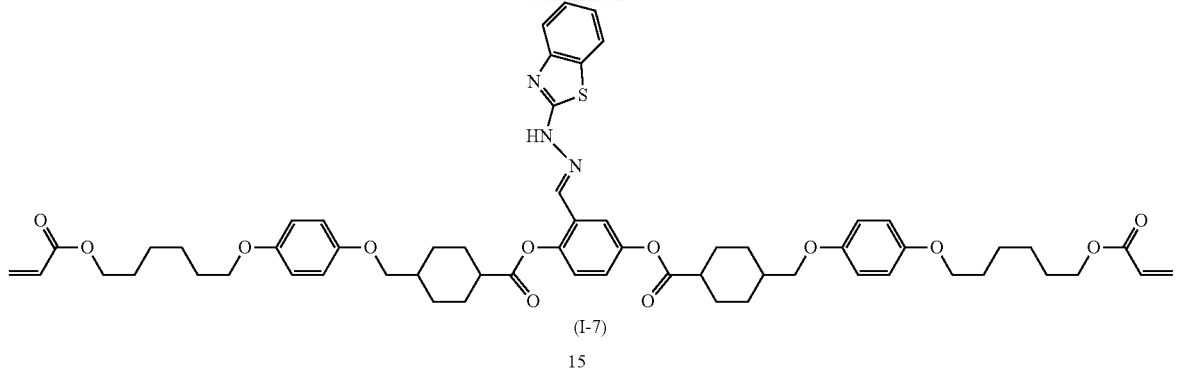

(I-7)

A compound represented by Formula (I-7-1), tert-butyl-alcohol, N,N-dimethylaminopyridine, and dichloromethane were put into a reaction container. With ice cooling, diisopropylcarbodiimide was dropped, followed by stirring at room temperature. The precipitate was filtered, and then washed with hydrochloric acid, water, and brine. Purification was performed by column chromatography (silica gel) to obtain a compound represented by Formula (I-7-2).

The compound represented by Formula (I-7-2), methanol, and an aqueous sodium hydroxide solution were put into a reaction container, followed by heating and stirring. The resultant product was neutralized with hydrochloric acid, diluted with chloroform, and then washed with water and brine. After solid was filtered by celite, the solvent was distilled away to obtain a compound represented by Formula (I-7-3).

The compound represented by Formula (I-7-3), triethylamine, and tetrahydrofuran were put into a reaction container. With ice cooling, ethyl chloroformate was dropped, followed by stirring at room temperature. The precipitate was filtered to obtain a solution. Sodium borohydride and tetrahydrofuran were put into another reaction container under a nitrogen atmosphere. With ice cooling, the solution was dropped, followed by stirring. A mixed liquid of methanol and water was dropped, followed by further stirring. After the addition of hydrochloric acid, extraction was performed with ethyl acetate. Purification was performed by column chromatography (alumina) to obtain a compound represented by Formula (I-7-4).

The compound represented by Formula (I-7-4), pyridine, and dichloromethane were put into a reaction container under a nitrogen atmosphere. With ice cooling, methanesulfonyl chloride was dropped, followed by stirring at room temperature. After ordinary post-treatment was performed, purification was performed by column chromatography (silica gel) to obtain a compound represented by Formula (I-7-5).

The compound represented by Formula (I-7-5), a compound represented by Formula (I-7-6), potassium carbonate, and N, N-dimethylformamide were put into a reaction container, followed by heating and stirring. The resultant product was diluted with dichloromethane, and then washed with water and brine. Purification was performed by column chromatography (alumina) to obtain a compound represented by Formula (I-7-7).

The compound represented by Formula (I-7-7), tetrahydrofuran, methanol, and concentrated hydrochloric acid were put into a reaction container, followed by stirring. After ordinary post-treatment was performed, drying was performed to obtain a compound represented by Formula (I-7-8).

The compound represented by Formula (I-7-8), a compound represented by Formula (I-7-9), potassium carbonate, and N, N-dimethylformamide were put into a reaction container, followed by heating and stirring. The resultant product was diluted with dichloromethane, and then washed with water and brine. Purification was performed by column chromatography (silica gel) to obtain a compound represented by Formula (I-7-10).

The compound represented by Formula (I-7-10), dichloromethane, and trifluoroacetic acid were put into a reaction container, followed by stirring. After dichloromethane was distilled away, diisopropyl ether was added, and the precipitated solid was filtered. The solid was washed with diisopropyl ether and dried to obtain a compound represented by Formula (I-7-11).

The compound represented by Formula (I-7-11), a compound represented by Formula (I-7-12), N,N-dimethylaminopyridine, and dichloromethane were put into a reaction container. With ice cooling, diisopropylcarbodiimide was dropped, followed by stirring at room temperature. The precipitate was filtered, and then washed with hydrochloric acid, water, and brine. Purification was performed by column chromatography (silica gel) and recrystallization to obtain a compound represented by Formula (I-7-13).

A compound represented by Formula (I-7) was obtained in the same manner as in Example 1.

LCMS: 1058 [M+1]

(Example 8) Preparation of Compound Represented by Formula (I-8)

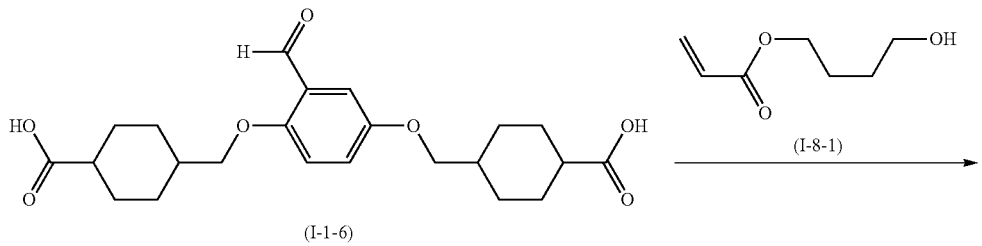

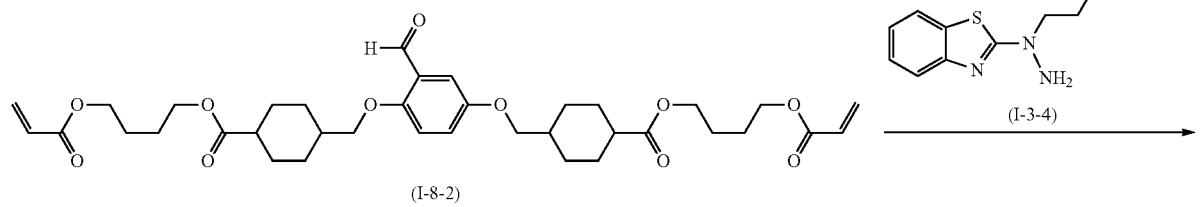

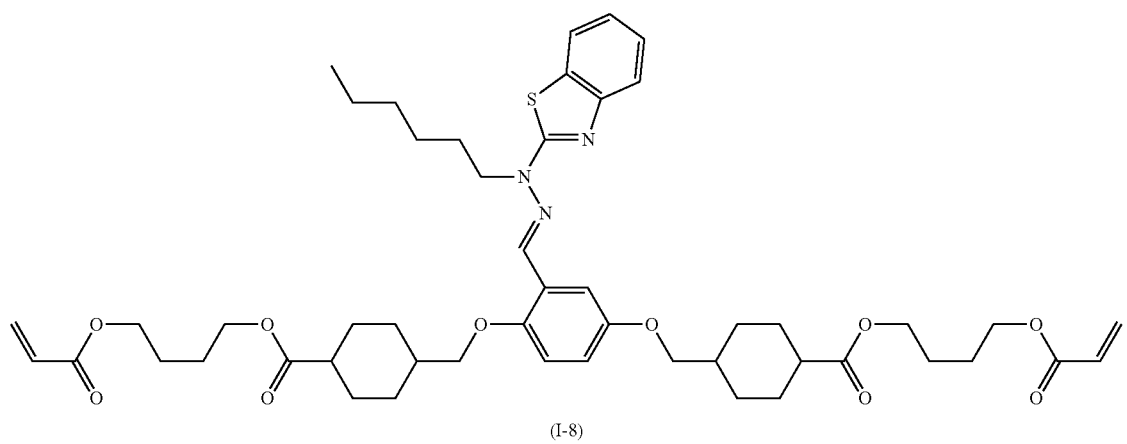

The compound represented by Formula (I-1-6), a compound represented by Formula (I-8-1), N,N-dimethylaminopyridine, and dichloromethane were put into a reaction container. With ice cooling, diisopropylcarbodiimide was dropped, followed by stirring at room temperature. The precipitate was filtered, and then washed with hydrochloric acid, water, and brine. Purification was performed by column chromatography (silica gel) and recrystallization to obtain a compound represented by Formula (I-8-2).

A compound represented by Formula (I-8) was obtained in the same manner as in Example 3.

LCMS: 902 [M+1]

(Example 9) Preparation of Compound Represented by Formula (I-9)

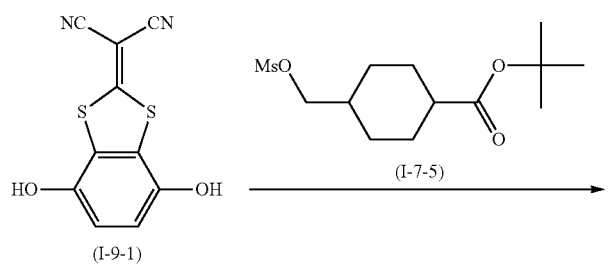

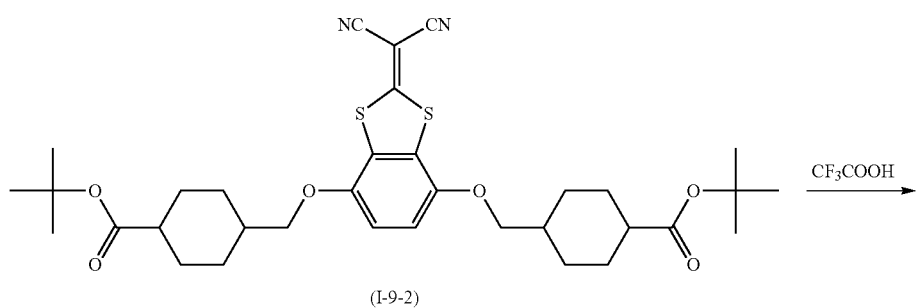

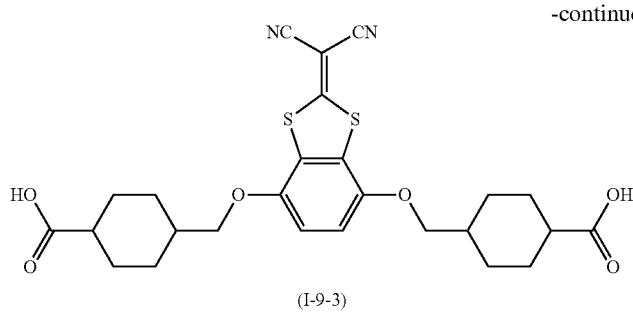
(I-9-3)

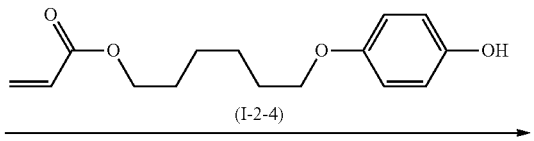
(I-2-4)

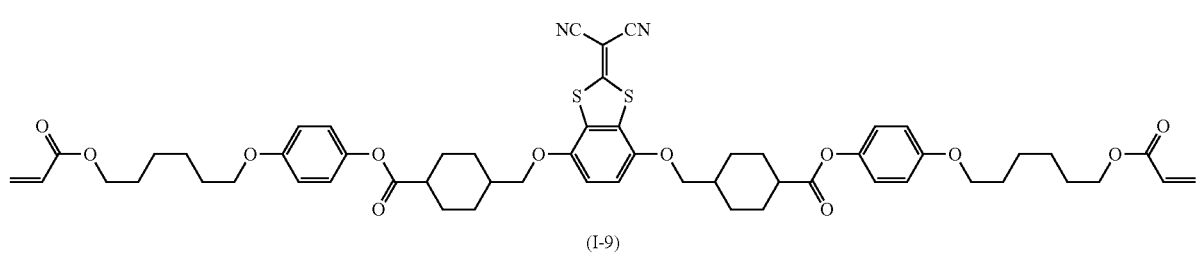
(I-9)

A compound represented by Formula (I-9-1) was prepared by ' ' the method described in JP-A-2008-107767. The compound represented by Formula (I-9-1), the compound represented by Formula (I-7-5), potassium carbonate, and N,N-dimethylformamide were put into a reaction container, followed by heating and stirring. The resultant product was diluted with dichloromethane, and then washed with water and brine. Purification was performed by column chromatography (silica gel) to obtain a compound represented by Formula (I-9-2).

The compound represented by Formula (I-9-2), dichloromethane, and trifluoroacetic acid were put into a reaction container, followed by stirring. After dichloromethane was distilled away, diisopropyl ether was added, and the precipitated solid was filtered. The solid was washed with diisopropyl ether and dried to obtain a compound represented by Formula (I-9-3).

The compound represented by Formula (I-9-3), the compound represented by Formula (I-2-4), N,N-dimethylaminopyridine, and dichloromethane were put into a reaction container. With ice cooling, diisopropylcarbodiimide was dropped, followed by stirring at room temperature. The precipitate was filtered, and then washed with hydrochloric acid, water, and brine. Purification was performed by column chromatography (silica gel) and recrystallization to obtain a compound represented by Formula (I-9).

LCMS: 1021 [M+1]

(Example 10) Preparation of Compound Represented by Formula (I-10)

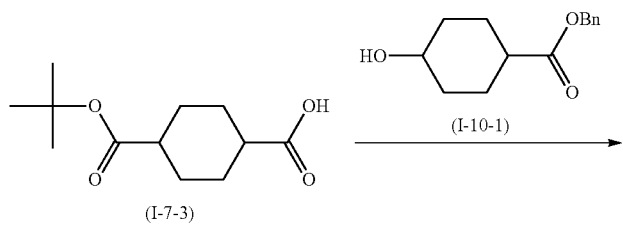
(I-7-3)    (I-10-1)

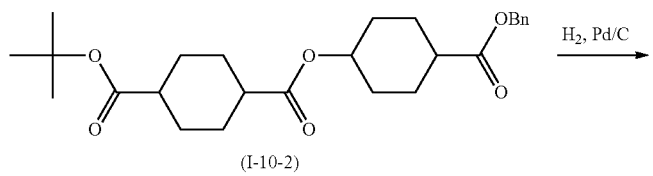
(I-10-2)

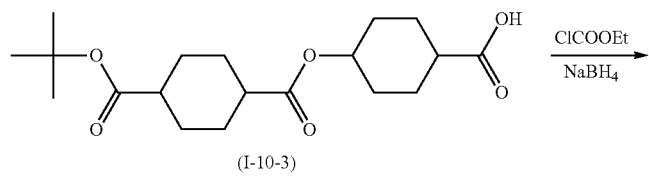
(I-10-3)

-continued
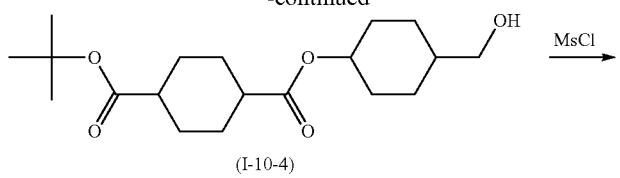
(I-10-4)
MsCl →
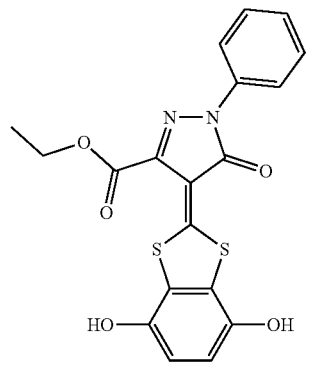
(I-10-6)
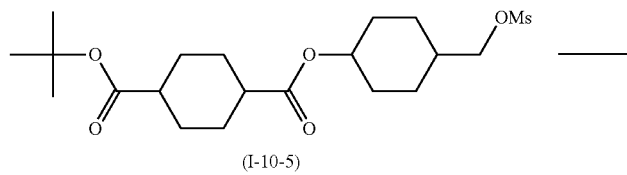
(I-10-5)
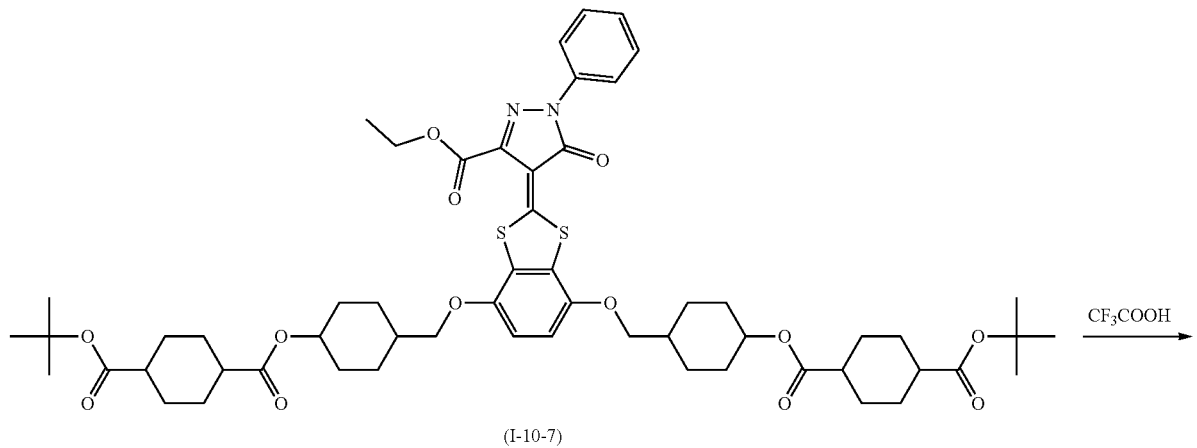
(I-10-7)
CF₃COOH →
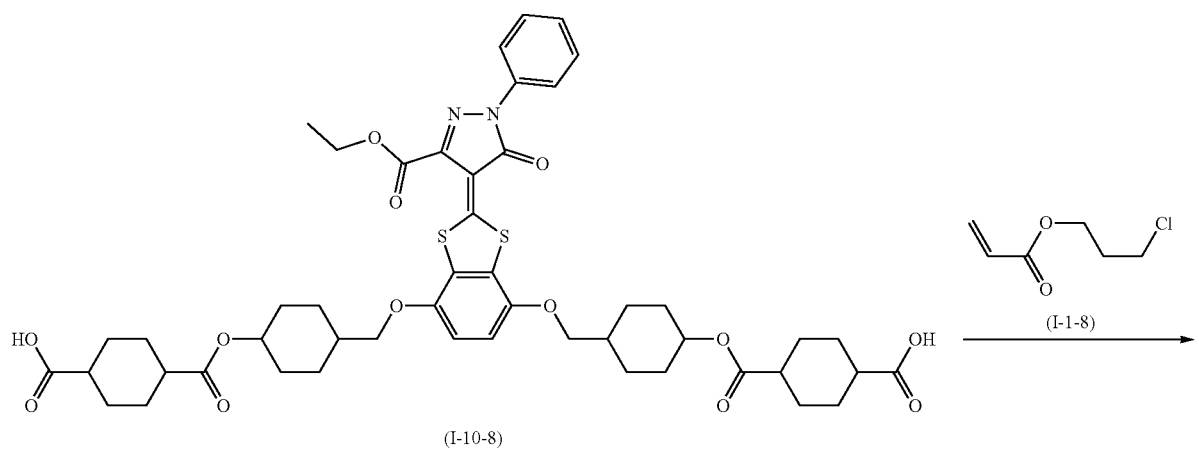
(I-10-8)
(I-1-8) →

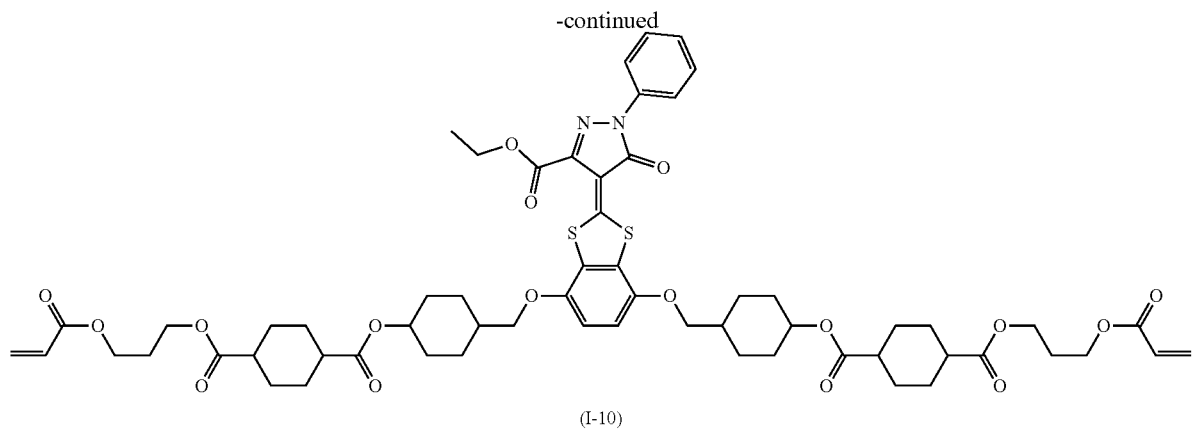

(I-10)

A compound represented by Formula (I-10-1) was prepared by the method described in JP-A-2009-179563. The compound represented by Formula (I-7-3), the compound represented by Formula (I-10-1), N, N-dimethylaminopyridine, and dichloromethane were put into a reaction container. With ice cooling, diisopropylcarbodiimide was dropped, followed by stirring at room temperature. The precipitate was filtered, and then washed with hydrochloric acid, water, and brine. Purification was performed by column chromatography (silica gel) and recrystallization to obtain a compound represented by Formula (I-10-2).

The compound represented by Formula (I-10-2), tetrahydrofuran, ethanol, and 5% palladium carbon were put into an autoclave, followed by heating and stirring at a hydrogen pressure of 0.5 MPa. After a catalyst is filtered, the solvent was distilled away and dried to obtain a compound represented by Formula (I-10-3).

The compound represented by Formula (I-10-3), triethylamine, and tetrahydrofuran were put into a reaction container. With ice cooling, ethyl chloroformate was dropped, followed by stirring at room temperature. The precipitate was filtered to obtain a solution. Sodium borohydride and tetrahydrofuran were put into another reaction container under a nitrogen atmosphere. With ice cooling, the solution was dropped, followed by stirring. A mixed liquid of methanol and water was dropped, followed by further stirring. After the addition of hydrochloric acid, extraction was performed with ethyl acetate. Purification was performed by column chromatography (alumina) to obtain a compound represented by Formula (I-10-4).

The compound represented by Formula (I-10-4), pyridine, and dichloromethane were put into a reaction container under a nitrogen atmosphere. With ice cooling, methanesulfonyl chloride was dropped, followed by stirring at room temperature. After ordinary post-treatment was performed, purification was performed by column chromatography (silica gel) to obtain a compound represented by Formula (I-10-5).

A compound represented by Formula (I-10-6) was prepared by the method described in JP-A-2009-179563. The compound represented by Formula (I-10-5), the compound represented by Formula (I-10-6), cesium carbonate, and dimethyl sulfoxide were put into a reaction container, followed by heating and stirring. The resultant product was diluted with dichloromethane, and then washed with water and brine. Purification was performed by column chromatography (silica gel) to obtain a compound represented by Formula (I-10-7). The compound represented by Formula (I-10-7), dichloromethane, and trifluoroacetic acid were put into a reaction container, followed by stirring. After dichloromethane was distilled away, diisopropyl ether was added, and the precipitated solid was filtered. The solid was washed with diisopropyl ether and dried to obtain a compound represented by Formula (I-10-8).

The compound represented by Formula (I-10-8), the compound represented by Formula (I-1-8), cesium carbonate, and dimethyl sulfoxide were put into a reaction container, followed by heating and stirring. The resultant product was diluted with dichloromethane, and then washed with water and brine.

Purification was performed by column chromatography (silica gel) and recrystallization to obtain a compound represented by Formula (I-10).

LCMS: 1171 [M+1]

(Example 11) Preparation of Compound Represented by Formula (I-11)

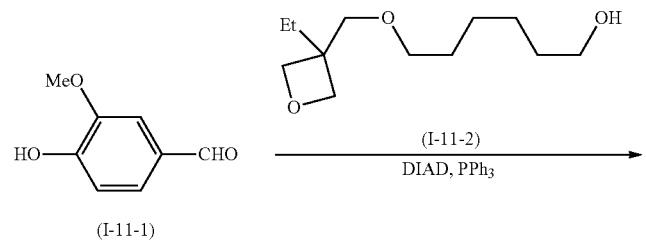

-continued
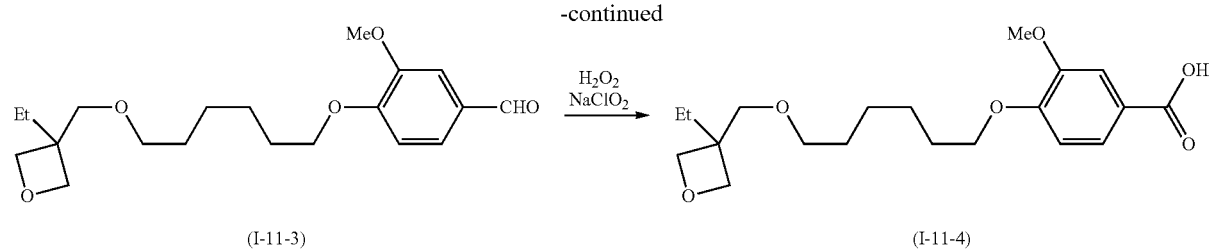
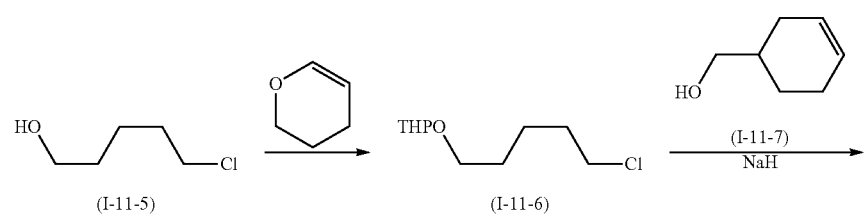
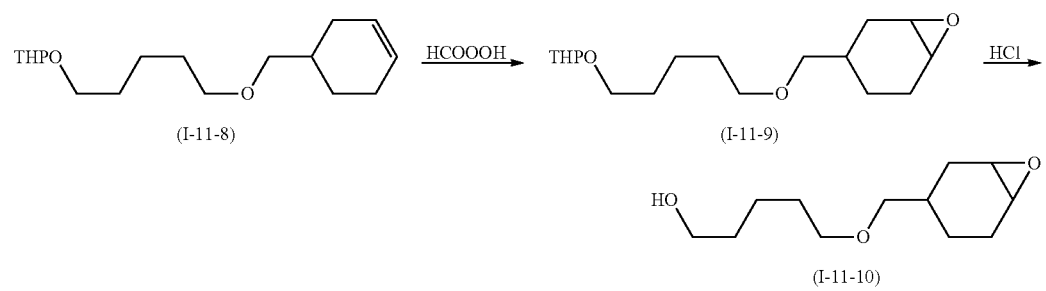
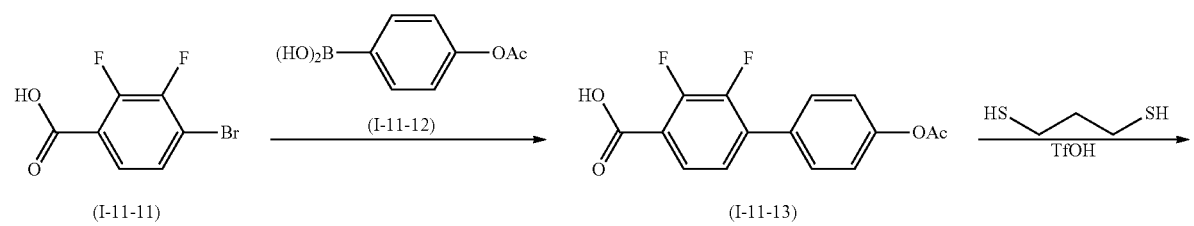
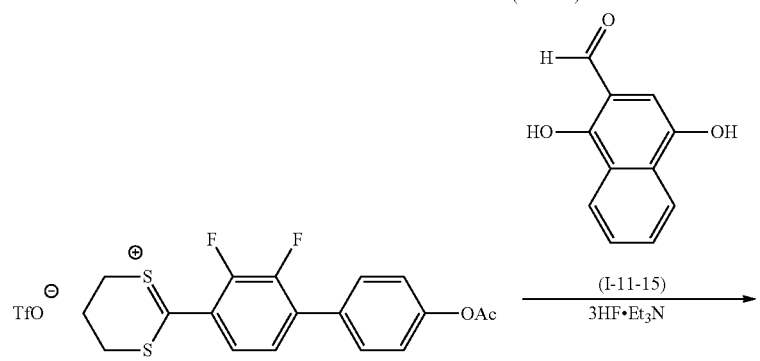
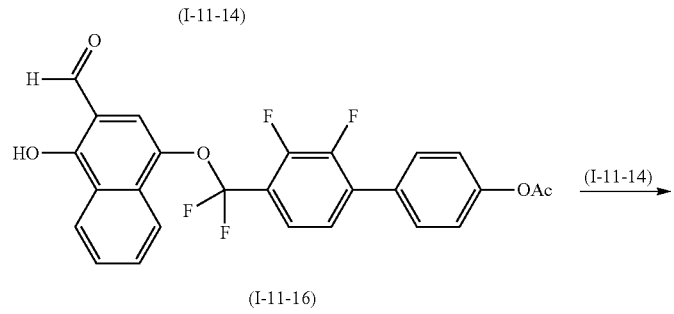

215
-continued
216
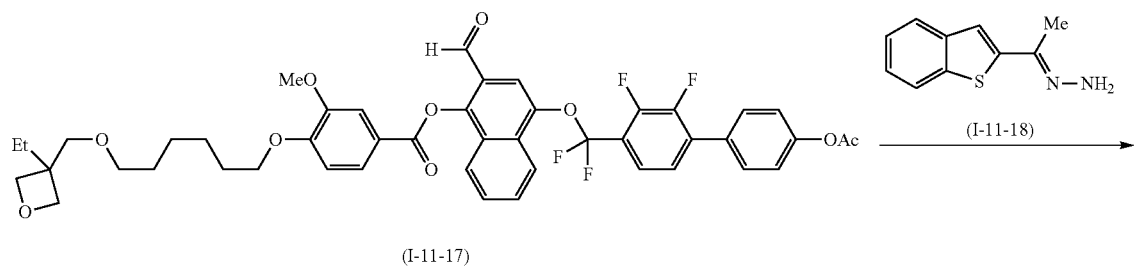
(I-11-17)              (I-11-18)
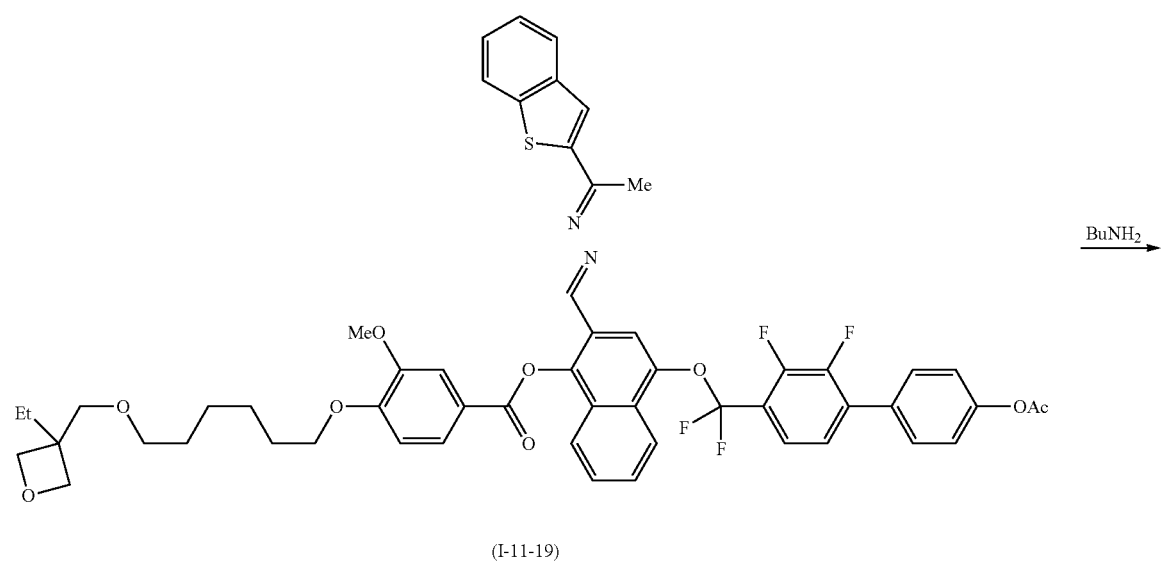
(I-11-19)
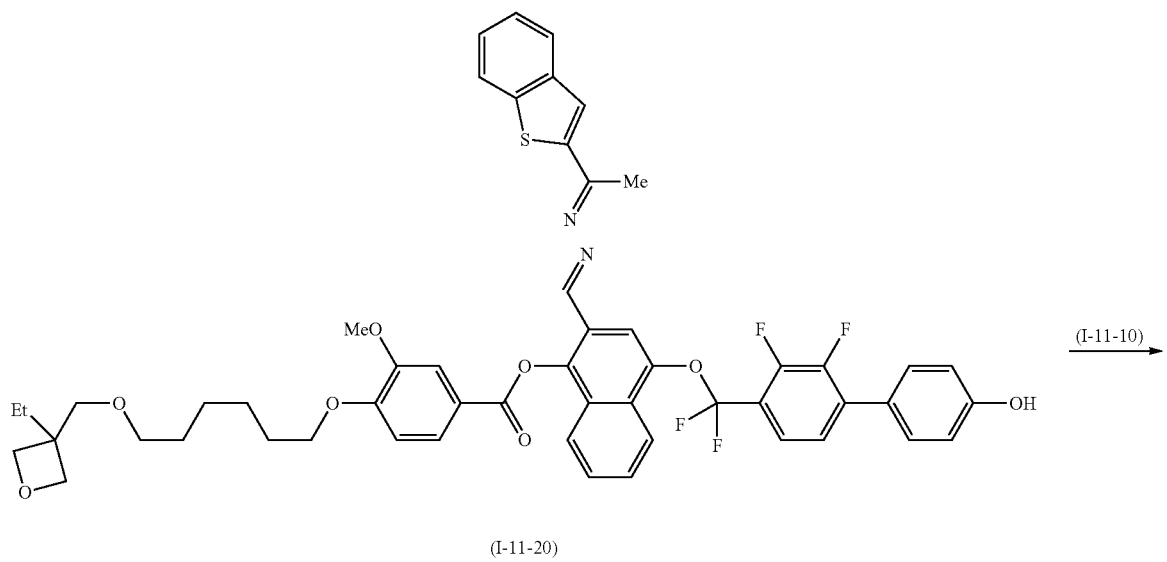
(I-11-20)                              (I-11-10)

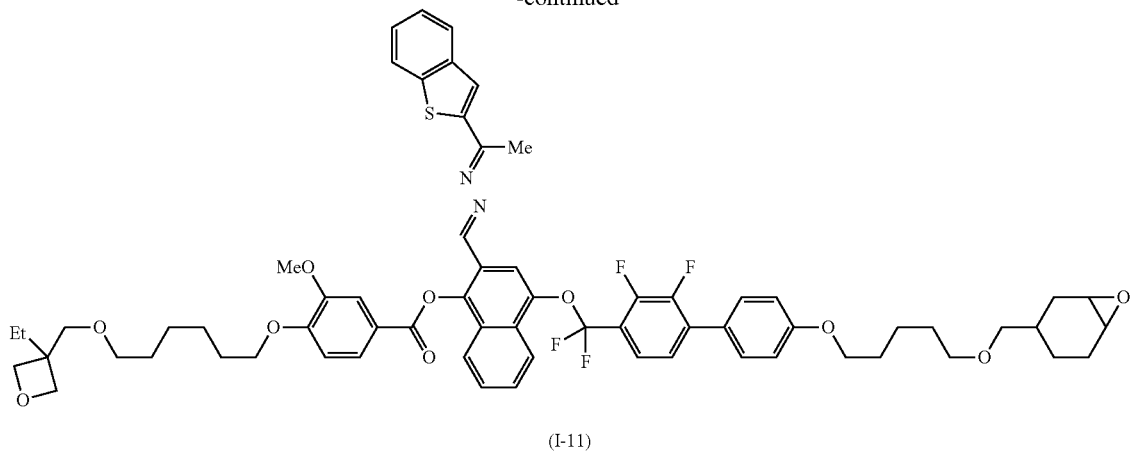

(I-11)

A compound represented by Formula (I-11-2) was obtained by the method described in the journal Macromolecular Chemistry and Physics (pages 531-541, No. 7, Vol. 210, 2009). A compound represented by Formula (I-11-1), the compound represented by Formula (I-11-2), triphenylphosphine, and tetrahydrofuran were added under a nitrogen atmosphere. With ice cooling, diisopropyl azodicarboxylate was added, followed by stirring. After ordinary post-treatment was performed, purification was performed by column chromatography to obtain a compound represented by Formula (I-11-3).

The compound represented by Formula (I-11-3), sodium dihydrogen phosphate dihydrate, methanol, water, and a hydrogen peroxide solution were put into a reaction container. An aqueous sodium chlorite solution was dropped, followed by heating and stirring. Cooling was performed by the addition of water, and the precipitate was filtered. Drying is performed to obtain a compound represented by Formula (I-11-4).

A compound represented by Formula (I-11-5), pyridinium p-toluenesulfonate, and dichloromethane were put into a reaction container under a nitrogen atmosphere. With ice cooling, 3,4-dihydro-2H-pyran was added, followed by stirring. After ordinary post-treatment was performed, purification was performed by column chromatography to obtain a compound represented by Formula (I-11-6).

A compound represented by Formula (I-11-7), tetrahydrofuran, and sodium hydride were put into a reaction container, followed by stirring. A tetrahydrofuran solution of the compound represented by Formula (I-11-6) was dropped, followed by heating and stirring. Water was dropped. After ordinary post-treatment was performed, purification was performed by column chromatography to obtain a compound represented by Formula (I-11-8).

Formic acid and hydrogen peroxide were put into a reaction container, followed by stirring. A dichloromethane solution of the compound represented by Formula (I-11-8) was dropped, followed by heating and stirring. After ordinary post-treatment was performed, purification was performed by column chromatography to obtain a compound represented by Formula (I-11-9).

The compound represented by Formula (I-11-9), methanol, tetrahydrofuran, and concentrated hydrochloric acid were put into a reaction container, followed by heating and stirring. After ordinary post-treatment was performed, purification was performed by column chromatography to obtain a compound represented by Formula (I-11-10).

A compound represented by Formula (I-11-11), a compound represented by Formula (I-11-12), potassium carbonate, tetrahydrofuran, water, and tetrakis (triphenylphosphine) palladium (0) were put into a reaction container under a nitrogen atmosphere, followed by heating and stirring. After ordinary post-treatment was performed, purification was performed by column chromatography (silica gel) to obtain a compound represented by Formula (I-11-13).

The compound represented by Formula (I-11-13), 1,3-propanedithiol, and trifluoroacetic acid were put into a reaction container under a nitrogen atmosphere, followed by heating and stirring. With cooling, tert-butyl methyl ether was added, and the precipitate was filtered. The resultant product was washed with tert-butyl methyl ether and dried to obtain a compound represented by Formula (I-11-14).

The compound represented by Formula (I-11-14), a compound represented by Formula (I-11-15), triethylamine trihydrofluoride, and dichloromethane were put into a reaction container cooled to −65° C. under a nitrogen atmosphere. Bromine was dropped, followed by stirring. An aqueous sodium hydroxide solution was added at room temperature, ordinary post-treatment was performed, and then purification was performed by column chromatography (silica gel) to obtain a compound represented by Formula (I-11-16).

The compound represented by Formula (I-11-16), the compound represented by Formula (I-11-4), N,N-dimethylaminopyridine, and dichloromethane were put into a reaction container. With ice cooling, diisopropylcarbodiimide was dropped, followed by stirring at room temperature. The precipitate was filtered, and then washed with hydrochloric acid, water, and brine. Purification was performed by column chromatography (silica gel) and recrystallization to obtain a compound represented by Formula (I-11-17).

A compound represented by Formula (I-11-18) was prepared by the method described in WO2012-141245A1. The compound represented by Formula (I-11-17), the compound represented by Formula (I-11-18), (±)-10-camphorsulfonic acid, tetrahydrofuran, and ethanol were put into a reaction container, followed by heating and stirring. The solvent was concentrated, and purification was performed by column chromatography (silica gel) and recrystallization to obtain a compound represented by Formula (I-11-19).

The compound represented by Formula (I-11-19), tetrahydrofuran, and butylamine were put into a reaction container, followed by stirring. After ordinary post-treatment was performed, purification was performed by column chromatography (silica gel) to obtain a compound represented by Formula (I-11-20).

The compound represented by Formula (I-11-20), the compound represented by Formula (I-11-10), triphenylphosphine, and tetrahydrofuran were added under a nitrogen atmosphere. With ice cooling, diisopropyl azodicarboxylate was added, followed by stirring. After ordinary post-treatment was performed, purification was performed by column chromatography (silica gel) and recrystallization to obtain a compound represented by Formula (I-11).

LCMS: 1159 [M+1]

(Example 12) Preparation of Compound Represented by Formula (I-12)

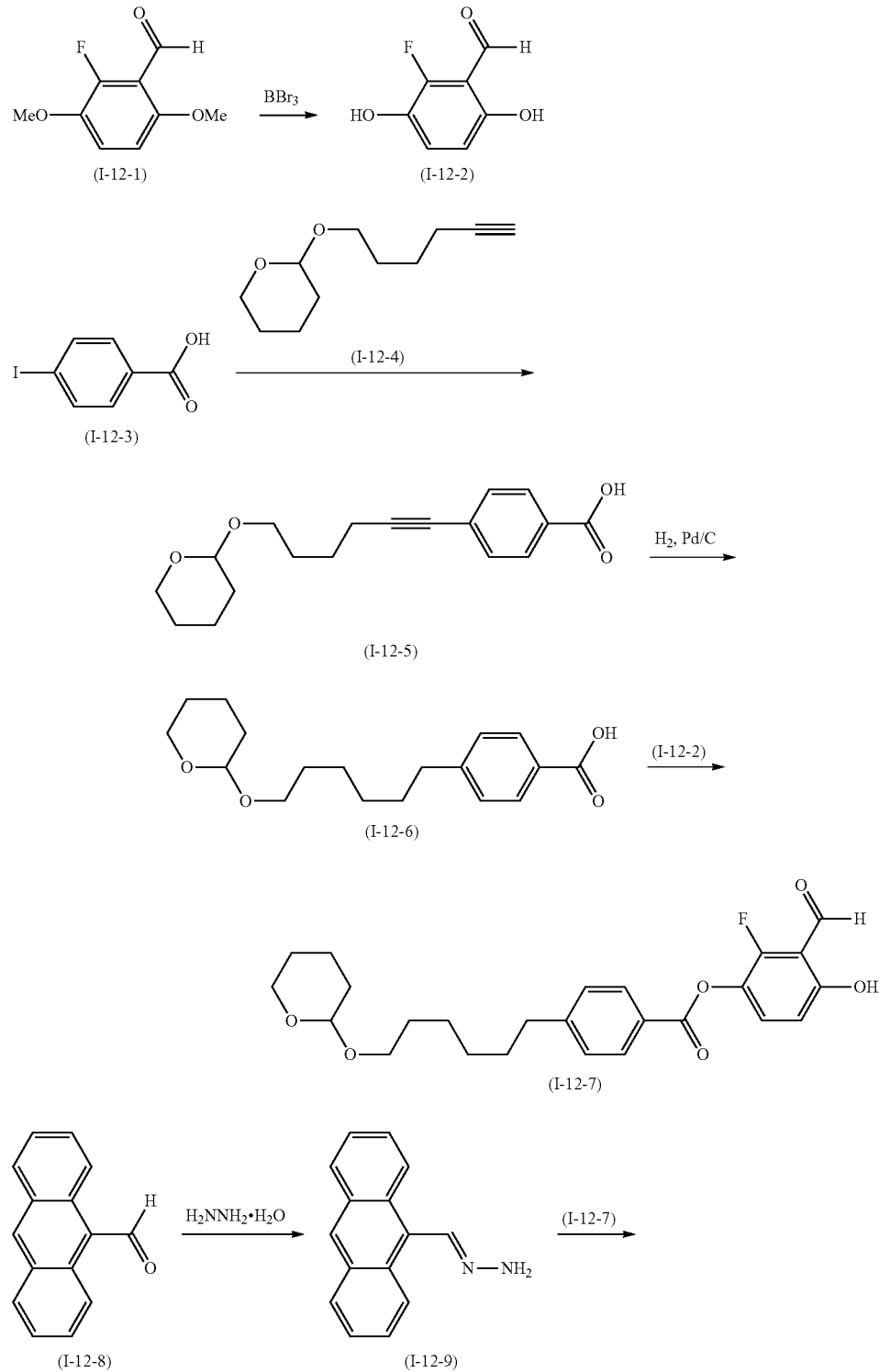

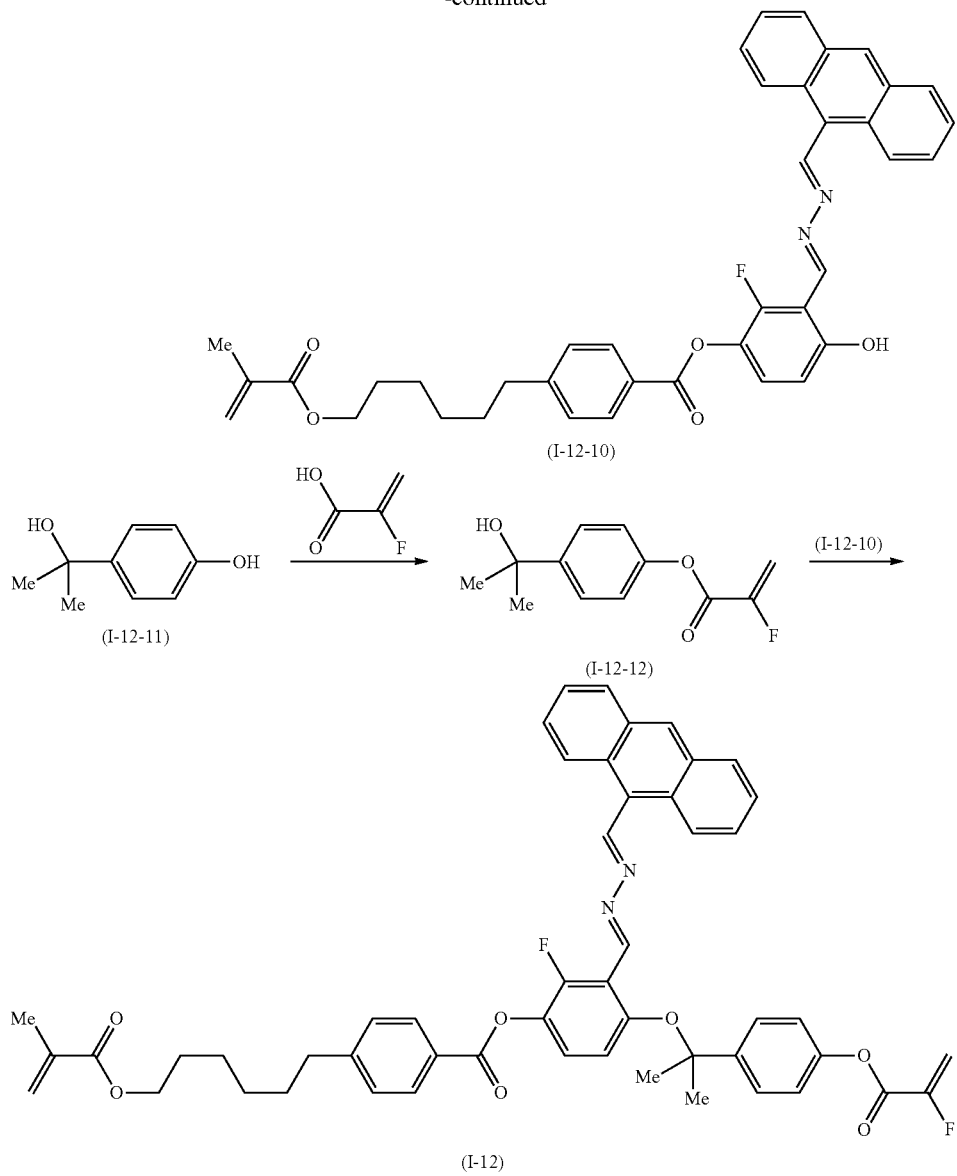

A compound represented by Formula (I-12-1) was obtained by the method described in the journal Bioorganic & Medicinal Chemistry Letters (pages 1675-1681, No. 6, Vol. 15, 2005). The compound represented by Formula (I-12-1) and dichloromethane were put into a reaction container. The reaction container was cooled to −78° C., and boron tribromide was dropped, followed by stirring. After ordinary post-treatment was performed, purification was performed by column chromatography to obtain a compound represented by Formula (I-12-2).

A compound represented by Formula (I-12-3), a compound represented by Formula (I-12-4), copper iodide (I), tetrakis (triphenylphosphine) palladium (0), triethylamine, and N,N-dimethylformamide were put into a reaction container under a nitrogen atmosphere, followed by heating and stirring. After ordinary post-treatment was performed, purification was performed by column chromatography to obtain a compound represented by Formula (I-12-5).

The compound represented by Formula (I-12-5), 5% palladium carbon, and tetrahydrofuran were put into a reaction container. Stirring was performed under a hydrogen atmosphere. A catalyst was filtered, and then purification was performed by column chromatography to obtain a compound represented by Formula (I-12-6).

The compound represented by Formula (I-12-6), the compound represented by Formula (I-12-2), N,N-dimethylaminopyridine, and dichloromethane were put into a reaction container. Diisopropylcarbodiimide was dropped, followed by stirring. After ordinary post-treatment was performed, purification was performed by column chromatography and recrystallization to obtain a compound represented by Formula (I-12-7).

Hydrazine monohydrate and ethanol were put into a reaction container. A tetrahydrofuran solution of a compound represented by Formula (I-12-8) was added, followed by stirring. After ordinary post-treatment was performed, purification was performed by recrystallization to obtain a compound represented by Formula (I-12-9).

The compound represented by Formula (I-12-9), the compound represented by Formula (I-12-7), (±)-10-camphorsulfonic acid, tetrahydrofuran, and ethanol were put into a reaction container, followed by stirring. After ordinary post-treatment was performed, purification was performed by column chromatography (silica gel) to obtain a compound represented by Formula (I-12-10).

A compound represented by Formula (I-12-11), 2-fluoroacrylic acid, N,N-dimethylaminopyridine, and dichloromethane were put into a reaction container. Diisopropylcarbodiimide was dropped, followed by stirring. After ordinary post-treatment was performed, purification was performed by column chromatography (silica gel) to obtain a compound represented by Formula (I-12-12).

The compound represented by Formula (I-12-12), the compound represented by Formula (I-12-10), triphenylphosphine, and tetrahydrofuran were added under a nitrogen atmosphere. With ice cooling, diisopropyl azodicarboxylate was added, followed by stirring. After ordinary post-treatment was performed, purification was performed by column chromatography (silica gel) and recrystallization to obtain a compound represented by Formula (I-12).

LCMS: 837 [M+1]

(Example 13) Preparation of Compound Represented by Formula (I-13)

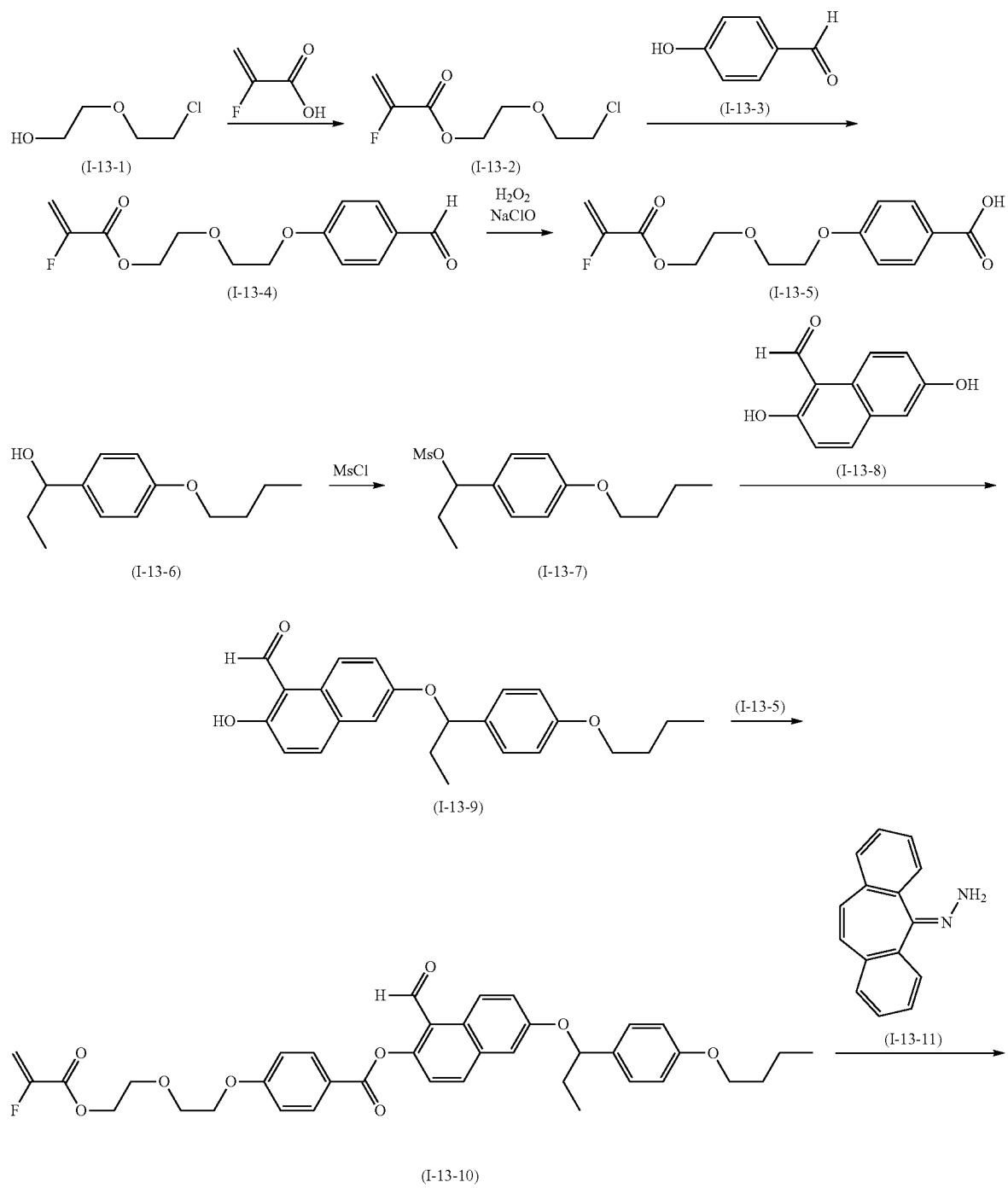

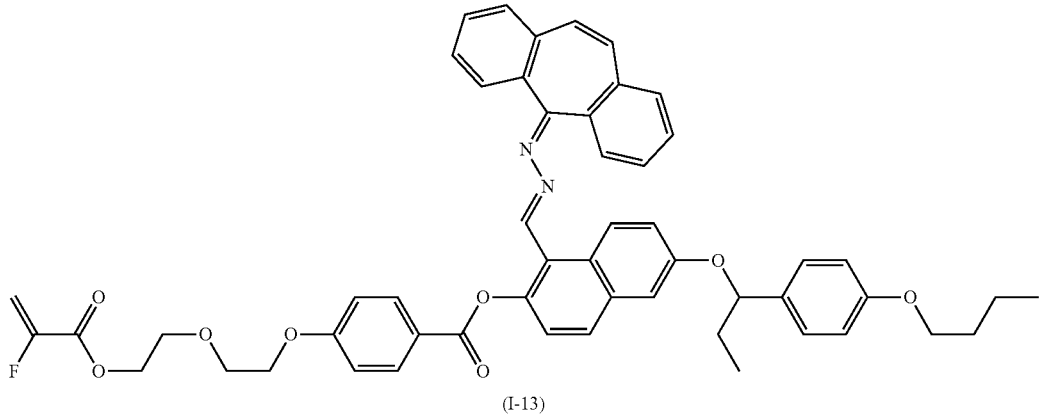

(I-13)

2-fluoroacrylic acid, a compound represented by Formula (I-13-1), N, N-dimethylaminopyridine, and dichloromethane were put into a reaction container under a nitrogen atmosphere. With ice cooling, diisopropylcarbodiimide was added, followed by stirring. After ordinary post-treatment was performed, purification was performed by column chromatography (silica gel) to obtain a compound represented by Formula (I-13-2).

The compound represented by Formula (I-13-2), a compound represented by Formula (I-13-3), cesium carbonate, and dimethyl sulfoxide were put into a reaction container, followed by heating and stirring. After ordinary post-treatment was performed, purification was performed by column chromatography (silica gel) to obtain a compound represented by Formula (I-13-4).

The compound represented by Formula (I-13-4), sodium dihydrogen phosphate dihydrate, methanol, water, and a hydrogen peroxide solution were put into a reaction container. An aqueous sodium chlorite solution was dropped, followed by heating and stirring. Cooling was performed by the addition of water, and the precipitate was filtered. Drying was per formed to obtain a compound represented by Formula (I-13-5).

A compound represented by Formula (I-13-6), pyridine, and dichloromethane were put into a reaction container under a nitrogen atmosphere. With ice cooling, methanesulfonyl chloride was dropped, followed by stirring at room temperature. After ordinary post-treatment was performed, purification was performed by column chromatography (silica gel) to obtain a compound represented by Formula (I-13-7).

The compound represented by Formula (I-13-7), a compound represented by Formula (I-13-8), cesium carbonate, and dimethyl sulfoxide were put into a reaction container, followed by heating and stirring. The resultant product was diluted with dichloromethane and then washed with water and brine. Purification was performed by column chromatography (silica gel) to obtain a compound represented by Formula (I-13-9).

The compound represented by Formula (I-13-9), the compound represented by Formula (I-13-5), N,N-dimethylaminopyridine, and dichloromethane were put into a reaction container. With ice cooling, diisopropylcarbodiimide was dropped, followed by stirring at room temperature. The precipitate was filtered, and then washed with hydrochloric acid, water, and brine. Purification was performed by column chromatography (silica gel) and recrystallization to obtain a compound represented by Formula (I-13-10).

A compound represented by Formula (I-13-11) was obtained by the method described in WO2012-14124 5A1. The compound represented by Formula (I-13-10), the compound represented by Formula (I-13-11), (±)-10-camphorsulfonic acid, tetrahydrofuran, and ethanol were put into a reaction container, followed by stirring. After ordinary post-treatment was performed, purification was performed by column chromatography (silica gel) and recrystallization to obtain a compound represented by Formula (I-13).

LCMS: 861 [M+1]

(Example 14) Preparation of Compound Represented by Formula (I-14)

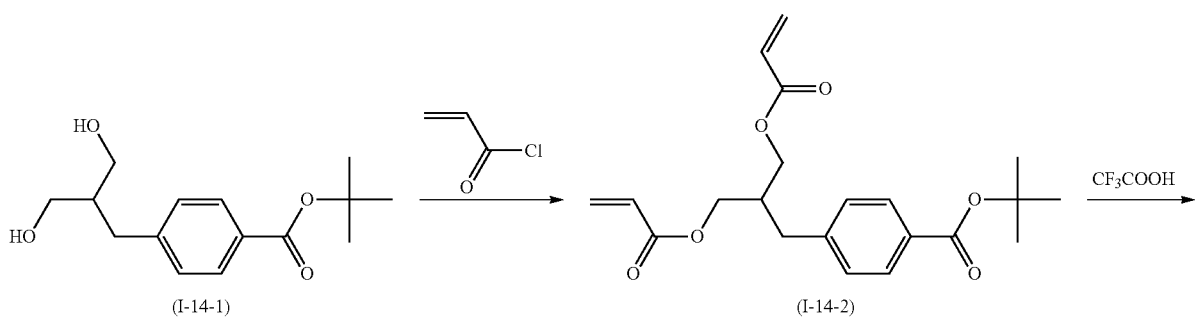

-continued
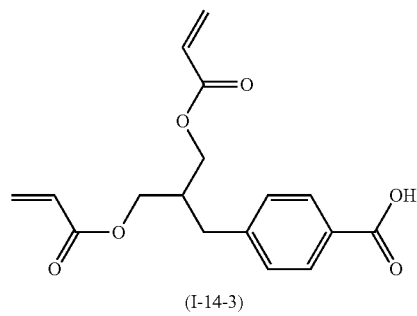
(I-14-3)
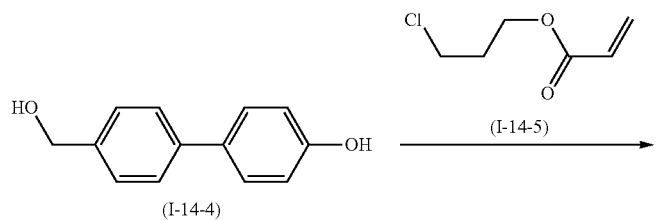
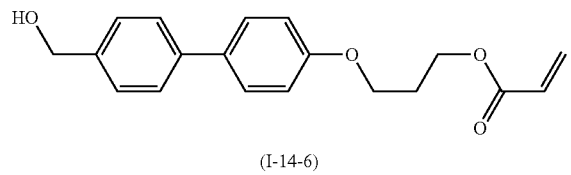
(I-14-6)
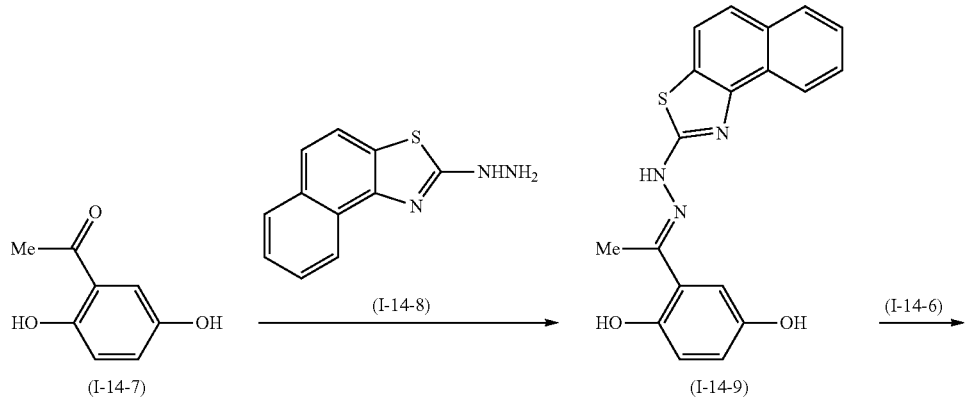
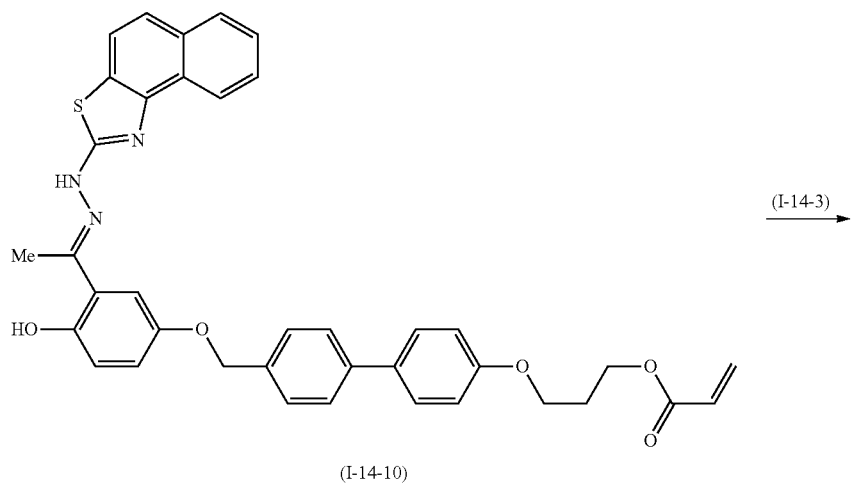
(I-14-10)

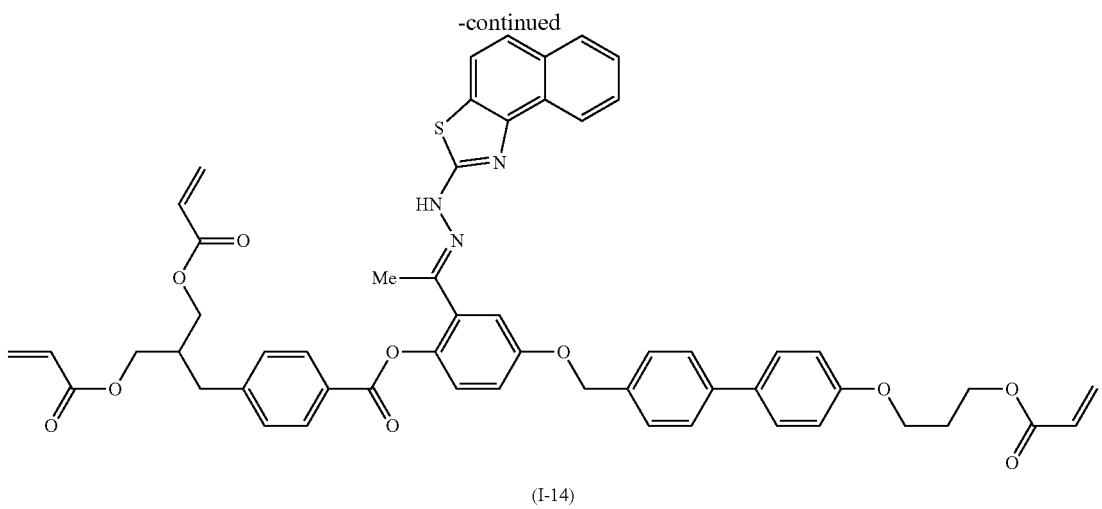

(I-14)

A compound represented by Formula (I-14-1) was obtained by the method described in WO2008-010985A1. The compound represented by Formula (I-14-1), N-ethyldiisopropylamine, and dichloromethane were put into a reaction container under a nitrogen atmosphere. With ice cooling, acryloyl chloride was added, followed by stirring. After ordinary post-treatment was performed, purification was performed by column chromatography (silica gel) to obtain a compound represented by Formula (I-14-2).

The compound represented by Formula (I-14-2) and dichloromethane were put into a reaction container. With ice cooling, trifluoroacetic acid was added, followed by stirring. After the solvent was distilled away, the resultant product was washed with water and dried to obtain a compound represented by Formula (I-14-3). A compound represented by Formula (I-14-4) was prepared by the method described in the journal European Journal of Organic Chemistry (pages 4482-4486, No. 21, 2014). The compound represented by Formula (I-14-4), a compound represented by Formula (I-14-5), cesium carbonate, and dimethyl sulfoxide were put into a reaction container, followed by heating and stirring. After ordinary post-treatment was performed, purification was performed by column chromatography (silica gel) to obtain a compound represented by Formula (I-14-6).

A compound represented by Formula (I-14-8) was prepared by the method described in WO2014/010325A1. A compound represented by Formula (I-14-7), the compound represented by Formula (I-14-8), tetrahydrofuran, and ethanol were put into a reaction container, followed by heating and stirring. The solvent was distilled away, and the resultant product was dried to obtain a compound represented by Formula (I-14-9).

The compound represented by Formula (I-14-9), the compound represented by Formula (I-14-6), triphenylphosphine, and tetrahydrofuran were added under a nitrogen atmosphere. With ice cooling, diisopropyl azodicarboxylate was added, followed by stirring. After ordinary post-treatment was performed, purification was performed by column chromatography (silica gel) to obtain a compound represented by Formula (I-14-10).

The compound represented by Formula (I-14-10), the compound represented by Formula (I-14-3), N,N-dimethylaminopyridine, and dichloromethane were put into a reaction container. With ice cooling, diisopropylcarbodiimide was dropped, followed by stirring at room temperature. The precipitate was filtered, and then washed with hydrochloric acid, water, and brine. Purification was performed by column chromatography (silica gel) and recrystallization to obtain a compound represented by Formula (I-14).

LCMS: 944 [M+1]

(Example 15) Preparation of Compound Represented by Formula (I-15)

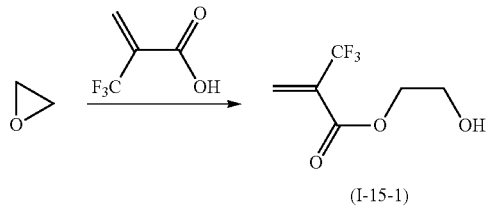

(I-15-1)

-continued
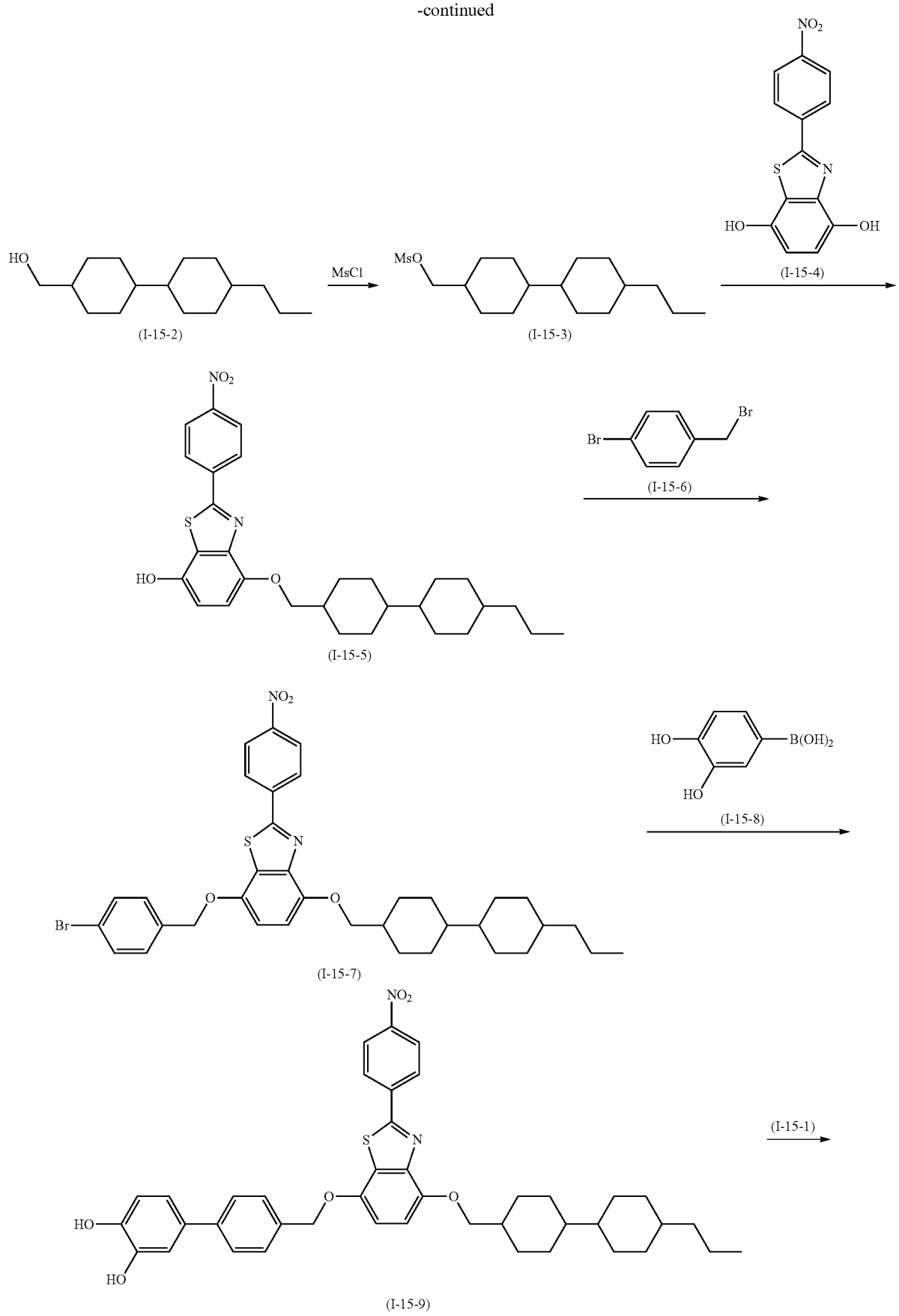

-continued

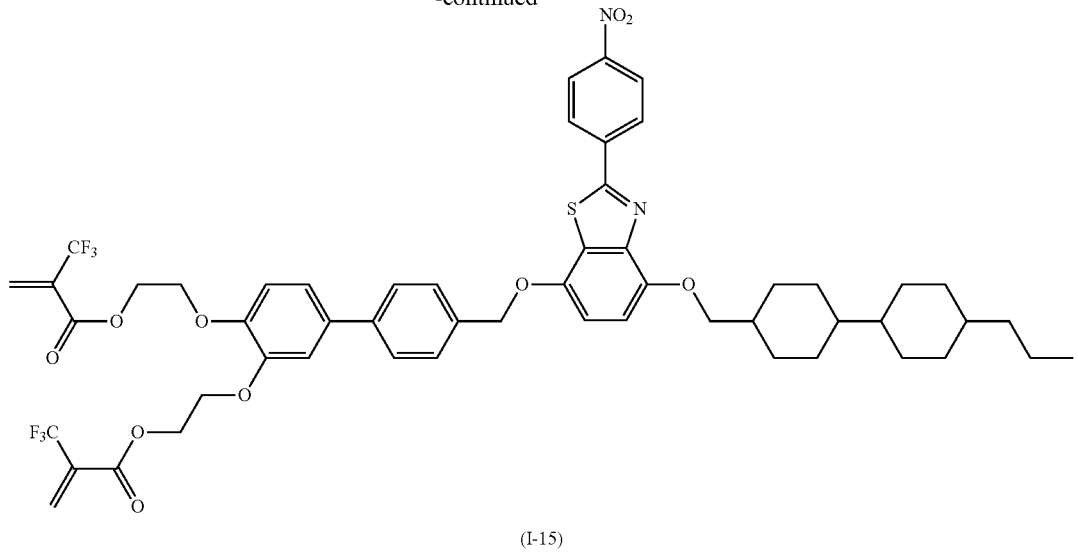

(I-15)

2-(trifluoromethyl) acrylate, ethylene oxide, and triethylamine were put into an autoclave, followed by heating and stirring. Reduced-pressure distillation was performed to obtain a compound represented by Formula (I-15-1).

A compound represented by Formula (I-15-2), pyridine, and dichloromethane were put into a reaction container under a nitrogen atmosphere. With ice cooling, methanesulfonyl chloride was dropped, followed by stirring at room temperature. After ordinary post-treatment was performed, purification was performed by column chromatography (silica gel) to obtain a compound represented by Formula (I-15-3).

The compound represented by Formula (I-15-3), a compound represented by Formula (I-15-4), cesium carbonate, and dimethyl sulfoxide were put into a reaction container, followed by heating and stirring. The resultant product was diluted with dichloromethane and then washed with water and brine. Purification was performed by column chromatography (silica gel) to obtain a compound represented by Formula (I-15-5).

The compound represented by Formula (I-15-5), a compound represented by Formula (I-15-6), cesium carbonate, and dimethyl sulfoxide were put into a reaction container, followed by heating and stirring. The resultant product was diluted with dichloromethane and then washed with water and brine. Purification was performed by column chromatography (silica gel) to obtain a compound represented by Formula (I-15-7).

The compound represented by Formula (I-15-7), a compound represented by Formula (I-15-8), potassium carbonate, tetrahydrofuran, water, and tetrakis (triphenylphosphine) palladium (0) were put into a reaction container under a nitrogen atmosphere, followed by heating and stirring. After ordinary post-treatment was performed, purification was performed by column chromatography (silica gel) to obtain a compound represented by Formula (I-15-9).

The compound represented by Formula (I-15-9), the compound represented by Formula (I-15-1), triphenylphosphine, and tetrahydrofuran were added under a nitrogen atmosphere. With ice cooling, diisopropyl azodicarboxylate was added, followed by stirring. After ordinary post-treatment was performed, purification was performed by column chromatography (silica gel) and recrystallization to obtain a compound represented by Formula (I-15).

LCMS: 1039 [M+1]

(Example 16) Preparation of Compound Represented by Formula (I-86)

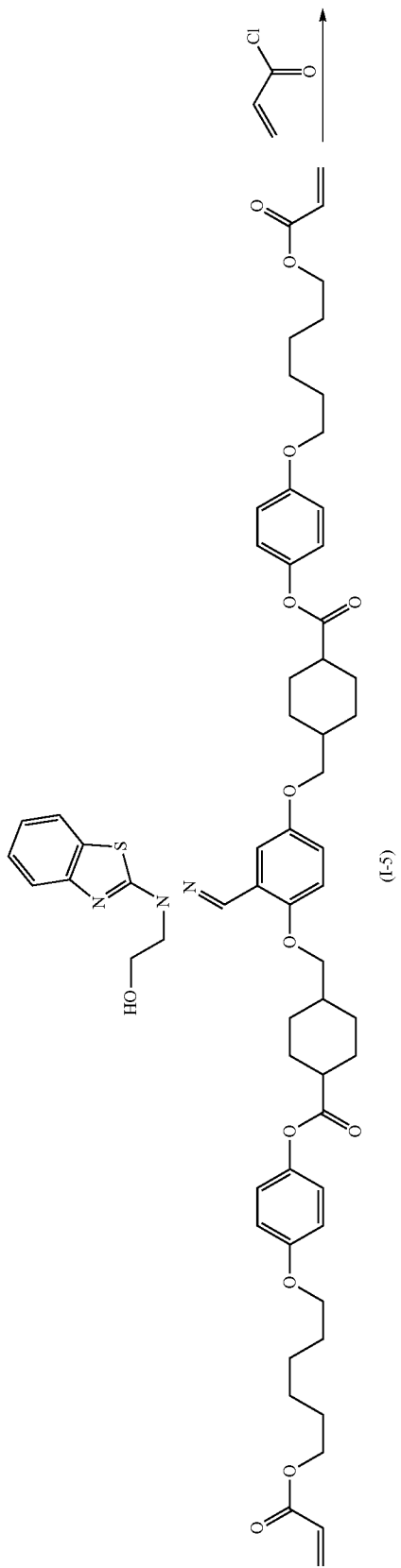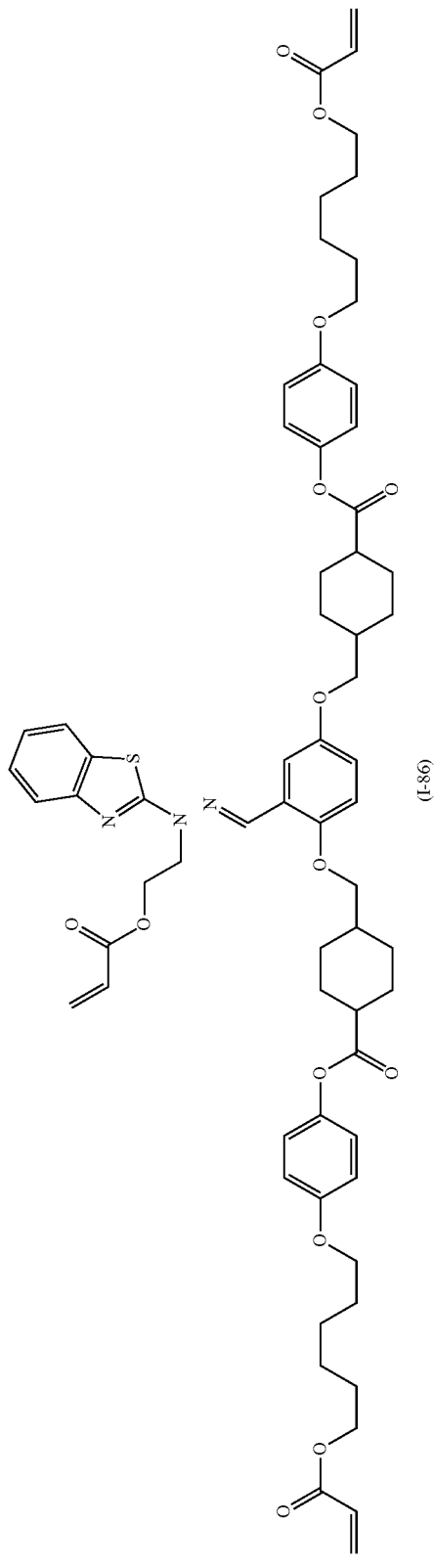

The compound represented by Formula (I-5), N-ethyldiisopropylamine, and dichloromethane were put into a reaction container under a nitrogen atmosphere. With ice cooling, acryloyl chloride was added, followed by stirring. After ordinary post-treatment was performed, purification was performed by column chromatography (silica gel) and recrystallization to obtain a compound represented by Formula (I-86).

Transition temperature (temperature rise rate 5° C./min) C 122 N 142 I $^1$H NMR (CDCl$_3$) δ 1.24 (m, 4H), 1.48 (m, 8H), 1.60-1.83 (m, 12H), 1.93 (m, 2H), 2.08 (t, 4H), 2.23 (m, AH), 2.54 (m, 2H), 3.86 (dd, 4H), 3.94 (t, 4H), 4.17 (t, 4H), 4.53 (t, 2H), 4.65 (t, 2H), 5.78 (dd, 1H), 5.82 (dd, 2H), 6.08 (dd, 1H), 6.12 (dd, 2H), 6.39 (dd, 1H), 6.40 (dd, 2H), 6.88 (m, 6H), 6.97 (dd, 4H), 7.16 (t, 1H), 7.34 (t, 1H), 7.54 (d, 1H), 7.66 (d, 1H), 7.70 (d, 1H), 8.36 (s, 1H) ppm.

(Example 17) Preparation of Compound Represented by Formula (I-89)

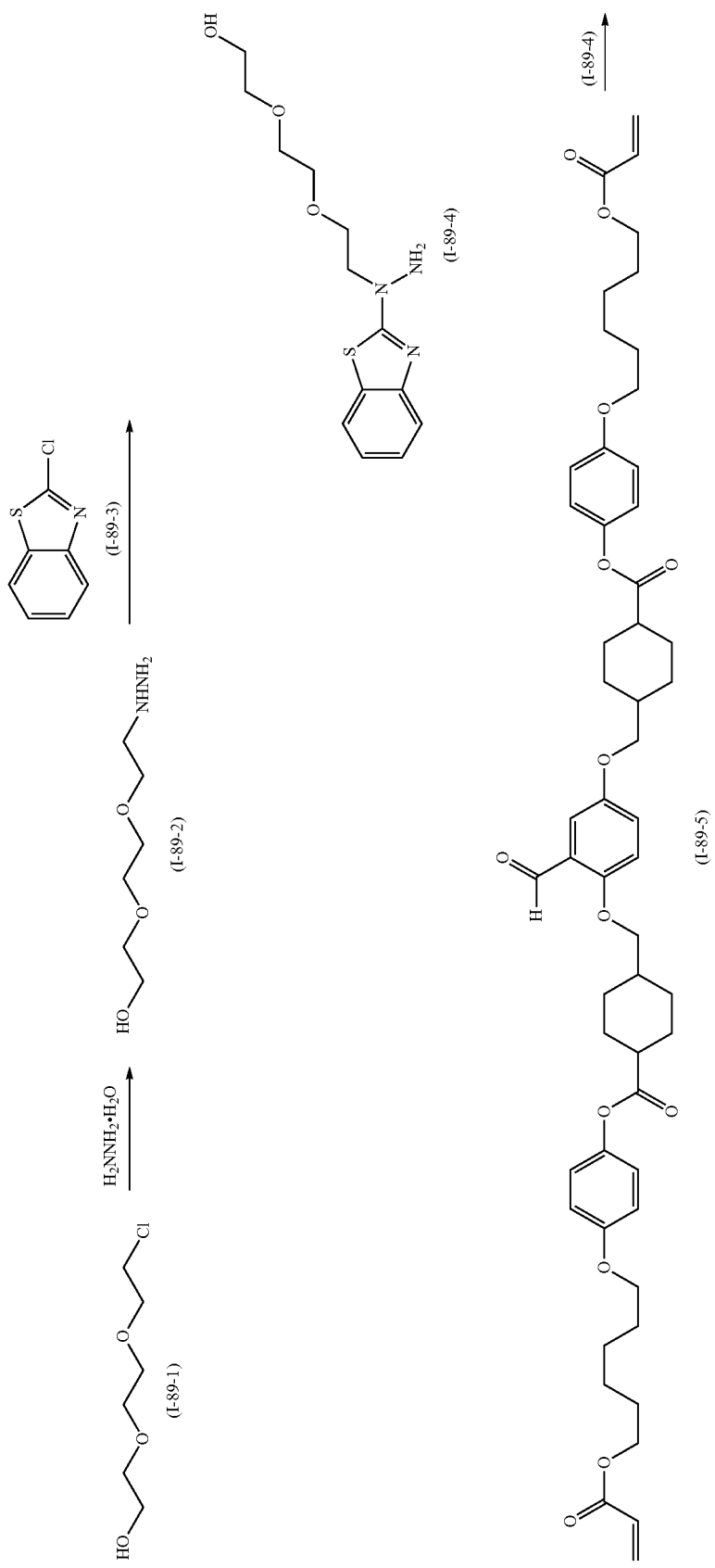

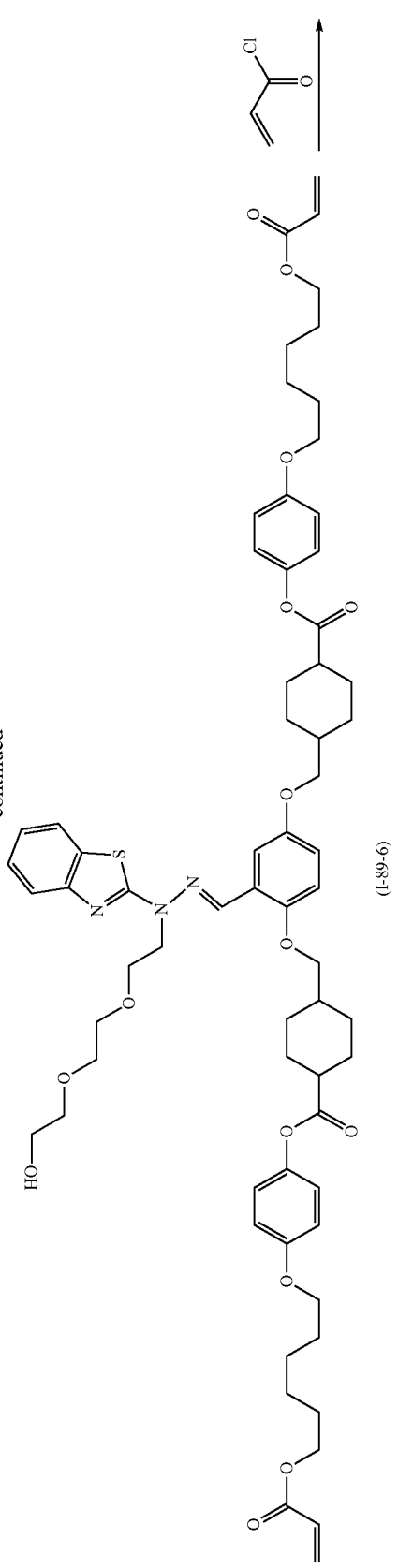
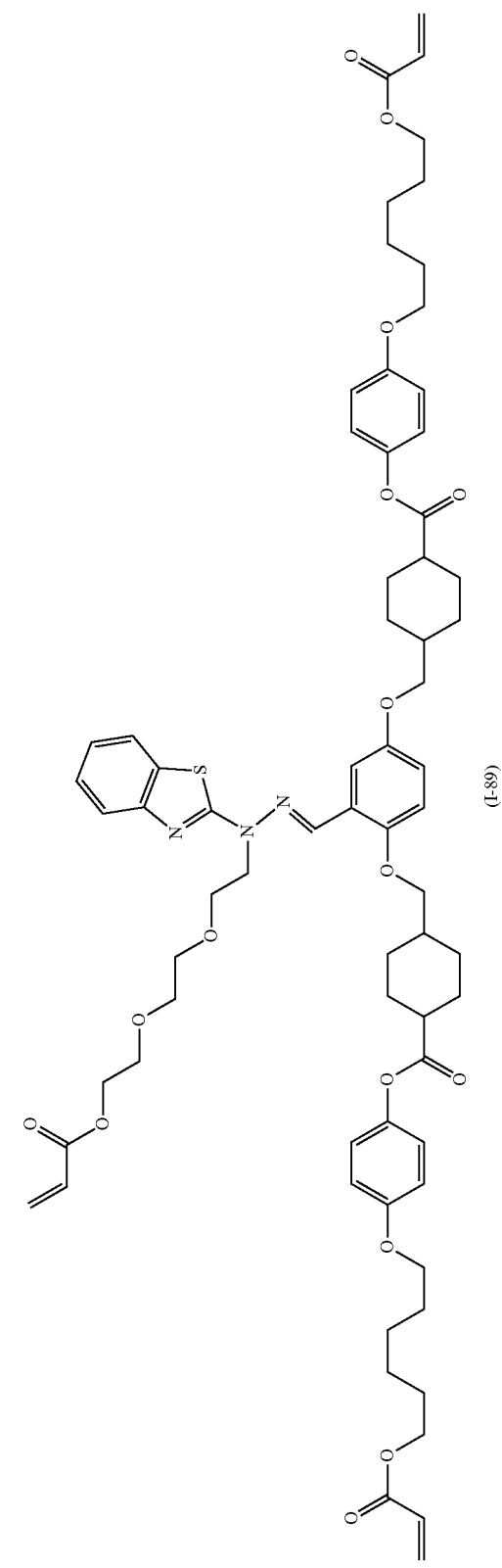

Hydrazine monohydrate and ethanol were put into a nitrogen-purged reaction container. With heating, a compound represented by Formula (I-89-1) was dropped, followed by stirring. The resultant product was concentrated to obtain a mixture containing a compound represented by Formula (I-89-2).

A compound represented by Formula (I-89-3), 1,2-dimethoxyethane, triethylamine, and a mixture containing a compound represented by Formula (I-89-2) were put into a reaction container under a nitrogen atmosphere, followed by heating and stirring. The resultant product was diluted with dichloromethane, and washed with water and brine. The solution was dried with sodium sulfate, and the solvent was concentrated to obtain a compound represented by Formula (I-89-4).

The compound represented by Formula (I-89-5), the compound represented by Formula (I-89-4), (±)-10-camphorsulfonic acid, tetrahydrofuran, and ethanol were put into a reaction container, followed by heating and stirring. The solvent was concentrated, and purification was performed by column chromatography (silica gel) and recrystallization to obtain a compound represented by Formula (I-89-6).

The compound represented by Formula (I-89-6), N-ethyldiisopropylamine, and dichloromethane were put into a reaction container under a nitrogen atmosphere. With ice cooling, acryloyl chloride was added, followed by stirring. After ordinary post-treatment was performed, purification was performed by column chromatography (silica gel) and recrystallization to obtain a compound represented by Formula (I-89).

Transition temperature (temperature rise rate 5° C./min) C 71 N 115 I $^1$H NMR (CDCl$_3$) δ 1.19-1.29 (m, 4H), 1.41-1.82 (m, 22H), 1.91 (m, 2H), 2.08 (m, 4H), 2.24 (m, 4H), 2.53 (m, 2H), 3.62 (m, 3H), 3.67 (m, 2H), 3.84-3.90 (m, 5H), 3.94 (t, 4H), 4.15-4.19 (m, 6H), 4.53 (t, 2H), 5.76 (dd, 1H), 5.82 (dd, 2H), 6.08 (dd, 1H), 6.12 (dd, 2H), 6.37 (dd, 1H), 6.40 (dd, 2H), 6.84-6.90 (m, 6H), 6.95-6.98 (m, 4H), 7.14 (t, 1H), 7.32 (t, 1H), 7.53 (d, 1H), 7.65 (d, 1H), 7.69 (d, 1H), 8.34 (s, 1H) ppm.

LCMS: 1244 [M+1]

(Example 18) Preparation of Compound Represented by Formula (I-121)

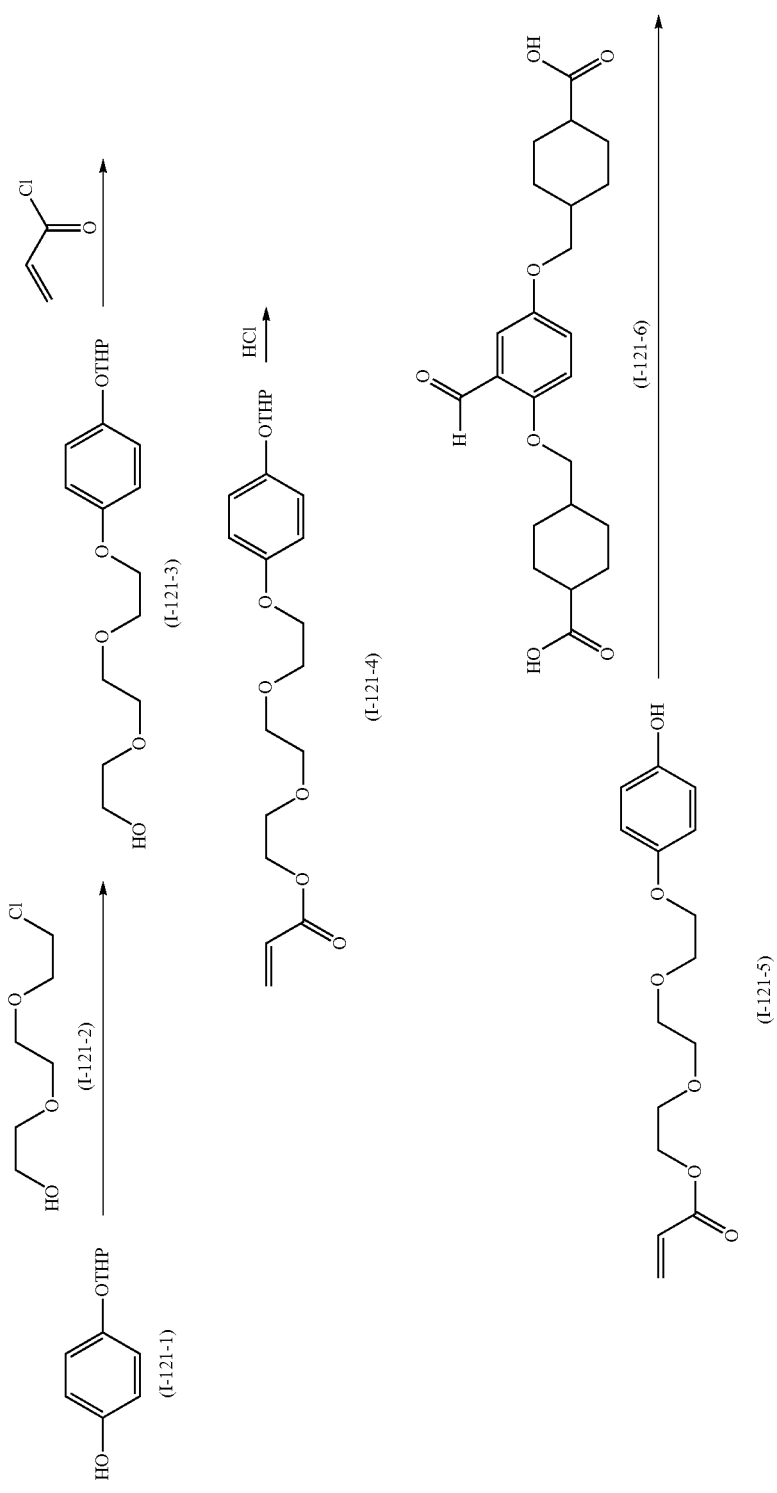

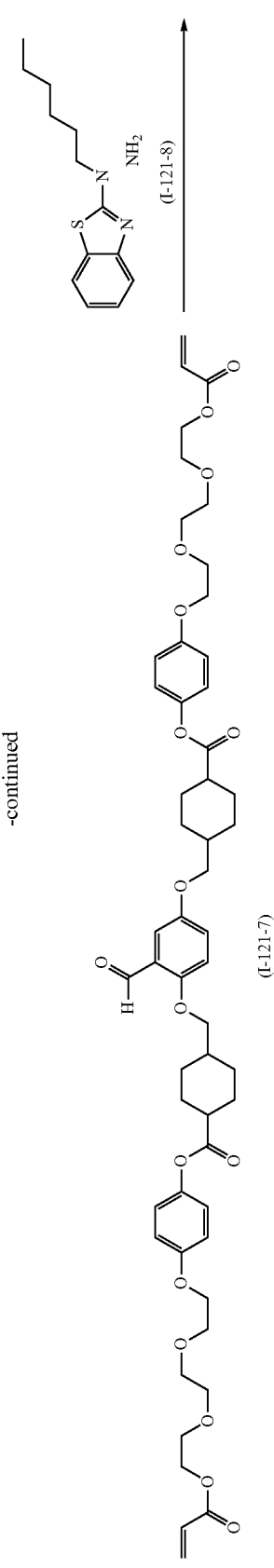
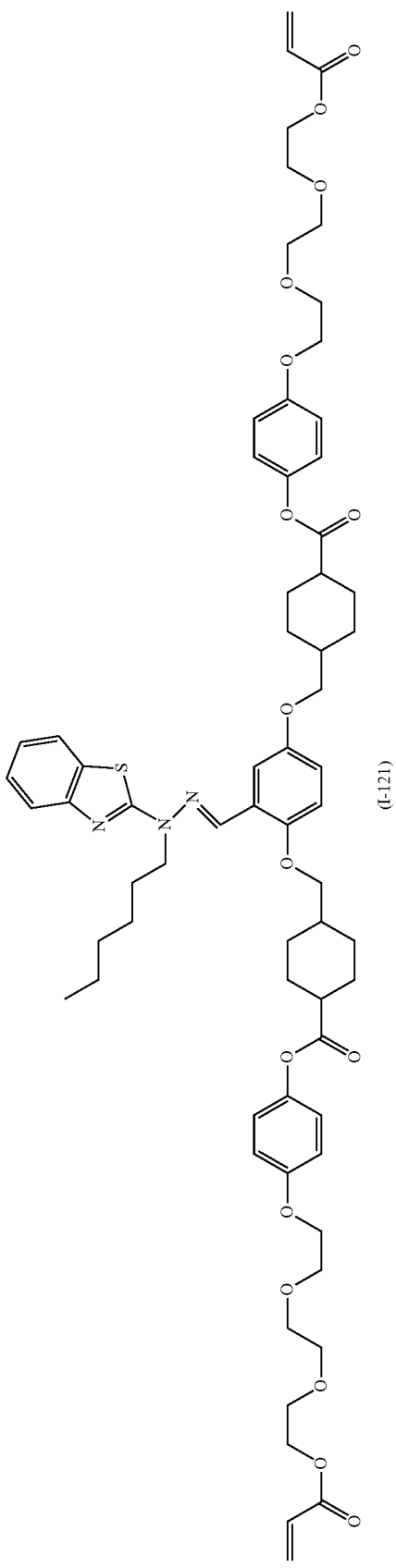

The compound represented by Formula (I-121-1), a compound represented by Formula (I-121-2), potassium carbonate, and N, N-dimethylformamide were put into a reaction container, followed by heating and stirring. The resultant product was diluted with dichloromethane, and then washed with water and brine. Purification was performed by column chromatography (alumina) to obtain a compound represented by Formula (I-121-3).

The compound represented by Formula (I-121-3), N-ethyldiisopropylamine, and dichloromethane were put into a reaction container under a nitrogen atmosphere. With ice cooling, acryloyl chloride was added, followed by stirring. After ordinary post-treatment was performed, purification was performed by column chromatography (alumina) and recrystallization to obtain a compound represented by Formula (I-121-4).

The compound represented by Formula (I-121-4), tetrahydrofuran, methanol, and concentrated hydrochloric acid were put into a reaction container, followed by stirring. After ordinary post-treatment was performed, drying was performed to obtain a compound represented by Formula (I-121-5).

The compound represented by Formula (I-121-5), a compound represented by Formula (I-121-6), N,N-dimethylaminopyridine, and dichloromethane were put into a nitrogen-purged reaction container. With ice cooling, diisopropylcarbodiimide was dropped, followed by stirring at room temperature. The precipitate was filtered, and then washed with hydrochloric acid, water, and brine. Purification was performed by column chromatography (silica gel) and recrystallization to obtain a compound represented by Formula (I-121-7).

The compound represented by Formula (I-121-7), the compound represented by Formula (I-121-8), (+)-10-camphorsulfonic acid, tetrahydrofuran, and ethanol were put into a reaction container, followed by stirring. The solvent was concentrated, and purification was performed by column chromatography (silica gel) and recrystallization to obtain a compound represented by Formula (I-121).

Transition temperature (temperature rise rate 5° C./min) C 77 S 90 N 109 I $^1$H NMR (CDCl$_3$) δ 0.89 (t, 3H), 1.20-1.35 (m, 10H), 1.61-1.69 (m, 6H), 1.78 (m, 2H), 1.90 (m, 2H), 2.07 (t, 4H), 2.23 (d, 4H), 2, 50 (m, 2H), 3.69-3.76 (m, 12H), 3.83-3.87 (m, 8H), 4.11 (t, 4H), 4.32 (t, 6H), 5.82 (d, 2H), 6.15 (q, 2H), 6.42 (d, 2H), 6.83-6.98 (m, 10H), 7.13 (t, 1H), 7.32 (t, 1H), 7.53 (t, 1H), 7.66 (t, 2H), 8.13 (s, 1H) ppm.

(Example 19) Preparation of Compound Represented by Formula (I-122)

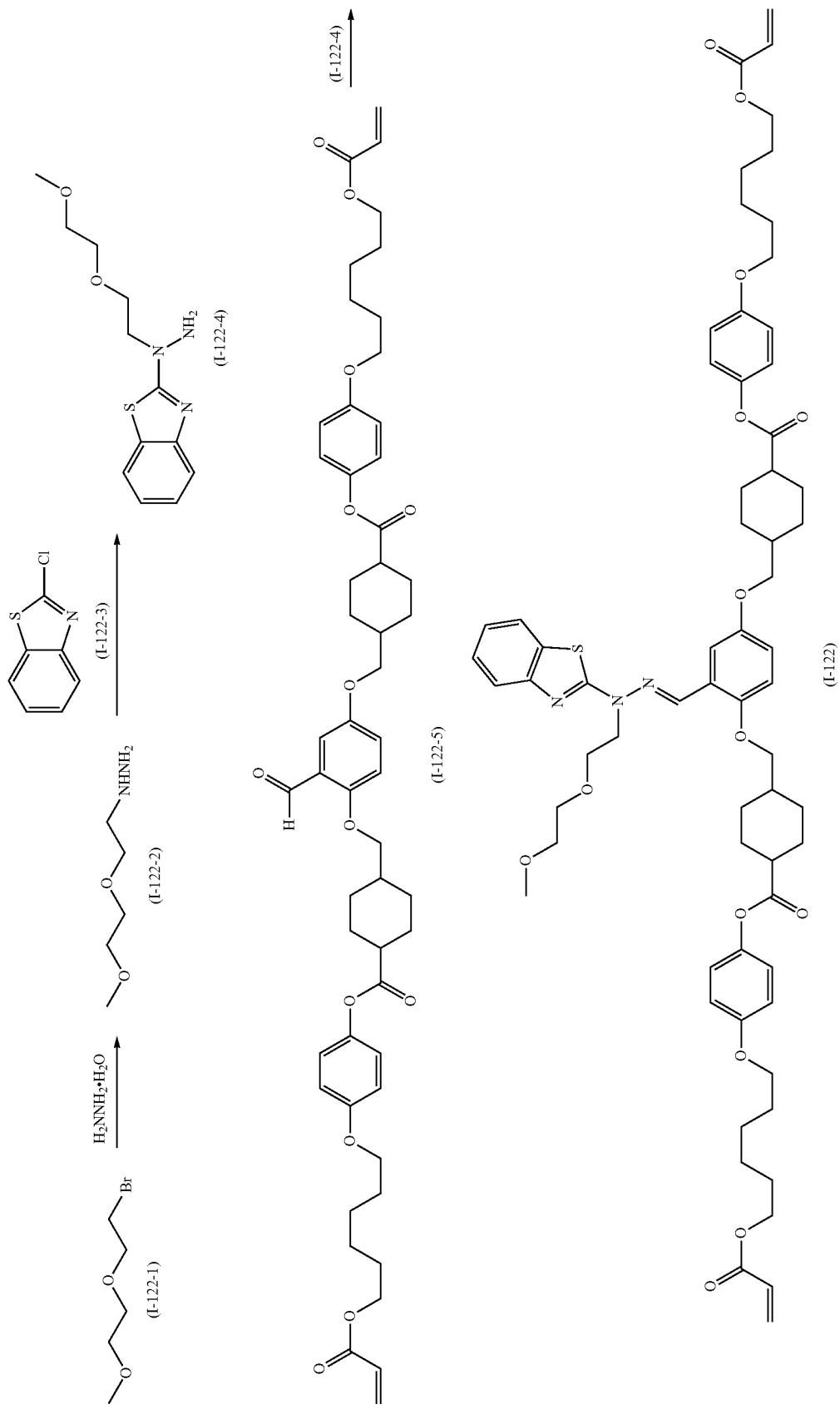

Hydrazine monohydrate and ethanol were put into a reaction container under a nitrogen atmosphere. A compound represented by Formula (I-122-1) was added, followed by heating and stirring. The resultant product was concentrated to obtain a mixture containing a compound represented by Formula (I-122-2).

A compound represented by Formula (I-122-3), 1,2-dimethoxyethane, triethylamine, and a mixture containing a compound represented by Formula (I-122-2) were put into a reaction container under a nitrogen atmosphere, followed by heating and stirring. The resultant product was diluted with dichloromethane, and washed with water and brine. The solution was dried with sodium sulfate, and the solvent was concentrated to obtain a compound represented by Formula (I-122-4).

The compound represented by Formula (I-122-5), the compound represented by Formula (I-122-4), (±)-10-camphorsulfonic acid, tetrahydrofuran, and ethanol were put into a reaction container, followed by heating and stirring. The solvent was concentrated, and purification was performed by column chromatography (silica gel) and recrystallization to obtain a compound represented by Formula (I-122).

Transition temperature (temperature rise rate 5° C./min) C 85 N 128 I $^1$H NMR (CDCl$_3$) 51.22-1.28 (m, 4H), 1.44-1.47 (m, 8H), 1.60-1.82 (m, 12H), 1.90 (m, 2H), 2.07 (t, 4H), 2.24 (d, 4H), 2.53 (m, 2H), 3.30 (s, 3H), 3.50 (t, 2H), 3.66 (t, 2H), 3.85-3.89 (m, 6H), 3.93 (t, 4H), 4.17 (t, 4H), 4.53 (t, 2H), 5.82 (d, 2H), 6.13 (q, 2H), 6.40 (d, 2H), 6.83-6.90 (m, 6H), 6.95-6.98 (m, 4H), 7.14 (t, 1H), 7.32 (t, 1H), 7.52 (t, 1H), 7.67 (t, 2H), 8.33 (s, 1H) ppm.

(Example 20) Preparation of Compound Represented by Formula (I-123)

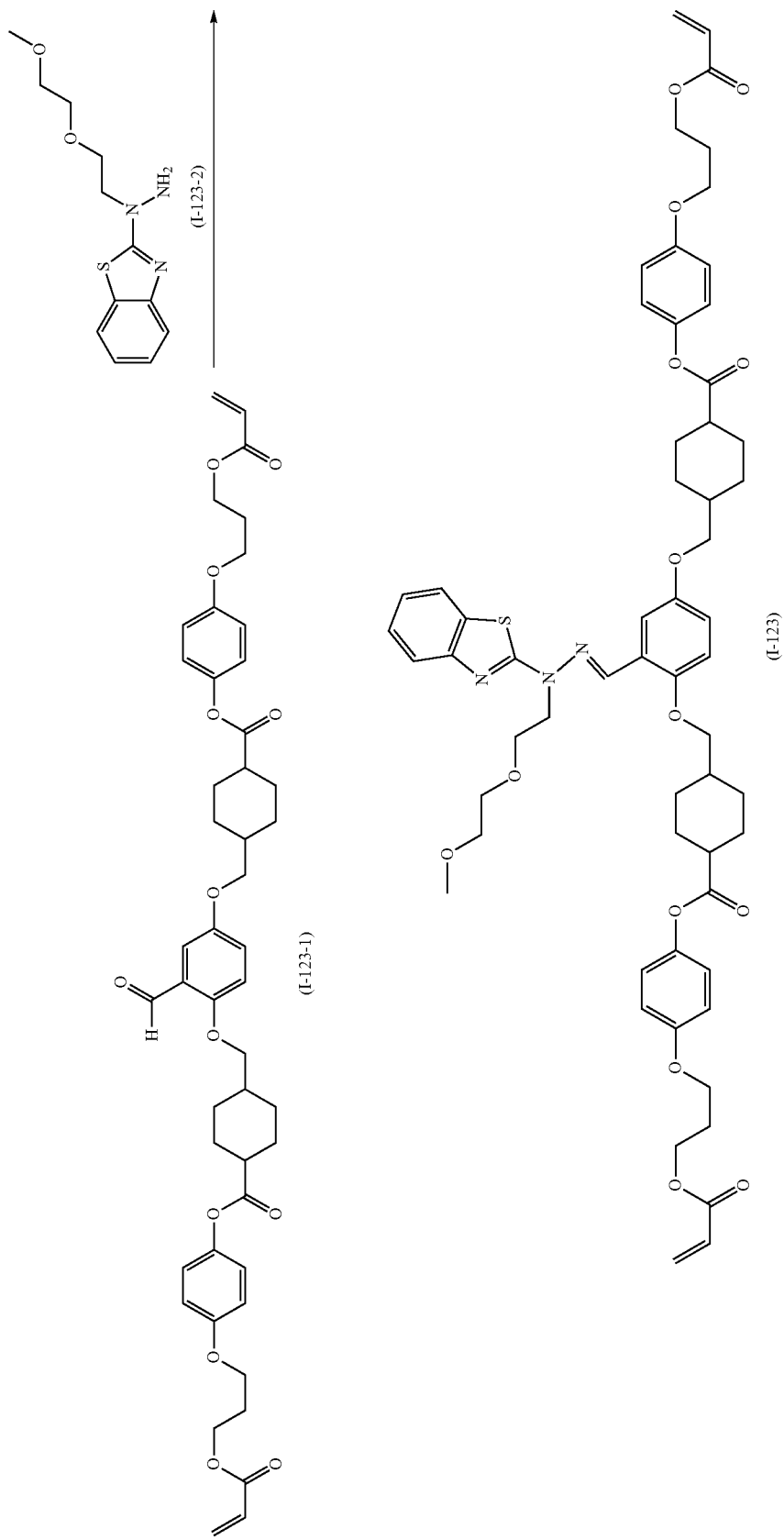

The compound represented by Formula (I-123-1), the compound represented by Formula (I-123-2), (±)-10-camphorsulfonic acid, tetrahydrofuran, and ethanol were put into a reaction container, followed by heating and stirring. The solvent was concentrated, and purification was performed by column chromatography (silica gel) and recrystallization to obtain a compound represented by Formula (I-123).

Transition temperature (temperature rise rate 5° C./min) C 89-95 N 145 I $^1$H NMR (CDCl$_3$) δ 1.24 (m, 4H), 1.65 (m, 4H), 1.91 (m, 2H), 2.05-2.25 (m, 12H), 2.55 (m, 2H), 3.30 (s, 3H), 3.51 (m, 2H), 3.67 (m, 2H), 3.84-3.89 (m, 6H), 4.05 (t, 4H), 4.36 (t, 4H), 4.54 (t, 2H), 5.84 (dd, 2H), 6.13 (dd, 2H), 6.41 (dd, 2H), 6.84-6.89 (m, 6H), 6.97-7.00 (m, 4H), 7.14 (t, 1H), 7.33 (t, 1H), 7.52 (d, 1H), 7.67 (dd, 2H), 8.34 (s, 1H) ppm.

(Example 21) Preparation of Compound Represented by Formula (I-124)

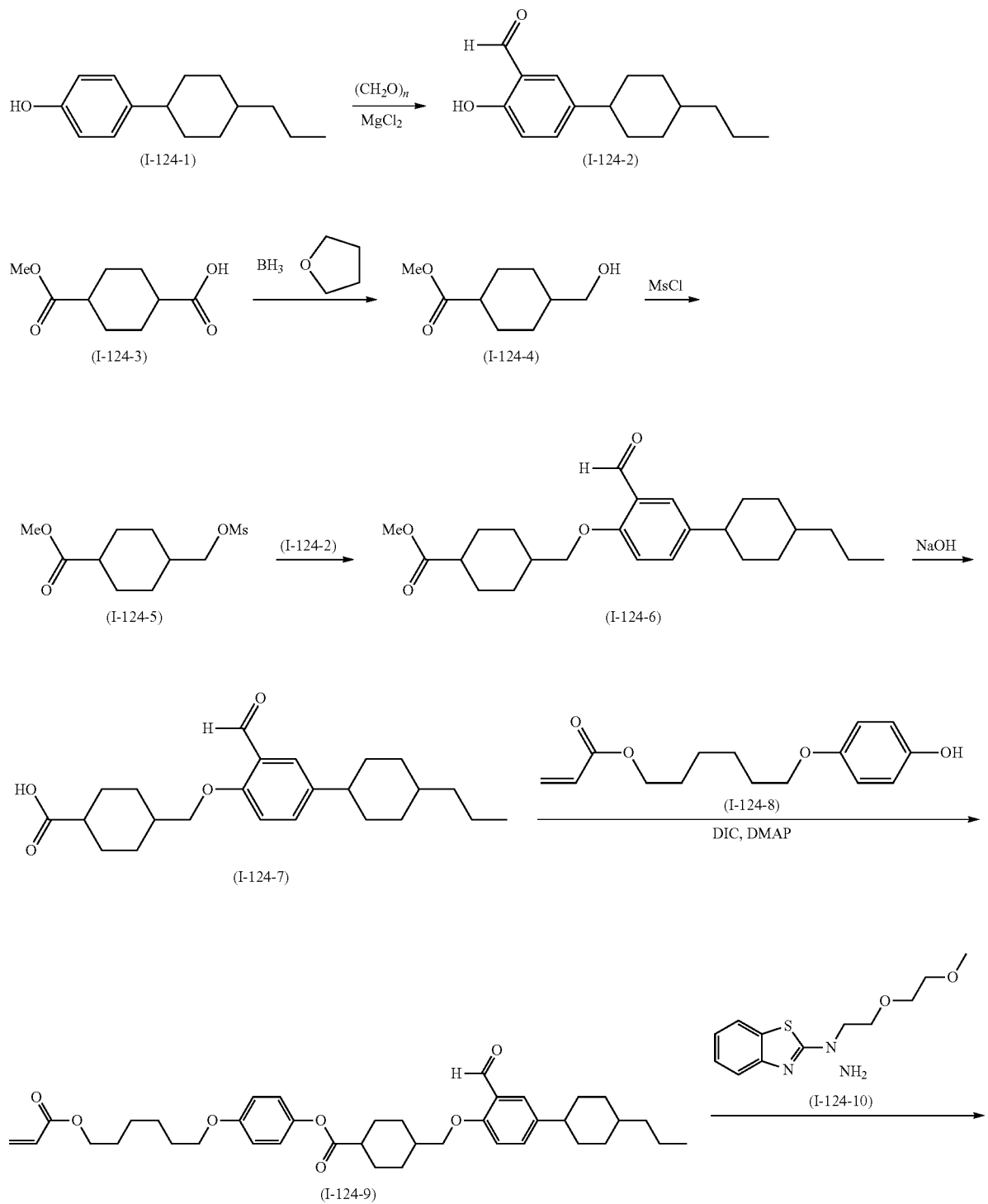

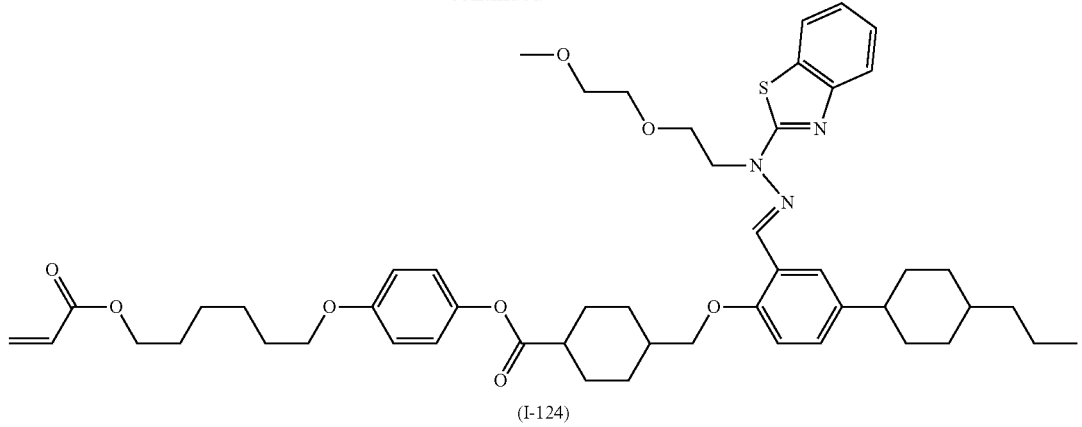

(I-124)

A compound represented by Formula (I-124-1), magnesium chloride, paraformaldehyde, triethylamine, acetonitrile were put into a reaction container, followed by heating and stirring. The resultant product was diluted with ethyl acetate, and washed with water and brine. Purification was performed by column chromatography (silica gel) and recrystallization to obtain a compound represented by Formula (I-124-2).

The compound represented by Formula (I-124-3) and tetrahydrofuran were put into a reaction container under a nitrogen atmosphere. With ice cooling, borane-tetrahydrofuran complex (0.9 mol/L) was dropped, followed by stirring. After ordinary post-treatment was performed, the solvent was concentrated to obtain a compound represented by Formula (I-124-4).

The compound represented by Formula (I-124-4), pyridine, and dichloromethane were put into a reaction container under a nitrogen atmosphere. With ice cooling, methanesulfonyl chloride was dropped, followed by stirring at room temperature. After ordinary post-treatment was performed, purification was performed by column chromatography (silica gel) to obtain a compound represented by Formula (I-124-5).

The compound represented by Formula (I-124-5), a compound represented by Formula (I-124-2), potassium carbonate, and N, N-dimethylformamide were put into a reaction container, followed by heating and stirring. After ordinary post-treatment was performed, purification was performed by column chromatography (silica gel) and recrystallization to obtain a compound represented by Formula (I-124-6).

The compound represented by Formula (I-124-6), methanol, and an aqueous sodium hydroxide solution were put into a reaction container, followed by heating and stirring. The resultant product was neutralized with hydrochloric acid, diluted with ethyl acetate, and then washed with water and brine. Purification was performed by column chromatography (alumina) to obtain a compound represented by Formula (I-124-7).

The compound represented by Formula (I-124-7), the compound represented by Formula (I-124-8), N,N-dimethylaminopyridine, and dichloromethane were put into a reaction container. With ice cooling, diisopropylcarbodiimide was dropped, followed by stirring at room temperature. The precipitate was filtered, and then washed with hydrochloric acid, water, and brine. Purification was performed by column chromatography (silica gel) and recrystallization to obtain a compound represented by Formula (I-124-9).

The compound represented by Formula (I-124-9), a compound represented by Formula (I-124-10), (±)-10-camphorsulfonic acid, tetrahydrofuran, and ethanol were put into a reaction container, followed by heating and stirring. The solvent was concentrated, and purification was performed by column chromatography (silica gel) and recrystallization to obtain a compound represented by Formula (I-124).

Transition temperature (temperature rise rate 5° C./min) C 101-105 (N 82) I $^1$H NMR (CDCl$_3$) δ 0.92 (t, 3H), 1.08-1.91 (m, 26H), 2.06 (d, 2H), 2.24 (d, 2H), 2.51 (m, 2H), 3.30 (s, 3H), 3.51 (dd, 2H), 3.67 (dd, 2H), 3.87 (quin, 4H), 3.94 (t, 2H), 4.17 (t, 2H), 4.54 (t, 2H), 5.82 (dd, 1H), 6.12 (dd, 1H), 6.40 (dd, 1H), 6.86 (m, 3H), 6.97 (m, 2H), 7.16 (m, 2H), 7.32 (t, 1H), 7.65 (d, 1H), 7.70 (d, 1H), 7.82 (d, 1H), 8.36 (s, 1H) ppm.

(Example 22) Preparation of Compound Represented by Formula (I-125)

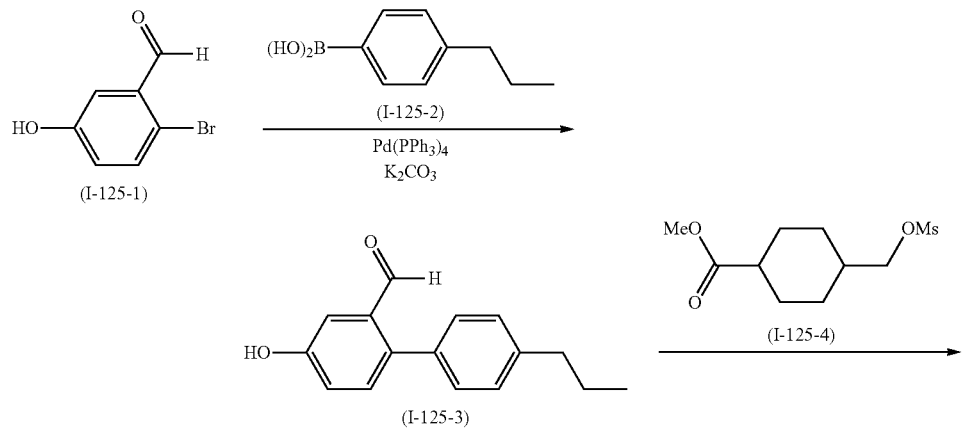

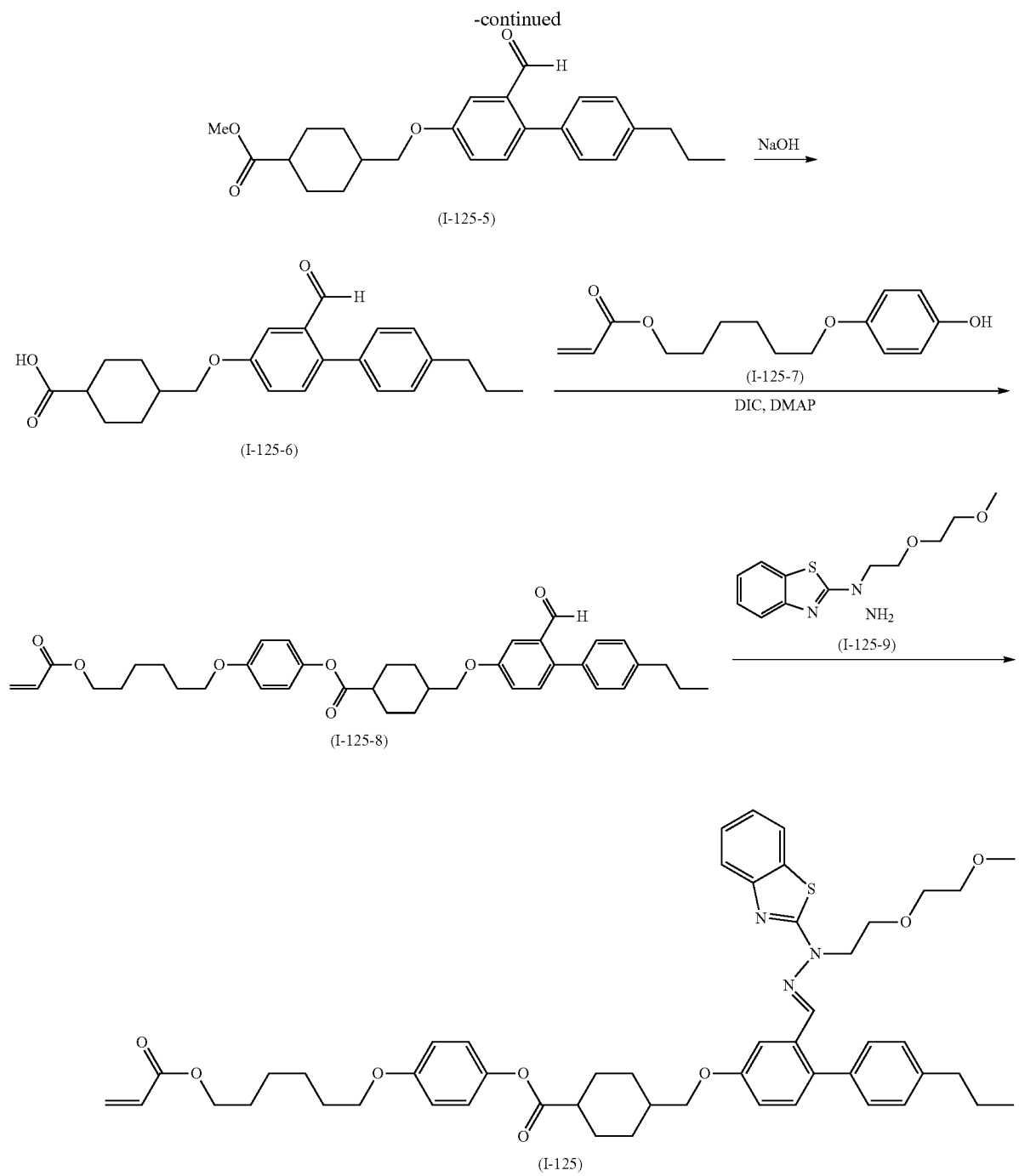

A compound represented by Formula (I-125-1), a compound represented by Formula (I-125-2), potassium carbonate, ethanol, water, and tetrakis (triphenylphosphine) palladium (0) were put into a reaction container under a nitrogen atmosphere, followed by heating and stirring. After ordinary post-treatment was performed, purification was performed by column chromatography (silica gel) to obtain a compound represented by Formula (I-125-3).

The compound represented by Formula (I-125-3), a compound represented by Formula (I-125-4), potassium carbonate, and N, N-dimethylformamide were put into a reaction container, followed by heating and stirring. The resultant product was diluted with dichloromethane, and then washed with water and brine.

Purification was performed by column chromatography (silica gel) and recrystallization to obtain a compound represented by Formula (I-125-5).

The compound represented by Formula (I-125-5), methanol, and an aqueous sodium hydroxide solution were put into a reaction container, followed by heating and stirring. The resultant product was neutralized with hydrochloric acid, diluted with ethyl acetate, and then washed with water and brine. Purification was performed by column chromatography (alumina) to obtain a compound represented by Formula (I-125-6).

The compound represented by Formula (I-125-6), the compound represented by Formula (I-125-7), N,N-dimethylaminopyridine, and dichloromethane were put into a reaction container. With ice cooling, diisopropylcarbodiimide was dropped, followed by stirring at room temperature. The precipitate was filtered, and then washed with hydrochloric acid, water, and brine. Purification was performed by column chromatography (silica gel) and recrystallization to obtain a compound represented by Formula (1-125-8).

The compound represented by Formula (I-125-8), a compound represented by Formula (I-125-9), (±)-10-camphorsulfonic acid, tetrahydrofuran, and ethanol were put into a reaction container, followed by heating and stirring. The solvent was concentrated, and purification was performed by column chromatography (silica gel) and recrystallization to obtain a compound represented by Formula (I-125).

Transition temperature (temperature rise rate 5° C./min) C 67-100 I $^1$H NMR (CDCl$_3$) δ 1.00 (t, 3H), 1.28 (m, 2H), 1.45-1.81 (m, 12H), 1.97 (br, 1H), 2.13 (m, 2H), 2.26 (m, 2H), 2.57 (tt, 1H), 2.65 (t, 2H), 3.27 (s, 3H), 3.37 (m, 2H), 3.50 (m, 2H), 3.70 (t, 2H), 3.95 (q, 4H), 4.17 (t, 2H), 4.33 (t, 2H), 5.82 (dd, 1H), 6.12 (dd, 1H), 6.40 (dd, 1H), 6.87 (d, 2H), 6.98 (m, 3H), 7.15 (t, 1H), 7.25 (m, 5H), 7.32 (t, 1H), 7.64 (m, 2H), 7.69 (d, 1H), 7.91 (s, 1H) ppm.

Compounds represented by Formulae (I-16) to (1-85), Formula (I-87), Formula (I-88), and Formulae (I-90) to (1-120) were prepared using the same methods as Examples 1 to 22 and known methods.

Examples 23 to 44 and Comparative Examples 1 to 3

Compounds represented by Formulae (I-1) to (1-15), Formula (I-86), Formula (I-89), and Formulae (I-121) to (1-125) described in Examples 1 to 22, a compound (R-1) described in Patent document 1, a compound (R-2) described in Patent document 2, and a compound (R-3) described in Patent document 3 were provided as compounds to be evaluated.

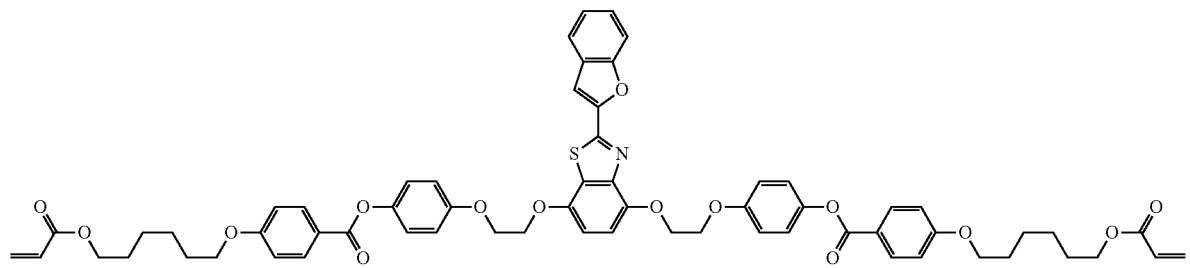
(R-1)

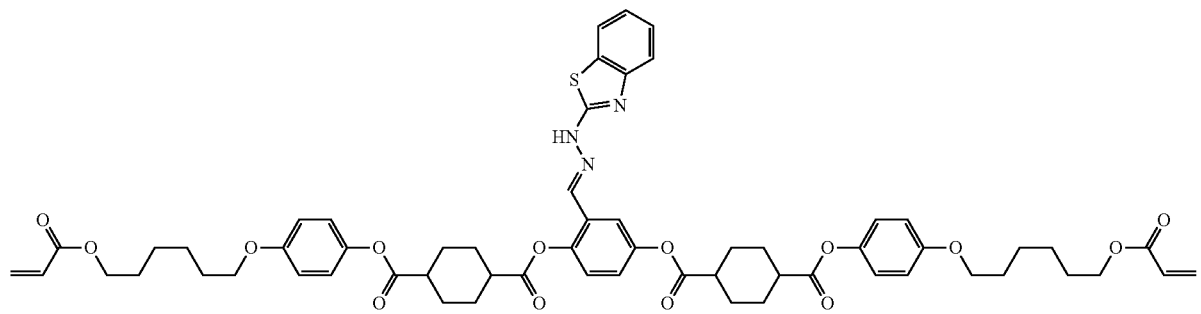
(R-2)

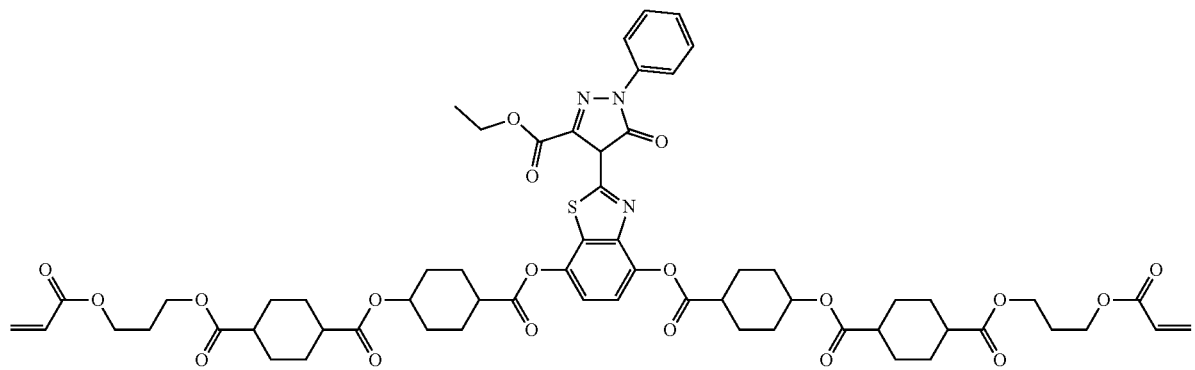
(R-3)

Further, a liquid crystal composition including 50% of a compound (X-1) described in JP-A-2005-015473, 30% of a compound (X-2) described in JP-A-10-87565, and 20% of a compound (X-3) described in JP-T-2002-537280 was provided as mother liquid crystal (X).

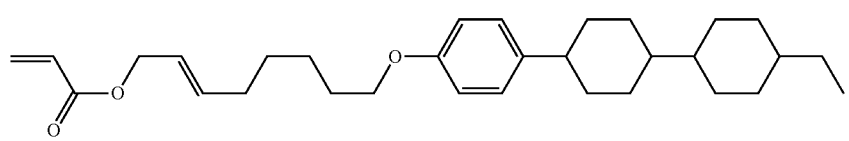
(X-1)

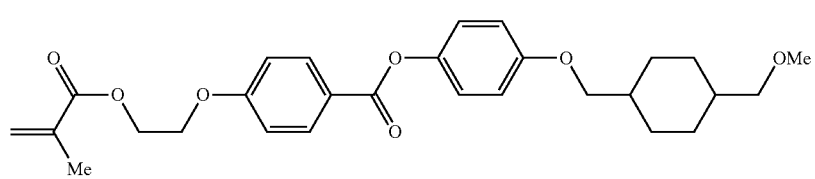
(X-2)

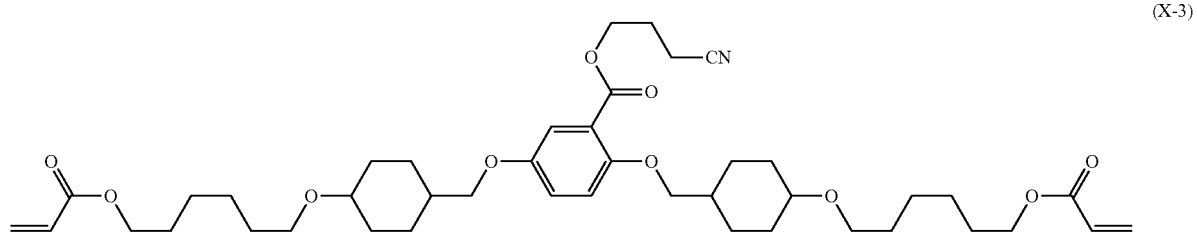
(X-3)

A polyimide solution for alignment film was applied onto a glass substrate having a thickness of 0.7 mm by spin coating, dried at 100° C. for 10 minutes, and then baked at 200° C. for 60 minutes to obtain a coating film. The obtained coating film was rubbed. The rubbing treatment was performed using a commercially available rubbing device.

1% of a photopolymerization initiator Irgacure 907 (manufactured by BASF Corporation), 0.1% of 4-methoxyphenol, and 80% of chloroform were added to each composition prepared by adding 40% of a compound to be evaluated to mother liquid crystal (X), so as to prepare a coating solution. The coating solution was applied onto the rubbed glass substrate by spin coating. The coating solution was dried at 80° C. for 1 minute, and further dried at 120° C. for 1 minute. Then, the dried coating solution was irradiated with ultraviolet rays at an intensity of 40 mW/cm² for 25 seconds using a high-pressure mercury pump, thereby fabricating films to be evaluated. The correspondence of the numbers of films of Examples to the compounds to be evaluated is shown in Table 1 below.

TABLE 1

| Film | Compound to be evaluated used |
| --- | --- |
| Example 23 | Compound (I-1) of the present invention |
| Example 24 | Compound (I-2) of the present invention |
| Example 25 | Compound (I-3) of the present invention |
| Example 26 | Compound (I-4) of the present invention |
| Example 27 | Compound (I-5) of the present invention |
| Example 28 | Compound (I-6) of the present invention |
| Example 29 | Compound (I-7) of the present invention |
| Example 30 | Compound (I-8) of the present invention |
| Example 31 | Compound (I-9) of the present invention |
| Example 32 | Compound (I-10) of the present invention |
| Example 33 | Compound (I-11) of the present invention |
| Example 34 | Compound (I-12) of the present invention |

TABLE 1-continued

| Film | Compound to be evaluated used |
| --- | --- |
| Example 35 | Compound (I-13) of the present invention |
| Example 36 | Compound (I-14) of the present invention |

TABLE 1-continued

| Film | Compound to be evaluated used |
| --- | --- |
| Example 37 | Compound (I-15) of the present invention |
| Example 38 | Compound (I-86) of the present invention |
| Example 39 | Compound (I-89) of the present invention |
| Example 40 | Compound (I-121) of the present invention |
| Example 41 | Compound (I-122) of the present invention |
| Example 42 | Compound (I-123) of the present invention |
| Example 43 | Compound (I-124) of the present invention |
| Example 44 | Compound (I-125) of the present invention |
| Comparative Example 1 | Comparative compound (R-1) |
| Comparative Example 2 | Comparative compound (R-2) |
| Comparative Example 3 | Comparative compound (R-3) |

The San test of each of the fabricated films was performed under conditions of 60 mW/cm², 26° C. and 120 J using Xenon lamp irradiation test machine (San test XLS, manufactured by ATLAS Corporation). The discoloration and alignment defect of each of the obtained films were evaluated.

<Discoloration>

The yellowness index (YI) of each of the films was measured. The difference (ΔYI) between the YI value before San test and the YI value after San test was calculated. The measurement of the yellowness index (YI) was performed using JASCO UV/VIS Spectrophotometer V-560, and the yellowness index (YI) was calculated by accessory color diagnostic program. Calculation Equation is represented by:

$$YI = 100(1.28X - 1.06Z)/Y \text{ (JIS K7373)}$$

(X, Y, Z represent three stimulus values in the XYZ color system). The smaller the ΔYI value, it means that there is less discoloration.

<Alignment Defect>

Each of the films was divided into areas of the total of 100 squares (vertical 10×horizontal 10). The number of the grids in which alignment defects occurred was counted by polarizing microscope observation. The smaller the value, it means that there are less alignment defects. The results thereof are summarized in Table 2 below.

TABLE 2

| Film | ΔYI | Alignment defect |
| --- | --- | --- |
| Example 23 | 0.6 | 0 |
| Example 24 | 0.6 | 0 |
| Example 25 | 0.4 | 0 |
| Example 26 | 0.4 | 0 |
| Example 27 | 0.5 | 0 |
| Example 28 | 0.8 | 1 |
| Example 29 | 0.8 | 1 |
| Example 30 | 0.5 | 2 |
| Example 31 | 1.4 | 6 |
| Example 32 | 1.4 | 7 |
| Example 33 | 1.1 | 4 |
| Example 34 | 1.2 | 4 |
| Example 35 | 1.3 | 5 |
| Example 36 | 1.3 | 6 |
| Example 37 | 1.3 | 7 |
| Example 38 | 0.4 | 0 |
| Example 39 | 0.4 | 0 |
| Example 40 | 0.5 | 2 |
| Example 41 | 0.4 | 0 |
| Example 42 | 0.4 | 0 |
| Example 43 | 0.5 | 1 |
| Example 44 | 0.5 | 1 |
| Comparative Example 1 | 1.5 | 8 |
| Comparative Example 2 | 2.7 | 7 |
| Comparative Example 3 | 5.2 | 9 |

From Table 2, it was understood that all of the films fabricated using the compounds of the present invention of Examples 23 to 44 are less likely to cause discoloration and alignment defects when being irradiated with ultraviolet rays. Therefore, each of the compounds of the present invention is useful as a component of the polymerizable composition. Further, the optically anisotropic body using the polymerizable liquid crystal composition containing the compound of the present invention is useful in applications such as optical films.

The invention claimed is:

1. A polymerizable low-wavelength dispersive or polymerizable reverse-wavelength dispersive compound, wherein the polymerizable low-wavelength dispersive or polymerizable reverse-wavelength dispersive compound is a compound represented by Formula (I) below,

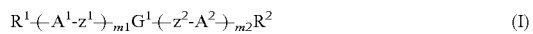

(in the formula, $R^1$ is represented by Formula (I-0-R) below,

(in the formula, $P^0$ represents a polymerizable group, $Sp^0$ represents a spacer group or a single bond, and if a plurality of $Sp^0$'s exist, they may be different from or identical to each other; $X^0$ represents —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—N=CH—, —CF=CF—, or a single bond, and if a plurality of $X^0$'s exist, they may be different from or identical to each other (provided that, $P^0$-(Sp$^0$-X$^0$)k0-does not contain a —O—O— bond); and k0 represents an integer of 0 to 10), $R^2$ represents a hydrogen atom, a fluorine atom, a chlorine atom, or a linear or branched alkyl group having 1 to 12 carbon atoms, in which one —CH$_2$— or two or more non-adjacent —CH$_2$—'s may be each independently substituted with —O—, —COO—, —OCO—, or —O—CO—O—, $A^1$ and $A^2$ each independently represent a 1,4-phenylene group, a 1,4-cyclohexylene group, a pyridine-2,5-diyl group, a pyrimidine-2,5-diyl group, a naphthalene-2,6-diyl group, a naphthalene-1,4-diyl group, a tetrahydronaphthalene-2,6-diyl group, a decahydronaphthalene-2,6-diyl group, or a 1,3-dioxane-2,5-diyl group, and these groups may be unsubstituted or may be substituted with one or more of substituent groups L, L represents a fluorine atom, a chlorine atom, a bromine atom, an iodine atom, a pentafluorosulfuranyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms, in which one —CH$_2$— or two or more non-adjacent —CH$_2$—'s may be each independently substituted with —O—, —S—, —CO—, —COO—, —OCO—, —CO—S—, —S—CO—, —O—CO—O—, —CO—NH—, —NH—CO—, and any hydrogen atom in the alkyl group may be substituted with a fluorine atom, and if a plurality of L's exist in the compound, they may be different from or identical to each other;

$Z^1$ and $Z^2$ each independently represent —O—, —S—, —OCH$_2$—, —CH$_2$O—, —CH$_2$CH$_2$-, —CO—, —COO—, —OCO—, —CO—S—, —S—CO—, —O—CO—O—, —CO—NH—, —NH—CO—, —OCO—NH—, —NH—COO—, —NH—CO—NH—, —NH—O—, —O—NH—, —SCH$_2$—, —CH$_2$S—, —CF$_2$O—, —OCF$_2$—, —CF$_2$S—, —SCF$_2$—, —CH=CH—COO—, —CH=CH—OCO—, —COO—CH=CH—, —OCO—CH=CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH=CH—, —N=N—, —CH=N—, —N=CH—, —CH=N—N=CH—, —CF=CF—, —C≡C—, a single bond, or a group represented by —CR$^{0-1}$R$^{0-2}$O— or OCR$^{0-1}$R$^{0-2}$—(in the formulas, R$^{0-1}$ and R$^{0-2}$ each independently represent a hydrogen atom, a fluorine atom, a chlorine atom, a bromine atom, an iodine atom, or a linear or branched alkyl group having 1 to 20 carbon atoms, in which one —CH$_2$— or two or more non-adjacent —CH$_2$—'s may be each independently substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, and any hydrogen atom in the alkyl group may be substituted with a fluorine atom or a chlorine atom; and two terminal groups in —CR$^{0-1}$R$^{0-2}$O— are connected to ring structures), if a plurality of $Z^1$'s exist, they may be different from or identical to each other, if a plurality of $Z^2$'s exist, they may be different from or identical to each other, and at least one of $Z^1$ and $Z^2$ represents a group represented by —$CR^{0-1}R^{0-2}O$— or —$OCR^{0-1}R^{0-2}$—;

$G^1$ represents a divalent group having at least one aromatic ring selected from the group consisting of aromatic hydrocarbon rings and aromatic heterocyclic rings, the number of π electrons contained in the aromatic ring of the group represented by $G^1$ is 12 or more, and the group represented by $G^1$ may be unsubstituted or may be substituted with one or more of substituent groups $L^G$;

$L^G$ represents a fluorine atom, a chlorine atom, a bromine atom, an iodine atom, a pentafluorosulfuranyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms, in which one —$CH_2$— or two or more non-adjacent —$CH_2$—'s may be each independently substituted with —O—, —S—, —CO—, —COO—, —OCO—, —CO—S—, —S—CO—, —O—CO—O—, —CO—NH—, —NH—CO—, and any hydrogen atom in the alkyl group may be substituted with a fluorine atom, and if a plurality of $L^G$'s exist in the compound, they may be different from or identical to each other; and m1 and m2 each independently represent an integer of 0 to 6, and m1+m2 represents an integer of 0 to 6).

2. The compound according to claim 1,
wherein $P^0$ in Formula (I-0-R) represents a group selected from Formulae (P-1) to (P-20) below:

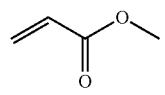
(P-1)

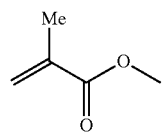
(P-2)

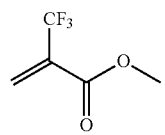
(P-3)

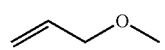
(P-4)

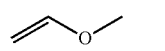
(P-5)

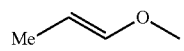
(P-6)

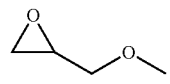
(P-7)

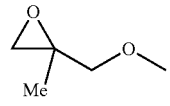
(P-8)

(P-9)

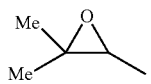
(P-10)

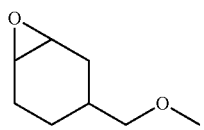
(P-11)

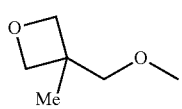
(P-12)

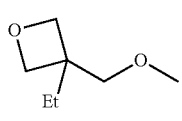
(P-13)

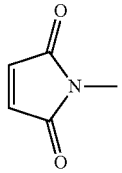
(P-14)

HS—
(P-15)

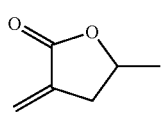
(P-16)

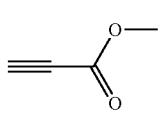
(P-17)

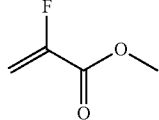
(P-18)

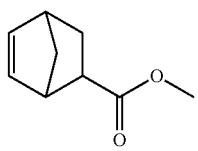
(P-19)

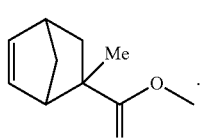
(P-20)

3. The compound according to claim 1,
wherein $Sp^0$'s in Formula (I-0-R) each independently represent an alkylene group having 1 to 20 carbon atoms, in which one —$CH_2$— or two or more non-adjacent —$CH_2$—'s may be each independently substituted with —O—, —COO—, —OCO—, —OCO—O—, —CO—NH—, —NH—CO—, —CH=CH—, or —C≡C—.

4. The compound according to claim 1,
wherein G¹ in Formula (I) represents a group selected from Formulae (M-1) to (M-6) below:

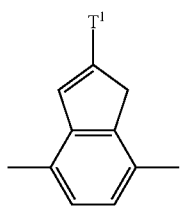
(M-1)

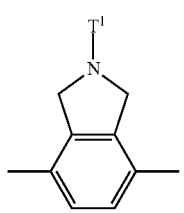
(M-2)

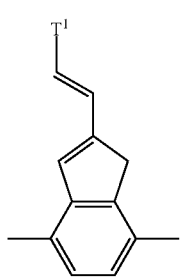
(M-3)

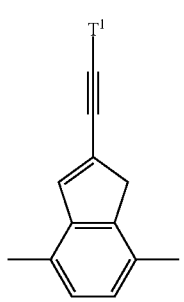
(M-4)

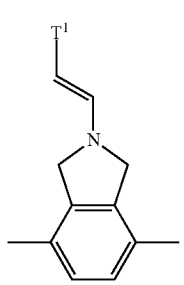
(M-5)

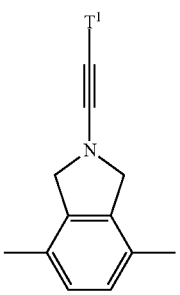
(M-6)

(in the formulae, these groups may be unsubstituted or substituted with one or more of the aforementioned substituent groups $L^G$, any —CH='s may be each independently substituted with —N=, —CH₂—'s may be each independently substituted with —O—, —S—, —NR$_T$-(in the formula, R$^T$ represents a hydrogen atom or an alkyl group having 1 to 20 carbon atoms), —CS—, or —CO—, and T¹ represents a group selected from Formulae (T1-1) to (T1-6) below:

(T1-1)

(T1-2)

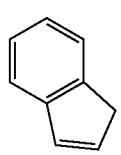
(T1-3)

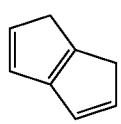
(T1-4)

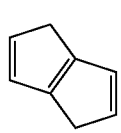
(T1-5)

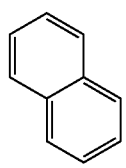
(T1-6)

(in the formulae, each of these groups may have a bond at any position, any —CH='s may be each independently substituted with —N=, —CH₂—'s may be each independently substituted with —O—, —S—, —NR$^T$-(in the formula, R$^T$ represents a hydrogen atom or an alkyl group having 1 to 20 carbon atoms), —CS—, or —CO—; and these groups may be unsubstituted or substituted with one or more of the aforementioned substituent groups $L^G$)); or a group selected from Formulae (M-7) to (M-14) below:

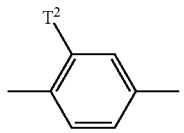 (M-7)

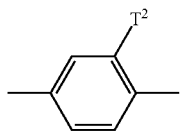 (M-8)

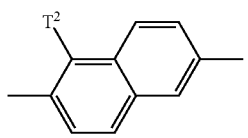 (M-9)

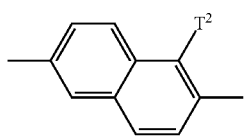 (M-10)

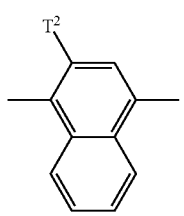 (M-11)

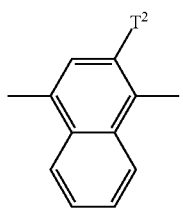 (M-12)

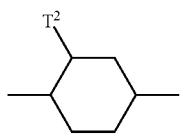 (M-13)

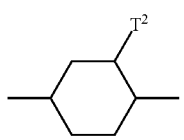 (M-14)

(in the formulae, these groups may be unsubstituted or substituted with one or more of the aforementioned substituent groups $L^G$, any —CH—'s may be each independently substituted with —N═, —CH$_2$—'s may be each independently substituted with —O—, —S—, —NR$^T$-(in the formula, R$^T$ represents a hydrogen atom or an alkyl group having 1 to 20 carbon atoms), —CS—, or —CO—, and T$^2$ represents a group selected from Formulae (T2-1) and (T2-2) below:

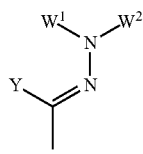 (T2-1)

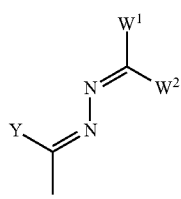 (T2-2)

(in the formula, W$^1$ represents a group containing an aromatic group and/or non-aromatic group having 1 to 40 carbon atoms, which may be substituted, the aromatic group may be a hydrocarbon ring or a heterocyclic ring, and the non-aromatic group may be a hydrocarbon group or a group in which any carbon atom in a hydrocarbon group is substituted with a heteroatom (provided that, oxygen atoms are not directly connected with each other), W$^2$ represents a hydrogen atom or a linear or branched alkyl group having 1 to 20 carbon atoms, in which one —CH$_2$— or two or more non-adjacent —CH$_2$—'s may be each independently substituted with —O—, —S—, —CO—, —COO—, —OCO—, —CO—S—, —S—CO—, —O—CO—O—, —CO—NH—, —NH—CO—, —CH═CH—COO—, —CH═CH—OCO—, —COO—CH═CH—, —OCO—CH═CH—, —CH═CH—, —CF═CF—, or —C≡C—, and any hydrogen atom in the alkyl group may be substituted with a fluorine atom, or W$^2$ may represent a group of 2 to 30 carbon atoms having at least one aromatic group, and the group may be unsubstituted or may be substituted with one or more of substituent groups L$^W$, or W$^2$ may represent a group represented by P$^W$-(Sp$^W$-X$^W$)kW-, where P$^W$ represents a polymerizable group, Sp$^W$ represents a spacer group or single bond, and if a plurality of Sp$^W$'s exist, they may be different from or identical to each other, X$^W$ represents —O—, —S—, —OCH$_2$—, —CH$_2$O—, —CO—, —COO—, —OCO—, —CO—S—, —S—CO—, —O—CO—O—, —CO—NH—, —NH—CO—, —SCH$_2$—, —CH$_2$S—, —CF$_2$O—, —OCF$_2$—, —CF$_2$S—, —SCF$_2$—, —CH═CH—COO—, —CH═CH—OCO—, —COO—CH═CH—, —OCO—CH═CH—, —COO—CH$_2$CH$_2$—, —OCO—CH$_2$CH$_2$—, —CH$_2$CH$_2$—COO—, —CH$_2$CH$_2$—OCO—, —COO—CH$_2$—, —OCO—CH$_2$—, —CH$_2$—COO—, —CH$_2$—OCO—, —CH═CH—, —N═N—, —CH═N—N═CH—, —CF═CF—, —C≡C—, or a single bond, and if a plurality of X$^W$'s exist, they may be different from or identical to each other (provided that, P$^W$-(Sp$^W$-X$^W$)kW-does not contain a —O—O— bond), and kW represents an integer of 0 to 10, L$^W$ represents a fluorine atom, a chlorine atom, a bromine atom, an iodine atom, a pentafluorosulfuranyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms, in which one —$CH_2$— or two or more non-adjacent —$CH_2$—'s may be each independently substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, and any hydrogen atom in the alkyl group may be substituted with a fluorine atom, or $L^W$ may represent a group represented by $P^{LW}$-$(Sp^{LW}$-$X^{LW})$kLW-, where $P^{LW}$ represents a polymerizable group, $Sp^{LW}$ represents a spacer group or single bond, and if a plurality of $Sp^{LW}$'s exist, they may be different from or identical to each other, $X^{LW}$ represents —O—, —S—, —$OCH_2$—, —$CH_2O$—, —CO—, —COO—, —OCO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —$SCF_2$—, —CH=CH—COO—, —CH=CH—OCO—, —COO—CH=CH—, —OCO—CH=CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$—COO—, —$CH_2$—OCO—, —CH=CH—, —N=N—, —CH=N—N=CH—, —CF=CF—, —C≡C—, or a single bond, and if a plurality of $X^{LW}$'s exist, they may be different from or identical to each other (provided that, $P^{LW}$-$(Sp^{LW}$-$X^{LW})$kLW-does not contain a —O— bond), and kLW represents an integer of 0 to 10, and if a plurality of $L^W$'s exist in the compound, they may be different from or identical to each other, and Y represents a hydrogen atom, a fluorine atom, a chlorine atom, a bromine atom, an iodine atom, a pentafluorosulfuranyl group, a nitro group, a cyano group, an isocyano group, an amino group, a hydroxyl group, a mercapto group, a methylamino group, a dimethylamino group, a diethylamino group, a diisopropylamino group, a trimethylsilyl group, a dimethylsilyl group, a thioisocyano group, or a linear or branched alkyl group having 1 to 20 carbon atoms, in which one —$CH_2$— or two or more non-adjacent —$CH_2$—'s may be each independently substituted with —O—, —S—, —CO—, —COO—, —OCO—, —CO—S—, —S—CO—, —O—CO—O—, —CO—NH—, —NH—CO—, —CH=CH—COO—, —CH=CH—OCO—, —COO—CH=CH—, —OCO—CH=CH—, —CH=CH—, —CF=CF—, or —C≡C—, and any hydrogen atom in the alkyl group may be substituted with a fluorine atom, or Y may represent a group represented by $P^Y$-$(Sp^Y$-$X^Y)$kY-, where $P^Y$ represents a polymerizable group, $Sp^Y$ represents a spacer group or single bond, and if a plurality of $Sp^Y$'s exist, they may be different from or identical to each other, $X^Y$ represents —O—, —S—, —$OCH_2$—, —$CH_2O$—, —CO—, —COO—, —OCO—, —CO—S—, —S—CO—, —O—CO—O—, —CO—NH—, —NH—CO—, —$SCH_2$—, —$CH_2S$—, —$CF_2O$—, —$OCF_2$—, —$CF_2S$—, —$SCF_2$—, —CH=CH—COO—, —CH=CH—OCO—, —COO—CH=CH—, —OCO—CH=CH—, —COO—$CH_2CH_2$—, —OCO—$CH_2CH_2$—, —$CH_2CH_2$—COO—, —$CH_2CH_2$—OCO—, —COO—$CH_2$—, —OCO—$CH_2$—, —$CH_2$COO—, —$CH_2$OCO—, —CH=CH—, —N=N—, —CH=N—N=CH—, —CF=CF—, —C≡C—, or a single bond, and if a plurality of $X^Y$'s exist, they may be different from or identical to each other (provided that, $P^Y$-$(Sp^Y$-$X^Y)$kY-does not contain a —O—O— bond), and kY represents an integer of 0 to 10, and $W^1$ and $W^2$ may form a ring structure by combining together).

5. The compound according to claim 1, wherein $R^1$ and $R^2$ in Formula (I) represent a group represented by Formula (I-0-R).

6. The compound according to claim 1, wherein the compound represented by Formula (I) is represented by Formula (IA) below,

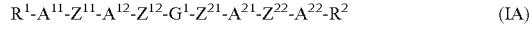

$$R^1\text{-}A^{11}\text{-}Z^{11}\text{-}A^{12}\text{-}Z^{12}\text{-}G^1\text{-}Z^{21}\text{-}A^{21}\text{-}Z^{22}\text{-}A^{22}\text{-}R^2 \quad \text{(IA)}$$

(in the formula, $R^1$, $R^2$, and $G^1$ have the same meaning as those in Formula (I), $A^{11}$ and $A^{22}$ have the same meaning as $A^1$ and $A^2$ in Formula (I), $Z^{11}$ and $Z^{22}$ have the same meaning as $Z^1$ and $Z^2$ in Formula (I), $A^{12}$ and $A^{22}$ represent a 1,4-cyclohexylene group which may be unsubstituted or may be substituted with one or more of the aforementioned substituent groups L, and $Z^{12}$ and $Z^{21}$ each independently represent a group represented by —$CR^{0\text{-}1}R^{0\text{-}2}$O— or —$OCR^{0\text{-}1}R^{0\text{-}2}$-(in the formula, $R^{0\text{-}1}$ and $R^{0\text{-}2}$ each independently have the same meaning as $R^{0\text{-}1}$ and $R^{0\text{-}2}$ in Formula (Z-0)).

7. The compound according to claim 4, wherein $G^1$ in Formula (I) or Formula (IA) is represented by Formula (M-7) or Formula (M-8).

8. A composition, comprising the compound according to claim 1.

9. A liquid crystal composition, comprising the compound according to claim 1.

10. A polymer, obtained by polymerizing the composition according to claim 8.

11. An optically anisotropic body, using the polymer according to claim 10.

12. A resin, a resin additive, an oil, a filter, an adhesive, a pressure-sensitive adhesive, oil and fat, an ink, pharmaceuticals, cosmetics, a detergent, a building material, a packaging material, a liquid crystal material, an organic EL material, an organic semiconductor material, an electronic material, a display element, an electronic device, a communication apparatus, an automobile part, an aircraft part, a machinery part, an agricultural chemical, and a food, each of which is obtained by using the compound according to claim 1, and a product using these.

* * * * *